(12) United States Patent
Zhao et al.

(10) Patent No.: US 11,248,006 B2
(45) Date of Patent: Feb. 15, 2022

(54) MACROCYCLIC DERIVATIVE OF PYRAZOL[3,4-D]PYRIMIDIN-3-ONE, PHARMACEUTICAL COMPOSITION AND USE THEREOF

(71) Applicant: SHANGHAI DE NOVO PHARMATECH CO., LTD., Shanghai (CN)

(72) Inventors: Zhiming Zhao, Shanghai (CN); Daxin Gao, Shanghai (CN); Shoujun Chen, Shanghai (CN); Zhiheng Wu, Shanghai (CN)

(73) Assignee: SHANGHAI DE NOVO PHARMATECH CO., LTD., Shanghai (CN)

( * ) Notice: Subject to any disclaimer, the term of this patent is extended or adjusted under 35 U.S.C. 154(b) by 129 days.

(21) Appl. No.: 16/496,534

(22) PCT Filed: Mar. 21, 2018

(86) PCT No.: PCT/CN2018/079866
§ 371 (c)(1),
(2) Date: Nov. 19, 2019

(87) PCT Pub. No.: WO2018/171633
PCT Pub. Date: Sep. 27, 2018

(65) Prior Publication Data
US 2020/0377520 A1   Dec. 3, 2020

(30) Foreign Application Priority Data

| Mar. 23, 2017 | (CN) | .............................. | 201710179860 |
| Aug. 25, 2017 | (CN) | .......................... | 201710741306.6 |
| Sep. 20, 2017 | (CN) | .............................. | 201710853561 |
| Jan. 5, 2018 | (CN) | .......................... | 201810012312.2 |

(51) Int. Cl.
*C07D 498/22* (2006.01)
*C07D 519/00* (2006.01)
*A61K 45/06* (2006.01)

(52) U.S. Cl.
CPC ......... *C07D 498/22* (2013.01); *C07D 519/00* (2013.01); *A61K 45/06* (2013.01)

(58) Field of Classification Search
CPC .............................. C07D 498/22; C07D 519/00
See application file for complete search history.

(56) References Cited

U.S. PATENT DOCUMENTS

| 2005/0215556 | A1 | 9/2005 | Lin et al. |
| 2010/0221211 | A1 | 9/2010 | Furuyama et al. |
| 2020/0325145 | A1* | 10/2020 | Qian .................... C07D 519/00 |

FOREIGN PATENT DOCUMENTS

| CN | 101432284 A | 5/2009 |
| EP | 3712150 A1 | 9/2020 |
| WO | WO-2005047294 A1 | 5/2005 |
| WO | WO-2007126122 A1 | 11/2007 |

OTHER PUBLICATIONS

Extended European Search Report issued in European Patent Application No. 18772694.8, dated Nov. 10, 2020.
Masaki et al., "Cyclins and cyclin-dependent kinases: comparative study of hepatocellular carcinoma versus cirrhosis", Hepatology, vol. 37, No. 3, 2003, pp. 534-543.
Iorns et al., "Integrated functional, gene expression and genomic analysis for the identification of cancer targets", PLOSONE, vol. 4, issue 4, 2009, e5120, pp. 1-11.
Magnussen et al., "High expression of wee1 is associated with malignancy in vulvar squamous cell carcinoma patients", BMC Cancer, vol. 13, No. 288, 2013, pp. 1-9.
Mueller et al., "Feasibility of genomics-enabled therapy for pediatric high-grade gliomas and diffuse pontine gliomas", Neuro-Oncology, vol. 16, No. v168, 2014 (Abstracts).
Mir et al., "In silico analysis of kinase expression identifies WEE1 as a gatekeeper against mitotic catastrophe in glioblastoma", Cancer Cell, vol. 18, 2010, pp. 244-257.
Music et al., "Expression and prognostic value ofthe WEE1 kinase in gliomas", J Neurooncol, vol. 127, 2016, pp. 381-389.
Harris et al., "Integrated genomic analysis identifies the mitotic checkpoint kinase WEE1 as a novel therapeutic target in medulloblastoma", Molecular Cancer, vol. 13, No. 72, 2014, pp. 1-14.
Tibes et al., "RNAi screening of the kinome with cytarabine in leukemias", Blood, vol. 119, No. 12, 2012, pp. 2863-2872.
Porter et al., "Integrated genomic analyses identify WEE1 as a critical mediator of cell fate and a novel therapeutic target in acute myeloid leukemia", Leukemia, vol. 26, 2012, pp. 1266-1276.
Magnussen et al., "High expression of wee1 is associated with poor disease-free survival in malignant melanoma: potential for targeted therapy", PLOSONE, vol. 7, issue 6, 2012, e38254, pp. 1-8.
Slipicevic et al., "Wee1 is a novel independent prognostic marker of poor survival in post chemotherapy ovarian carinoma effusions", Gynecologic Oncology, vol. 135, 2014, pp. 118-124.
Pfister, et al, "Inhibiting WEE1 selectively kills histone H3K36me3-deficient cancers by dNTP starvation", Cancer Cell, vol. 28, 2015, pp. 1-12.
International Search Report (in English and Chinese) and Written Opinion (in English and Chinese) of PCT/CN2018/079866 dated Jun. 21, 2018; ISA/CN.

* cited by examiner

*Primary Examiner* — Matthew P Coughlin
(74) *Attorney, Agent, or Firm* — Harness, Dickey & Pierce, P.L.C.

(57) ABSTRACT

A macrocyclic derivative of pyrazol[3,4-d]pyrimidin-3-one as represented by formula (I) and/or a pharmaceutically acceptable salt thereof, a composition comprising the compound as represented by formula (I) and/or a pharmaceutically acceptable salt thereof, a preparation method therefor, use thereof as a Wee1 inhibitor and use thereof as a sensitizer in chemotherapy or a radiotherapy of cancers. The macrocyclic derivative of pyrazol[3,4-d]pyrimidin-3-one can effectively inhibit Wee1 and relating signaling pathways, having good therapeutic and relieving effects on cancers.

20 Claims, No Drawings

MACROCYCLIC DERIVATIVE OF PYRAZOL[3,4-D]PYRIMIDIN-3-ONE, PHARMACEUTICAL COMPOSITION AND USE THEREOF

CROSS-REFERENCE TO RELATED APPLICATIONS

The present application is a 371 National Phase of International Application No. PCT/CN2018/079866, filed Mar. 21, 2018, which claims the benefit of Chinese Patent Application CN201710179860.X, filed on Mar. 23, 2017, the Chinese Patent Application CN201710741306.6, filed on Aug. 25, 2017, the Chinese Patent Application CN201710853561.X, filed on Sep. 20, 2017 and the Chinese Patent Application CN201810012312.2, filed on Jan. 5, 2018. The entire disclosures of the above applications are incorporated herein by reference.

FIELD OF INVENTION

The present disclosure relates to a macrocyclic derivative of pyrazole[3,4-d]pyrimidin-3-one, a preparation method thereof, a pharmaceutical composition thereof and a use thereof.

PRIOR ARTS

Wee1 (Wee1 G2 checkpoint kinase; gene number: 7465) is a member of the serine/threonine protein kinase family, which can directly phosphorylate cyclin-dependent kinase 1 (CDK1). The phosphorylation site is thetyrosine 15 residue of CDK1, and said site is an inhibitory phosphorylation site that negatively regulates the activity of CDK1. Activation of the G2 checkpoint is primarily through the inhibition of mitosis, promoting the cyclin B-CDK1 complex. Normal cells repair damaged DNA during the G1 arrest period. However, cancer cell G1-S detection sites are often deficient, and it is necessary to rely on the function of G2-M detection sites for DNA repair. For example, P53-deficient tumor cells are lack of the function of the G1 checkpoint, and thus rely on the G2 checkpoint as a response reaction to DNA damage in cell cycle arrest. After DNA damage, the G2 checkpoint prevents damaged cells from starting mitosis, thereby protecting them from mitotic catastrophe and apoptosis. Wee1 is an indispensable factor in the function of the G2 checkpoint. Abolishing the G2 detection site by Wee1 inhibitor may selectively sensitize the P53-deficient cancer cells to DNA damage and avoid affecting surrounding normal tissues. Wee1 also regulates CDK activity in S-phase, preventing the induction of DNA damage during normal S-phase progression. Besides, Wee1 plays an active mediating role in homologous recombination (HR) repair, and homologous recombination repair is an important pathway for DNA double-strand break repair.

Up-regulation of Wee1 appears in a number of different types of cancer, including hepatocellular carcinoma (Masaki, et al, 2003), breast cancer, cervical cancer, lung cancer (Iom, et al, 2009), squamous-cell carcinoma (Magnussen, et Al, 2013), neuroglioma DIPG (Mueller, et al, 2014), spongioblastoma (Mir, et al, 2010; Music, et al, 2016), medulloblastoma (Harris, et al, 2014), Leukemia (Tibas, et al, 2012; Porter, et al, 2012), melanoma (Magnussen, et al, 2012), and oophoroma (Slipicevic, et al, 2014). Furthermore, the high expression of Wee1 is related to poor prognosis of many types of cancer. Inhibition of Wee1 may induce apoptosis in some P53 inactivated tumor cells. Inhibition of Wee1 can make cancer cells that are resistant to chemotherapy and radiation therapy become sensitive. The latest study (Pfister, et al, 2015) demonstrates the interaction between synthetic lethal and H3K36me3 deficiency, epigenetic changes in some cancer cells and Wee1 inhibition, thereby providing strong evidences for the relation between Wee1 inhibition and specific cancer patients with more precise targeted gene changes.

Thus, Wee1 is currently a highly attractive therapeutic target in the field of cancer therapy. In addition to the existing research on Wee1, there are still many opportunities to expand and benefit from its application. There are currently no drugs using Wee1 as therapeutic target in the market. The compound, the composition thereof and the use thereof described in the present disclosure will contribute to the development of Wee1 inhibitor to meet clinically unmet drug needs.

CONTENT OF THE PRESENT DISCLOSURE

The technical problem to be solved in the present disclosure is to provide a novel macrocyclic derivative of pyrazole [3,4-d]pyrimidin-3-one, a preparation method, a pharmaceutical composition and a use thereof. The macrocyclic derivative of pyrazole[3,4-d]pyrimidin-3-one of the present disclosure has good inhibitory effect on Wee1 and related signaling pathway, and can effectively treat and/or alleviate cancer.

The present disclosure provides a compound of formula (I), an isomer, a prodrug, a stable isotope derivative or a pharmaceutically acceptable salt thereof;

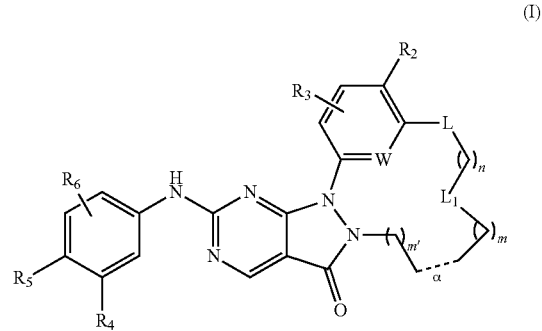

wherein, α bond is a single bond, a double bond or a triple bond;

L is CRR', O or NR'; $L_1$ is CRR$_1$, O or C(O); W is N or CR$_7$;

each of R and R$_1$ is independently H, halogene, —OR$_a$, —C(O)OR$_a$, —C(O)R$_a$, —C(O)NR$_a$R$_b$, —C(O)NR$_a$S(O)$_2$R$_b$, —S(O)$_{1-2}$R$_b$, —S(O)$_2$NR$_a$R$_b$, —S(O)$_2$N(R$_a$)C(O)R$_b$, —S(O)(=NCN)R$_a$, —S(O)(=NR$_c$)R$_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —NH$_2$, —NO$_2$, —SH, halogen, $C_{1-3}$ alkyl, $C_{1-3}$ alkoxyl and $C_{1-3}$ alkylamino; or R and R$_1$ together with the C atom to which they attached form a 3-8 membered cycloalkyl;

R' is H, —C(O)OR$_a$, —C(O)R$_a$, —C(O)NR$_a$R$_b$, —C(O)NR$_a$S(O)$_2$R$_b$, —S(O)$_{1-2}$R$_b$, —S(O)$_2$NR$_a$R$_b$, —S(O)$_2$N(R$_a$)

C(O)$R_b$, —S(O)(=NCN)$R_a$, —S(O)(=N$R_c$)$R_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —NH$_2$, —NO$_2$, —SH, halogen, $C_{1-3}$ alkyl, $C_{1-3}$ alkoxyl and $C_{1-3}$ alkylamino;

$R_2$ is H, halogen, hydroxyl, cyano, nitro, sulfydryl, amino, alkyl, alkoxyl, alkylthio, haloalkyl, haloalkoxyl, $C_{2-6}$ alkynyl, $C_{2-6}$ alkenyl, aryl, cycloalkyl, heterocycloalkyl, heteroaryl, —OC(O)$R_c$, —OC(O)O$R_c$, —OC(O)N($R_c$)$_2$, —C(O)O$R_c$, —C(O)$R_c$, —C(O)N($R_c$)$_2$, —N($R_c$)$_2$, —NHC(O)$R_c$, —NHC(O)O$R_c$, —NHC(O)N($R_c$)$_2$, —NHS(O)$_2R_c$, —S(O)$_{0-2}R_c$ or —S(O)$_2$N($R_c$)$_2$;

each of R' and $R_2$ is independently a substituent, or R' and $R_2$ are bonded to each other to form ring A; the ring A is substituted or unsubstituted $C_{3-15}$ cycloalkyl or substituted or unsubstituted 3-15 membered heterocycloalkyl; when the ring A is substituted, it is optionally substituted at any position by one or more substituents selected from the group consisting of oxo, thio, halogen, —CN, —O$R_d$, —OC(O)$R_d$, —OC(O)O$R_d$, —OC(O)N$R_dR_e$, —C(O)O$R_d$, —C(O)$R_d$, —C(O)N$R_dR_e$, —N$R_dR_e$, —N$R_d$C(O)$R_e$, —N($R_d$)C(O)O$R_e$, —N($R_d$)C(O)N$R_dR_e$, —N$R_d$S(O)$_2R_c$, —N$R_d$C(=NH)$R_e$, —N$R_d$C(=NH)N$R_dR_e$, —S(O)$_{1-2}R_e$, —S(O)$_2$N$R_dR_e$, —N$R_d$S(O)$_2$N$R_dR_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, and substituted or unsubstituted alkynyl; when the alkyl, cycloalkyl, heterocycloalkyl, cycloalkylalkyl, heterocycloalkylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —S$R_c$, —O$R_c$, —OC(O)$R_c$, —OC(O)O$R_c$, —OC(O)N($R_c$)$_2$, —C(O)O$R_c$, —C(O)$R_c$, —C(O)N($R_c$)$_2$, —N($R_c$)$_2$, —NHC(O)$R_c$, —NHC(O)O$R_c$, —NHC(O)N($R_c$)$_2$, —NHS(O)$_2R_c$, —NHC(=NH)$R_c$, —NHC(=NH)N($R_c$)$_2$, —S(O)$_{1-2}R_c$, —S(O)$_2$N($R_c$)$_2$ and —NHS(O)$_2$N($R_c$)$_2$;

$R_3$ is H, halogen, hydroxyl, cyano, nitro, sulfydryl, amino, alkyl, alkoxyl, alkylthio, haloalkyl, haloalkoxyl, $C_{2-6}$ alkynyl, $C_{2-6}$ alkenyl, aryl, cycloalkyl, heterocycloalkyl, heteroaryl, —OC(O)$R_c$, —OC(O)O$R_c$, —OC(O)N($R_c$)$_2$, —C(O)O$R_c$, —C(O)$R_c$, —C(O)N($R_c$)$_2$, —N($R_c$)$_2$, —NHC(O)$R_c$, —NHC(O)O$R_c$, —NHC(O)N($R_c$)$_2$, —NHS(O)$_2R_c$, —S(O)$_{0-2}R_c$ or —S(O)$_2$N($R_c$)$_2$;

each of $R_4$ and $R_5$ is independently H, substituted or unsubstituted alkyl, substituted or unsubstituted alkoxyl, substituted or unsubstituted alkylamino, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, alkoxyl, alkylamino, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —S$R_d$, —O$R_d$, —OC(O)$R_d$, —OC(O)O$R_d$, —OC(O)N$R_dR_e$, —C(O)O$R_d$, —C(O)$R_d$, —C(O)N$R_dR_e$, —N$R_dR_e$, —N$R_d$C(O)$R_e$, —N($R_d$)C(O)O$R_e$, —N($R_d$)C(O)N$R_dR_e$, —N$R_d$S(O)$_2R_e$, —N$R_d$C(=NH)$R_e$, —N$R_d$C(=NH)N$R_dR_e$, —S(O)$_{1-2}R_e$, —S(O)$_2$N$R_dR_e$ and —N$R_d$S(O)$_2$N$R_dR_e$;

each of $R_4$ and $R_5$ is independently a substituent, or, $R_4$ and $R_5$ together with the ring atom to which they attached form ring B, the ring B is substituted or unsubstituted monocyclic cycloalkyl, substituted or unsubstituted monocyclic heterocycloalkyl, substituted or unsubstituted spirocycloalkyl, substituted or unsubstituted spiroheterocyclyl, substituted or unsubstituted phenyl, or substituted or unsubstituted 5-12 membered heteroaryl; when the ring B is substituted, it is optionally substituted at any position by one or more substituents selected from the group consisting of oxo, halogen, —CN, —NO$_2$, —S$R_d$, —O$R_d$, —OC(O)$R_d$, —OC(O)O$R_d$, —OC(O)N$R_dR_e$, —C(O)O$R_d$, —C(O)$R_d$, —C(O)N$R_dR_e$, —N$R_dR_e$, —N$R_d$C(O)$R_e$, —N($R_d$)C(O)O$R_e$, —N($R_d$)C(O)N$R_dR_e$, —N$R_d$S(O)$_2R_e$, —N$R_d$C(=NH)$R_e$, —N$R_d$C(=NH)N$R_dR_e$, —S(O)$_{1-2}R_e$, —S(O)$_2$N$R_dR_e$, —N$R_d$S(O)$_2$N$R_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, and substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —S$R_c$, —O$R_c$, —OC(O)$R_c$, —OC(O)O$R_c$, —OC(O)N($R_c$)$_2$, —C(O)O$R_c$, —C(O)$R_c$, —C(O)N($R_c$)$_2$, —N($R_c$)$_2$, —NHC(O)$R_c$, —NHC(O)O$R_c$, —NHC(O)N($R_c$)$_2$, —NHS(O)$_2R_c$, —NHC(=NH)$R_c$, —NHC(=NH)N($R_c$)$_2$, —S(O)$_{1-2}R_c$, —S(O)$_2$N($R_c$)$_2$ and —NHS(O)$_2$N($R_c$)$_2$;

each of $R_6$ and $R_7$ is independently H, halogen, hydroxyl, sulfydryl, cyano, nitro, carboxyl, amino, alkyl, alkoxyl, alkylthio, alkylamino, haloalkyl, haloalkoxyl, $C_{2-6}$ alkynyl, $C_{2-6}$ alkenyl, hydroxyalkyl, aminoalkyl, aryl, cycloalkyl, substituted or unsubstituted heterocycloalkyl, or heteroaryl; when the heterocycloalkyl is substituted, it is optionally substituted at any position by 1-3 substituents selected from the group consisting of halogen, $C_{1-3}$ alkyl, $C_{1-3}$ alkoxyl and halo-$C_{1-3}$ alkyl;

each of $R_a$ and $R_b$ is independently H, halogen, $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, 5-6 membered heteroaryl, $C_{3-8}$ cycloalkyl-$C_{1-6}$ alkyl, 3-8 membered heterocycloalkyl-$C_{1-6}$ alkyl, phenyl-$C_{1-6}$ alkyl, or 5-6 membered heteroaryl 1-6 alkyl; the $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, or 5-6 membered heteroaryl is unsubstituted or optionally substituted at any position by 1-3 substituents selected from the group consisting of halogen, hydroxyl, amino, carboxyl, $C_{1-6}$ alkyl, halo-$C_{1-6}$ alkyl, $C_{1-6}$ alkoxyl and halo-$C_{1-6}$ alkoxyl;

each of $R_c$ is independently H, $C_{1-6}$ alkyl, halo-$C_{1-6}$ alkyl, $C_{3-8}$ cycloalkyl, 3-8 membered heterocycloalkyl, phenyl, 5-6 membered heteroaryl, 3-8 membered heterocycloalkyl-$C_{1-6}$ alkyl, $C_{3-8}$ cycloalkyl-$C_{1-6}$ alkyl, phenyl-$C_{1-6}$ alkyl or 5-6 membered heteroaryl-$C_{1-6}$ alkyl;

each of $R_d$ and $R_e$ is independently H, halogen, $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, 5-6 membered heteroaryl, $C_{3-8}$ cycloalkyl-$C_{1-6}$ alkyl, 3-8 membered heterocycloalkyl-$C_{1-6}$ alkyl, phenyl-$C_{1-6}$ alkyl, or 5-6 membered heteroaryl-$C_{1-6}$ alkyl; the $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_6$-10 aryl, or 5-6 membered heteroaryl is unsubstituted or optionally substituted at any position by 1-3 substituents selected from the group consisting of halogen, hydroxyl, amino, carboxyl, $C_{1-6}$ alkyl, halo-$C_{1-6}$ alkyl, $C_{1-6}$ alkoxyl, $C_{1-6}$ alkylamino and halo-$C_{1-6}$ alkoxyl;

m' is an integer between 1-3;

each of m and n is independently an integer between 0-5.

In the present disclosure, m' is preferably 1.

In the present disclosure, the α bond is preferably a single bond.

In the present disclosure, the α bond is preferably a double bond.

In the present disclosure, the α bond is preferably a triple bond.

In some embodiments, the compound of formula (I) and/or the pharmaceutically acceptable salt thereof is the compound of formula (I') and/or the pharmaceutically acceptable thereof:

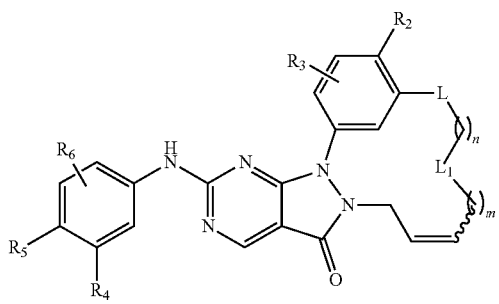

(I')

wherein, L is CRR', O or NR'; $L_1$ is $CRR_1$, O or C(O); W is N or $CR_7$;

each of R and $R_1$ is independently H, halogen, —$OR_a$, —C(O)$OR_a$, —C(O)$R_a$, —C(O)$NR_aR_b$, —C(O)$NR_aS(O)_2R_b$, —S(O)$_{1-2}R_b$, —S(O)$_2NR_aR_b$, —S(O)$_2N(R_a)C(O)R_b$, —S(O)(=NCN)$R_a$, —S(O)(=$NR_c$)$R_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —$NH_2$, —$NO_2$, —SH, halogen, $C_{1-3}$ alkyl, $C_{1-3}$ alkoxyl and $C_{1-3}$ alkylamino; or R and $R_1$ together with the C atom to which they attached form a 3-8 membered cycloalkyl;

R' is H, —C(O)$OR_a$, —C(O)$R_a$, —C(O)$NR_aR_b$, —C(O)$NR_aS(O)_2R_b$, —S(O)$_{1-2}R_b$, —S(O)$_2NR_aR_b$, —S(O)$_2N(R_a)C(O)R_b$, —S(O)(=NCN)$R_a$, —S(O)(=$NR_c$)$R_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —$NH_2$, —$NO_2$, —SH, halogen, $C_{1-3}$ alkyl, $C_{1-3}$ alkoxyl and $C_{1-3}$ alkylamino;

$R_2$ is H, halogen, hydroxyl, cyano, nitro, sulfydryl, amino, alkyl, alkoxyl, alkylthio, haloalkyl, haloalkoxyl, $C_{2-6}$ alkynyl, $C_{2-6}$ alkenyl, aryl, cycloalkyl, heterocycloalkyl, heteroaryl, —OC(O)$R_c$, —OC(O)$OR_c$, —OC(O)N($R_c)_2$, —C(O)$OR_c$, —C(O)$R_c$, —C(O)N($R_c)_2$, —N($R_c)_2$, —NHC(O)$R_c$, —NHC(O)$OR_c$, —NHC(O)N($R_c)_2$, —NHS(O)$_2R_c$, —S(O)$_{0-2}R_c$ or —S(O)$_2$N($R_c)_2$;

each of R' and $R_2$ is independently a substituent, or $R_2$ and R' are bonded to each other to form ring A; the ring A is substituted or unsubstituted $C_{3-15}$ cycloalkyl or substituted or unsubstituted 3-15 membered heterocycloalkyl; when the ring A is substituted, it is optionally substituted at any position by one or more substituents selected from the group consisting of oxo, thio, halogen, —CN, —$SR_d$, —$OR_d$, —OC(O)$R_d$, —OC(O)$OR_d$, —OC(O)$NR_dR_e$, —C(O)$OR_d$, —C(O)$R_d$, —C(O)$NR_dR_e$, —$NR_dR_e$, —$NR_dC(O)R_e$, —N($R_d$)C(O)$OR_e$, —N($R_d$)C(O)$NR_dR_e$, —$NR_dS(O)_2R_c$, —$NR_dC(=NH)R_e$, —$NR_dC(=NH)NR_dR_e$, —S(O)$_{1-2}R_e$, —S(O)$_2NR_dR_e$, —$NR_dS(O)_2NR_dR_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, and substituted or unsubstituted alkynyl; when the alkyl, cycloalkyl, heterocycloalkyl, cycloalkylalkyl, heterocycloalkylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —$NO_2$, —$SR_c$, —$OR_c$, —OC(O)$R_c$, —OC(O)$OR_c$, —OC(O)N($R_c)_2$, —C(O)$OR_c$, —C(O)$R_c$, —C(O)N($R_c)_2$, —N($R_c)_2$, —NHC(O)$R_c$, —NHC(O)$OR_c$, —NHC(O)N($R_c)_2$, —NHS(O)$_2R_c$, —NHC(=NH)$R_c$, —NHC(=NH)N($R_c)_2$, —S(O)$_{1-2}R_c$, —S(O)$_2$N($R_c)_2$ and —NHS(O)$_2$N($R_c)_2$;

$R_3$ is H, halogen, hydroxyl, cyano, nitro, sulfydryl, amino, alkyl, alkoxyl, alkylthio, haloalkyl, haloalkoxyl, $C_{2-6}$ alkynyl, $C_{2-6}$ alkenyl, aryl, cycloalkyl, heterocycloalkyl, heteroaryl, —OC(O)$R_c$, —OC(O)$OR_c$, —OC(O)N($R_c)_2$, —C(O)$OR_c$, —C(O)$R_c$, —C(O)N($R_c)_2$, —N($R_c)_2$, —NHC(O)$R_c$, —NHC(O)$OR_c$, —NHC(O)N($R_c)_2$, —NHS(O)$_2R_c$, —S(O)$_{0-2}R_c$ or —S(O)$_2$N($R_c)_2$;

each of $R_4$ and $R_5$ is independently H, substituted or unsubstituted alkyl, substituted or unsubstituted alkoxyl, substituted or unsubstituted alkylamino, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroaryl alkyl, substituted or unsubstituted alkenyl, substituted or unsubstituted alkynyl; when the alkyl, alkoxyl, alkylamino, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —$NO_2$, —$SR_d$, —$OR_d$, —OC(O)$R_d$, —OC(O)$OR_d$, —OC(O)$NR_dR_e$, —C(O)$OR_d$, —C(O)$R_d$, —C(O)$NR_dR_e$, —$NR_dR_e$, —$NR_dC(O)R_e$, —N($R_d$)C(O)$R_e$, —N($R_d$)C(O)$OR_e$, —N($R_d$)C(O)$NR_dR_e$, —$NR_dS(O)_2R_e$, —$NR_dC(=NH)R_e$, —$NR_dC(=NH)NR_dR_e$, —S(O)$_{1-2}R_e$, —S(O)$_2NR_dR_e$ and —$NR_dS(O)_2NR_dR_e$;

each of R₄ and R₅ is independently a substituent, or R₄ and R₅ together with the ring atom to which they attached form a ring B, the ring B is substituted or unsubstituted monocyclic cycloalkyl, substituted or unsubstituted monocyclic heterocycloalkyl, substituted or unsubstituted spirocycloalkyl, substituted or unsubstituted spiroheterocyclyl, substituted or unsubstituted phenyl, or substituted or unsubstituted 5-12 membered heteroaryl; when the ring B is substituted, it is optionally substituted at any position by one or more substituents selected from the group consisting of oxo, halogen, —CN, —NO₂, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)₂R$_e$, —NR$_d$C(=NH)R$_e$, —NR$_d$C(=NH)NR$_d$R$_e$, —S(O)$_{1-2}$R$_e$, —S(O)₂NR$_d$R$_e$, —NR$_d$S(O)₂NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, and substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO₂, —SR$_c$, —OR$_c$, —OC(O)R$_c$, —OC(O)OR$_c$, —OC(O)N(R$_c$)₂, —C(O)OR$_c$, —C(O)R$_c$, —C(O)N(R$_c$)₂, —N(R$_c$)₂, —NHC(O)R$_c$, —NHC(O)OR$_c$, —NHC(O)N(R$_c$)₂, —NHS(O)₂R$_c$, —NHC(=NH)R$_c$, —NHC(=NH)N(R$_c$)₂, —S(O)$_{1-2}$R$_c$, —S(O)₂N(R$_c$)₂ and —NHS(O)₂N(R$_c$)₂;

each of R₆ and R₇ is independently H, halogen, hydroxyl, sulfydryl, cyano, nitro, carboxyl, amino, alkyl, alkoxyl, alkylthio, alkylamino, haloalkyl, haloalkoxyl, C$_{2-6}$ alkynyl, C$_{2-6}$ alkenyl, hydroxyalkyl, aminoalkyl, aryl, cycloalkyl, heterocycloalkyl, or heteroaryl; or in R₆ or R₇, the heterocycloalkyl is unsubstituted, or optionally substituted at any position by 1-3 substituents selected from the group consisting of halogen, C$_{1-3}$ alkyl, C$_{1-3}$ alkoxyl and halo-C$_{1-3}$ alkyl;

each of R$_a$ and R$_b$ is independently H, halogen, C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_{6-10}$ aryl, 5-6 membered heteroaryl, C$_{3-8}$ cycloalkyl-C$_{1-6}$ alkyl, 3-8 membered heterocycloalkyl-C$_{1-6}$ alkyl, phenyl-C$_{1-6}$ alkyl, or 5-6 membered heteroaryl-C$_{1-6}$ alkyl; the C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_6$-10 aryl, or 5-6 membered heteroaryl is unsubstituted or optionally substituted at any position by 1-3 substituents selected from the group consisting of halogen, hydroxyl, amino, carboxyl, C$_{1-6}$ alkyl, halo-C$_{1-6}$ alkyl, C$_{1-6}$ alkoxyl and halo-C$_{1-6}$ alkoxyl;

each of R$_c$ is independently H, C$_{1-6}$ alkyl, halo-C$_{1-6}$ alkyl, C$_{3-8}$ cycloalkyl, 3-8 membered heterocycloalkyl, phenyl, 5-6 membered heteroaryl, 3-8 membered heterocycloalkyl-C$_{1-6}$ alkyl, C$_{3-8}$ cycloalkyl-C$_{1-6}$ alkyl, phenyl-C$_{1-6}$ alkyl or 5-6 membered heteroaryl-C$_{1-6}$ alkyl;

each of R$_d$ and R$_e$ is independently H, halogen, C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_{6-10}$ aryl, 5-6 membered heteroaryl, C$_{3-8}$ cycloalkyl-C$_{1-6}$ alkyl, 3-8 membered heterocycloalkyl-C$_{1-6}$ alkyl, phenyl-C$_{1-6}$ alkyl, or 5-6 membered heteroaryl-C$_{1-6}$ alkyl; the C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_6$-10 aryl, or 5-6 membered heteroaryl is unsubstituted or optionally substituted at any position by 1-3 substituents selected from the group consisting of halogen, hydroxyl, amino, carboxyl, C$_{1-6}$ alkyl, halo-C$_{1-6}$ alkyl, C$_{1-6}$ alkoxyl, C$_{1-6}$ alkylamino and halo-C$_1$-6 alkoxyl;

each of m and n is independently an integer between 0-5.

In some embodiments, the compound of formula (I) and/or the pharmaceutically acceptable salt thereof is the compound of formula (I″) and/or the pharmaceutically acceptable salt thereof:

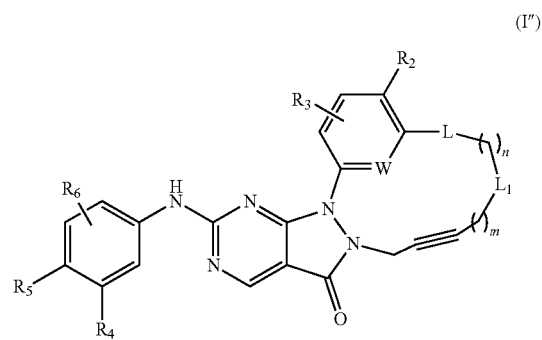

(I″)

wherein, L is CRR', O or NR'; L₁ is CRR₁, O or C(O); W is N or CR₇;

each of R and R₁ is independently H, halogen, —OR$_a$, —C(O)OR$_a$, —C(O)R$_a$, —C(O)NR$_a$R$_b$, —C(O)NR$_a$S(O)₂R$_b$, —S(O)$_{1-2}$R$_b$, —S(O)₂NR$_a$R$_b$, —S(O)₂N(R$_a$)C(O)R$_b$, —S(O)(=NCN)R$_a$, —S(O)(=NR$_c$)R$_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —NH₂, —NO₂, —SH, halogen, C$_{1-3}$ alkyl, C$_{1-3}$ alkoxyl and C$_{1-3}$alkylamino; or R and R₁ together with the C atom to which they attached form a 3-8 membered cycloalkyl;

R' is H, —C(O)OR$_a$, —C(O)R$_a$, —C(O)NR$_a$R$_b$, —C(O)NR$_a$S(O)₂R$_b$, —S(O)$_{1-2}$R$_b$, —S(O)₂NR$_a$R$_b$, —S(O)₂N(R$_a$)C(O)R$_b$, —S(O)(=NCN)R$_a$, —S(O)(=NR$_c$)R$_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —NH₂, —NO₂, —SH, halogen, C$_{1-3}$ alkyl, C$_{1-3}$ alkoxyl and C$_{1-3}$ alkylamino;

R₂ is H, halogen, hydroxyl, cyano, nitro, sulfydryl, amino, alkyl, alkoxyl, alkylthio, haloalkyl, haloalkoxyl, C$_{2-6}$ alkynyl, C$_{2-6}$ alkenyl, aryl, cycloalkyl, heterocycloalkyl, heteroaryl, —OC(O)R$_c$, —OC(O)OR$_c$, —OC(O)N(R$_c$)₂, —C(O)OR$_c$, —C(O)R$_c$, —C(O)N(R$_c$)₂, —N(R$_c$)₂, —NHC(O)R$_c$, —NHC(O)OR$_c$, —NHC(O)N(R$_c$)₂, —NHS(O)₂R$_c$, —S(O)$_{0-2}$R$_c$ or —S(O)₂N(R$_c$)₂;

each of R' and R₂ is independently a substituent, or R₂ and R' are bonded to each other to form ring A; the ring A is substituted or unsubstituted C$_{3-15}$ cycloalkyl or substituted or unsubstituted 3-15 membered heterocycloalkyl; when the ring A is substituted, it is optionally substituted at any position by one or more substituents selected from the group consisting of oxo, thio, halogen, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, and substituted or unsubstituted alkynyl; when the alkyl, cycloalkyl, heterocycloalkyl, cycloalkylalkyl, heterocycloalkylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_3$ is H, halogen, hydroxyl, cyano, nitro, sulfydryl, amino, alkyl, alkoxyl, alkylthio, haloalkyl, haloalkoxyl, C$_{2-6}$ alkynyl, C$_{2-6}$ alkenyl, aryl, cycloalkyl, heterocycloalkyl, heteroaryl, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —S(O)$_{0-2}$R$_c$ or —S(O)$_2$N(R$_c$)$_2$;

each of R$_4$ and R$_5$ is H, substituted or unsubstituted alkyl, substituted or unsubstituted alkoxyl, substituted or unsubstituted alkylamino, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, alkoxyl, alkylamino, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$ and —NR$_d$S(O)$_2$NR$_d$R$_e$;

each of R$_4$ and R$_5$ is independently a substituent, or R$_4$ and R$_5$ together with the ring atom to which they attached form a ring B, the ring B is substituted or unsubstituted monocyclic cycloalkyl, substituted or unsubstituted monocyclic heterocycloalkyl, substituted or unsubstituted spirocycloalkyl, substituted or unsubstituted spiroheterocyclyl, substituted or unsubstituted phenyl, or substituted or unsubstituted 5-12 membered heteroaryl; when the ring B is substituted, it is optionally substituted at any position by one or more substituents selected from the group consisting of oxo, halogen, —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, and substituted or unsubstituted alkynyl; when the alkyl, cycloalkyl, heterocycloalkyl, aryl, heteroaryl, cycloalkylalkyl, heterocycloalkylalkyl, aryl alkyl, heteroaryl alkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

each of R$_6$ and R$_7$ is independently H, halogen, hydroxyl, sulfydryl, cyano, nitro, carboxyl, amino, alkyl, alkoxyl, alkylthio, alkylamino, haloalkyl, haloalkoxyl, C$_{2-6}$ alkynyl, C$_{2-6}$ alkenyl, hydroxyalkyl, aminoalkyl, aryl, cycloalkyl, heterocycloalkyl, or heteroaryl; the heterocycloalkyl is unsubstituted or optionally substituted at any position by 1-3 substituents selected from the group consisting of halogen, C$_{1-3}$ alkyl, C$_{1-3}$ alkoxyl and halo-C$_{1-3}$ alkyl;

each of R$_a$ and R$_b$ is independently H, halogen, C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_{6-10}$ aryl, 5-6 membered heteroaryl, C$_{3-8}$ cycloalkyl-C$_{1-6}$ alkyl, 3-8 membered heterocycloalkyl-C$_{1-6}$ alkyl, phenyl-C$_{1-6}$ alkyl, or 5-6 membered heteroaryl-C$_{1-6}$ alkyl; the C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_6$-10 aryl, or 5-6 membered heteroaryl is unsubstituted or optionally substituted at any position by 1-3 substituents selected from the group consisting of halogen, hydroxyl, amino, carboxyl, C$_{1-6}$ alkyl, halo-C$_{1-6}$ alkyl, C$_{1-6}$ alkoxyl and halo-C$_{1-6}$ alkoxyl;

each of R$_c$ is independently H, C$_{1-6}$ alkyl, halo-C$_{1-6}$ alkyl, C$_{3-8}$ cycloalkyl, 3-8 membered heterocycloalkyl, phenyl, 5-6 membered heteroaryl, 3-8 membered heterocycloalkyl-C$_{1-6}$ alkyl, C$_{3-8}$ cycloalkyl-C$_{1-6}$ alkyl, phenyl-C$_{1-6}$ alkyl or 5-6 membered heteroaryl-C$_{1-6}$ alkyl;

each of R$_d$ and R$_e$ is independently H, halogen, C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_{6-10}$ aryl, 5-6 membered heteroaryl, C$_{3-8}$ cycloalkyl-C$_{1-6}$ alkyl, 3-8 membered heterocycloalkyl-C$_{1-6}$ alkyl, phenyl-C$_{1-6}$ alkyl, or 5-6 membered heteroaryl-C$_{1-6}$ alkyl; the C$_{1-6}$ alkyl, C$_{1-6}$ alkoxyl, C$_{2-6}$ alkenyl, C$_{2-6}$ alkynyl, C$_{3-8}$ cycloalkyl, 3-8 membered heterocycloalkyl, C$_6$-10 aryl, or 5-6 membered heteroaryl is unsubstituted or optionally substituted at any position by 1-3 substituents selected from the group consisting of halogen, hydroxyl, amino, carboxyl, C$_{1-6}$ alkyl, halo-C$_{1-6}$ alkyl, C$_{1-6}$ alkoxyl, C$_{1-6}$ alkylamino and halo-C$_1$-6 alkoxyl;

each of m and n is independently an integer between 0-5.

In the present disclosure, L is preferably CRR'; when L$_1$ is O; m is 0, 1, 2 or 3;

and n is 1 or 2.

In the present disclosure, L is preferably O, or NR'; when L$_1$ is O; m is 1, 2 or 3; and n is 1 or 2.

In the present disclosure, L is preferably CRR', O, or NR'; when L$_1$ is C(O); m is 0; and n is 1, 2 or 3.

In the present disclosure, L is preferably NR', when L$_1$ is O; m is 1, 2 or 3; and n is 1 or 2.

In the present disclosure, L is preferably NR' or O, when $L_1$ is $CRR_1$; m is 1, 2 or 3; and n is 1, 2 or 3.

In the present disclosure, in $L_1$, $R_1$ is preferably H, F, —OH, $C_{1-6}$ alkoxyl, $C_{1-4}$ alkyl(for example, methyl, ethyl, propyl or isopropyl) or $C_{3-8}$ cycloalkyl.

In the present disclosure, in $L_1$, $R_1$ is more preferably H.

In the present disclosure, $L_1$ is more preferably $CH_2$ or O.

In the present disclosure, R is preferably H, halogen, —$OR_a$, —$C(O)OR_a$, —$C(O)R_a$, —$C(O)NR_aR_b$, —$C(O)NHS(O)_2R_b$, —$S(O)_{1-2}R_b$, —$S(O)_2NR_aR_b$, —$S(O)_2NHC(O)R_b$, —$S(O)(=NCN)R_a$, —$S(O)(=NH)R_a$, $C_{1-6}$ alkyl, or $C_{3-8}$ cycloalkyl; $R_a$ and $R_b$ are defined as above. $R_a$ is preferably H or $C_{1-4}$ alkyl; $R_b$ is preferably H or $C_{1-4}$ alkyl; R is more preferably H, F, Cl, —OH, or —$CH_3$.

In the present disclosure, R' is preferably H, —$C(O)OR_a$, —$C(O)R_a$, —$C(O)NR_aR_b$, —$C(O)NHS(O)_2R_b$, —$S(O)_{1-2}R_b$, —$S(O)_2NR_aR_b$, —$S(O)_2NHC(O)R_b$, —$S(O)(=NCN)R_a$, —$S(O)(=NH)R_a$, $C_{1-6}$ alkyl, or $C_{3-8}$ cycloalkyl; $R_a$ and $R_b$ are as defined above. $R_a$ is preferably H or $C_{1-4}$ alkyl; $R_b$ is preferably H or $C_{1-4}$ alkyl. R' is preferably H, —$CH_3$, or —$C(O)CH_3$.

In the present disclosure, $R_2$ is preferably H.

In the present disclosure, each of $R_2$ and R' is independently a substituent, or $R_2$ and R' are bonded to each other to form ring A; the ring A is preferably substituted or unsubstituted 5-8 membered heterocycloalkyl; the ring A is more preferably substituted or unsubstituted 5-6 membered heterocycloalkyl.

In the present disclosure, when the ring A is substituted, it is preferably substituted at any position by 1-4 substituents; more preferably substituted at any position by 1-3 substituents or by 1-2 substituents. The substituent is as defined above.

In the present disclosure, when the ring A is substituted, the substituent is preferably oxo, thio, halogen, or $C_{1-6}$ alkyl.

In the present disclosure, $R_3$ is preferably H, F, —OH, or $C_{1-6}$ alkoxyl.

In the present disclosure, $R_3$ is more preferably H.

In the present disclosure, $R_4$ is preferably H.

In the present disclosure, $R_4$ is preferably substituted or unsubstituted $C_{1-6}$ alkyl, substituted or unsubstituted $C_{1-6}$ alkylamino, substituted or unsubstituted $C_{3-8}$ cycloalkyl, substituted or unsubstituted 3-9 membered heterocycloalkyl, substituted or unsubstituted phenyl, substituted or unsubstituted 5-6 membered heteroaryl, substituted or unsubstituted $C_{3-8}$ cycloalkyl-$C_{1-6}$ alkyl, substituted or unsubstituted 3-8 membered heterocycloalkyl-$C_{1-6}$ alkyl, substituted or unsubstituted phenyl-$C_{1-6}$ alkyl, substituted or unsubstituted 5-6 membered heteroaryl-$C_{1-6}$ alkyl, substituted or unsubstituted $C_{2-6}$ alkenyl, substituted or unsubstituted $C_{2-6}$ alkynyl.

In the present disclosure, $R_4$ is more preferably H or substituted or unsubstituted 3-9 membered heterocycloalkyl.

In the present disclosure, in $R_4$, when the alkyl, alkylamino, cycloalkyl, heterocyclyl, aryl, heteroaryl, cycloalkylalkyl, heterocycloalkylalkyl, arylalkyl, heteroarylalkyl, alkenyl or alkynyl is substituted, it is preferably substituted at any position by 1-4 substituents; more preferably substituted at any position by 1-3 substituents; the substituent is as defined above.

In the present disclosure, when $R_4$ is substituted, the substituent is preferably F, Cl, $C_{1-6}$ alkyl, halo-$C_{1-3}$ alkyl, halo-$C_{1-3}$ alkoxyl, hydroxy-$C_{1-3}$ alkyl, amino-$C_{1-3}$ alkyl, $C_{2-6}$ alkenyl, $C_{2-6}$ alkynyl, —CN, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, or —$NR_dS(O)_2NR_dR_e$; wherein $R_d$ and $R_e$ are as defined above. $R_d$ is preferably H or $C_{1-4}$ alkyl; $R_e$ is preferably H or $C_{1-4}$ alkyl.

In the present disclosure, when $R_4$ is substituted, the substituent is more preferably $C_{1-6}$ alkyl (for example, methyl).

In the present disclosure, $R_4$ is more preferably

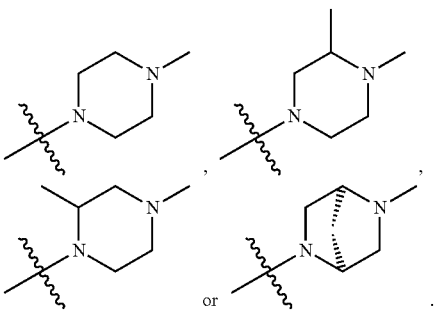

In the present disclosure, $R_5$ is preferably H.

In the present disclosure, $R_5$ is preferably substituted or unsubstituted $C_{1-6}$ alkyl, substituted or unsubstituted $C_{1-6}$ alkylamino, substituted or unsubstituted $C_{3-8}$ cycloalkyl, substituted or unsubstituted 3-9 membered heterocycloalkyl, substituted or unsubstituted phenyl, substituted or unsubstituted 5-6 membered heteroaryl, substituted or unsubstituted $C_{3-8}$ cycloalkyl-$C_{1-6}$ alkyl, substituted or unsubstituted 3-8 membered heterocycloalkyl-$C_{1-6}$ alkyl, substituted or unsubstituted phenyl-$C_{1-6}$ alkyl, substituted or unsubstituted 5-6 membered heteroaryl-$C_{1-6}$ alkyl, substituted or unsubstituted $C_{2-6}$ alkenyl, substituted or unsubstituted $C_{2-6}$ alkynyl.

In the present disclosure, in $R_5$, when the alkyl, alkylamino, cycloalkyl, heterocyclyl, aryl, heteroaryl, cycloalkylalkyl, heterocycloalkylalkyl, arylalkyl, heteroarylalkyl, alkenyl or alkynyl is substituted, it is preferably substituted at any position by 1-4 substituents; more preferably substituted at any position by 1-3 substituents; the substituent is as defined above.

In the present disclosure, when $R_5$ is substituted, the substituent is preferably F, Cl, $C_{1-6}$ alkyl, halo-$C_{1-3}$ alkyl, halo-$C_{1-3}$ alkoxyl, hydroxyl $C_{1-3}$ alkyl, amino$C_{1-3}$ alkyl, $C_{2-6}$ alkenyl, $C_{2-6}$ alkynyl, —CN, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, or —$NR_d S(O)_2NR_dR_e$; wherein, $R_d$ and $R_e$ are as defined above. $R_d$ is preferably H or $C_{1-4}$ alkyl; $R_e$ is preferably H or $C_{1-4}$ alkyl.

In the present disclosure, when $R_5$ is substituted, the substituent is more preferably $C_{1-6}$ alkyl (for example, methyl) or —$NR_dR_e$, wherein $R_d$ and $R_e$ are as defined above.

$R_5$ is more preferably

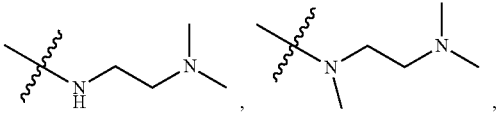

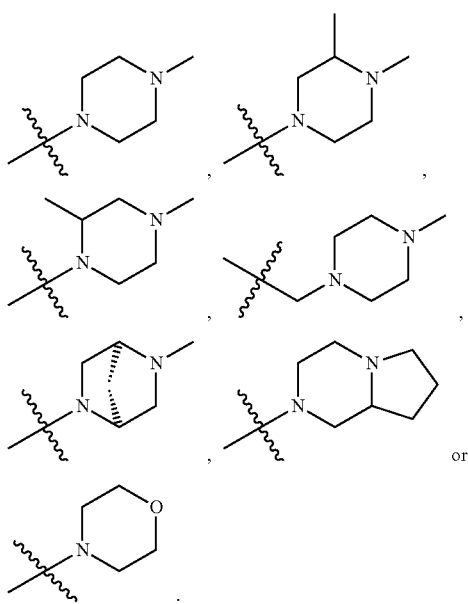

In the present disclosure, each of $R_4$ and $R_5$ is independently a substituent, or $R_4$ and $R_5$ together with the ring atom to which they attached preferably form a ring B, the ring B is preferably substituted or unsubstituted $C_{4-8}$ monocyclic cycloalkyl, substituted or unsubstituted 4-8 membered monocyclic heterocycloalkyl, substituted or unsubstituted $C_{7-12}$ spirocycloalkyl, substituted or unsubstituted 7-12 membered spiroheterocyclyl, substituted or unsubstituted phenyl, substituted or unsubstituted 5-6 membered monocyclic heteroaryl, or substituted or unsubstituted 8-10 membered fused ring heteroaryl.

In the present disclosure, ring B is more preferably selected from the group consisting of

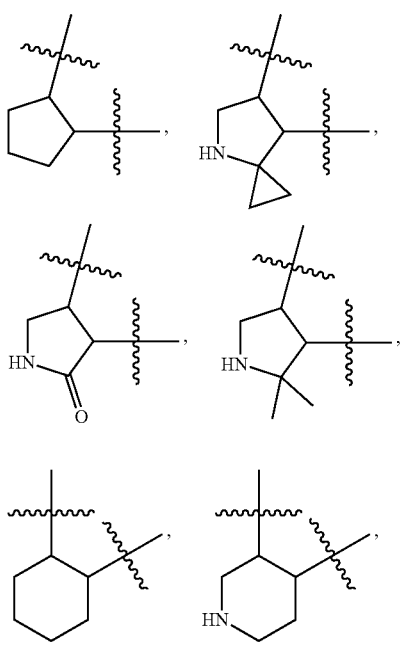

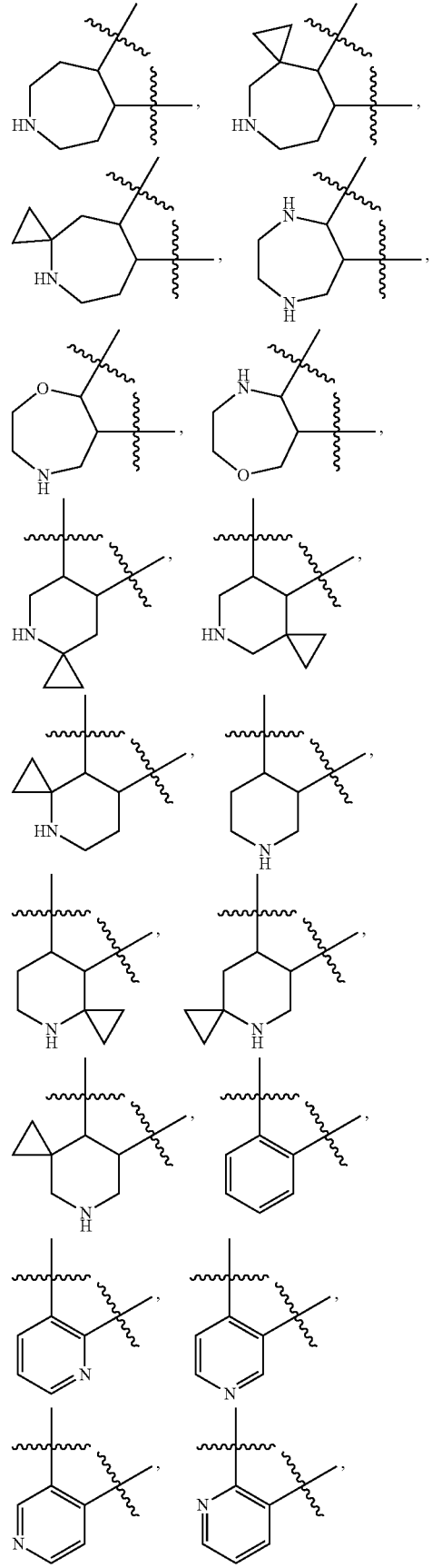

-continued

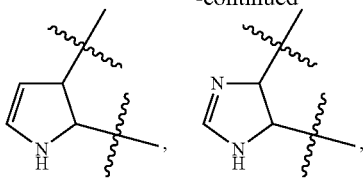

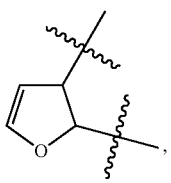

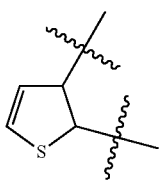 and 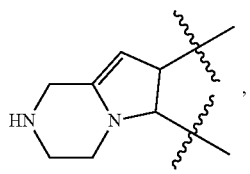

each of which is substituted or unsubstituted;

in the present disclosure, ring B is more preferably substituted or unsubstituted

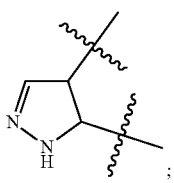 [SMILES: *C1C=NNC1*];

in the present disclosure, ring B is more preferably substituted or unsubstituted

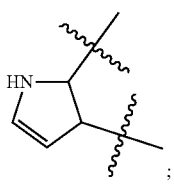;

In the present disclosure, when the ring B is substituted, it is preferably substituted at any position by 1-6 substituents; more preferably substituted at any position by 1-4 substituents; more preferably substituted at any position by 1-3 substituents; the substituent is as defined above.

In the present disclosure, $R_6$ is preferably H, F, —CH$_3$, —OCH$_3$, —OCF$_3$, —CH$_2$OH or —CH$_2$OCH$_3$.

In the present disclosure, $R_6$ is preferably C$_{1-6}$ alkylamino, or substituted or unsubstituted 3-8 membered heterocycloalkyl; wherein the 3-8 membered heterocycloalkyl is optionally substituted at any position by 1 or 1-2 substituent(s) selected from the group consisting of F, Cl, —CH$_3$, —OCH$_3$, —OCF$_3$, —CF$_3$, and —CHF$_2$.

In the present disclosure, the moiety

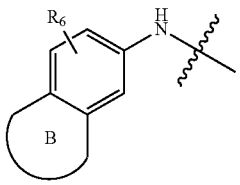

is more preferably

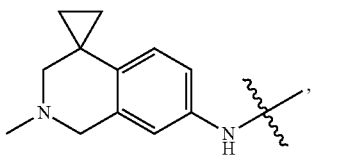,

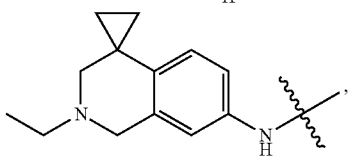,

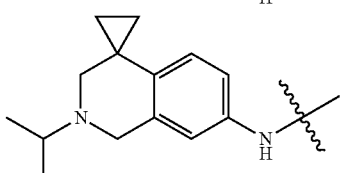,

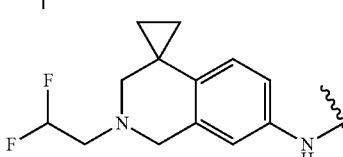,

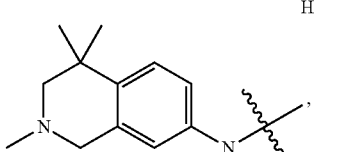,

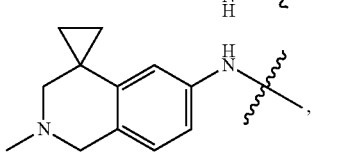,

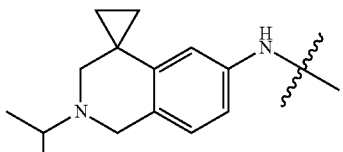,

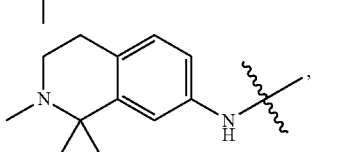,

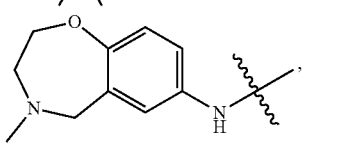,

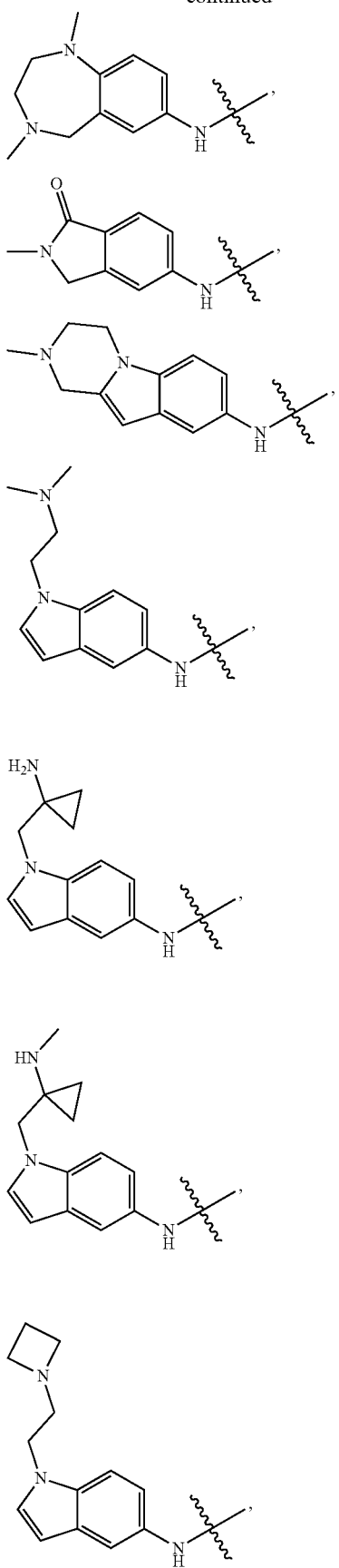
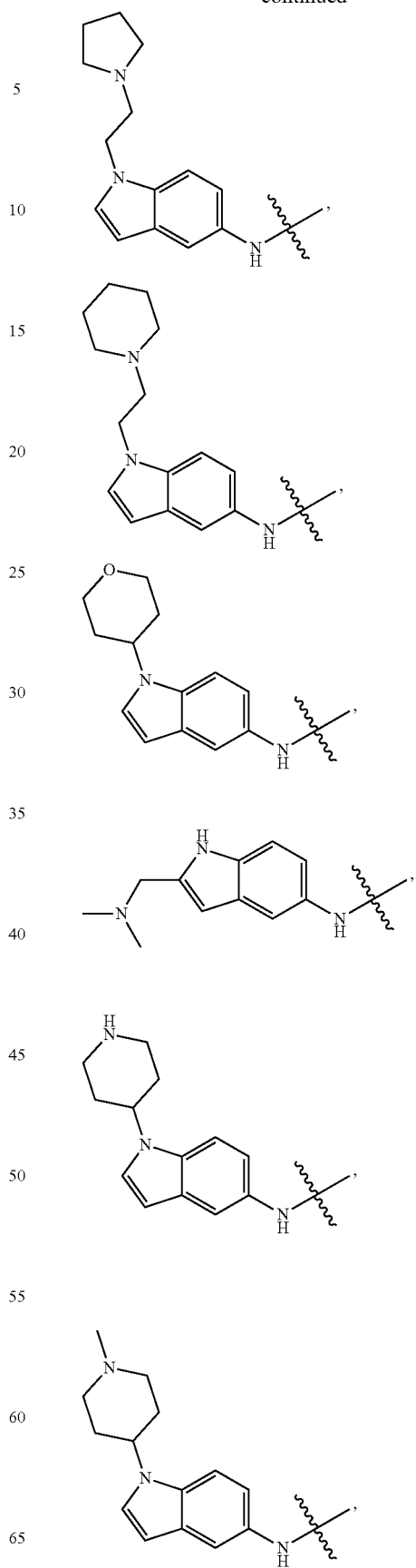

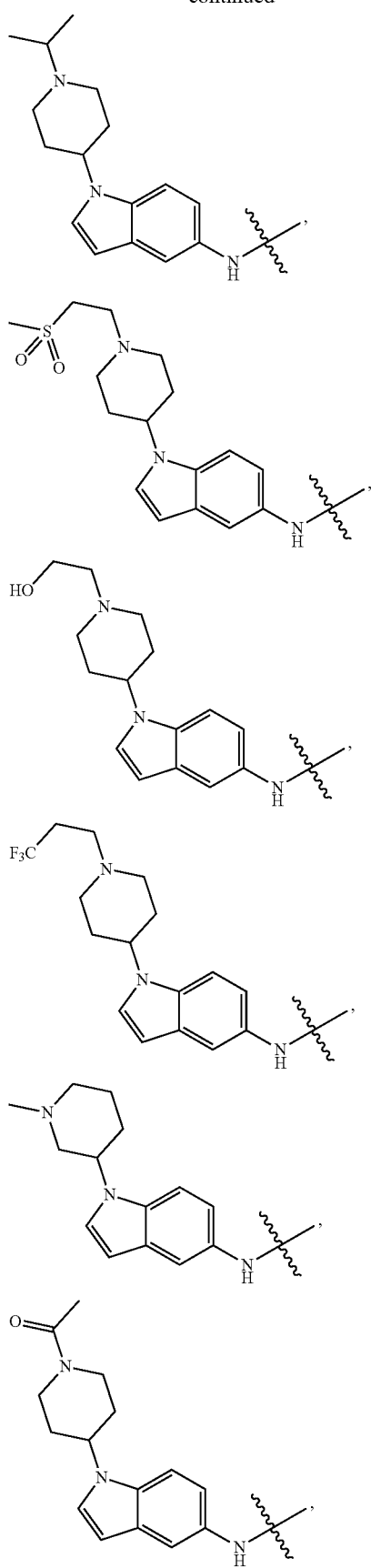
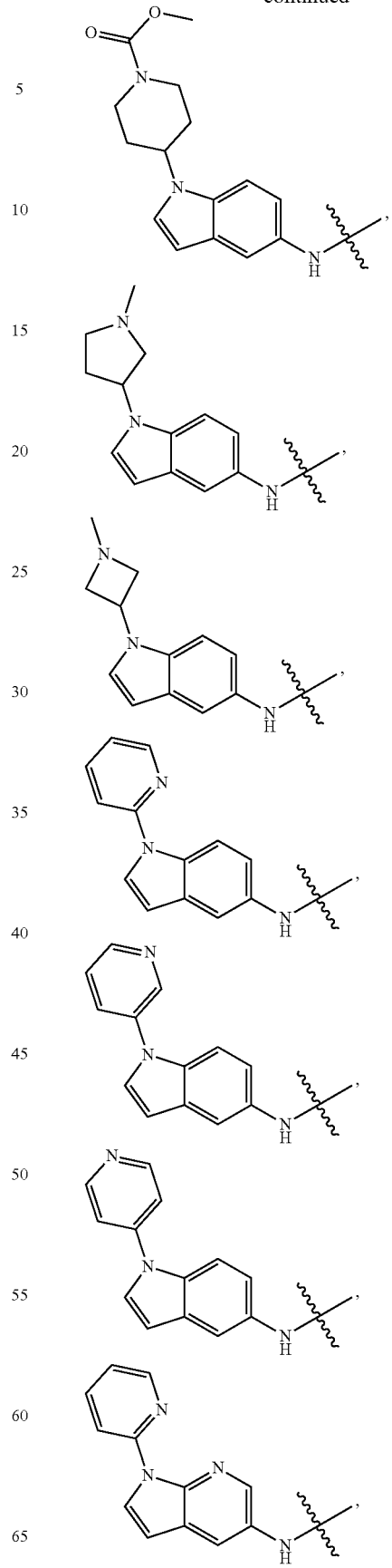

-continued
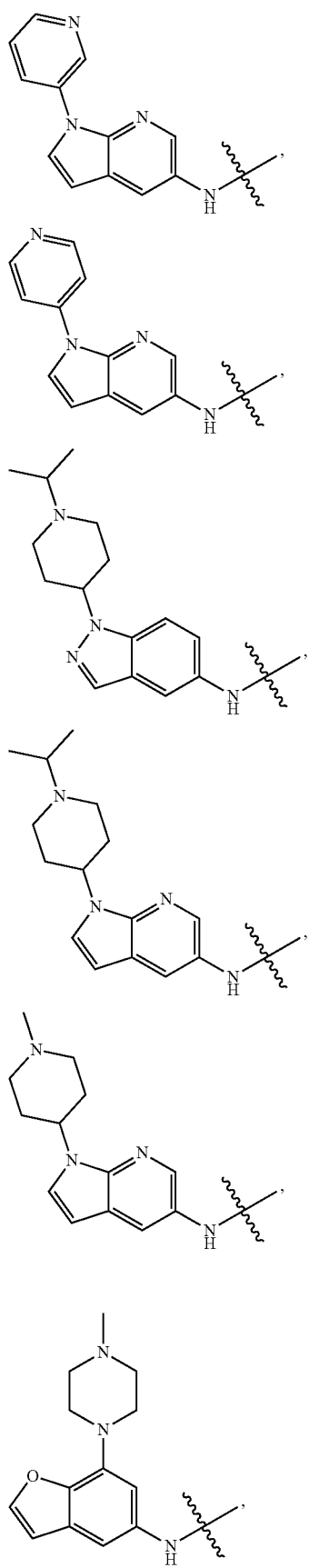
-continued
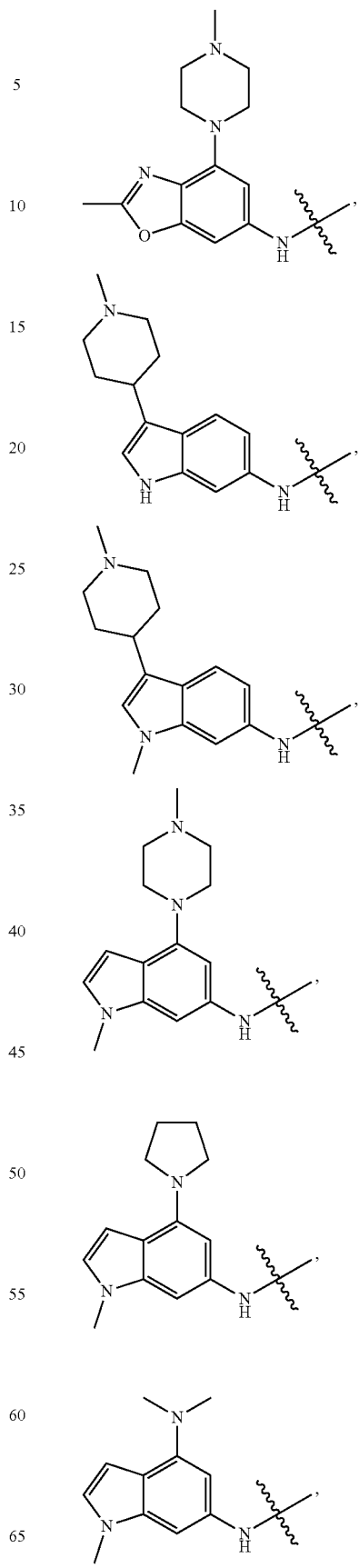

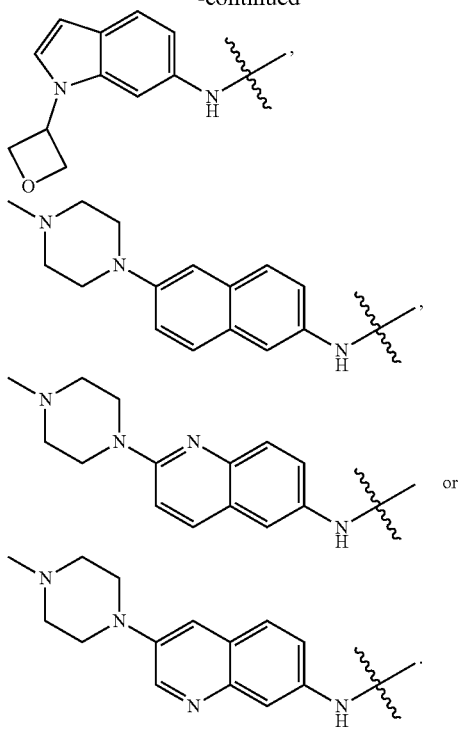

In the present disclosure, $R_7$ is preferably H.

In the present disclosure, W is preferably N.

In some embodiments, the compound of formula (I) and/or the pharmaceutically acceptable salt thereof is the compound of formula (II) and/or the pharmaceutically acceptable salt thereof:

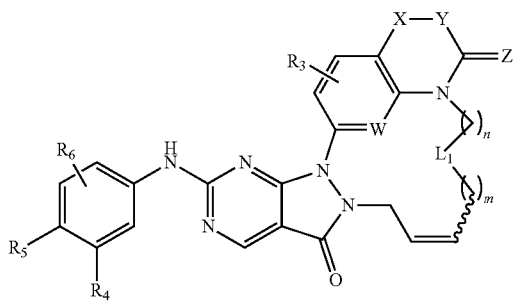

(II)

each of X and Y is a bond, —CR$_8$R$_{8a}$—, —NR$_9$—, —O—, —C(O)— or —S(O)$_{1-2}$—;

Z is H/H, O or S;

each of R$_8$ and R$_9$ is H, halogen, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, substituted or unsubstituted alkynyl; when the alkyl, cycloalkyl, heterocycloalkyl, cycloalkylalkyl, heterocycloalkylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

each of R$_{8a}$ is independently H, halogen or alkyl;

or, each of R$_8$ and R$_{8a}$ together with the C atom to which they attached form a 3-8 membered cycloalkyl or heterocycloalkyl; the heterocycloalkyl comprises 1-2 heteroatoms or groups selected from the group consisting of N, O and S(O)$_{1-2}$;

R$_3$, R$_4$, R$_5$, R$_6$, W, L$_1$, m, n, R$_c$, R$_d$, R$_e$ are as defined above.

Each of the following situations is included in the definition of formula (II):

in one of the preferable embodiments, X is O, Y is CR$_8$R$_{8a}$;

in one of the preferable embodiments, X is CR$_8$R$_{8a}$, Y is CR$_8$R$_{8a}$;

in one of the preferable embodiments, X is a bond, Y is CR$_8$R$_{8a}$;

in one of the preferable embodiments, Z is preferably O.

In one of the preferable embodiments, Z is preferably H/H.

In one of the preferable embodiments, R$_8$ is H, F or C$_{1-6}$ alkyl (for example, methyl, ethyl, isopropyl).

In one of the preferable embodiments, R$_{8a}$ is H, F or C$_{1-6}$ alkyl(for example, methyl, ethyl, isopropyl).

In one of the preferable embodiments, R$_3$ is H.

In some embodiments, the compound of formula (I) and/or the pharmaceutically acceptable salt thereof is the compound of formula (II') and/or the pharmaceutically acceptable salt thereof:

(II')

each of X and Y is a bond, —CR$_8$R$_{8a}$—, —NR$_9$—, —O—, —C(O)—, or —S(O)$_{1-2}$—;

Z is H/H, O or S;

each of R$_8$ and R$_9$ is independently H, halogen, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, substituted or unsubstituted alkynyl; when the alkyl, cycloalkyl, heterocycloalkyl, cycloalkylalkyl, heterocycloalkylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

each of R$_{8a}$ is independently H, halogen or alkyl;

or, each of R$_8$ and R$_{8a}$ together with the C atom to which they attached form a 3-8 membered cycloalkyl or heterocycloalkyl; the heterocycloalkyl comprises 1-2 heteroatoms or groups selected from the group consisting of N, O and S(O)$_{1-2}$;

R$_3$, R$_4$, R$_5$, R$_6$, W, L$_1$, m, n, R$_c$, R$_d$, R$_e$ are as defined above.

Each of the following situations is included in the definition of formula (II'):

in one of the preferable embodiments, X is O, Y is CR$_8$R$_{8a}$;

in one of the preferable embodiments, X is CR$_8$R$_{8a}$, Y is CR$_8$R$_{8a}$;

in one of the preferable embodiments, X is a connecting bond, Y is CR$_8$R$_{8a}$;

in one of the preferable embodiments, Z is preferably O.

In one of the preferable embodiments, Z is preferably H/H.

In one of the preferable embodiments, R$_8$ is H, F or C$_{1-6}$ alkyl (for example, methyl, ethyl, isopropyl).

In one of the preferable embodiments, R$_{8a}$ is H, F or C$_{1-6}$ alkyl(for example, methyl, ethyl, isopropyl).

In one of the preferable embodiments, R$_3$ is H.

In some embodiments, the compound of formula (I) and/or the pharmaceutically acceptable salt thereof is the compound of formula (I-1) and/or the pharmaceutically acceptable salt thereof:

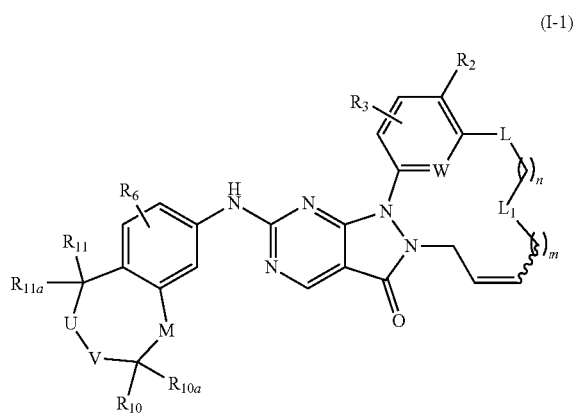

(I-1)

wherein, M is a bond, —CR$_{12}$R$_{12a}$—, —NR$_{13}$—, or —O—;

U is a bond, —CR$_{12}$R$_{12a}$—, —NR$_{13}$—, —C(O)—, or —S(O)$_{1-2}$—;

V is a bond, —NR$_{13}$—, —O—, or —CR$_{12}$R$_{12a}$—;

each of R$_{10}$, R$_{11}$ and R$_{12}$ is independently H, halogen, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

each of R$_{10a}$, R$_{11a}$ and R$_{12a}$ is independently H, hydroxyl, alkoxyl, halogen or alkyl;

or, each of R$_{10}$ and R$_{10a}$, R$_{11}$ and R$_{11a}$, or R$_{12}$ and R$_{12a}$ together with the C atom to which they attached form a 3-8 membered cycloalkyl or heterocycloalkyl; the heterocycloalkyl comprises 1-2 heteroatoms or groups selected from the group consisting of N, O and S(O)$_{1-2}$;

or, each of R$_{10}$ and R$_{10a}$, R$_{11}$ and R$_{11a}$, or R$_{12}$ and R$_{12a}$ together with the C atom to which they attached form a —C(=O)—;

R$_{13}$ is H, —OR$_d$, —C(O)OR$_d$, —C(O)R$_d$, —C(O)NR$_d$R$_e$, —S(O)$_{1-2}$R$_e$, —S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_2$, R$_3$, R$_6$, m, n, R$_c$, R$_d$, R$_e$, L and L$_1$ are as defined above.

In some embodiments, the compound of formula (I) and/or the pharmaceutically acceptable salt thereof is the compound of formula (II-I) and/or the pharmaceutically acceptable salt thereof:

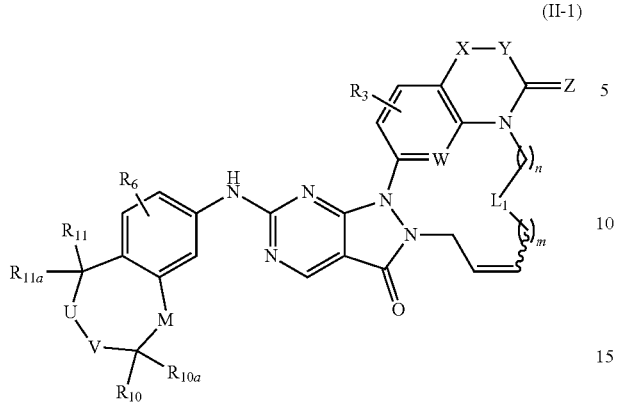

(II-1)

wherein, each of X and Y is a bond, —CR$_8$R$_{8a}$—, —NR$_9$—, O, —C(O)—, or —S(O)$_{1-2}$—;

Z is H/H, O or S;

R$_3$, R$_6$, R$_{8a}$, R$_8$, R$_9$, R$_{10a}$, R$_{10}$, R$_{11a}$, R$_{11}$, m, n, U, V and M are as defined above.

Each of the following situations is included in the definition of formula (II-1):

in one of the preferable embodiments, X is a bond or O; Y is —CH$_2$—, —CHCH$_3$—, or —C(CH$_3$)$_2$—.

Each of the following situations is included in the definition of formula (I-I) or (II-1):

in one of the preferable embodiments, each of R$_{10}$, R$_{11}$ and R$_{12}$ is independently H or C$_{1-4}$ alkyl;

in one of the preferable embodiments, each of R$_{10a}$, R$_{11a}$ and R$_{12a}$ is independently H or C$_{1-4}$ alkyl;

in one of the preferable embodiments, R$_{10}$ and R$_{10a}$ together with the C atom to which they attached form a 3 membered cycloalkyl;

in one of the preferable embodiments, R$_{11}$ and R$_{11a}$ together with the C atom to which they attached form a 3 membered cycloalkyl;

in one of the preferable embodiments, R$_{12}$ and R$_{12a}$ together with the C atom to which they attached form a 3 membered cycloalkyl;

in one of the preferable embodiments, U is —CH$_2$—, —CHCH$_3$—, —C(CH$_3$)$_2$— or

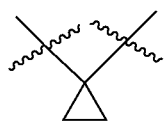

;

in one of the preferable embodiments, V is —NR$_{13}$—, R$_{13}$ is H or substituted or unsubstituted C$_{1-4}$ alkyl; when the alkyl is substituted, it is optionally substituted at any position by 1-3 fluorine;

in one of the preferable embodiments, R$_{10}$ and R$_{10a}$ together with the C atom to which they attached form a 3 membered cycloalkyl, U is —CH$_2$—, R$_{11}$ and R$_{11a}$ are H, and M is a bond;

in one of the preferable embodiments, R$_{11}$ and R$_{11a}$ together with the C atom to which they attached form a 3 membered cycloalkyl, U is —CH$_2$—, R$_{10}$ and R$_{10a}$ are H and M is a bond;

in one of the preferable embodiments, R$_{11}$ and R$_{11a}$ are H, U is

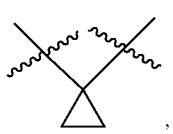 [SMILES: *C1(*)CC1]

,

R$_{10}$ and R$_{10a}$ are H, and M is a bond;

in one of the preferable embodiments, R$_3$ is H.

In some embodiments, the compound of formula (I) and/or the pharmaceutically acceptable salt thereof is the compound of formula (I-2) and/or the pharmaceutically acceptable salt thereof:

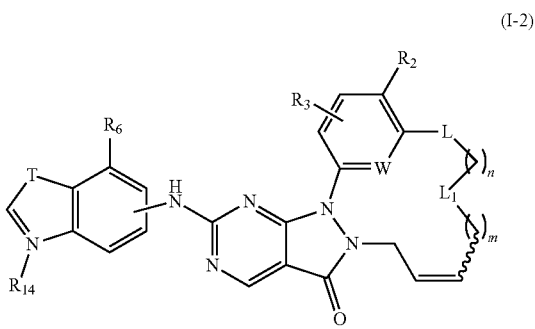

(I-2)

wherein, T is N or CR$_{14}$';

each of R$_{14}$ and R$_{14}$' is H, —OR$_d$, —C(O)OR$_d$, —C(O)R$_d$, —C(O)NR$_d$R$_e$, —S(O)$_{1-2}$R$_e$, —S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O) S(O)$_2$N(R$_c$)$_2$ and —NHS(O)$_2$N(R$_c$)$_2$;

R$_2$, R$_3$, R$_6$, R$_c$, R$_d$, R$_e$, m, n, L and L$_1$ are as defined above.

In some embodiments, the compound of formula (I) and/or the pharmaceutically acceptable salt thereof is the compound of formula (II-2) and/or the pharmaceutically acceptable salt thereof:

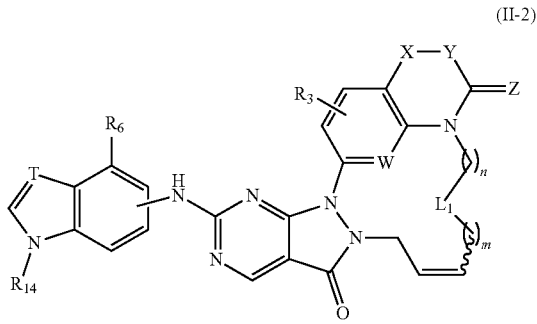

(II-2)

wherein, T is N or $CR_{14}'$;

$R_3$, $R_6$, $R_{14}$, $R_{14}'$, m, n, L and $L_1$ are as defined above.

Each of the following situations is included in the definition of the structure formula (II-2):

in one of the preferable embodiments, X is a bond or O; Y is —$CH_2$—, —$CHCH_3$— or —$C(CH_3)_2$—.

Each of the following situations is included in the definition of the formula (I-2) or (II-2):

in one of the preferable embodiments, $R_3$ is H;

in one of the preferable embodiments, $R_6$ is H;

in one of the preferable embodiments, T is N or CH; $R_{14}$ is substituted or unsubstituted $C_{1-6}$ alkyl, substituted or unsubstituted $C_{3-8}$ cycloalkyl, substituted or unsubstituted 3-8 membered heterocycloalkyl, substituted or unsubstituted $C_{3-8}$ cycloalkyl-$C_{1-6}$ alkyl, or substituted or unsubstituted 3-8 membered heterocycloalkyl-$C_{1-6}$ alkyl; the $C_{1-6}$ alkyl, $C_{3-8}$ cycloalkyl, 3-8 membered heterocycloalkyl, $C_{3-8}$ cycloalkyl-$C_{1-6}$ alkyl or 3-8 membered heterocycloalkyl-$C_{1-6}$ alkyl is optionally substituted at any position by 1-3 substituents selected from the group consisting of halogen, $C_{1-4}$ alkyl, halo-$C_{1-3}$ alkyl, halo-$C_{1-3}$ alkoxyl, hydroxy-$C_{1-3}$ alkyl, amino-$C_{1-3}$ alkyl, —CN, —$OR_d$, —$C(O)OR_d$, —$C(O)R_d$, —$C(O)NR_dR_e$, —$NR_dR_e$, —$S(O)_{1-2}R_e$, —$S(O)_2NR_dR_e$ and —$NR_dS(O)_2NR_dR_e$; each of $R_d$ and $R_e$ is independently H or $C_{1-4}$ alkyl;

in one of the preferable embodiments, T is $CR_{14}'$; $R_{14}'$ is substituted or unsubstituted $C_{1-6}$ alkyl, substituted or unsubstituted $C_{3-8}$ cycloalkyl, substituted or unsubstituted 3-8 membered heterocycloalkyl, substituted or unsubstituted $C_{3-8}$ cycloalkyl-$C_{1-6}$ alkyl, or substituted or unsubstituted 3-8 membered heterocycloalkyl-$C_{1-6}$ alkyl; the $C_{1-6}$ alkyl, $C_{3-8}$ cycloalkyl, 3-8 membered heterocycloalkyl, $C_{3-8}$ cycloalkyl-$C_{1-6}$ alkyl or 3-8 membered heterocycloalkyl-$C_{1-6}$ alkyl is optionally substituted at any position by 1-3 substituents selected from the group consisting of halogen, $C_{1-4}$ alkyl, halo-$C_{1-3}$ alkyl, halo-$C_{1-3}$ alkoxyl, hydroxy-$C_{1-3}$ alkyl, amino-$C_{1-3}$ alkyl, —CN, —$OR_d$, —$C(O)OR_d$, —$C(O)R_d$, —$C(O)NR_dR_e$, —$NR_dR_e$, —$S(O)_{1-2}R_e$, —$S(O)_2NR_dR_e$ and —$NR_dS(O)_2NR_dR_e$; each of $R_d$ and $R_e$ is independently H or $C_{1-4}$ alkyl; $R_{14}$ is H;

in one of the preferable embodiments, T is CH; $R_{14}$ is H or $C_{1-6}$ alkyl; $R_6$ is —$N(CH_3)_2$, piperazinyl, piperidyl, pyrrolidinyl or azacyclobutyl; wherein, the piperazinyl, piperidyl, pyrrolidinyl or azacyclobutyl is optionally substituted at any position by one substituent selected from F, Cl, —$CH_3$, —$OCH_3$, —$OCF_3$, —$CF_3$, or —$CHF_2$;

in one of the preferable embodiments, the moiety

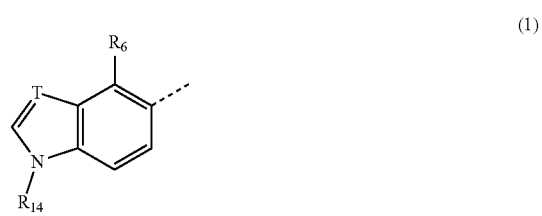

(1)

is attached to the parent molecular moiety through site (1) of the benzene ring;

in one of the preferable embodiments, the moiety

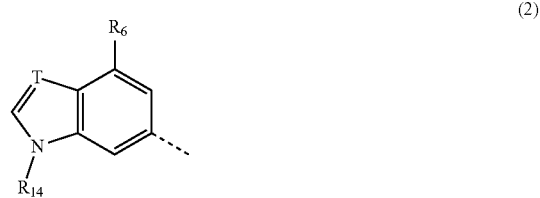

(2)

is attached to the parent molecular moiety through site (2) of the benzene ring.

In some embodiments, the compound of formula (I) and/or the pharmaceutically acceptable salt thereof is the compound of formula (I-3) and/or the pharmaceutically acceptable salt thereof:

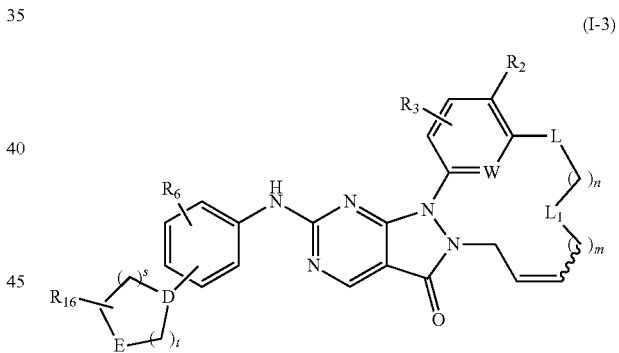

(I-3)

D is $CR_{17}$, or N;

E is —$CR_{17}R_{17a}$— or —$NR_{15}$—;

s is 0, 1 or 2;

t is 0, 1 or 2;

$R_{15}$ is H, —$OR_d$, —$C(O)OR_d$, —$C(O)R_d$, —$C(O)NR_dR_e$, —$S(O)_{1-2}R_e$, —$S(O)_2NR_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_d$, —C(O)R$_d$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{16}$ is H, halogen, oxo, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, aryl alkyl, heteroaryl alkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_d$, —C(O)R$_d$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{17}$ is H, halogen, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, aryl alkyl, heteroaryl alkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{17a}$ is H, halogen or alkyl;

R$_2$, R$_3$, R$_6$, m, n, R$_c$, R$_d$, R$_e$, L and L$_1$ are as defined above.

In some embodiments, the compound of formula (I) and/or the pharmaceutically acceptable salt thereof is the compound of formula (II-3) and/or the pharmaceutically acceptable salt thereof:

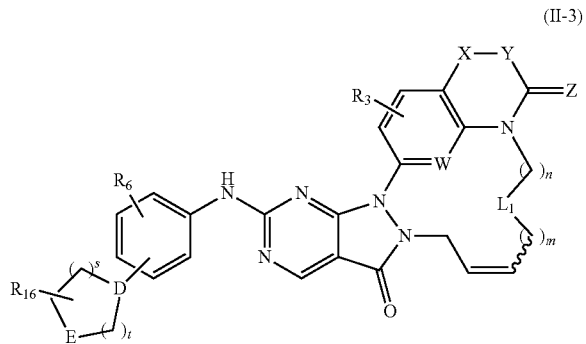

(II-3)

wherein, each of X and Y is a bond, —CR$_8$R$_{8a}$—, —NR$_9$—, O, —C(O)—, or —S(O)$_{1-2}$—;

Z is H/H, O or S;

R$_3$, R$_{8a}$, R$_8$, R$_9$, R$_6$, R$_{16}$, m, n, s, t, E, D and L$_1$ are as defined above.

Each of the following situations is included in the definition of formula (II-3):

in one of the preferable embodiments, X is a bond or O; Y is —CH$_2$—, —CHCH$_3$—, or —C(CH$_3$)$_2$—.

Each of the following situations is included in the definition of formula (I-3) or (II-3).

in one of the preferable embodiments, R$_3$ is H;

in one of the preferable embodiments, s is 1 and t is 1 or 2;

in one of the preferable embodiments, D is N or CH;

in one of the preferable embodiments, R$_6$ is H, F, Cl, —CN, —CH$_3$, —CH$_2$OH, or —CH$_2$OCH$_3$;

in one of the preferable embodiments, E is NR$_{15}$, R$_{15}$ is H, —OR$_d$, —C(O)OR$_d$, —C(O)R$_d$, —C(O)NR$_d$R$_e$, —S(O)$_{1-2}$R$_e$, —S(O)$_2$NR$_d$R$_e$, substituted or unsubstituted C$_{1-4}$ alkyl;

the C$_{1-4}$ alkyl is optionally substituted at any position by 1-3 substituents selected from the group consisting of halogen, halo-C$_{1-3}$ alkyl, —CN, —OR$_c$ and —N(R$_c$)$_2$; each of R$_c$, R$_d$ and R$_e$ is independently H or C$_{1-4}$ alkyl;

in one of the preferable embodiments, R$_{16}$ is H, —CH$_3$, —CH$_2$OH, or —CH$_2$OCH$_3$.

in one of the preferable embodiments, the moiety

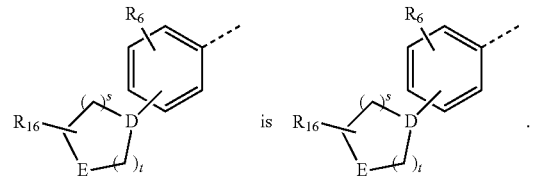

in one of the preferable embodiments, the moiety

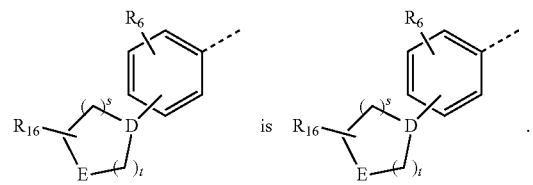

In some embodiments, the compound of formula (I) and/or the pharmaceutically acceptable salt thereof is the compound of formula (I-4) and/or the pharmaceutically acceptable salt thereof:

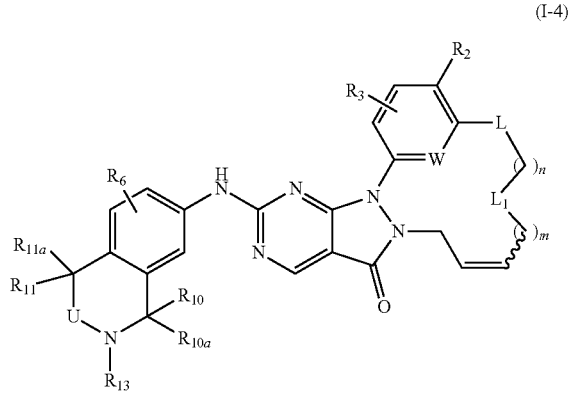

(I-4)

wherein, L is O or NR'; R' is H, $C_{1-6}$ alkyl or —C(O)—$C_{1-6}$ alkyl; $R_2$ is H;

$R_3$, $R_6$, $R_{10a}$, $R_{10}$, $R_{11a}$, $R_{11}$, $R_{13}$, $L_1$, m and n are as defined above.

In some embodiments, the compound of formula (I) and/or the pharmaceutically acceptable salt thereof is the compound of formula (II-4) and/or the pharmaceutically acceptable salt thereof:

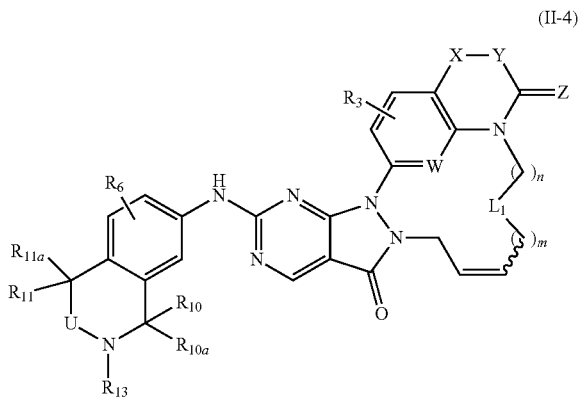

(II-4)

wherein, X is a bond or O; Y is —CH$_2$—, —CHCH$_3$—, or —C(CH$_3$)$_2$—;

Z is H/H, O or S;

$R_3$, $R_6$, $R_{10a}$, $R_{10}$, $R_{11a}$, $R_{11}$, m, n, U, W and $L_1$ are as defined above.

In some embodiments, the compound of formula (I) and/or the pharmaceutically acceptable salt thereof is the compound of formula (I-5) and/or the pharmaceutically acceptable salt thereof:

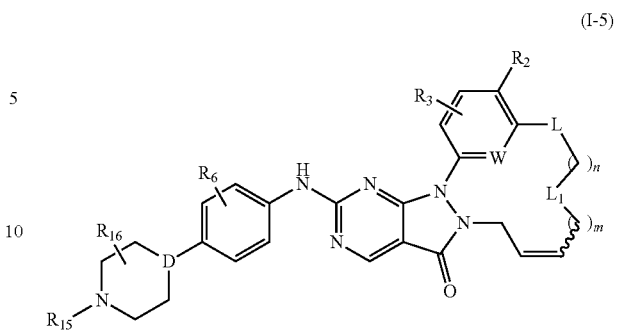

(I-5)

wherein, L is O or NR'; R' is H, $C_{1-6}$ alkyl or —C(O)—$C_{1-6}$ alkyl; $R_2$ is H;

$R_3$, $R_6$, $R_{15}$, $R_{16}$, m, n, $L_1$ and D are as defined above.

In some embodiments, the compound of formula (I) and/or the pharmaceutically acceptable salt thereof is the compound of formula (II-5) and/or the pharmaceutically acceptable salt thereof:

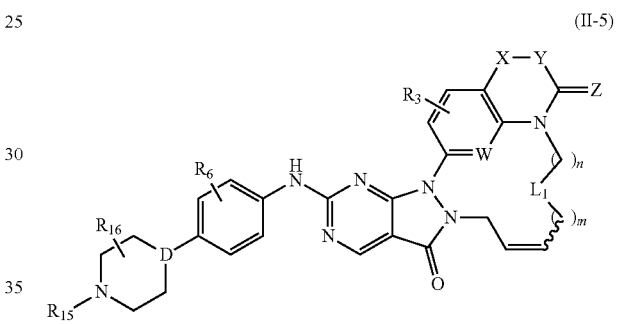

(II-5)

wherein, X is a bond or O; Y is —CH$_2$—, —CHCH$_3$— or —C(CH$_3$)$_2$—; Z is H/H, O or S;

$R_3$, $R_6$, $R_{15}$, $R_{16}$, m, n, $L_1$, W and D are as defined above.

In some embodiments, the compound of formula (I) and/or the pharmaceutically acceptable salt thereof is the compound of formula (I-6) and/or the pharmaceutically acceptable salt thereof:

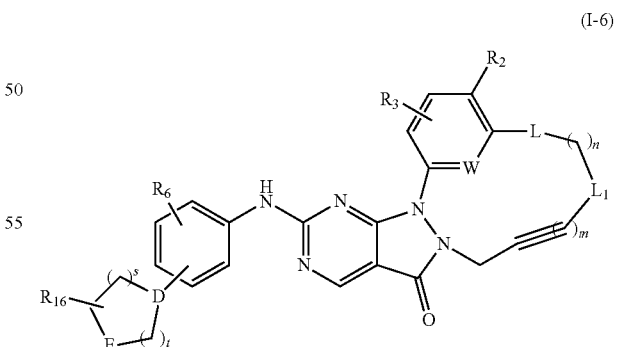

(I-6)

D is $CR_{17}$ or N;
E is —$CR_{17}R_{17a}$— or —$NR_{15}$—;
s is 0, 1 or 2;
t is 0, 1 or 2;
$R_{15}$ is H, —OR$_d$, —C(O)OR$_d$, —C(O)R$_d$, —C(O)NR$_d$R$_e$, —S(O)$_{1-2}$R$_e$, —S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, aryl alkyl, heteroaryl alkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_d$, —C(O)R$_d$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{16}$ is H, halogen, oxo, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, aryl alkyl, heteroaryl alkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_d$, —C(O)R$_d$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{17}$ is H, halogen, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroaryl alkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, aryl alkyl, heteroaryl alkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{17a}$ is H, halogen or alkyl;

R$_2$, R$_3$, R$_6$, m, n, R$_c$, R$_d$, R$_e$, L and L$_1$ are as defined above.

In some embodiments, the compound of formula (I) and/or the pharmaceutically acceptable salt thereof is the compound of formula (II-6) and/or the pharmaceutically acceptable salt thereof:

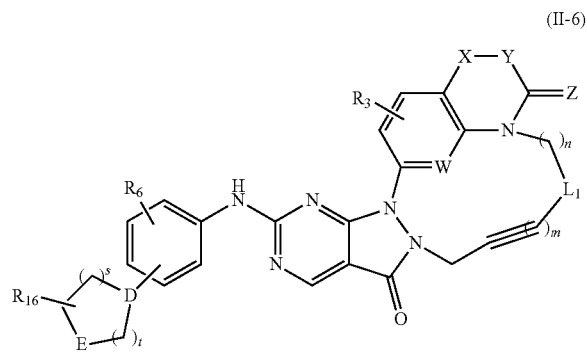

(II-6)

wherein, each of X and Y is a bond, —CR$_8$R$_{8a}$—, —NR$_9$—, O, —C(O)—, or —S(O)$_{1-2}$—;

Z is H/H, O or S;

R$_3$, R$_6$, R$_{8a}$, R$_8$, R$_9$, R$_{16}$, m, n, s, t, E, D and L$_1$ are as defined above.

Each of the following situations is included in the definition of formula (II-3):

in one of the preferable embodiments, X is a bond or O; Y is —CH$_2$—, —CHCH$_3$— or —C(CH$_3$)$_2$—.

Each of the following situations is included in the definition of formula (I-6) or (II-6):

in one of the preferable embodiments, R$_3$ is H;

in one of the preferable embodiments, s is 1, and t is 1 or 2;

in one of the preferable embodiments, D is N or CH;

in one of the preferable embodiments, R$_6$ is H, F, Cl, —CN, —CH$_3$, —CH$_2$OH, or —CH$_2$OCH$_3$;

in one of the preferable embodiments, E is NR$_{15}$; R$_{15}$ is H, —OR$_d$, —C(O)OR$_d$, —C(O)R$_d$, —C(O)NR$_d$R$_e$, —S(O)$_{1-2}$R$_e$, —S(O)$_2$NR$_d$R$_e$, substituted or unsubstituted C$_{1-4}$ alkyl; the C$_{1-4}$ alkyl is optionally substituted at any position by 1-3 substituents selected from the group consisting of halogen, halo-C$_{1-3}$ alkyl, —CN, —OR$_c$ and —N(R$_c$)$_2$; each of R$_c$, R$_d$ and R$_e$ is independently H or C$_{1-4}$ alkyl;

in one of the preferable embodiments, R$_{16}$ is H, —CH$_3$, —CH$_2$OH, or —CH$_2$OCH$_3$.

in one of the preferable embodiments, the moiety

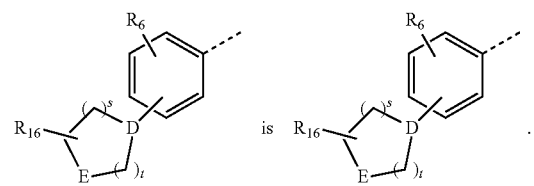

in one of the preferable embodiments, the moiety
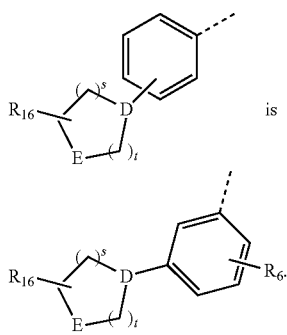 is
In some embodiments, the compound of formula (I) and/or the pharmaceutically acceptable salt thereof is preferably selected from the group consisting of:
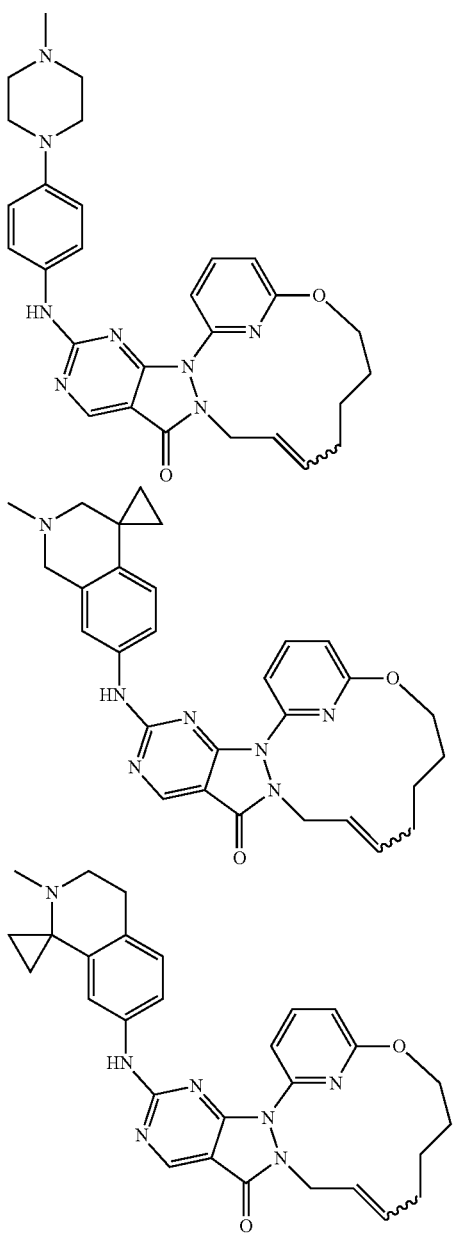
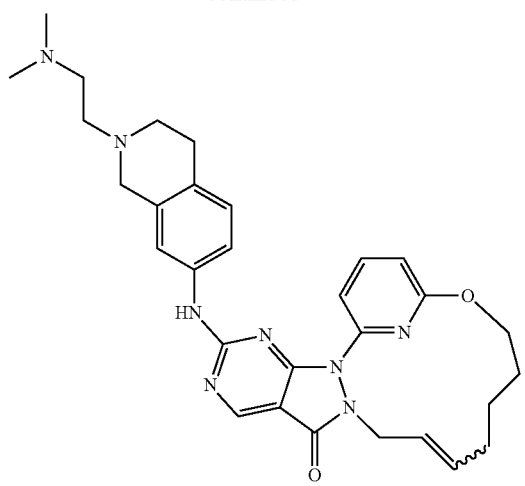
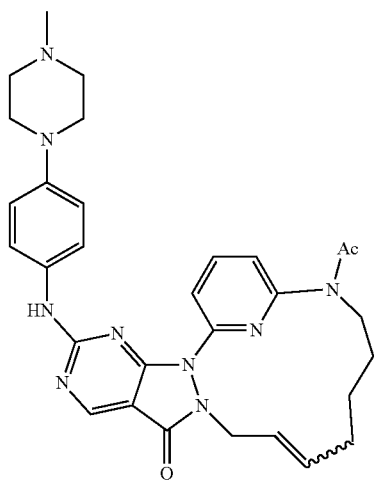
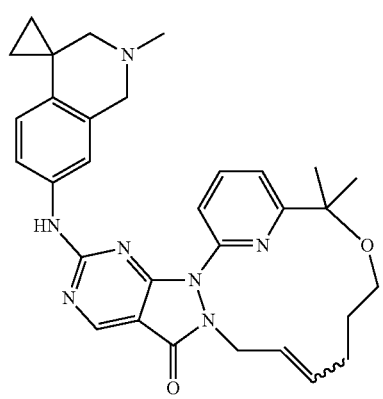

39
-continued
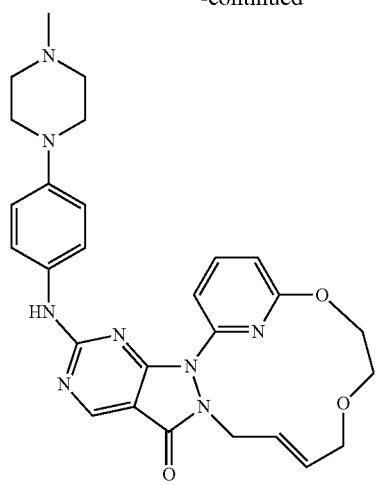
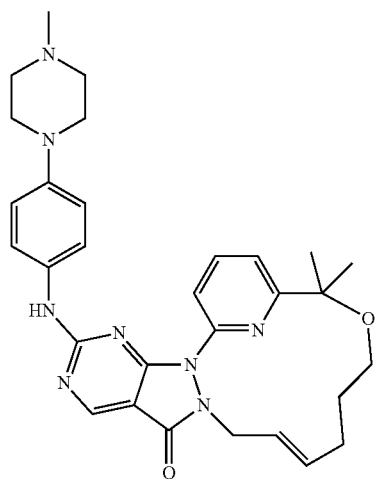
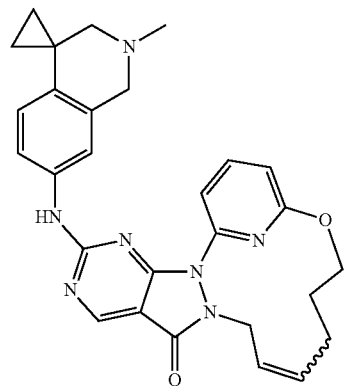
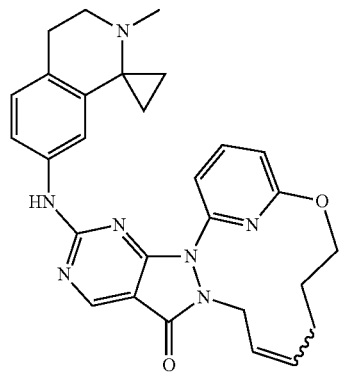
40
-continued
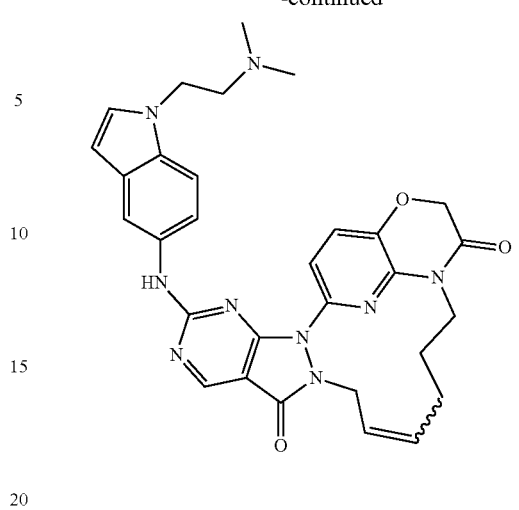
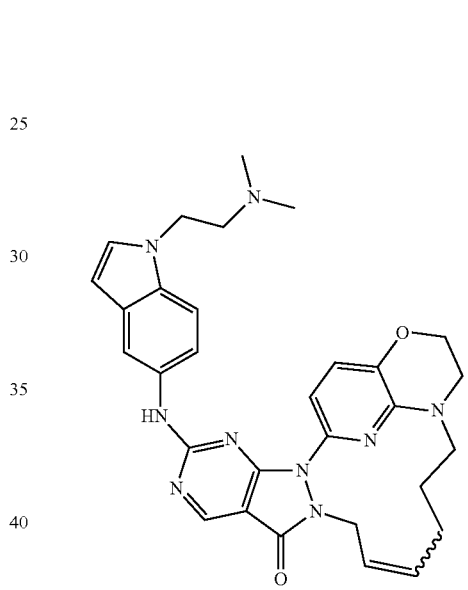

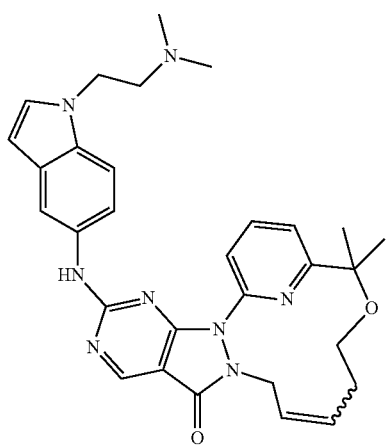
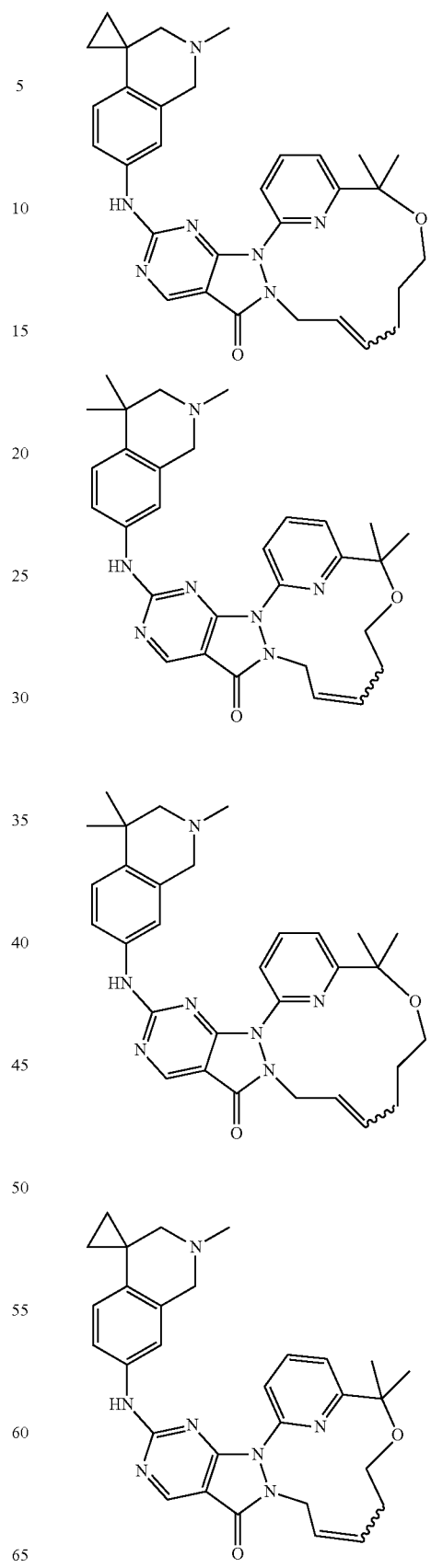

43
-continued
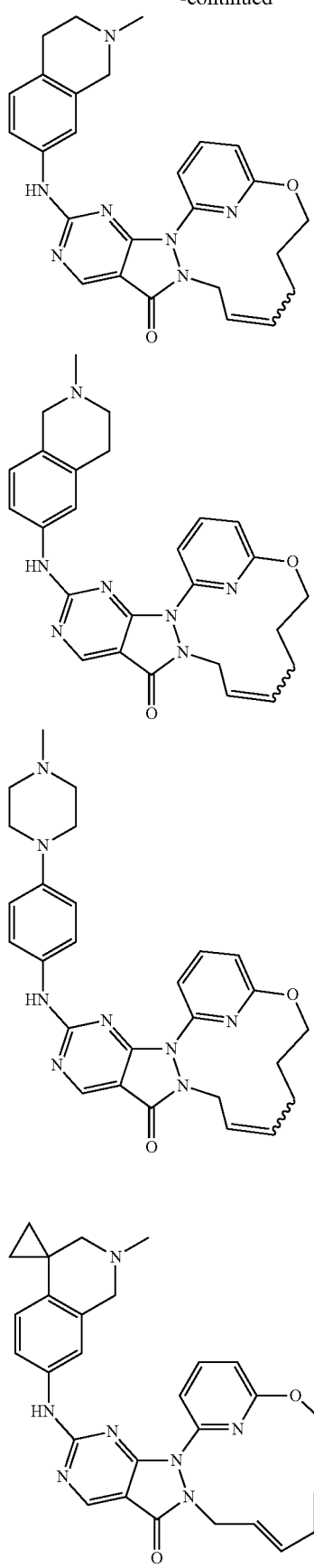
44
-continued
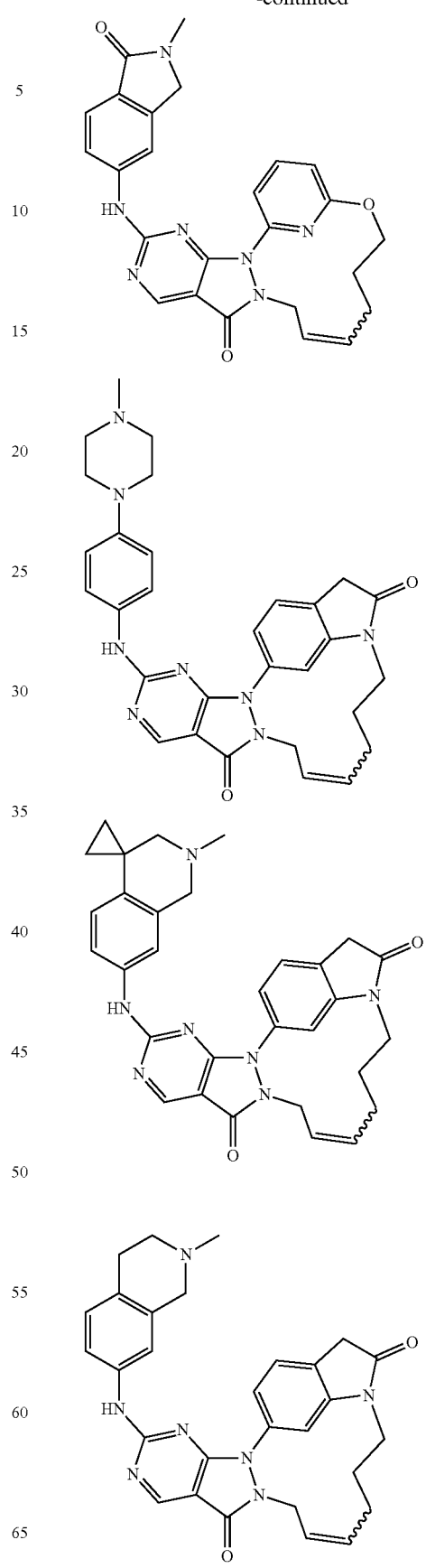

45
-continued
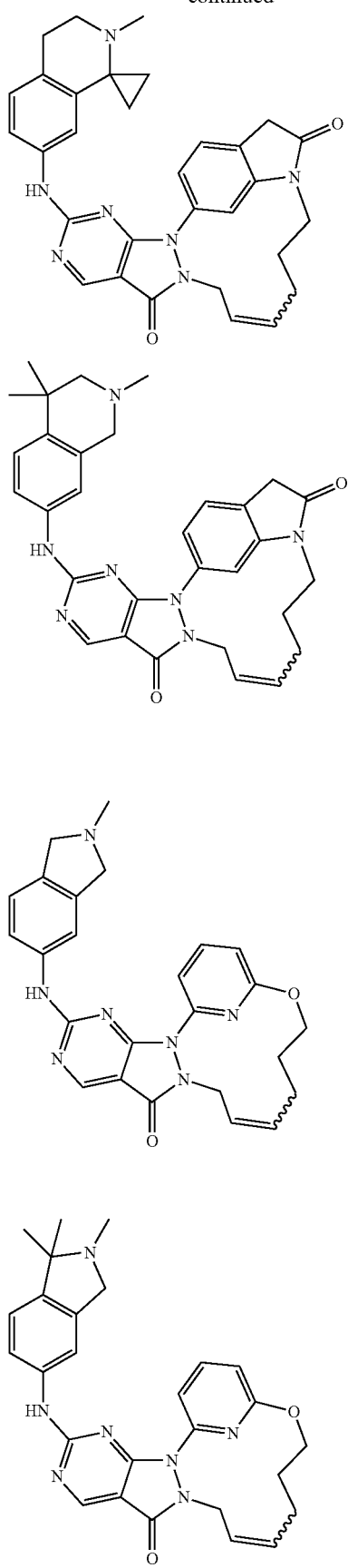
46
-continued
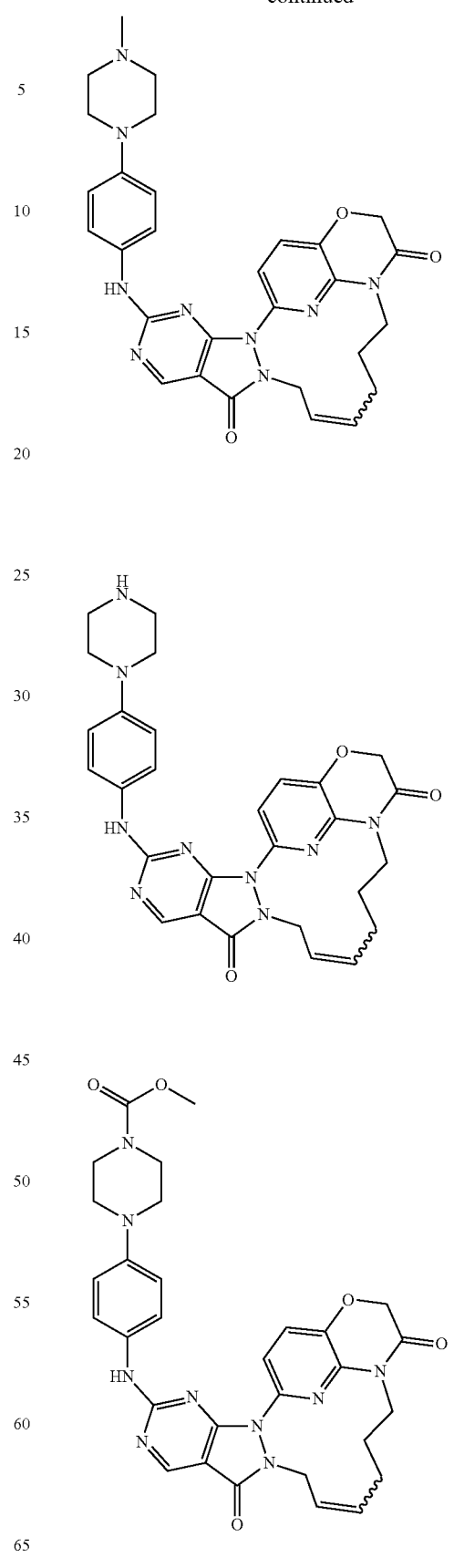

47
-continued
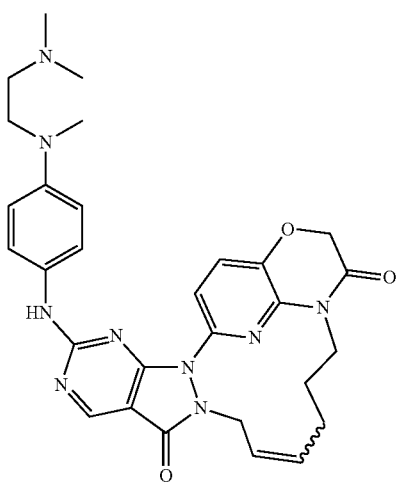
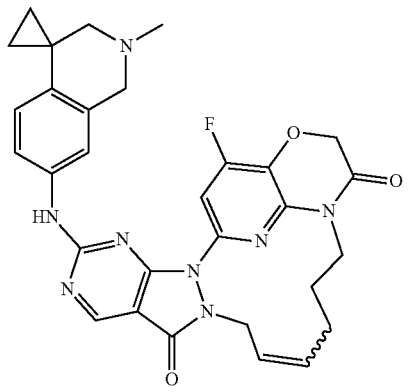
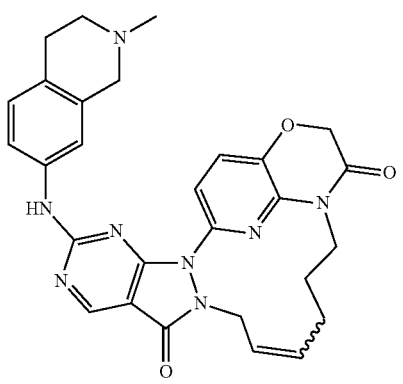 [SMILES: CN1CCc2ccc(Nc3ncc4c(=O)n5n(c4n3)-c3ccc4c(c3)N(CCCC=CC5)C(=O)CO4)cc2C1]
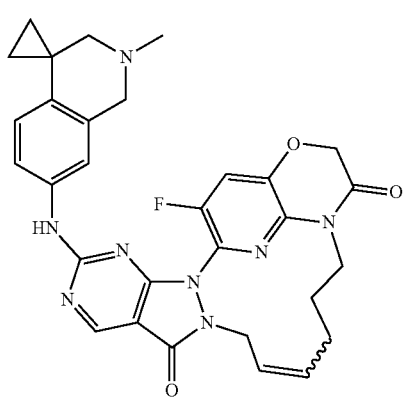
48
-continued
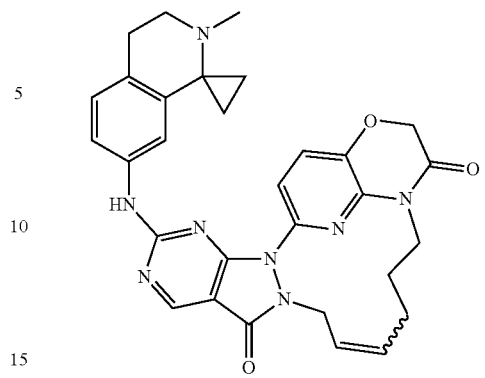
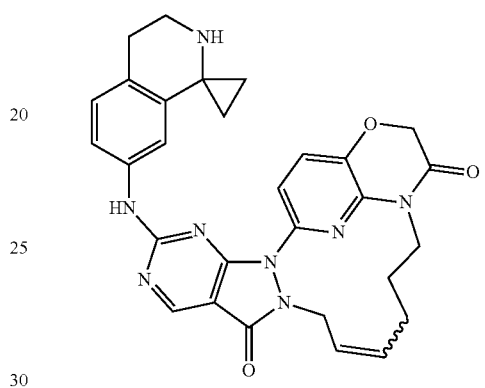
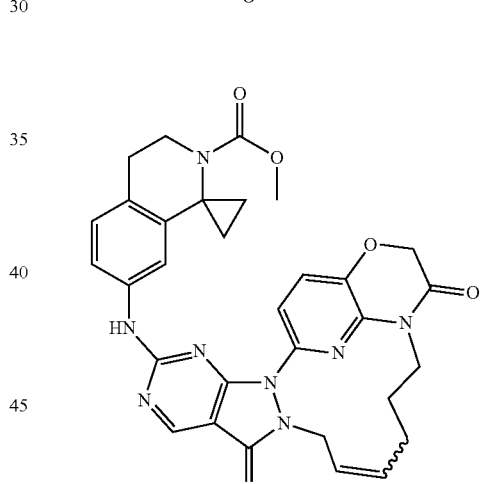
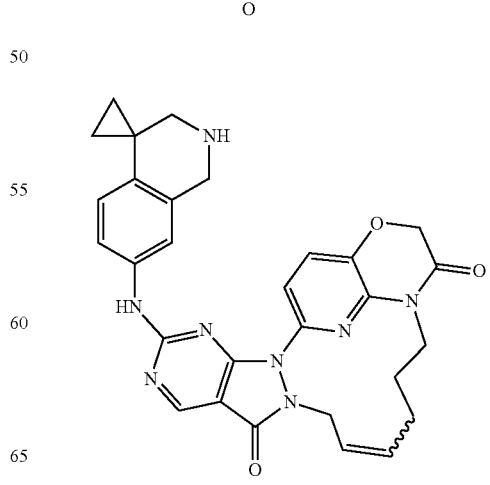

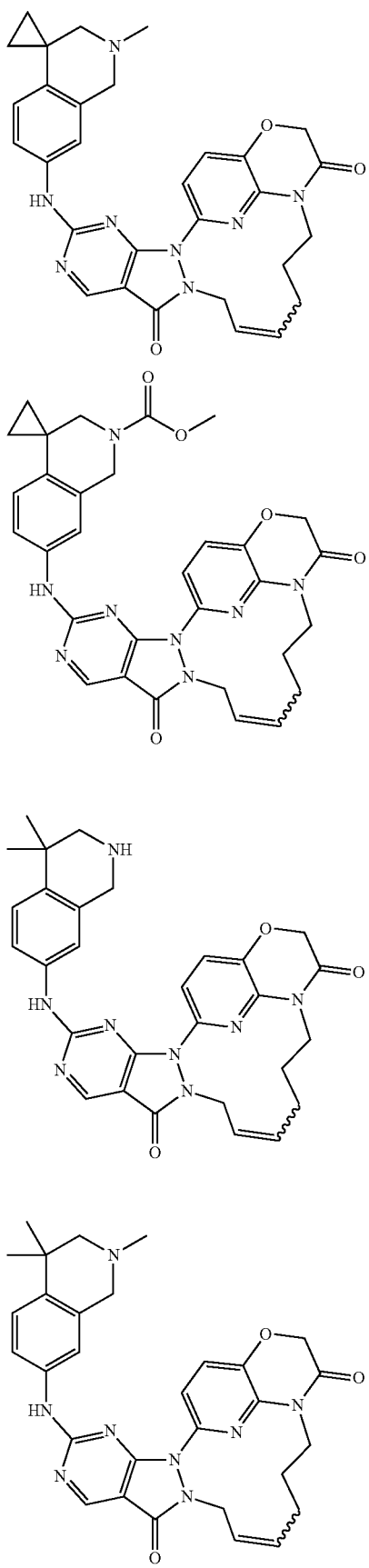
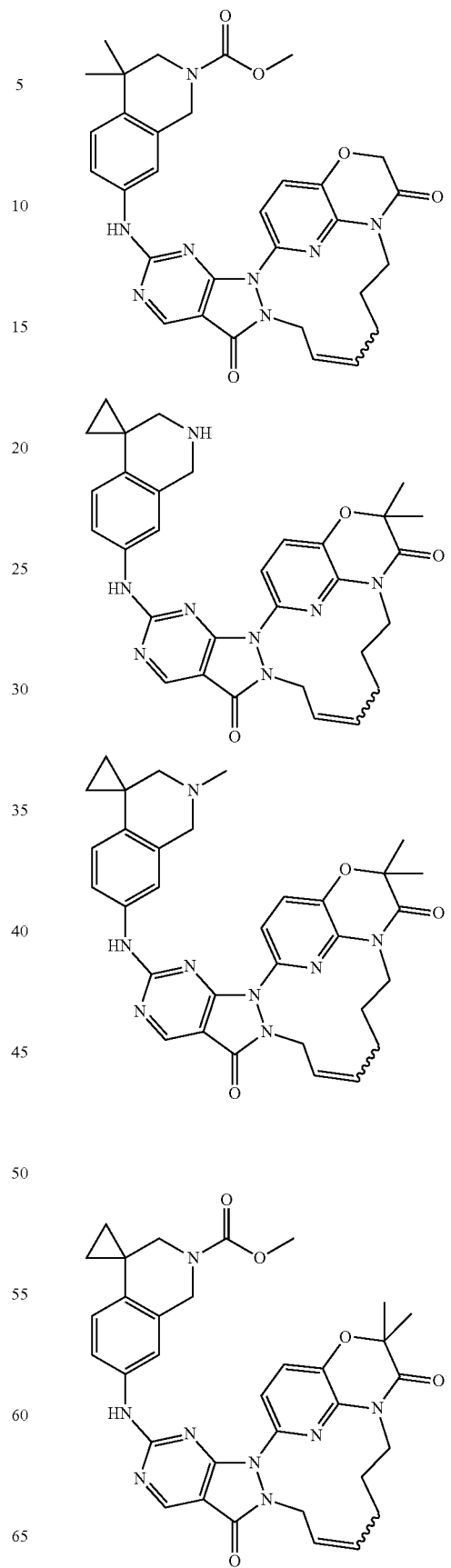

51
-continued
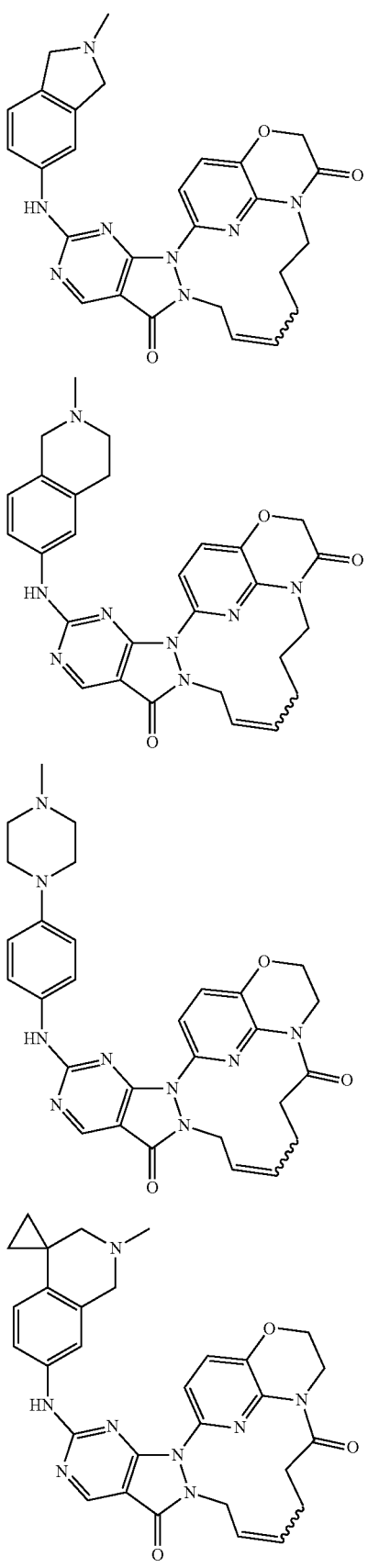
52
-continued
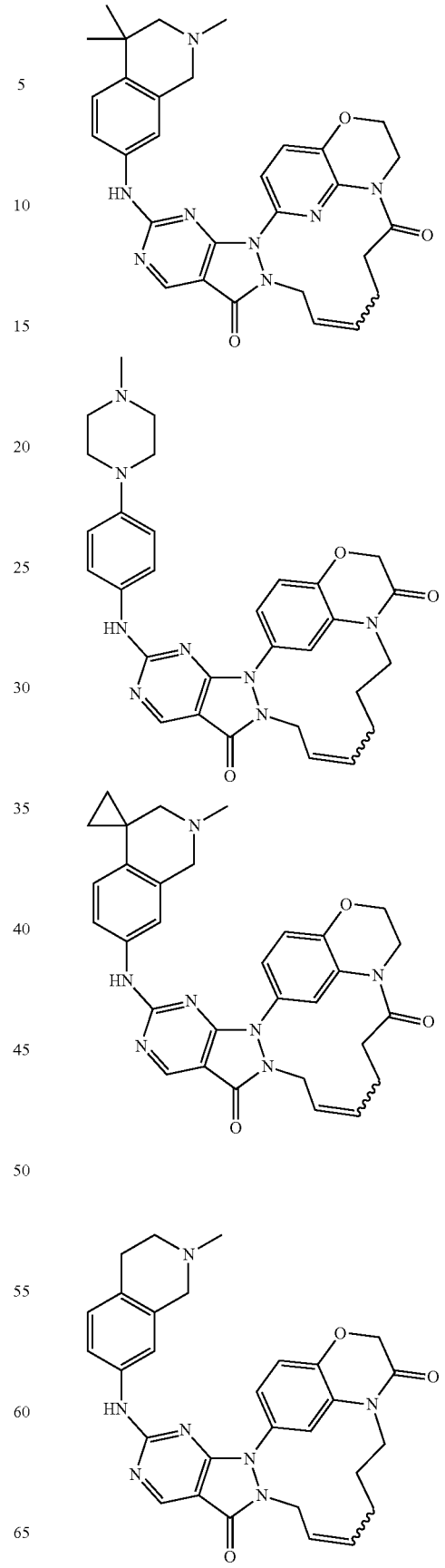

53
-continued
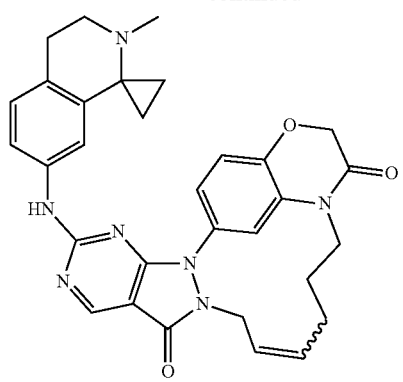
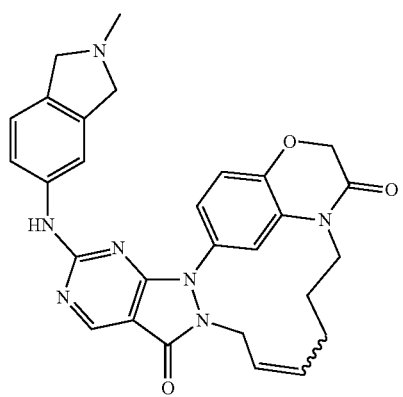
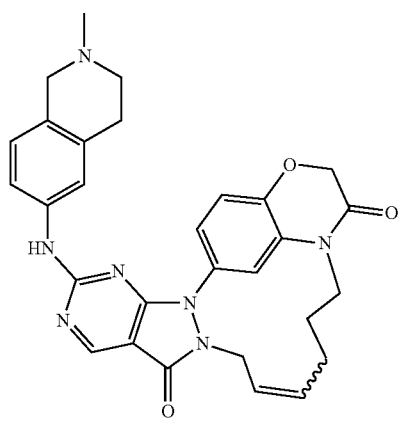
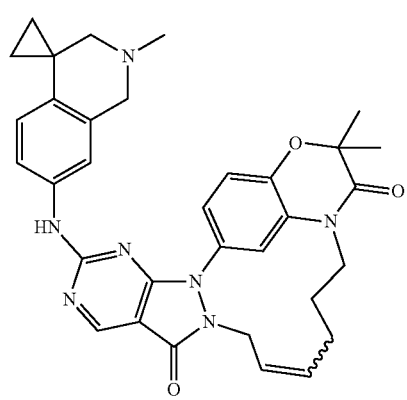
54
-continued
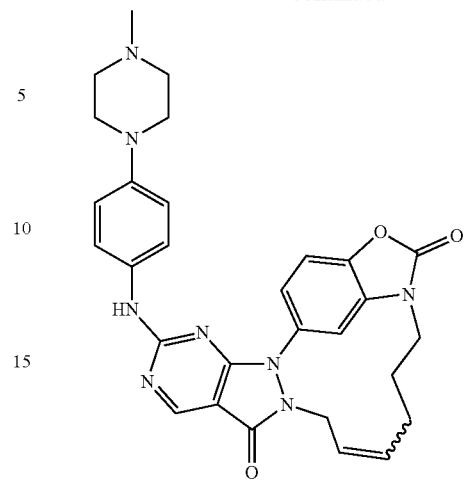
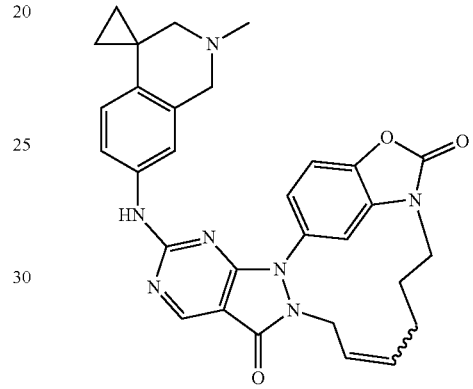
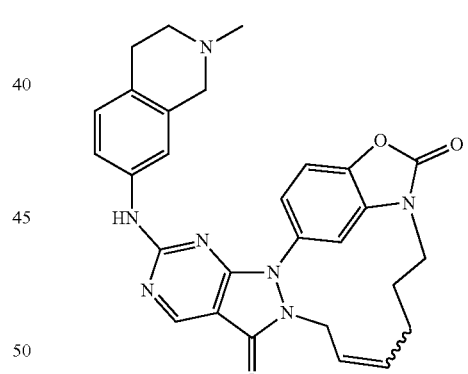
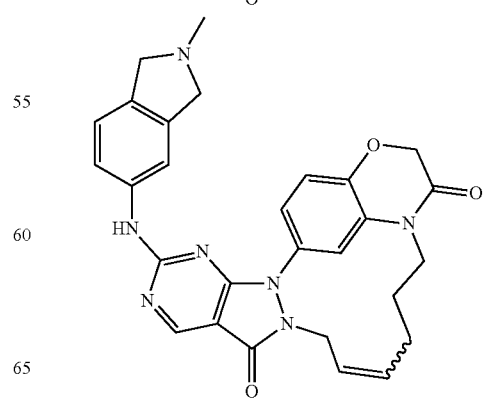

55
-continued
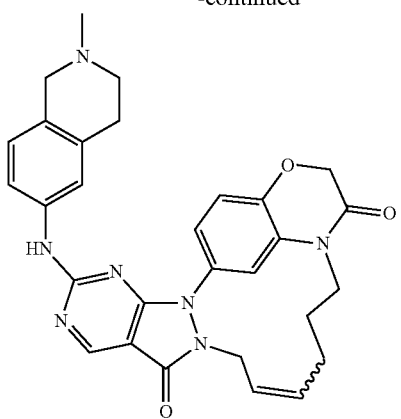
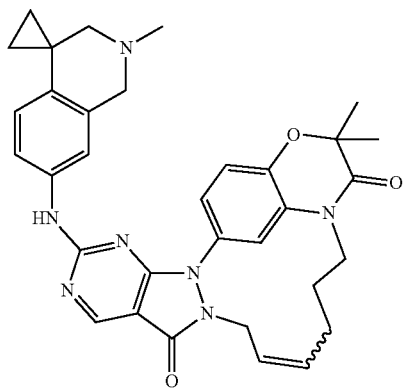
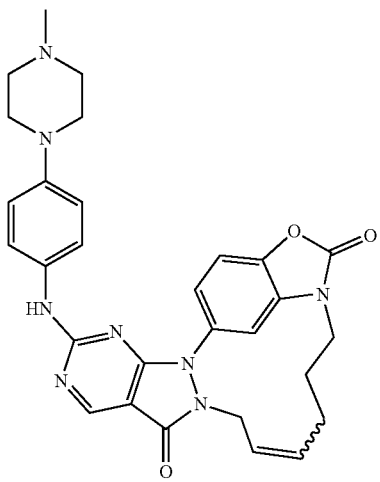
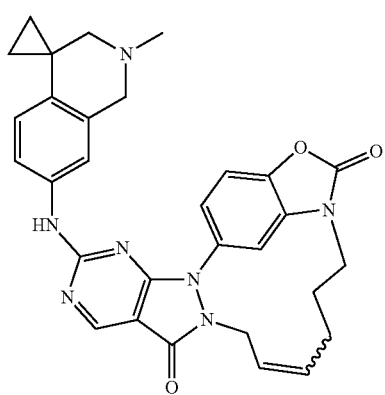
56
-continued
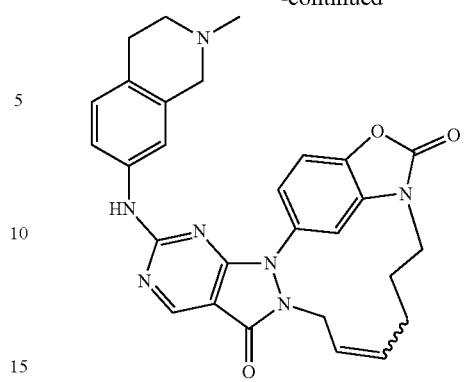
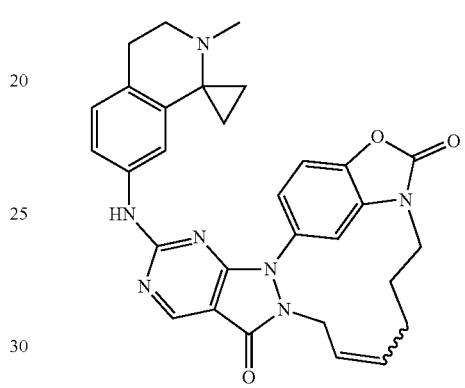
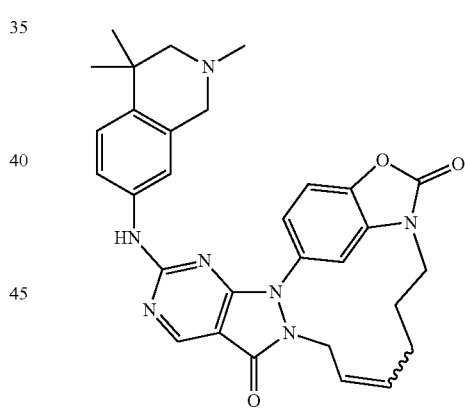
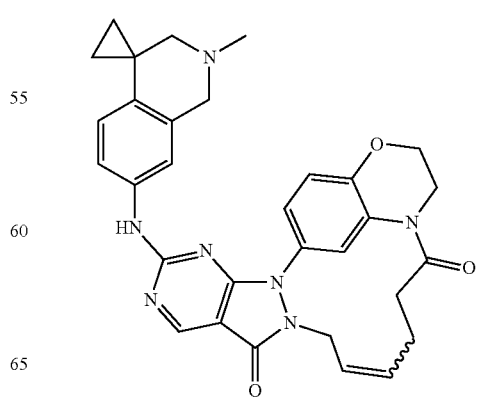

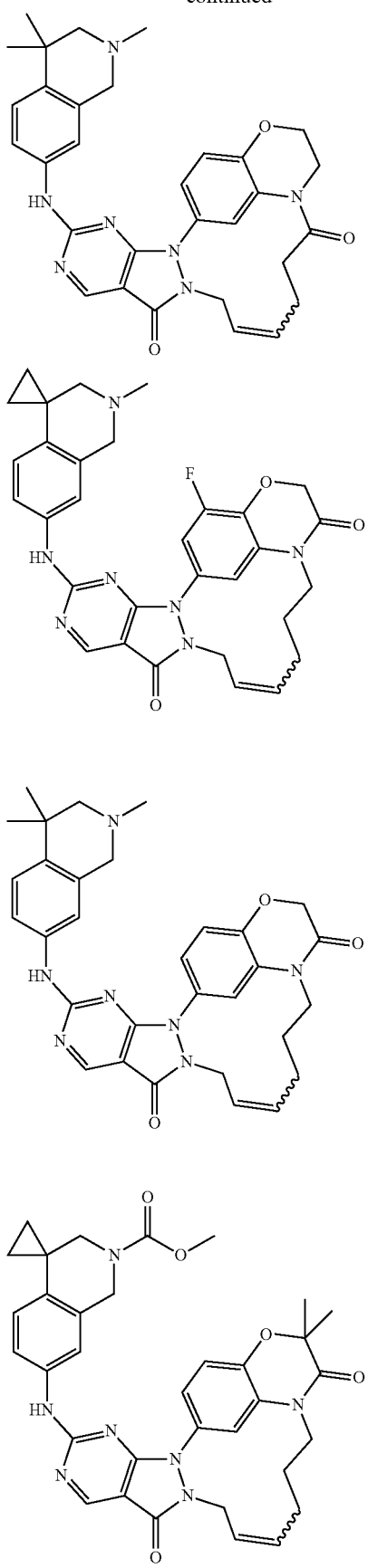
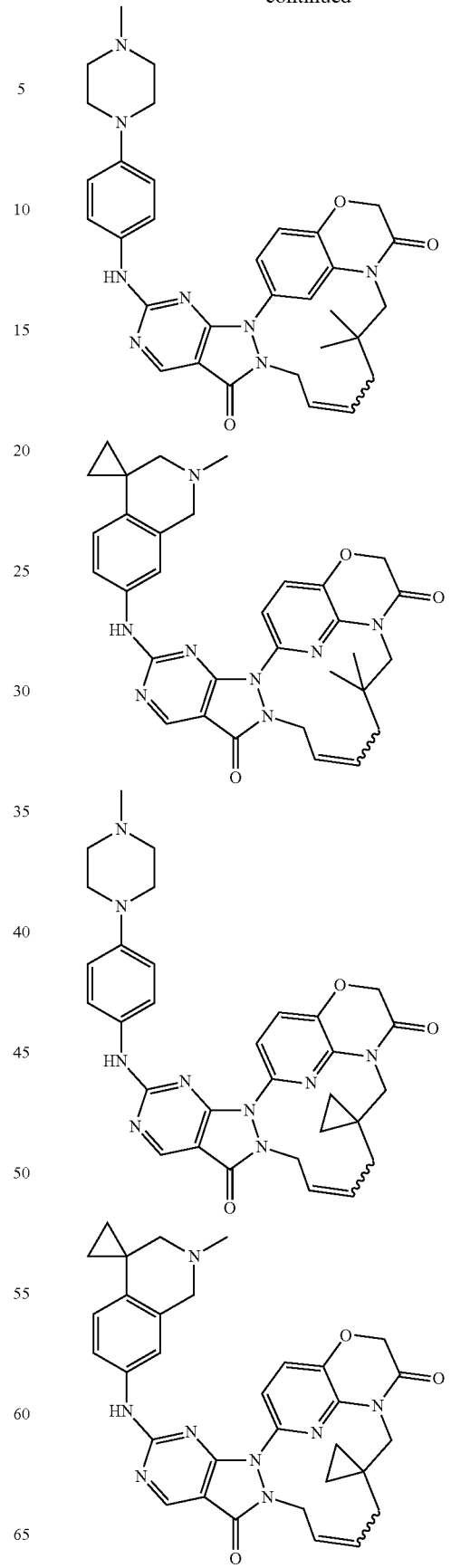

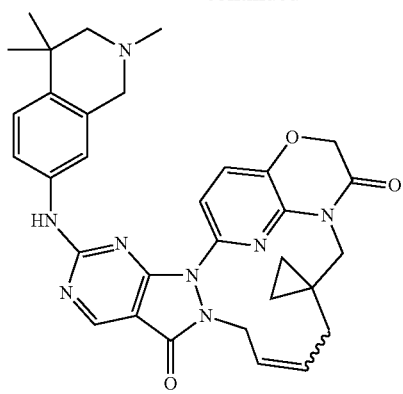
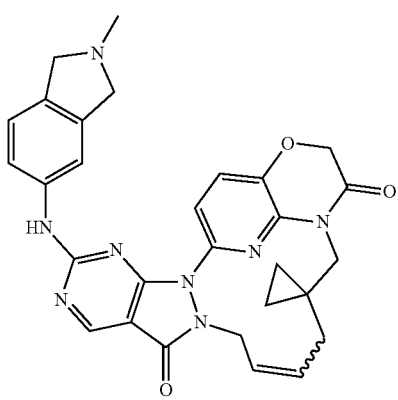
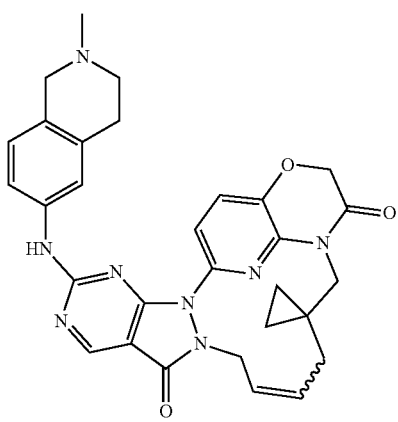
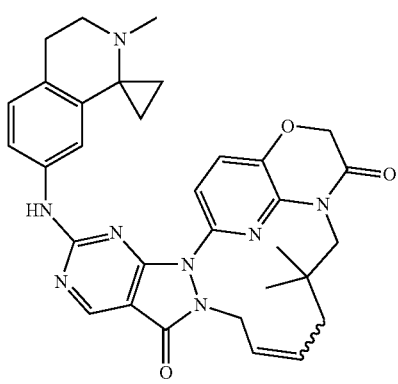
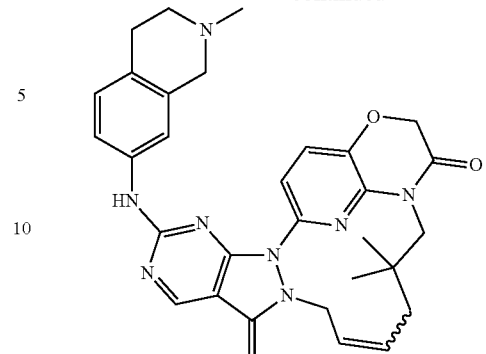
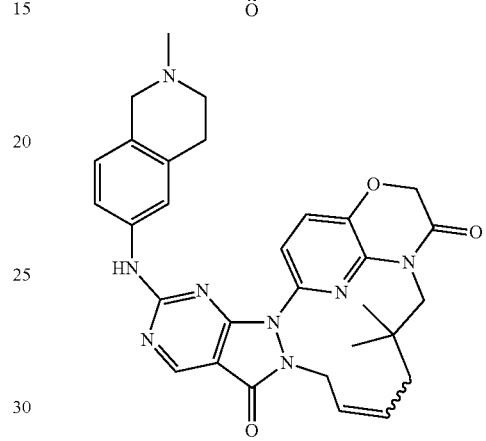
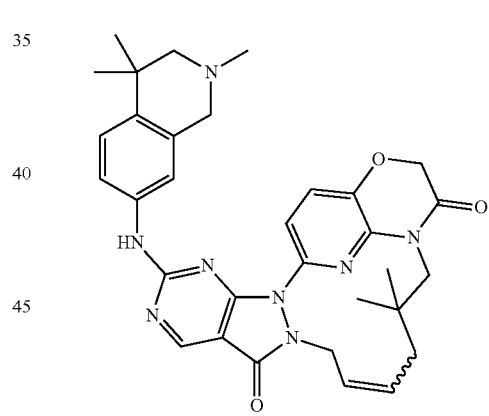
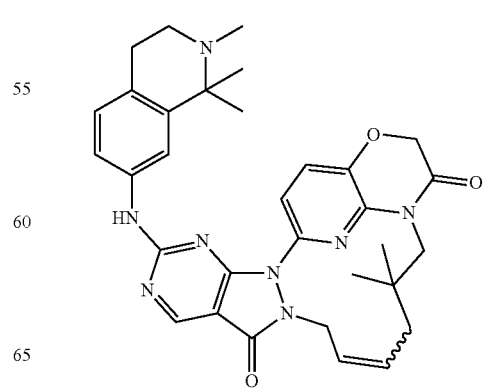

61
-continued
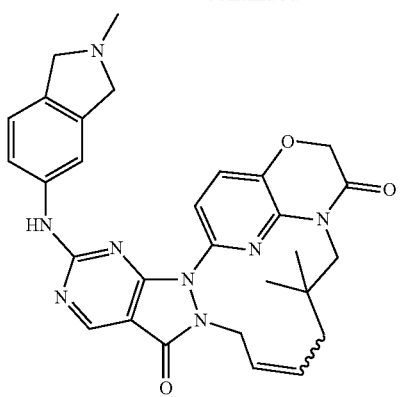
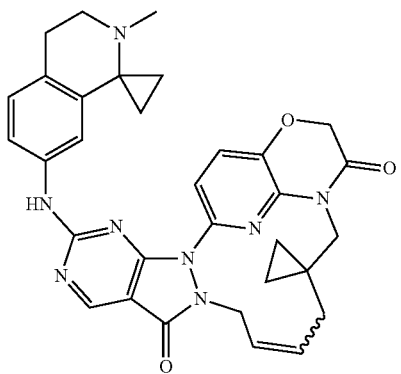
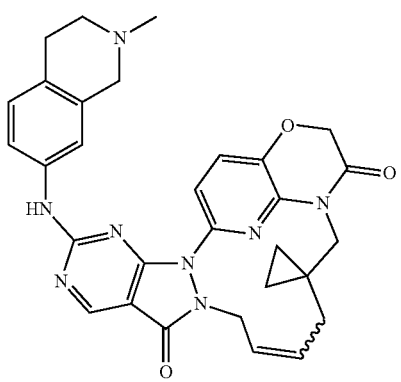
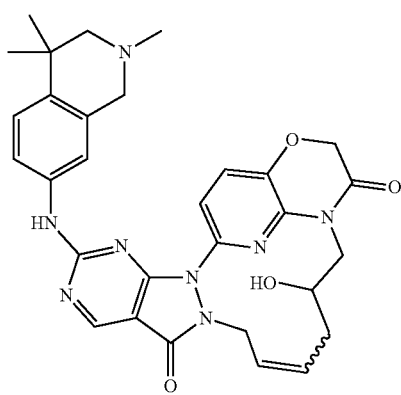
62
-continued
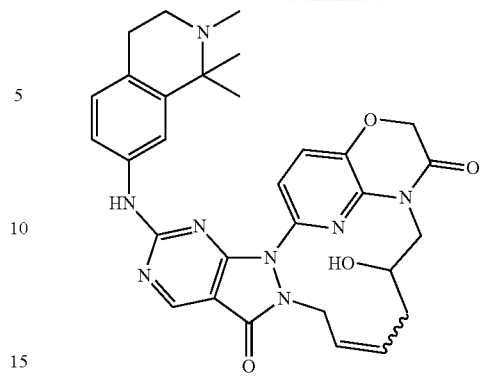
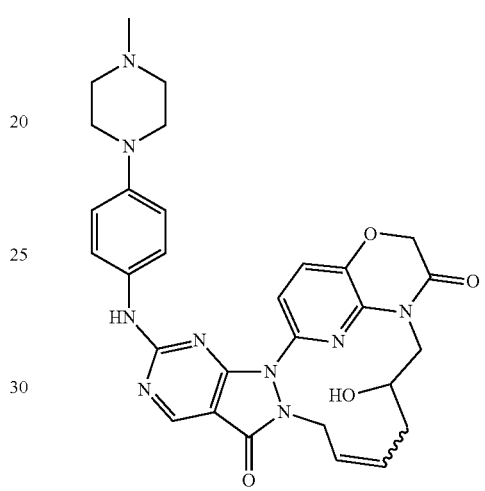
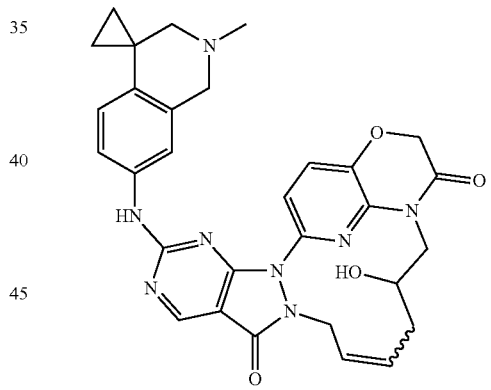
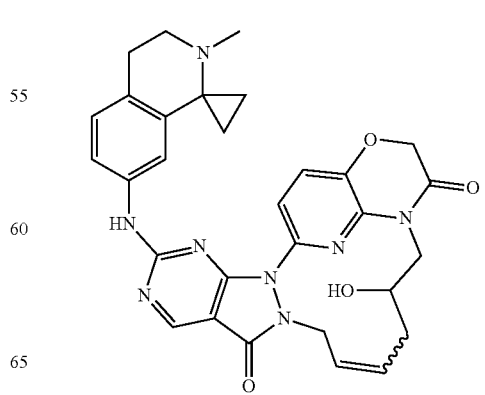

63
-continued
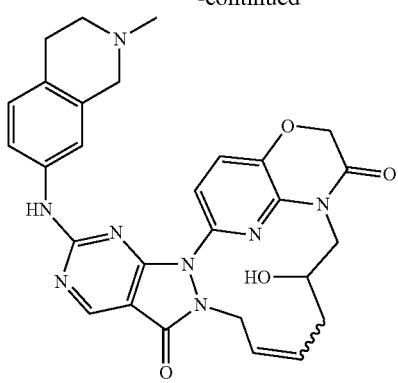
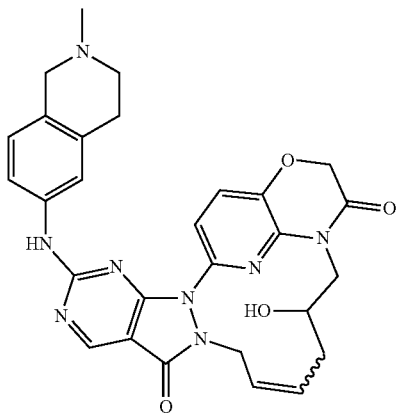
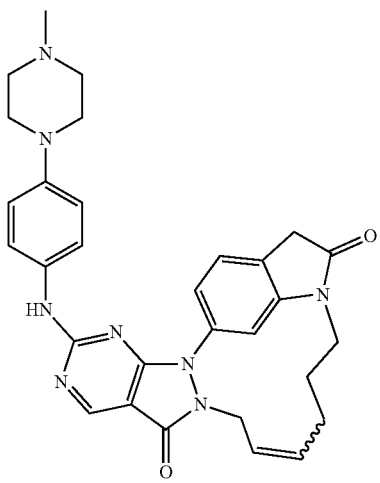
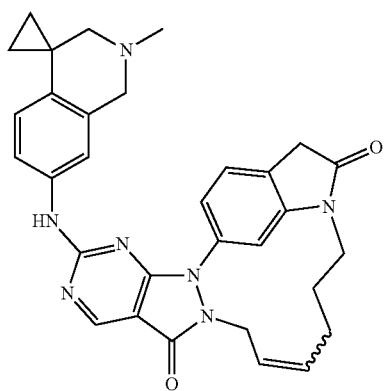
64
-continued
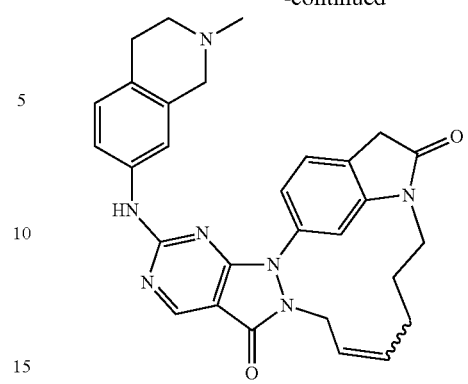
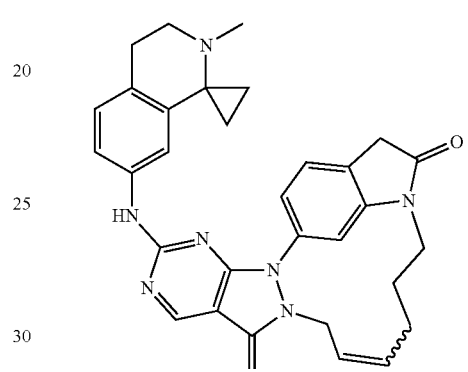
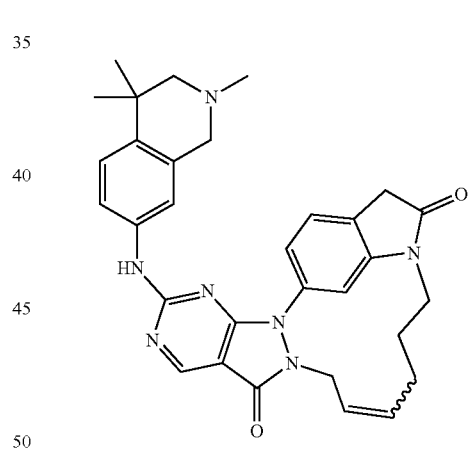
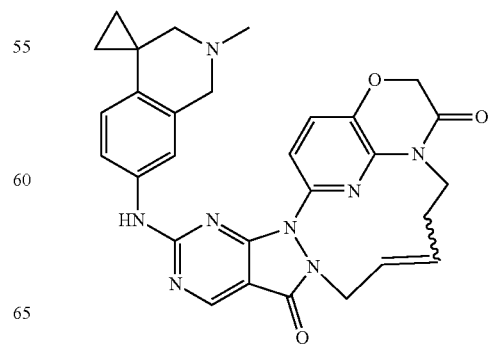

65
-continued
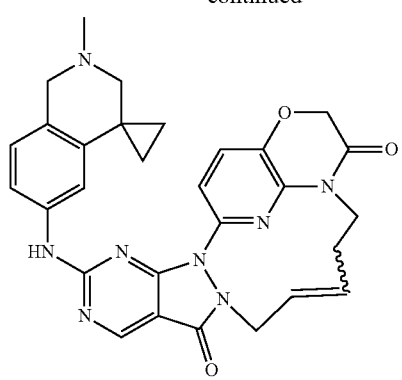
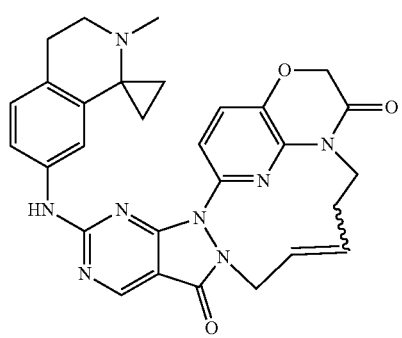
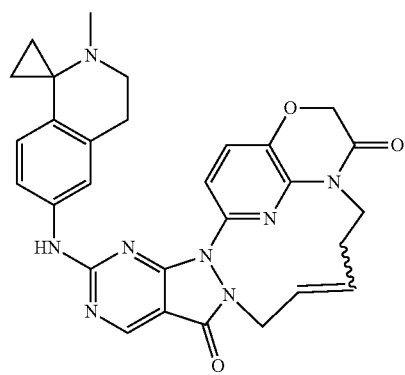
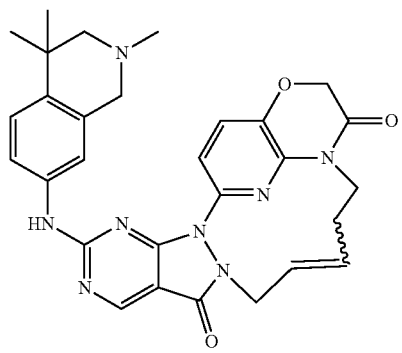
66
-continued
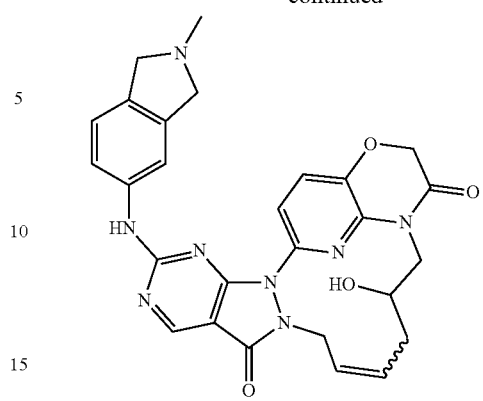
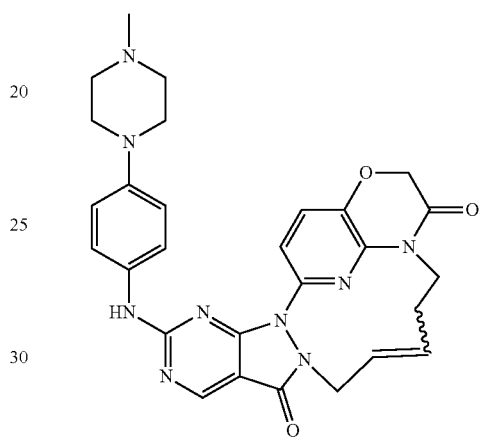
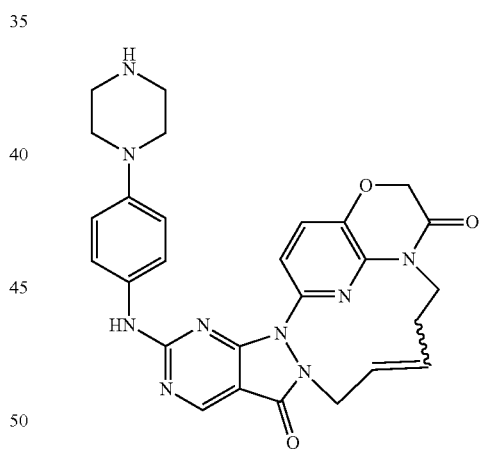
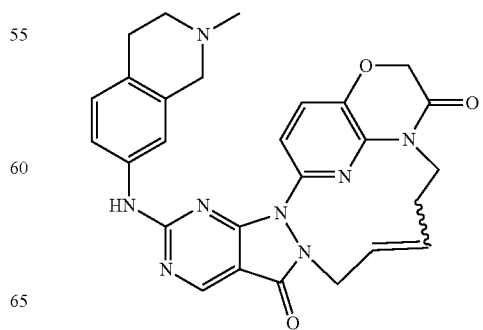

67
-continued
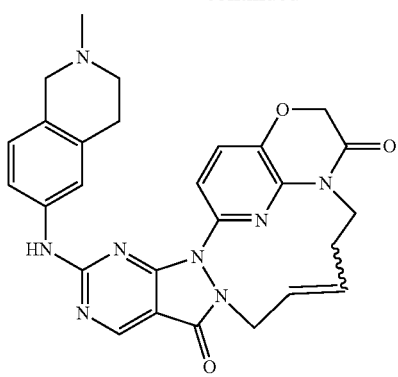
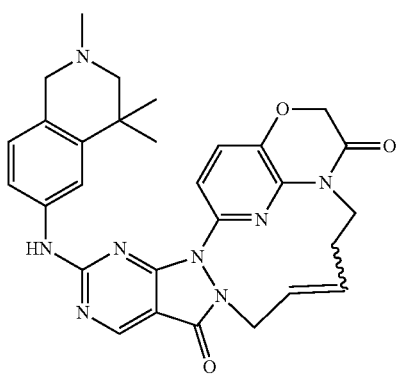
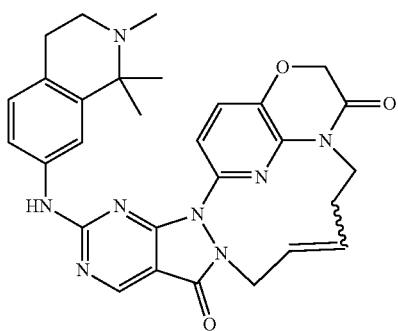
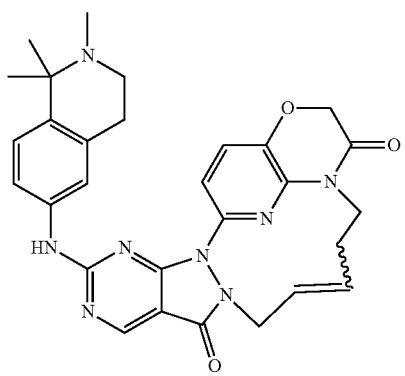
68
-continued
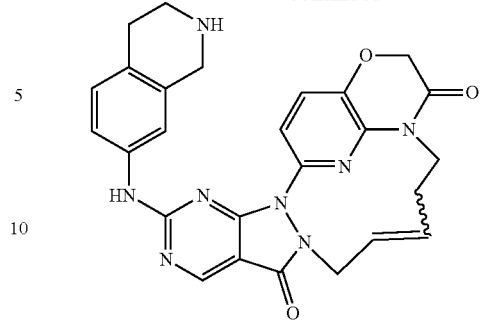
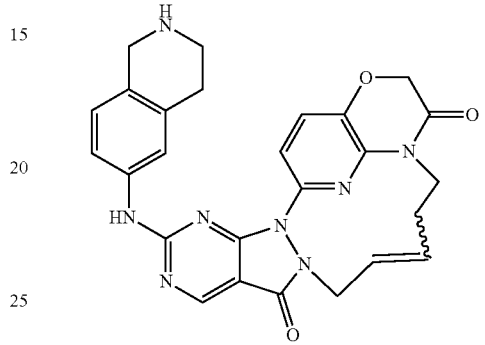
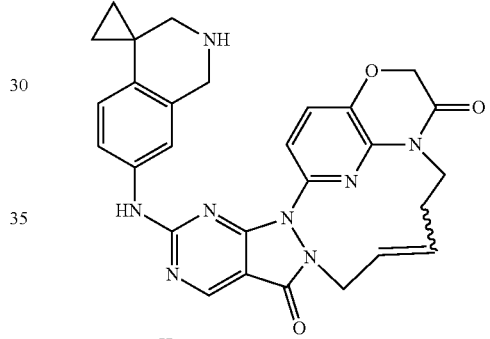
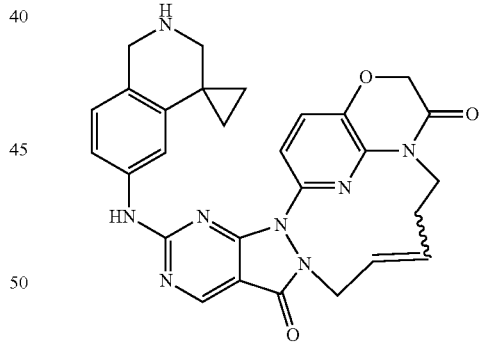
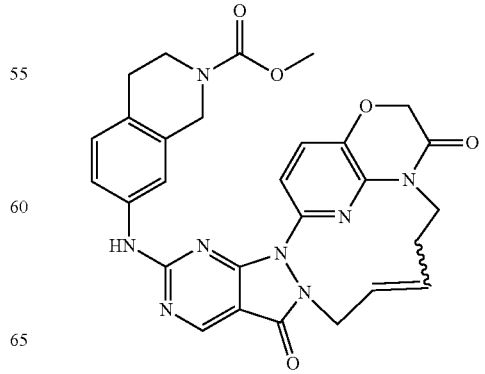

69
-continued
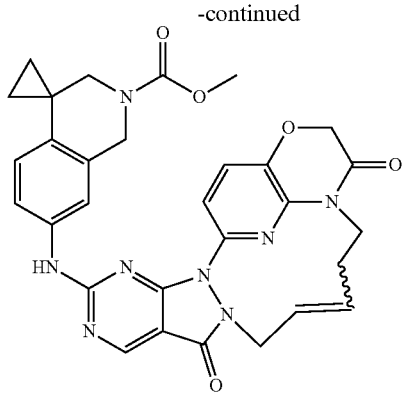
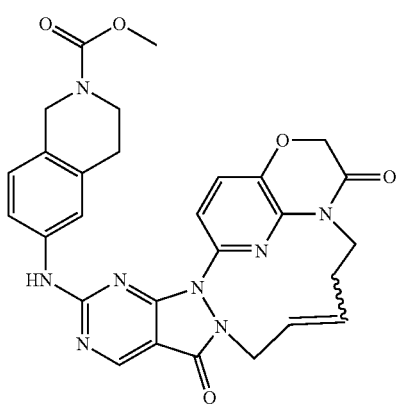
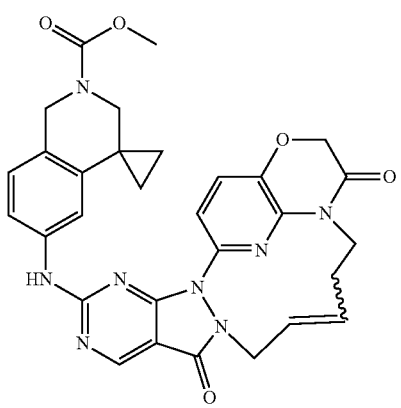
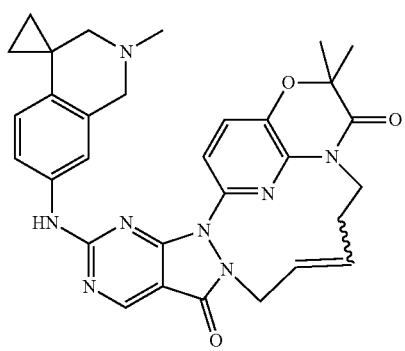
70
-continued
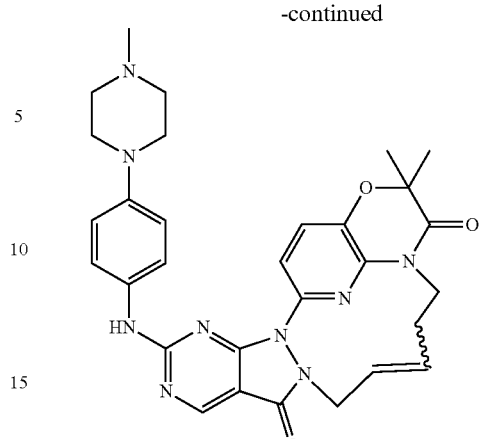
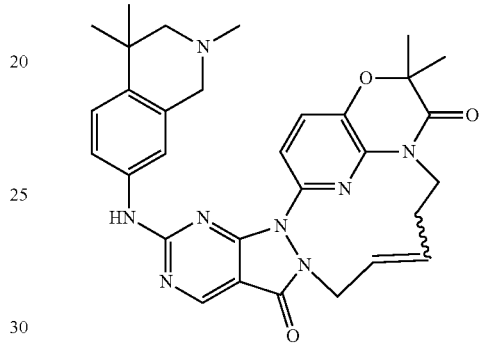
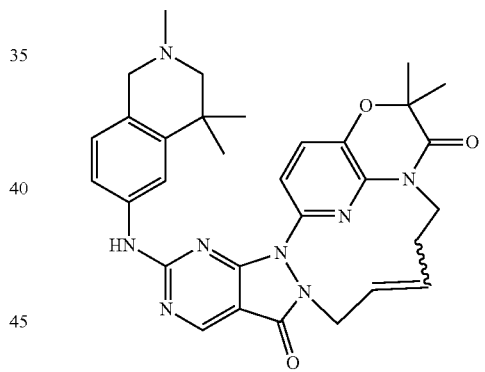
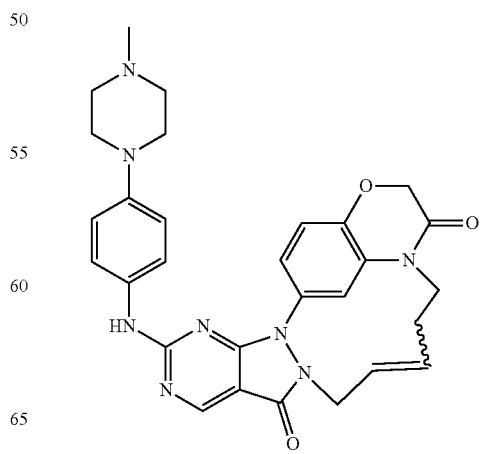

71
-continued
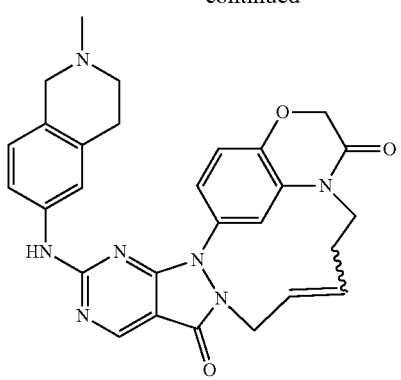
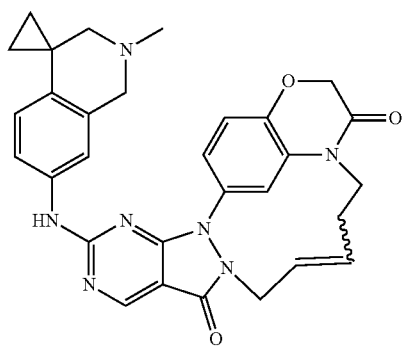
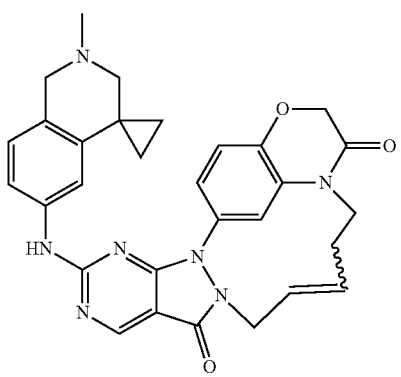
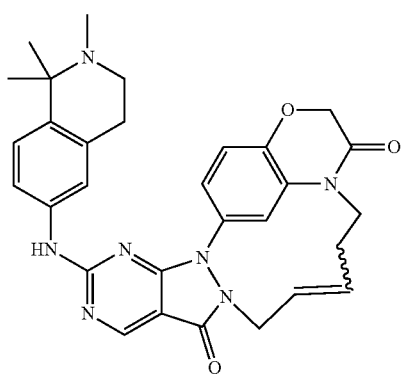
72
-continued
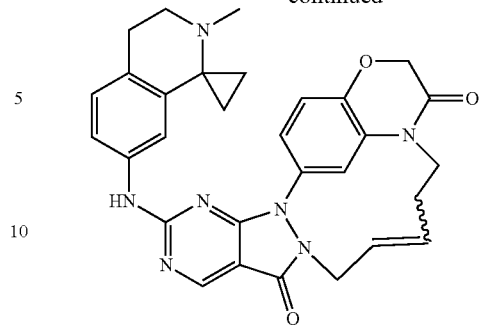
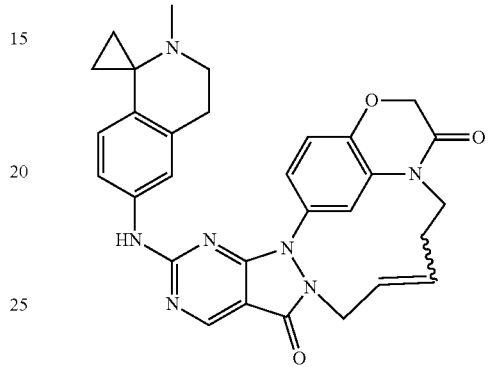
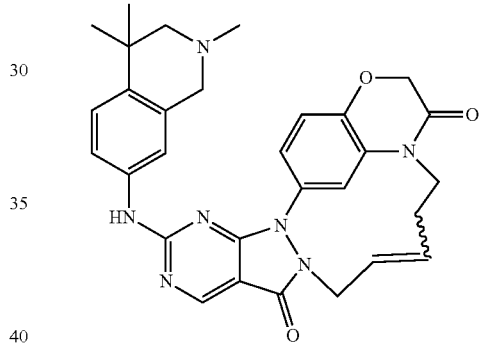
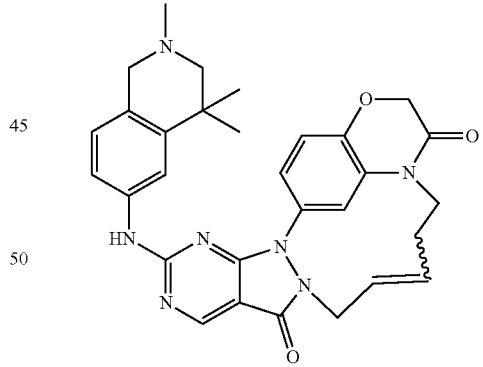
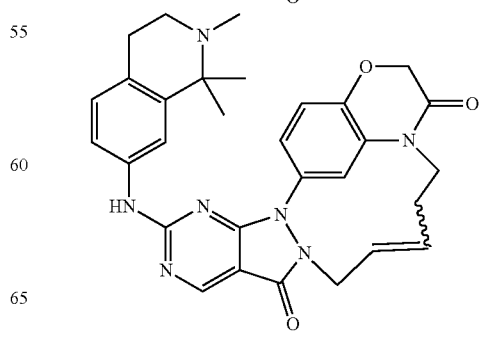

73
-continued
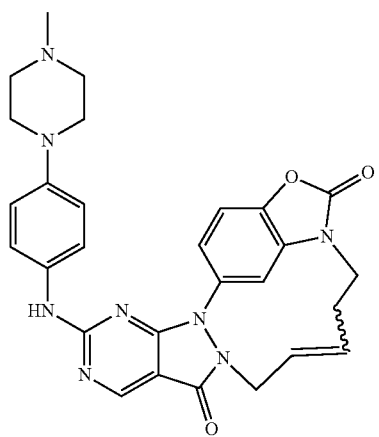
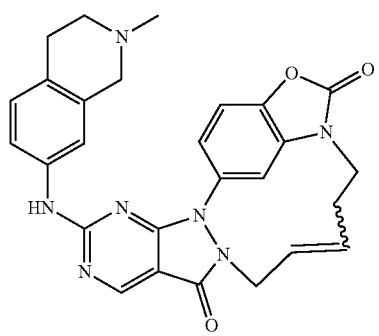
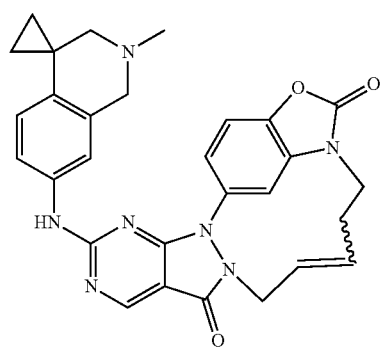
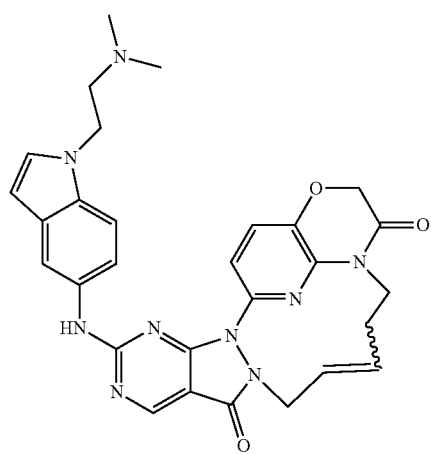
74
-continued
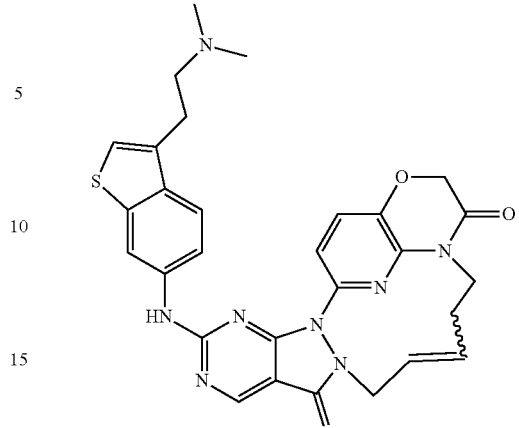
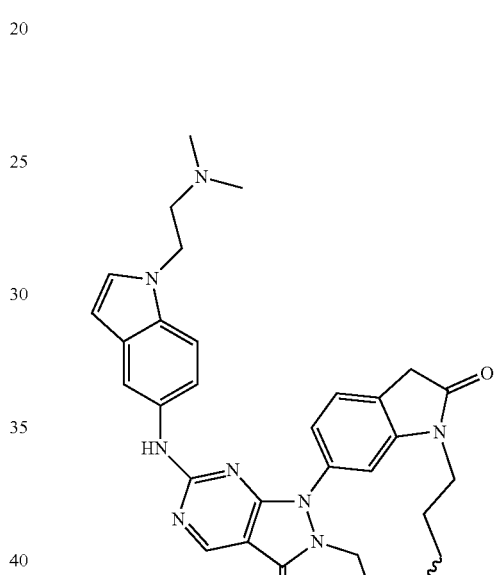
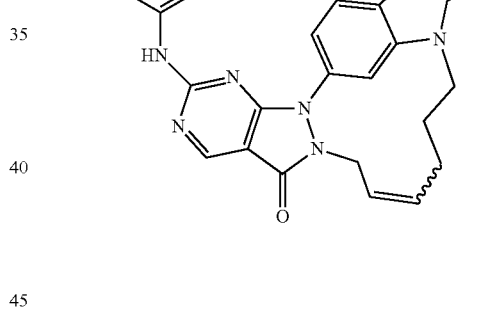
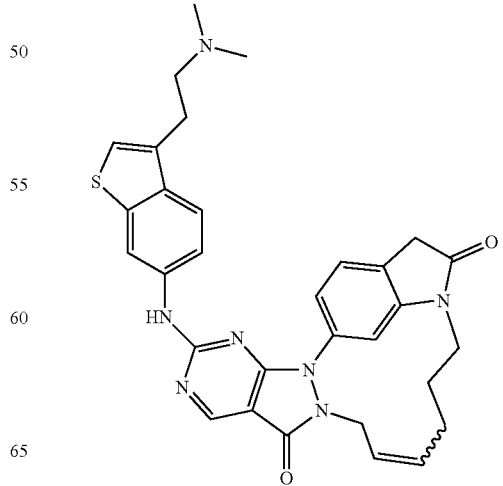

75
-continued
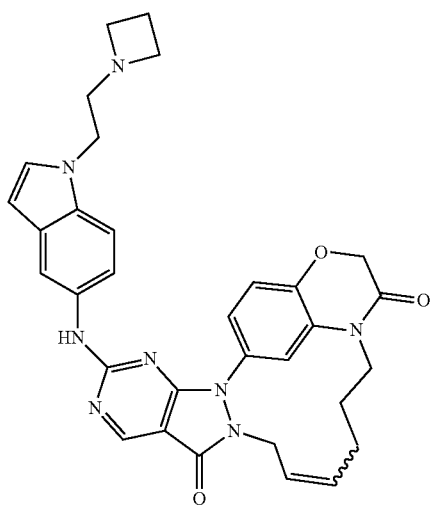
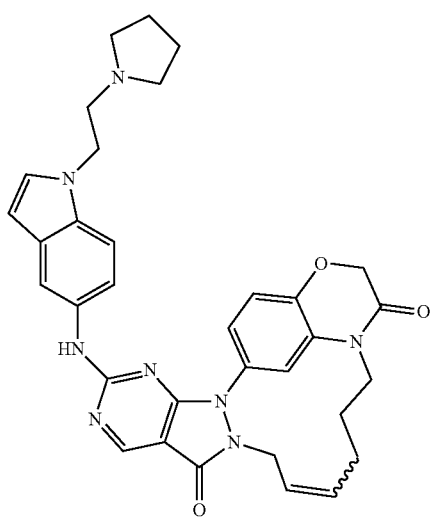
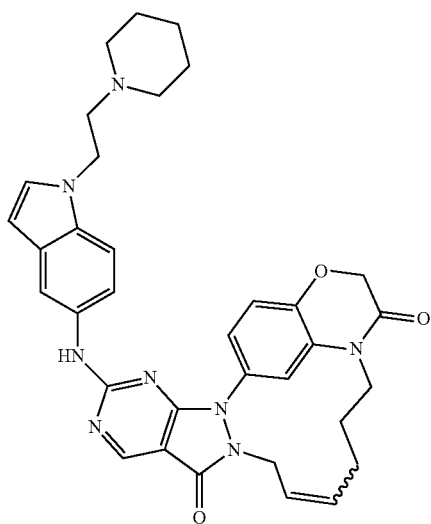
76
-continued
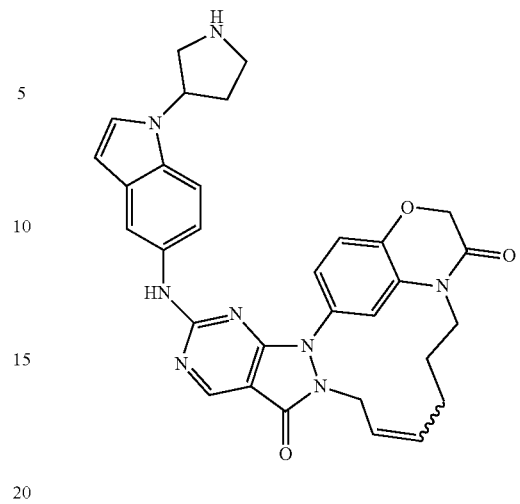
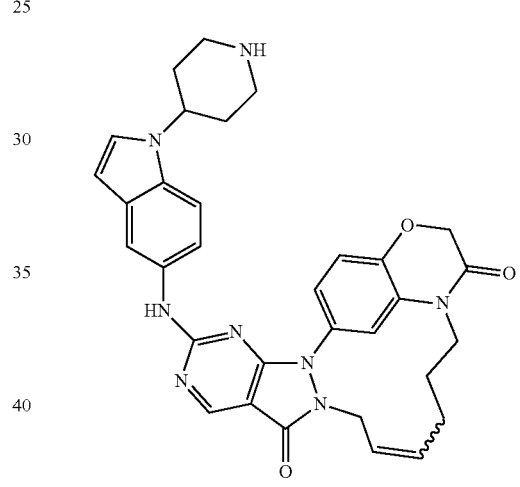
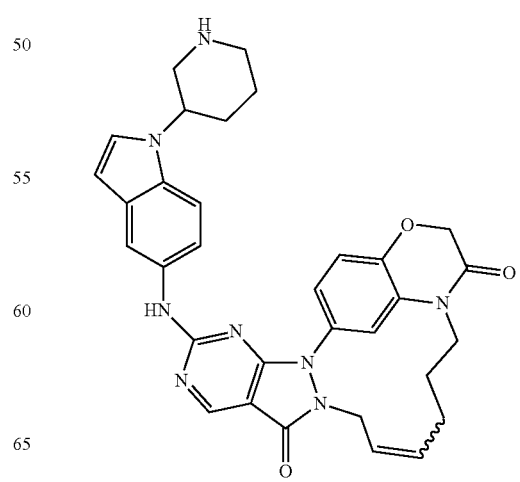

| 77 -continued | 78 -continued |
|---|---|
| 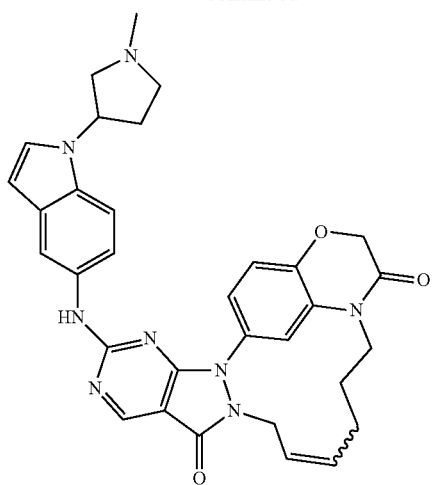 | 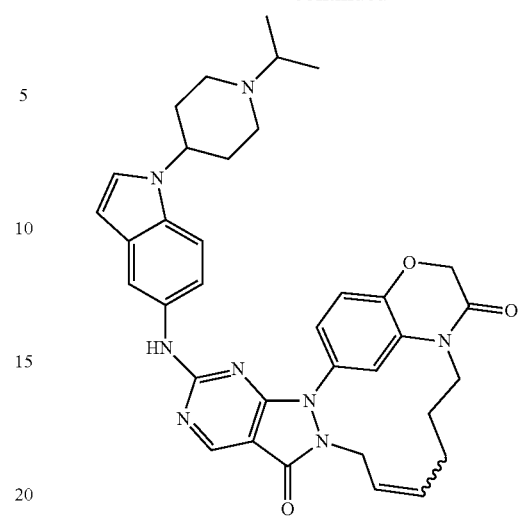 |
| 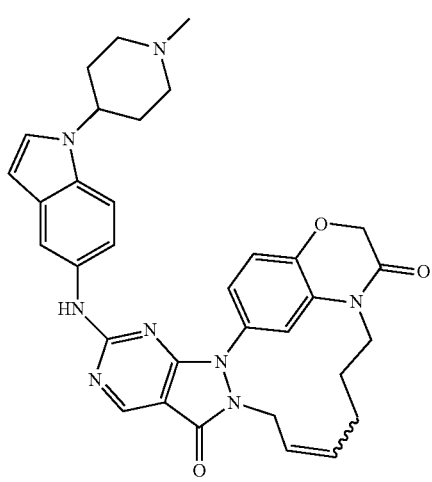 | 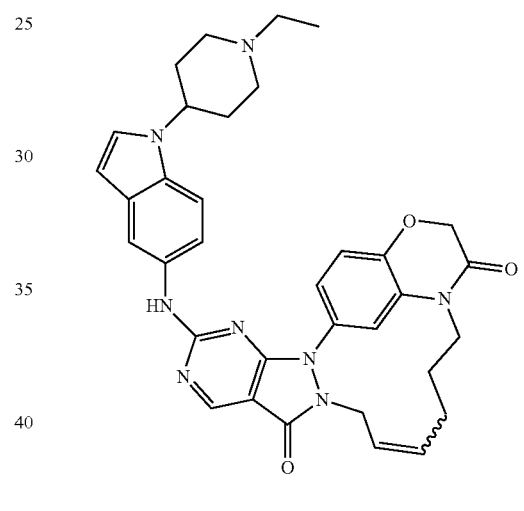 |
| 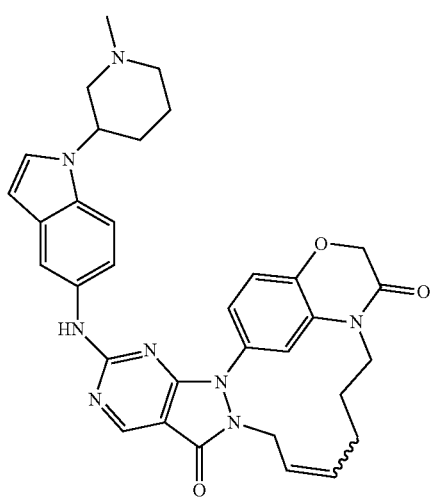 | 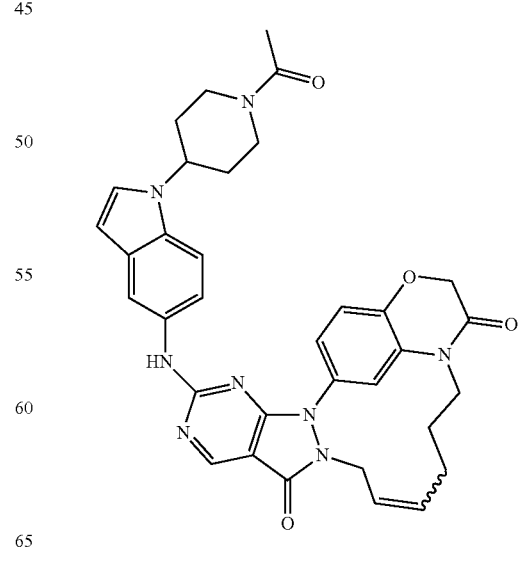 |

| 79 -continued | 80 -continued |
|---|---|
| 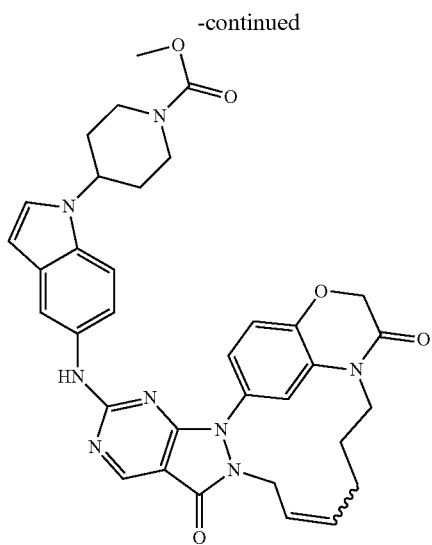 | 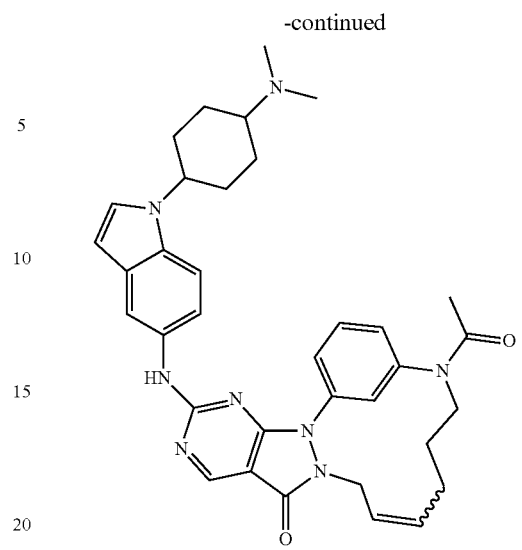 |
| 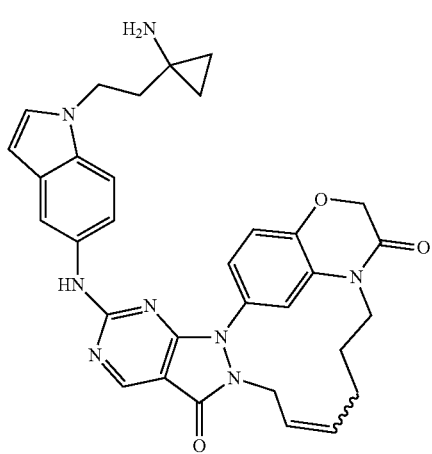 | 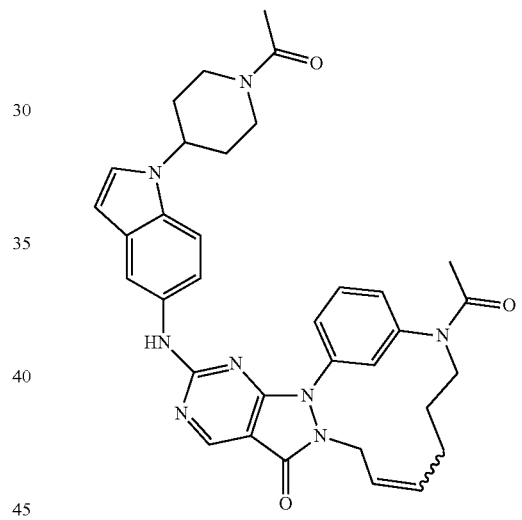 |
| 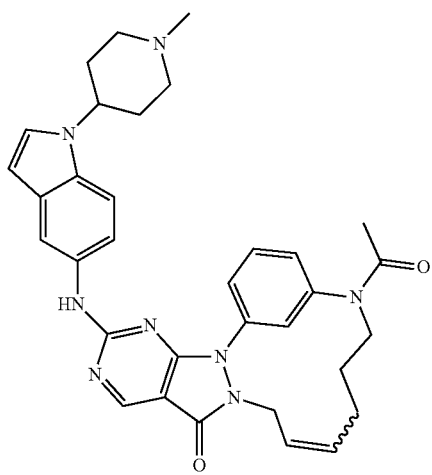 | 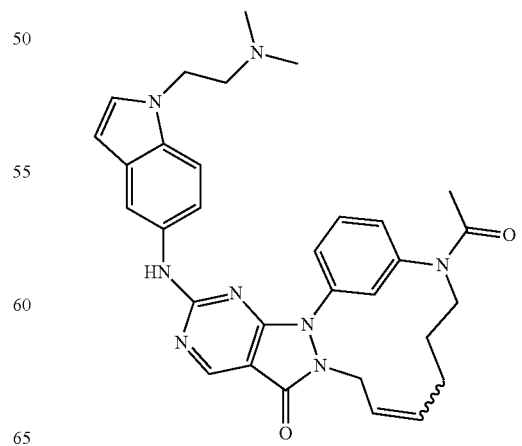 |

81
-continued
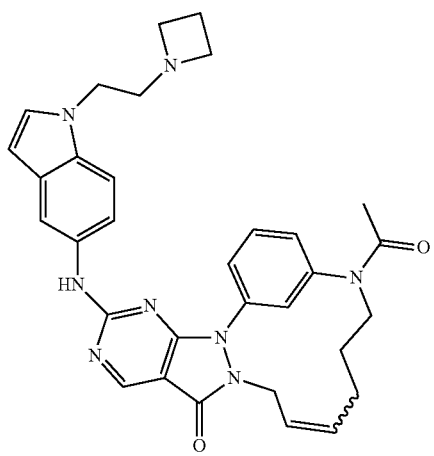
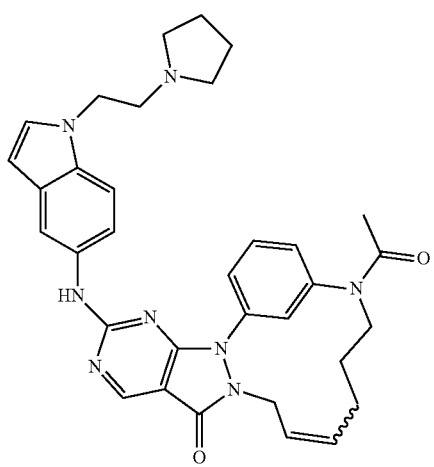
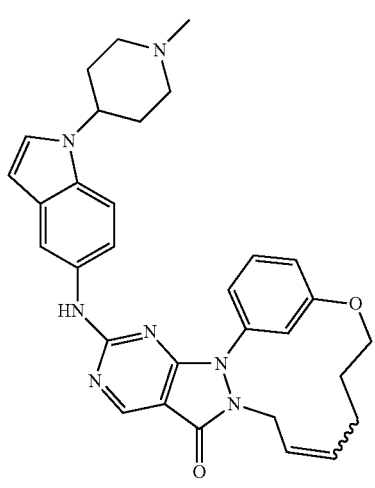
82
-continued
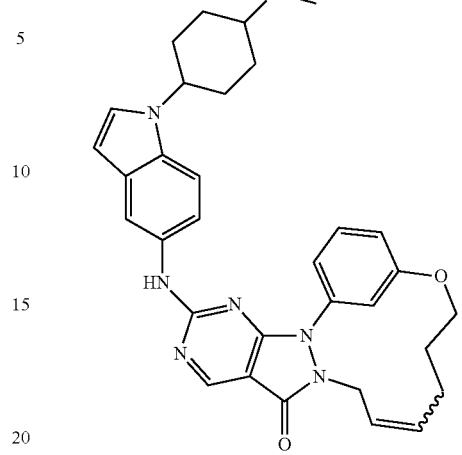
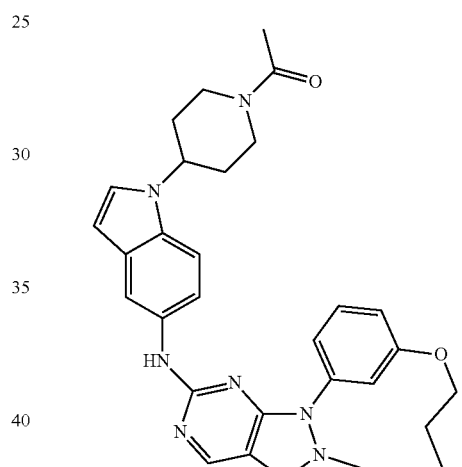
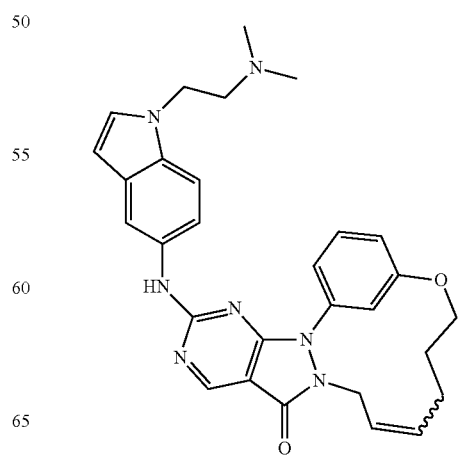

83
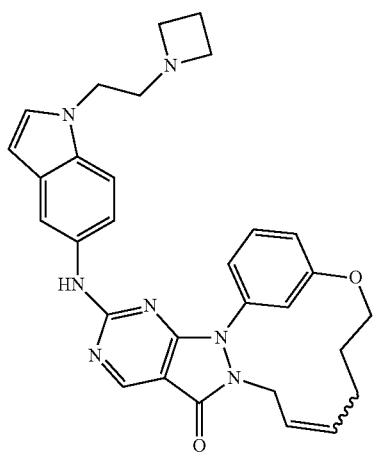
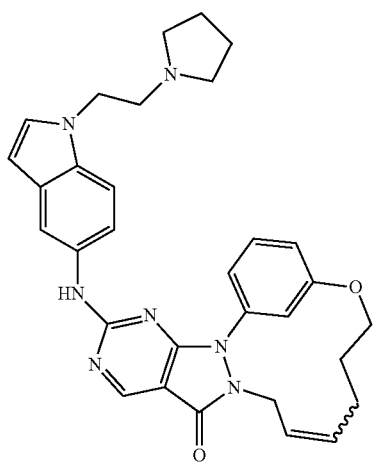
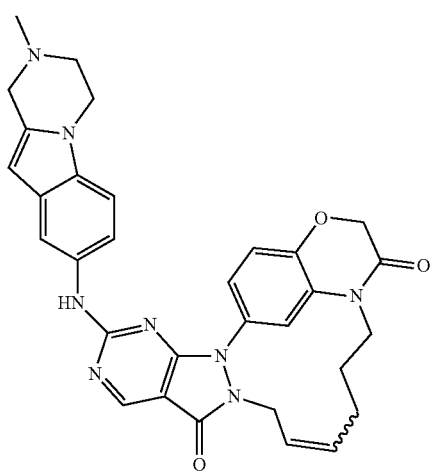
84
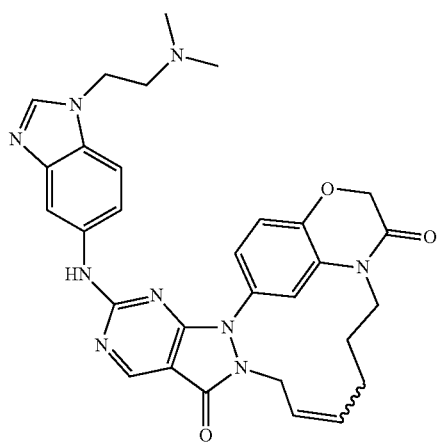
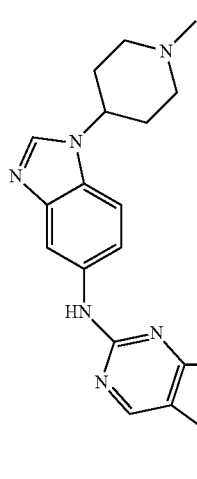
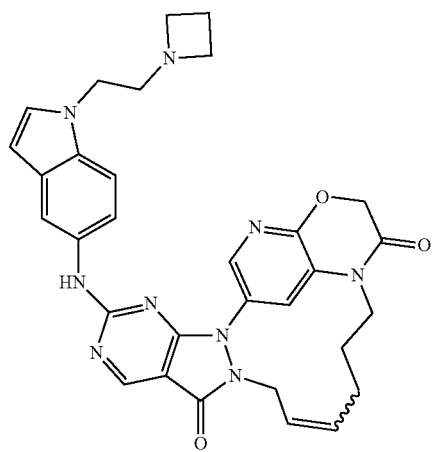

85
-continued
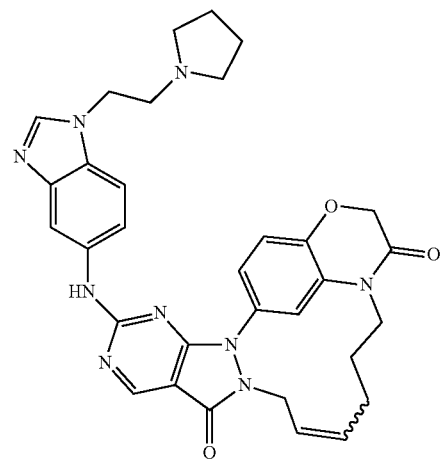
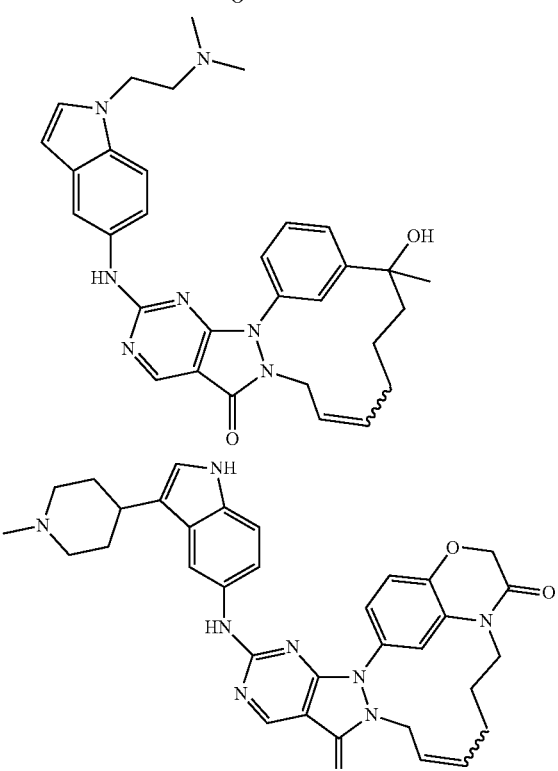
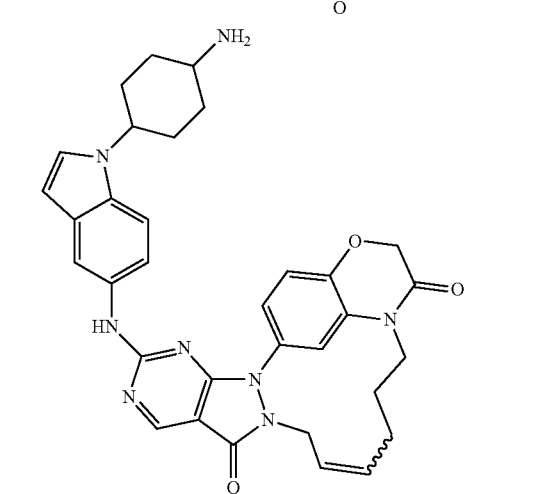
86
-continued
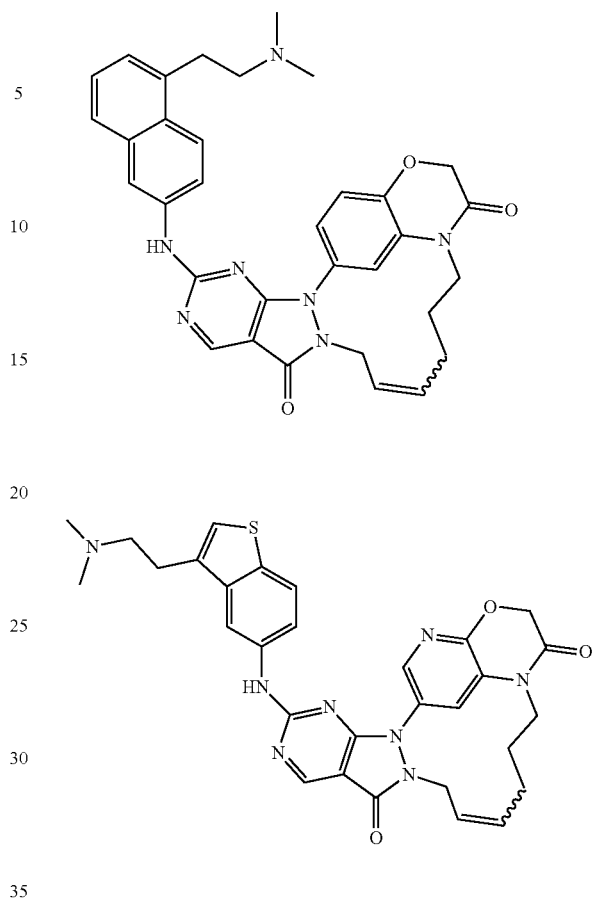
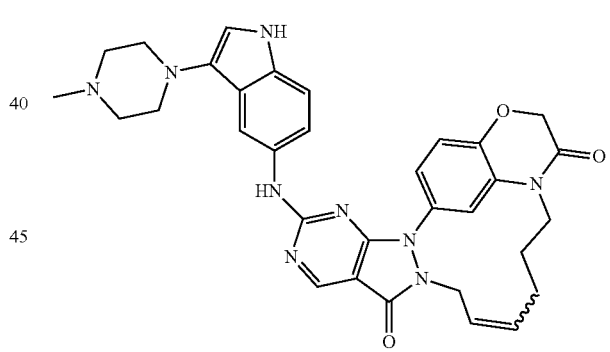
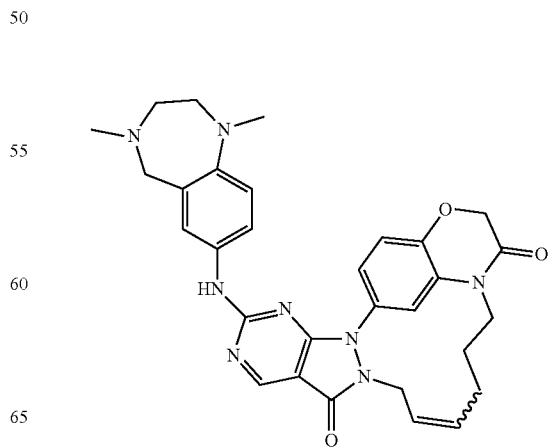

87
-continued
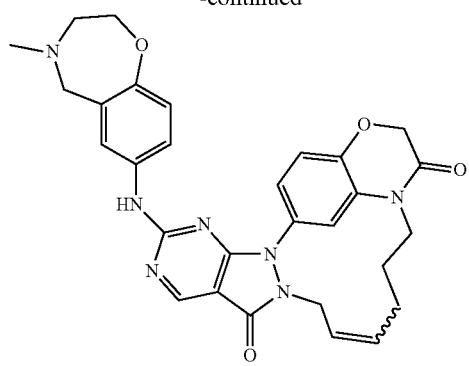
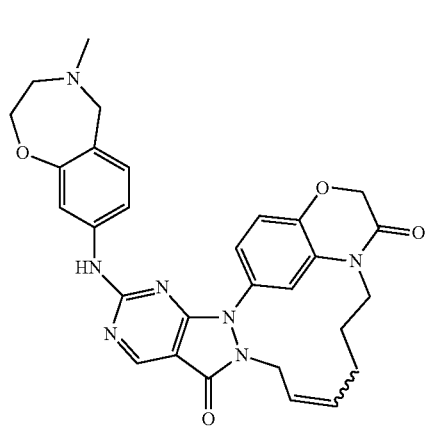
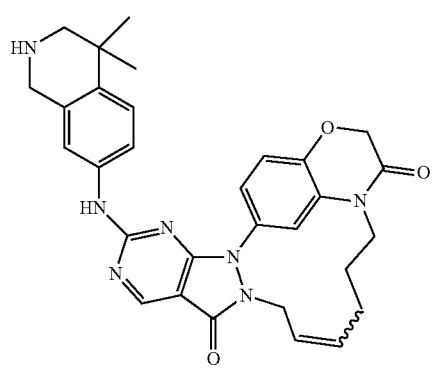
88
-continued
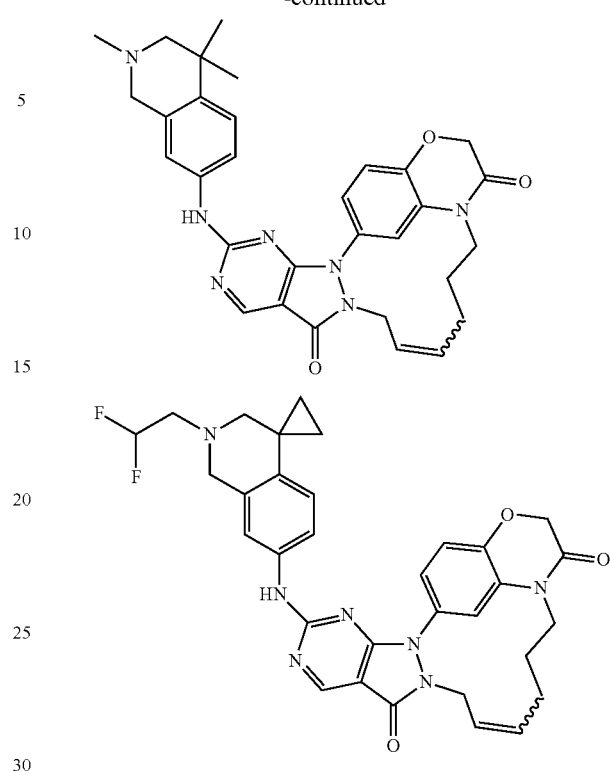
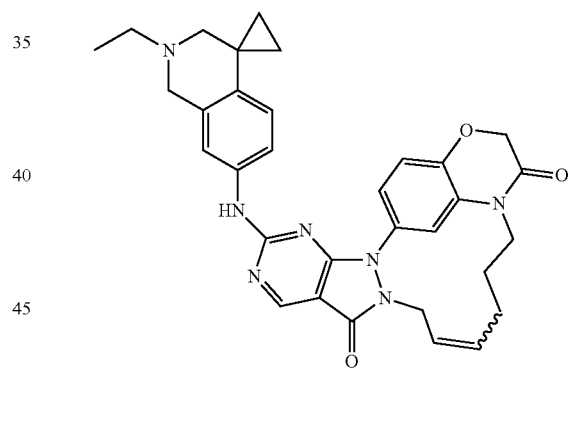
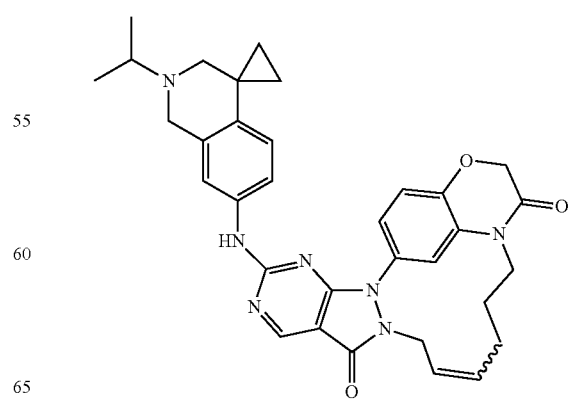

89
-continued
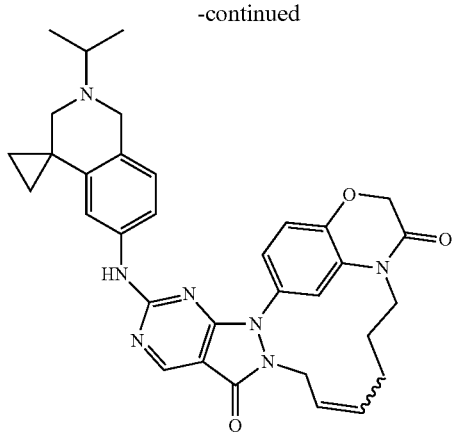
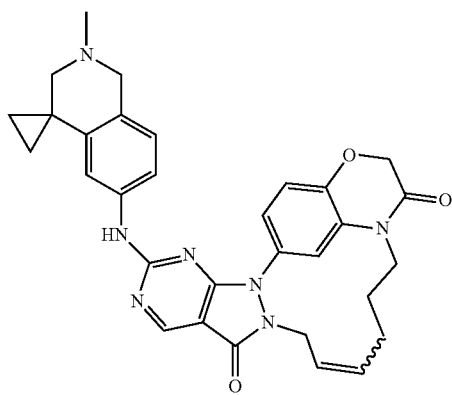
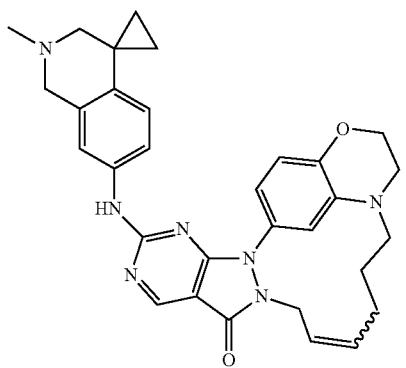
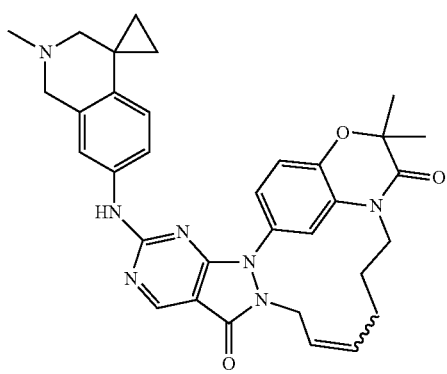
90
-continued
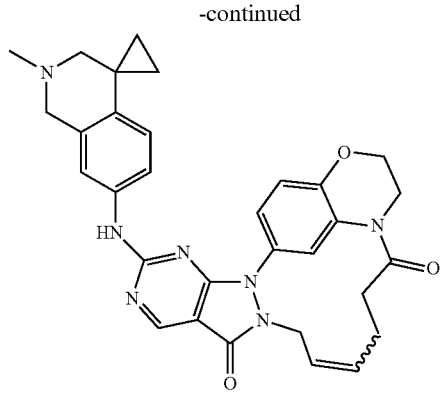
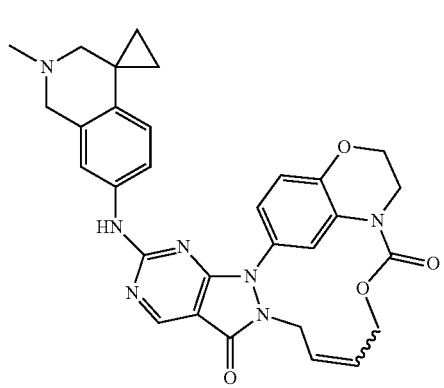
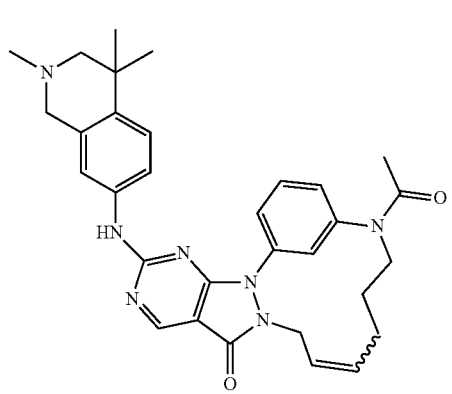
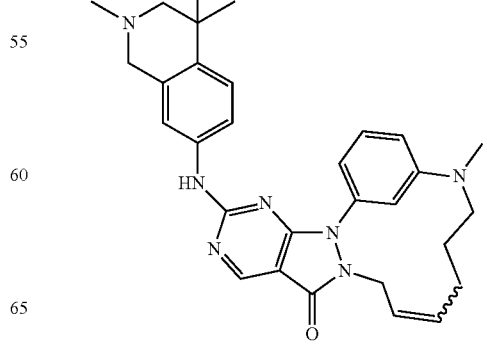

91
-continued
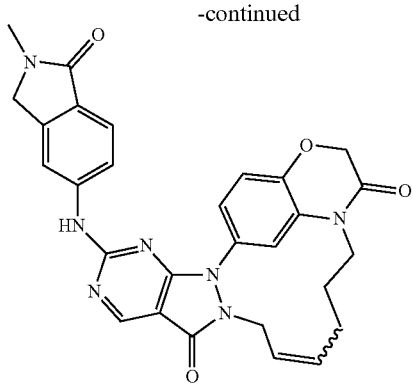
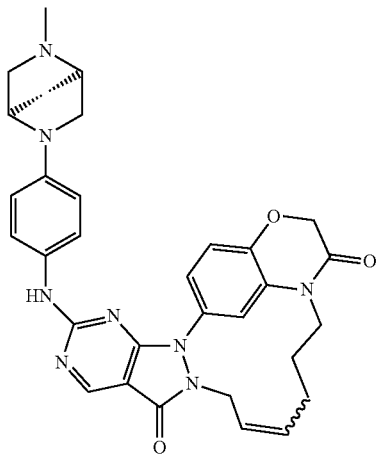
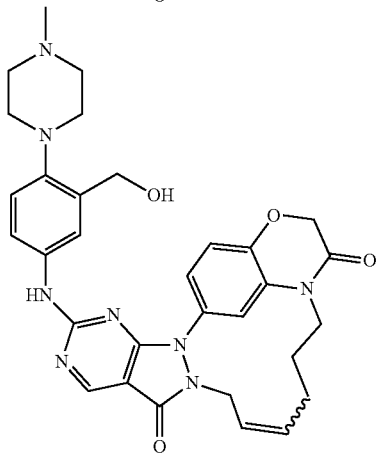
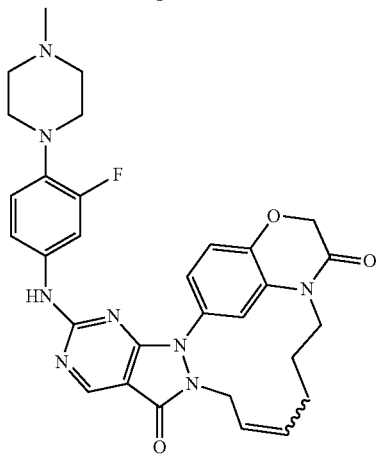
92
-continued
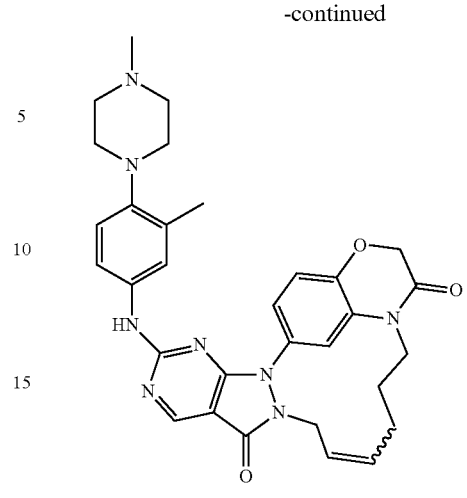
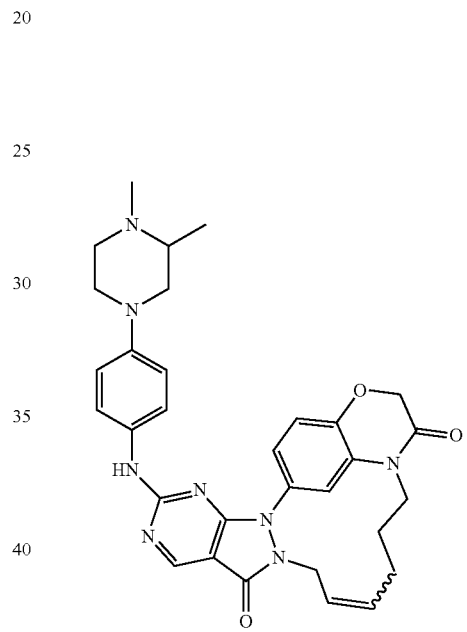
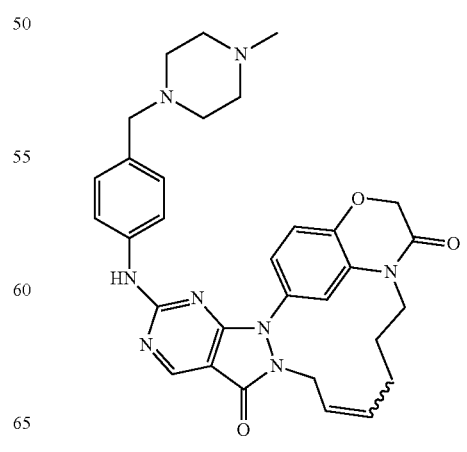

93
-continued
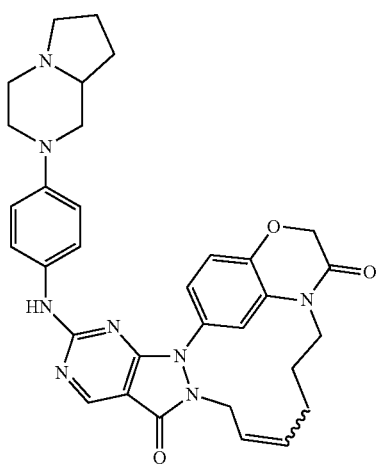
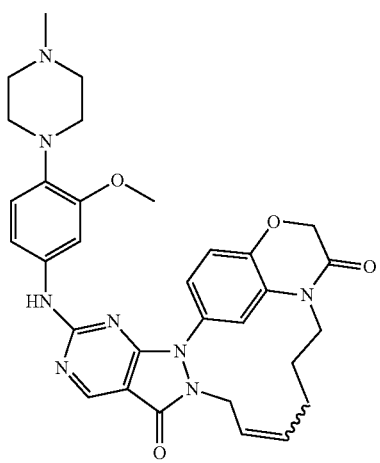
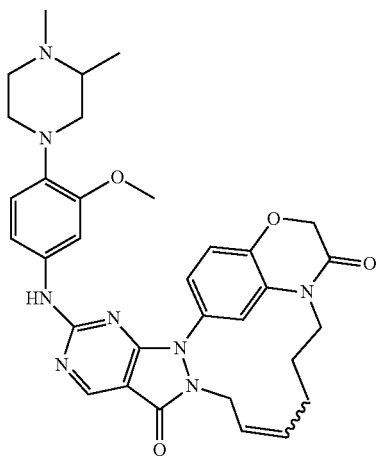
94
-continued
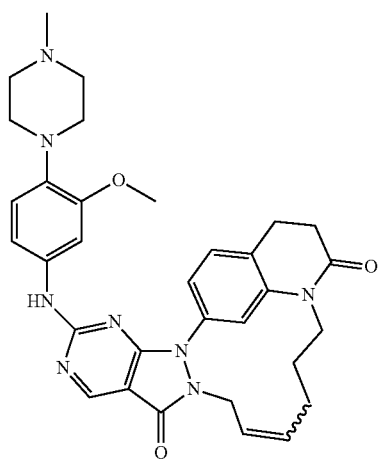
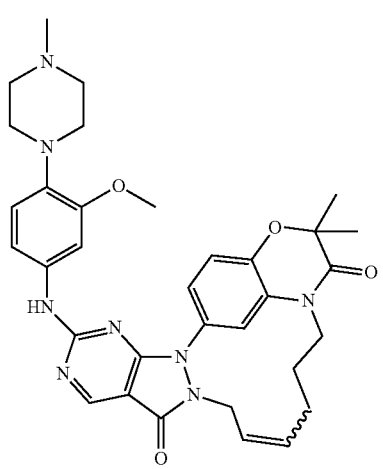
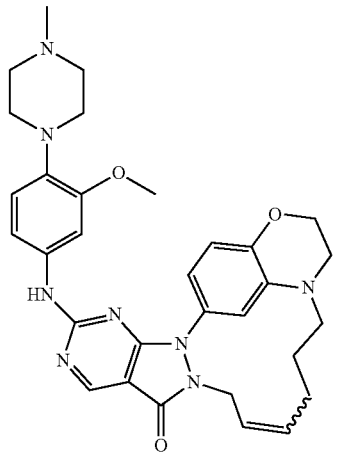

95
-continued
96
-continued
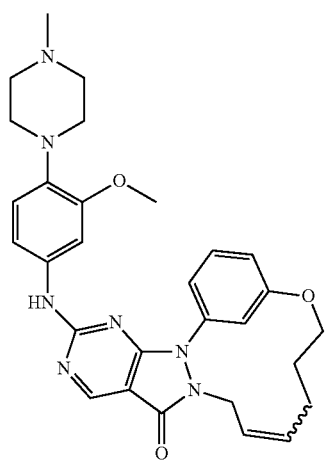
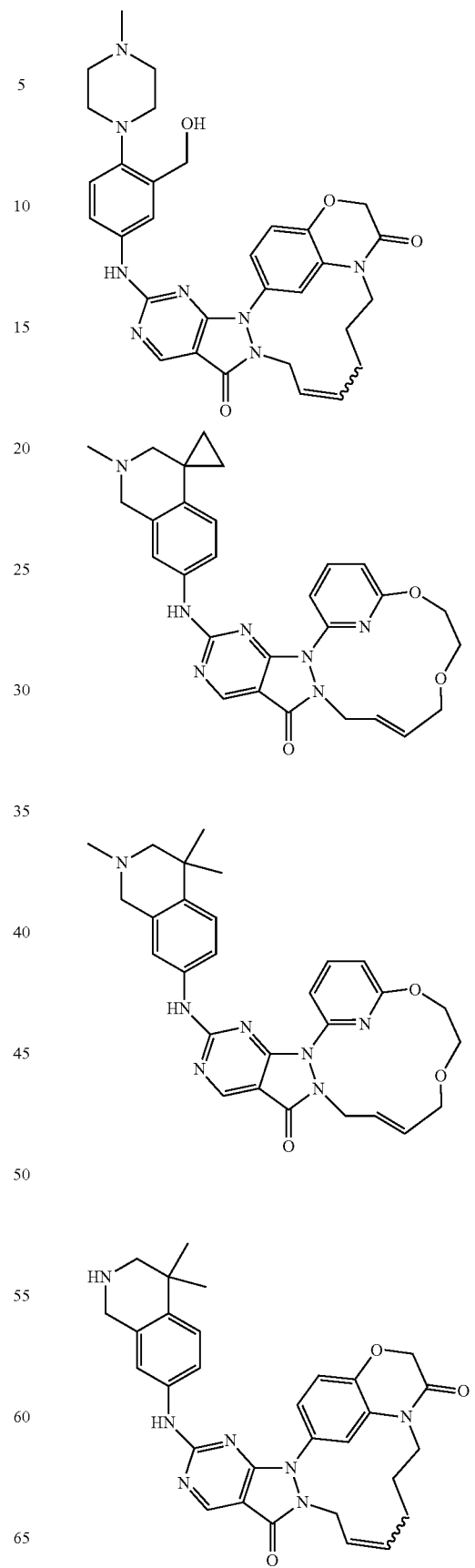

97
-continued
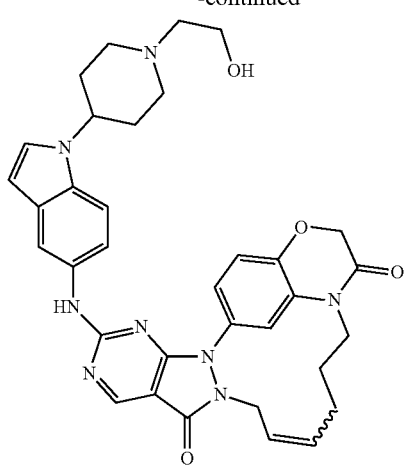
98
-continued
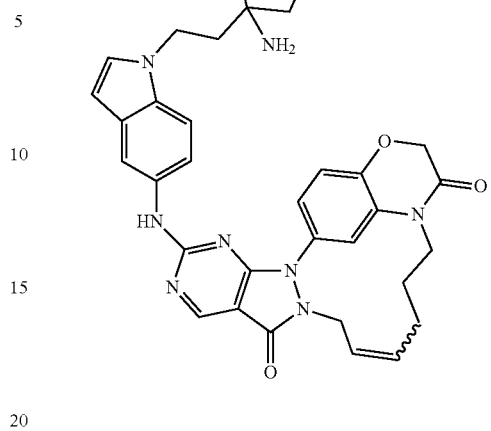
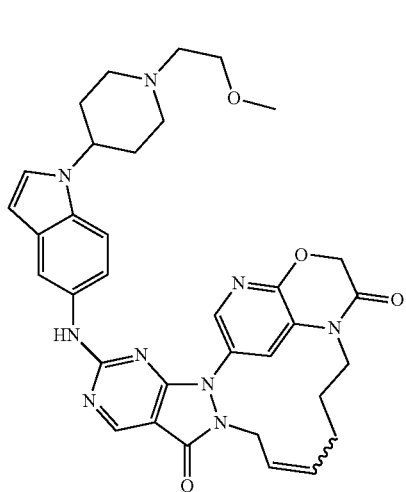
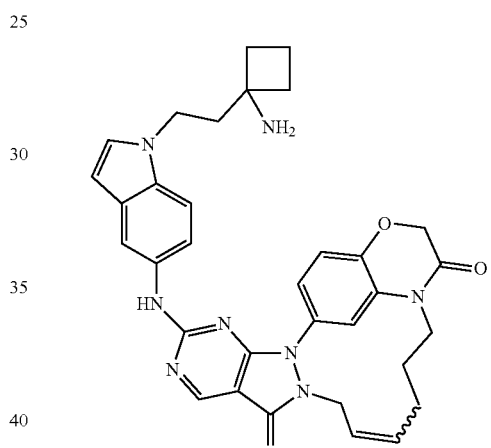
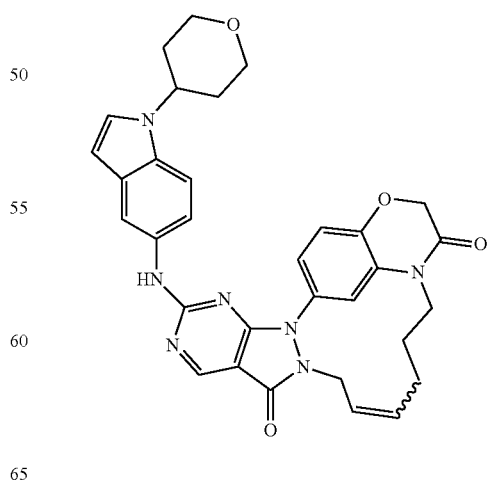

99
-continued
100
-continued
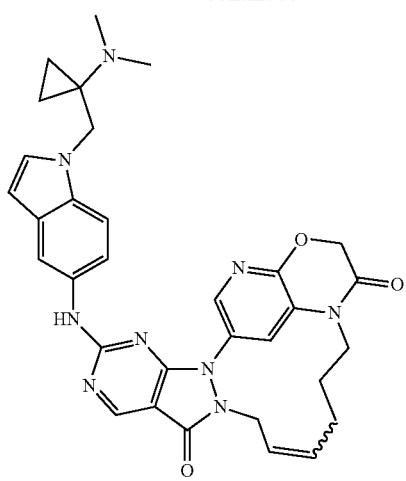
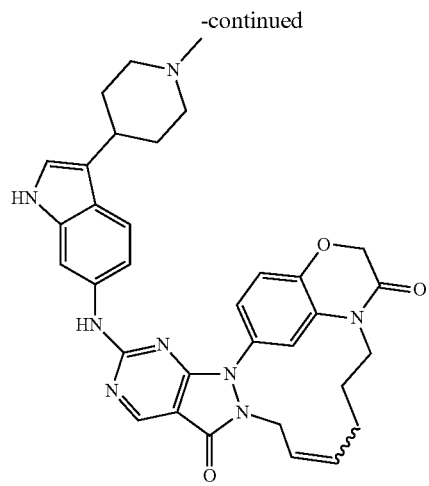
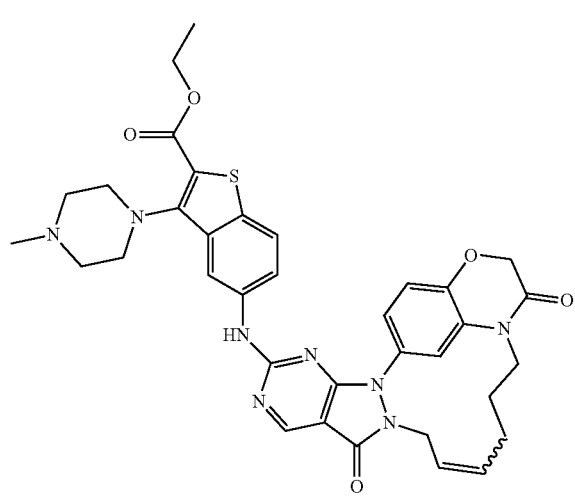

101
-continued
102
-continued
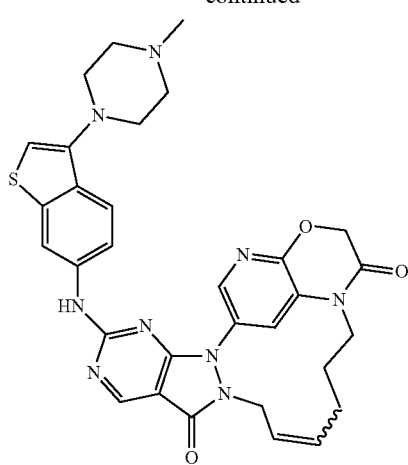
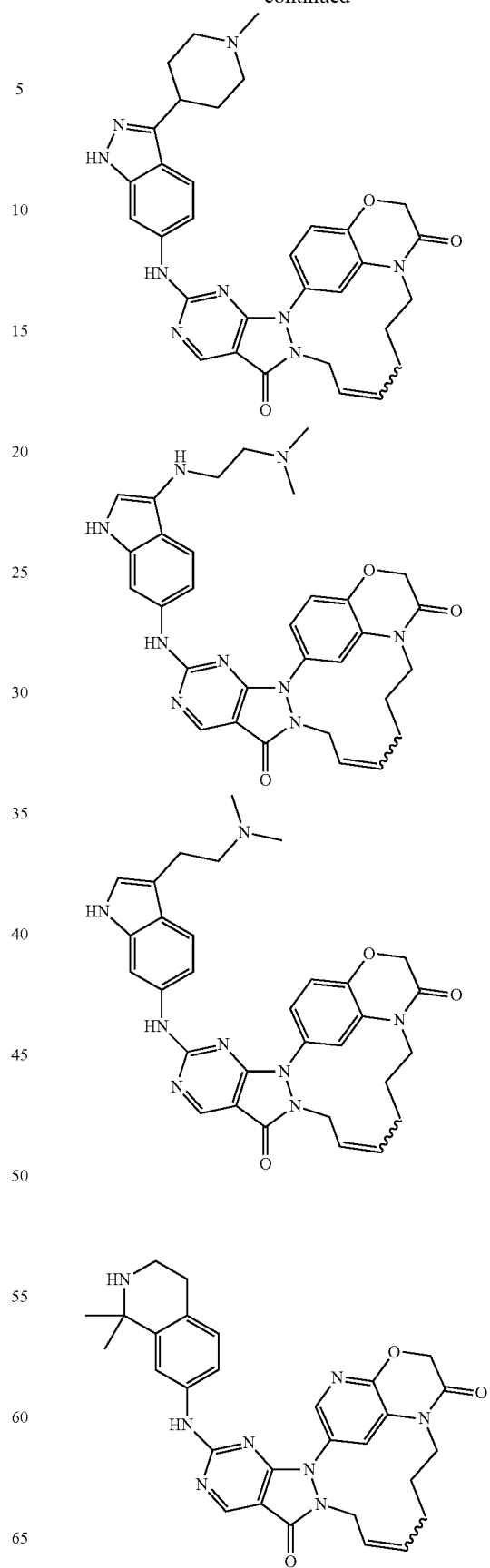

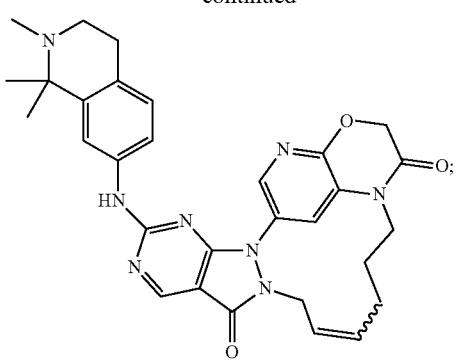
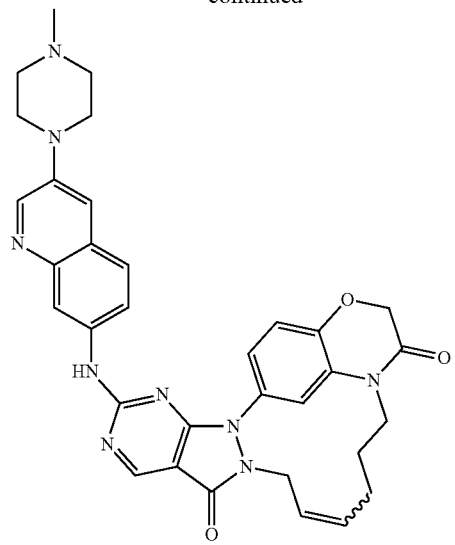
wherein " ⁓ " refers to a cis-configuration, a trans-configuration, or an isomeric mixture of double bond.
In some embodiments, the compound of formula (I) and/or the pharmaceutically acceptable salt thereof is selected from the group consisting of:
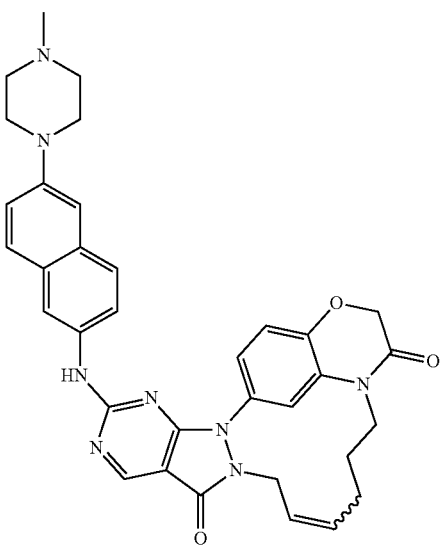
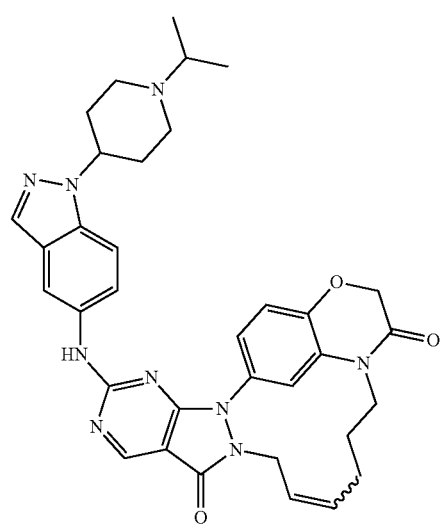
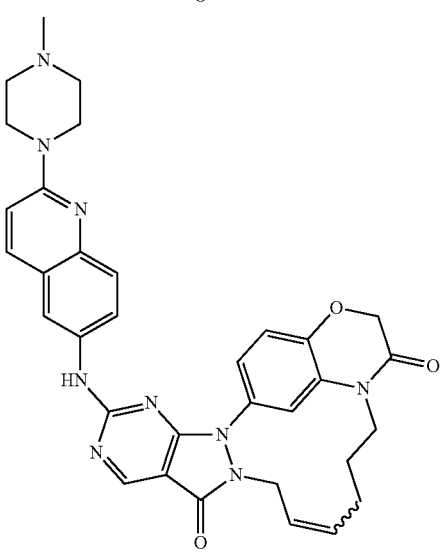
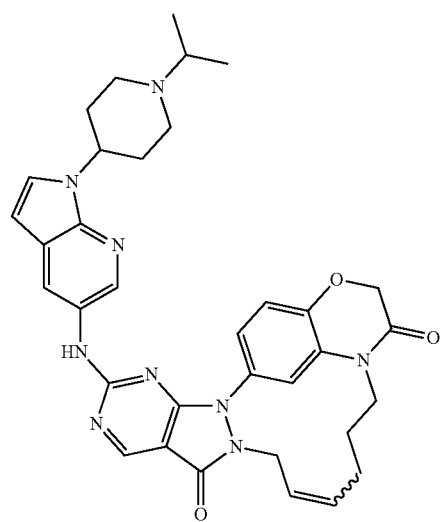

105
-continued
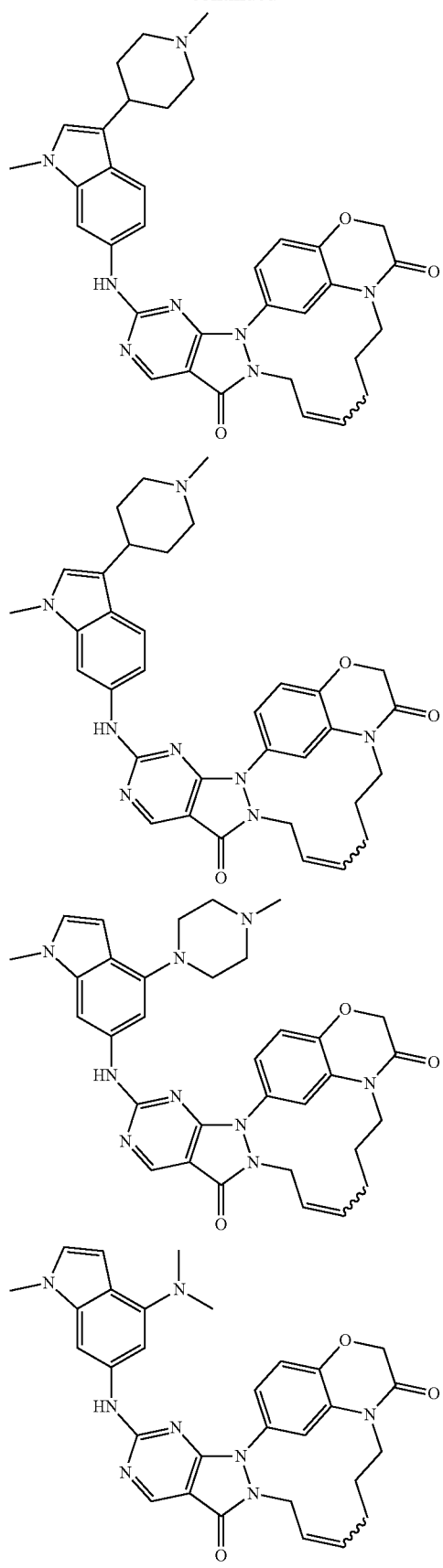
106
-continued
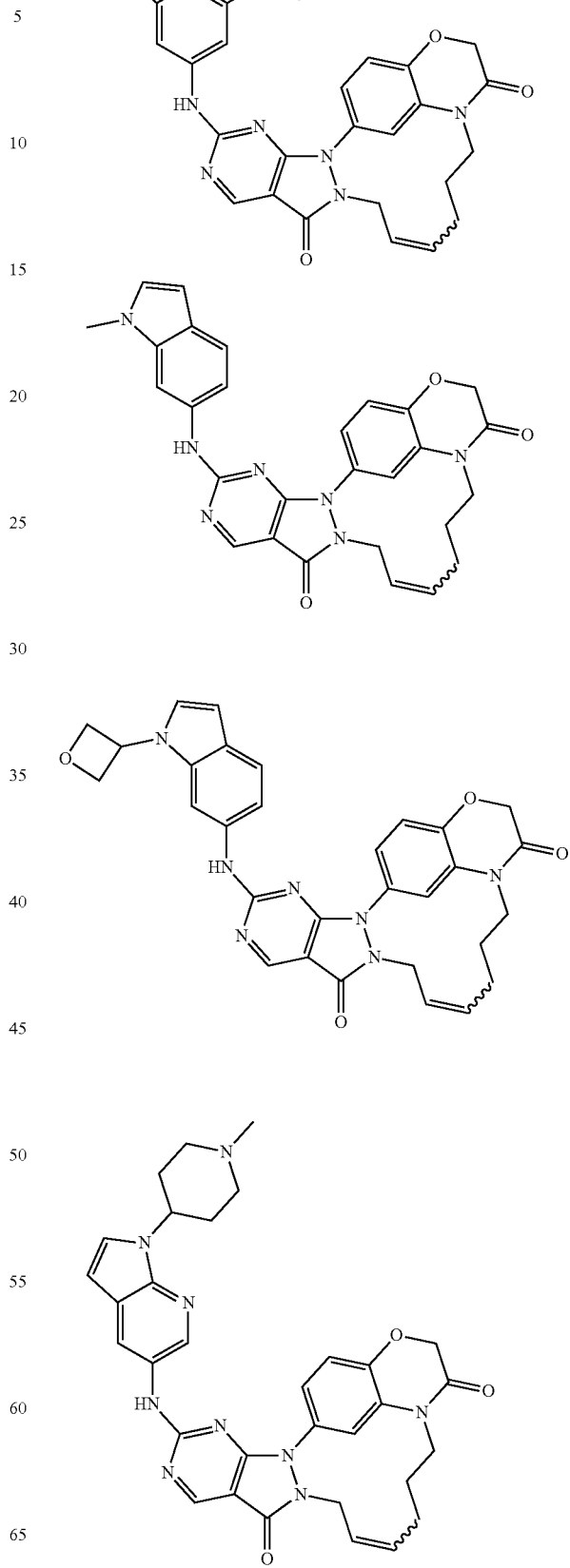

107
-continued
108
-continued
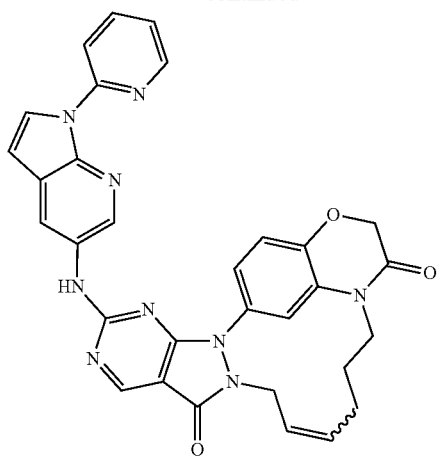
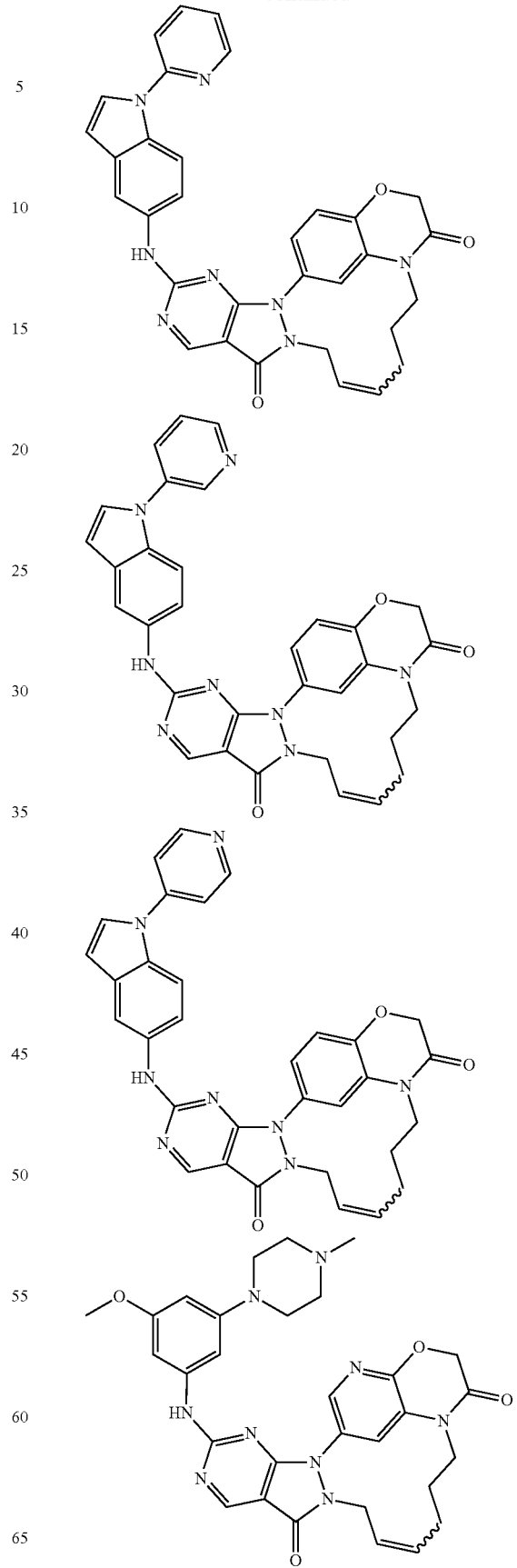

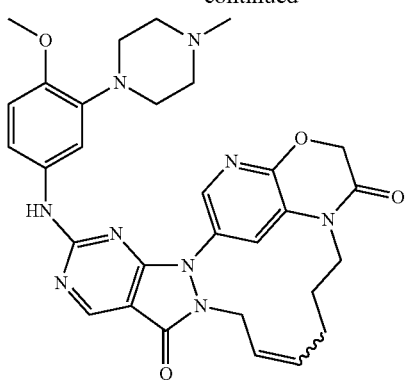
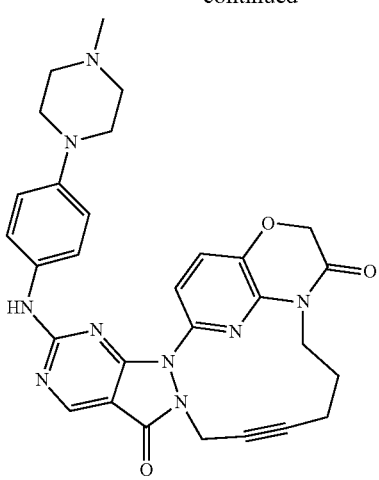
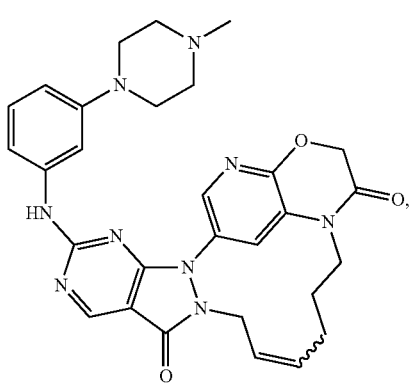
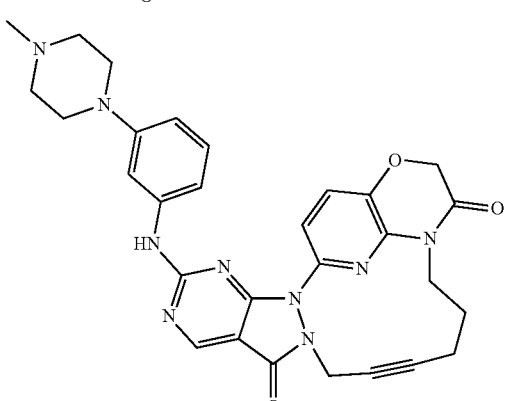
wherein " ∼ " refers to a cis-configuration, a trans-configuration, or an isomeric mixture of double bond.
In some embodiments, the compound of formula (I) and/or the pharmaceutically acceptable salt thereof is preferably selected from the group consisting of:
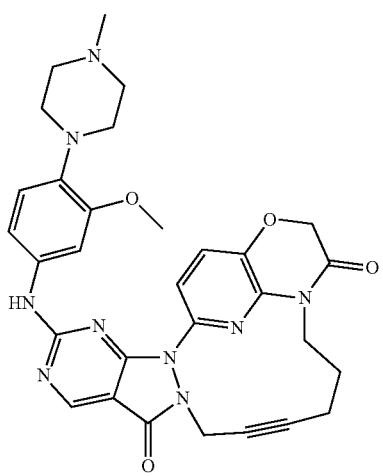
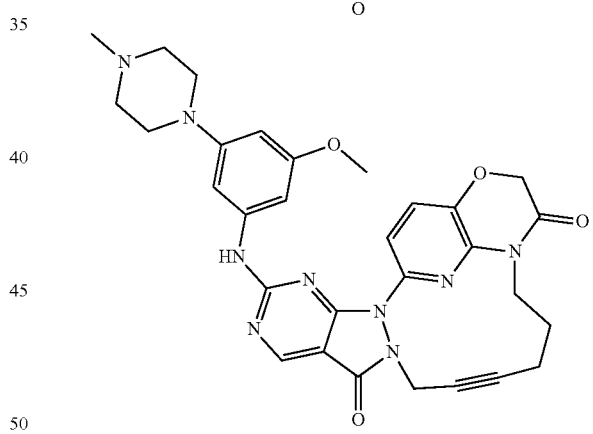
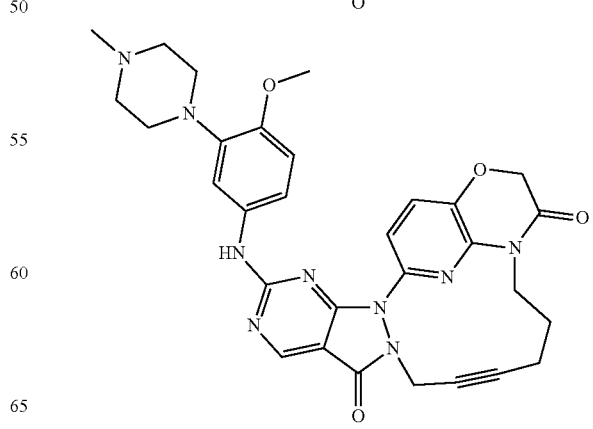

111
-continued
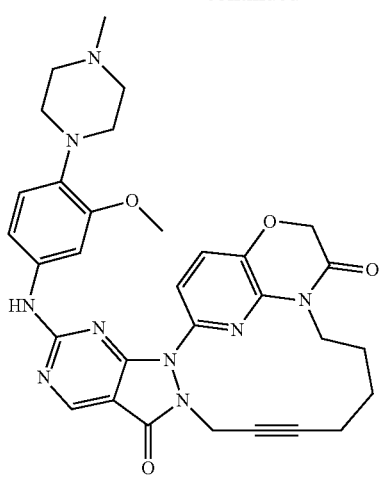
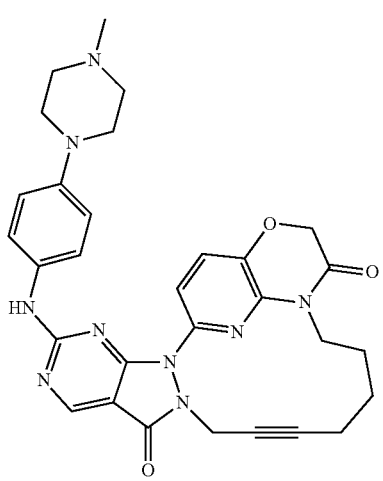
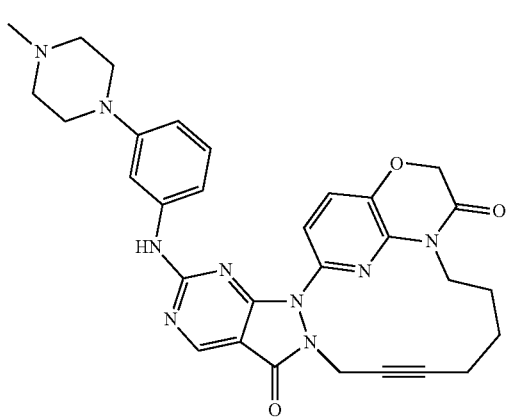
112
-continued
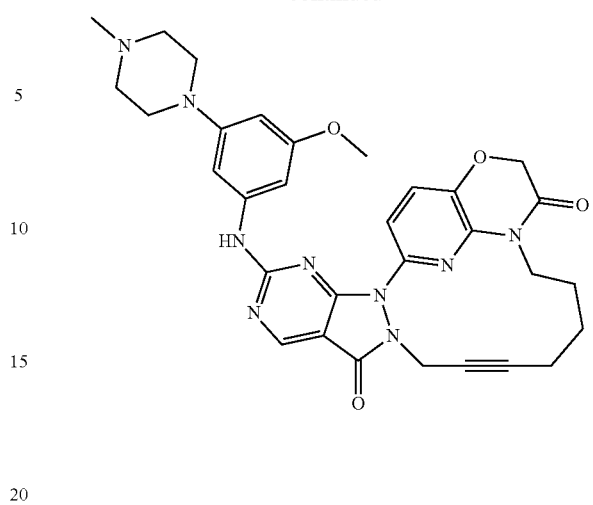
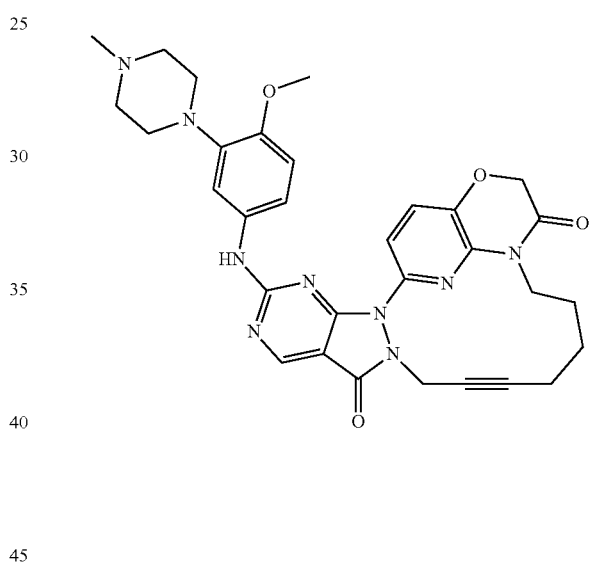
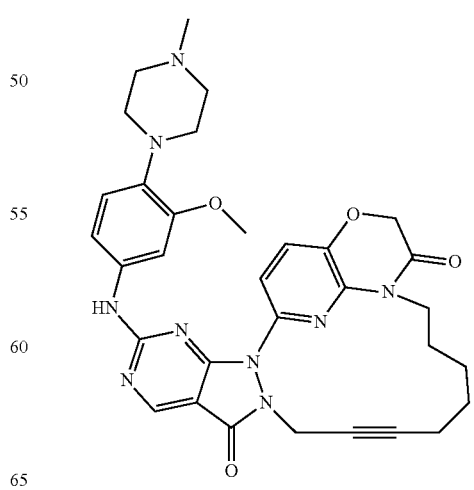

113
-continued
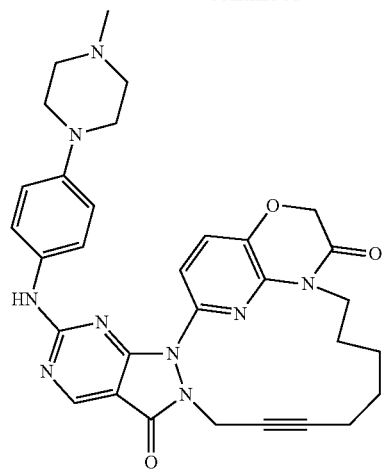
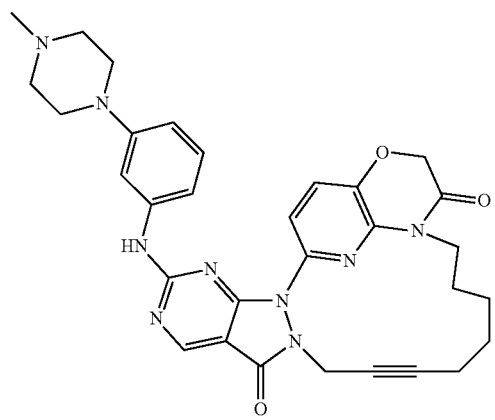
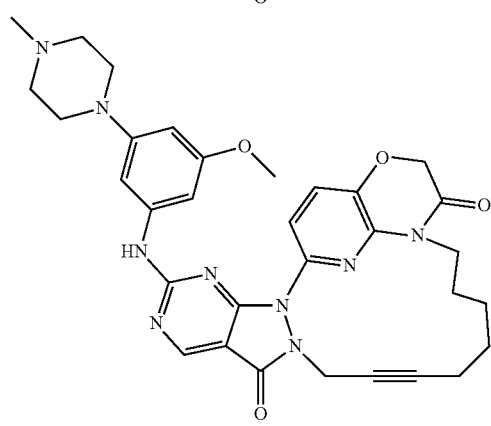
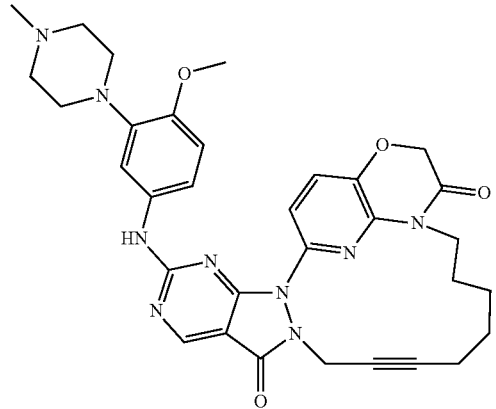
114
-continued
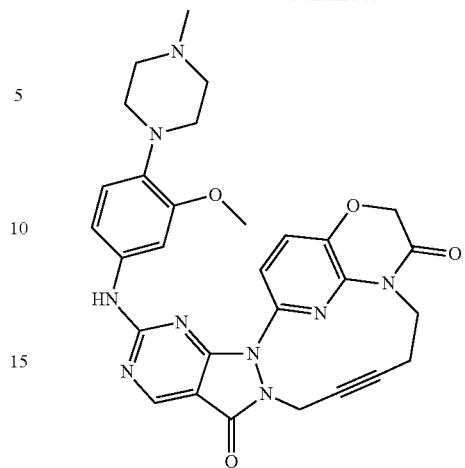
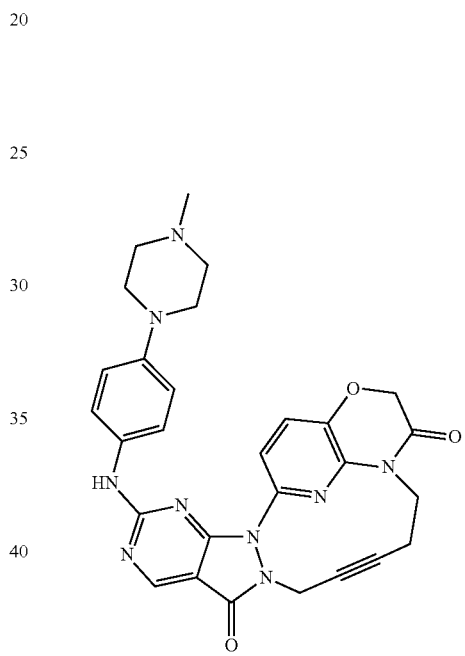
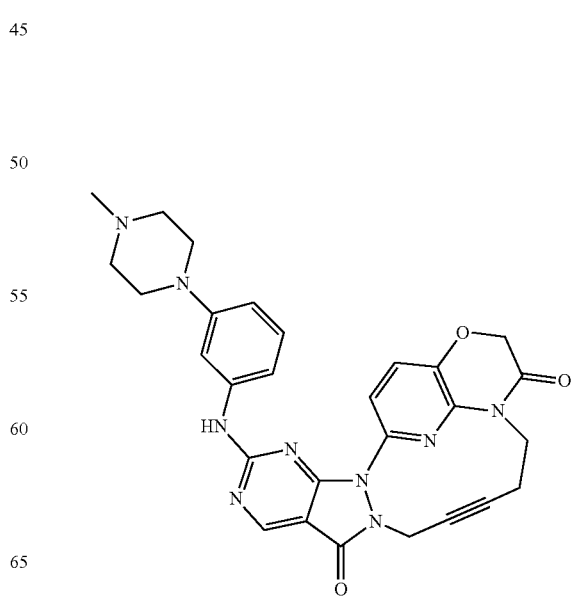

-continued

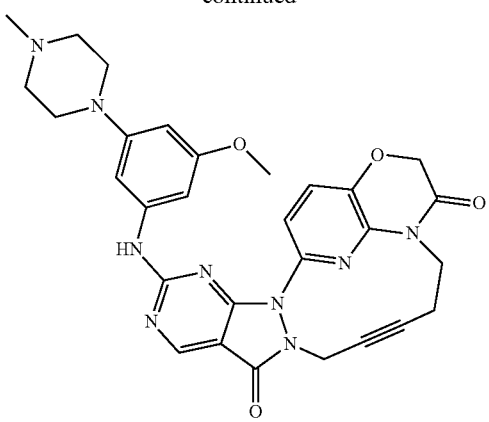

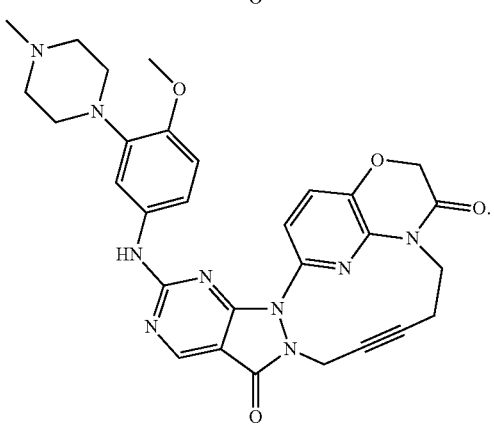

The present disclosure also provides a preparation method for a compound of formula (I), an isomer, a prodrug, a stable isotope derivative or a pharmaceutically acceptable salt thereof, the preparation method is any one of the following methods:

Method 1:

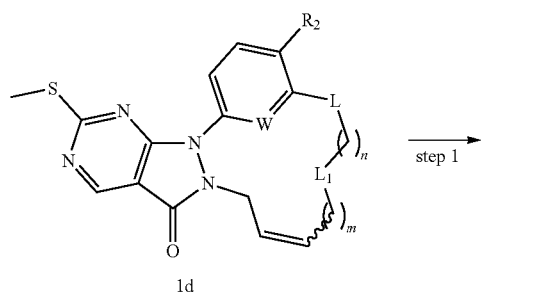

1d

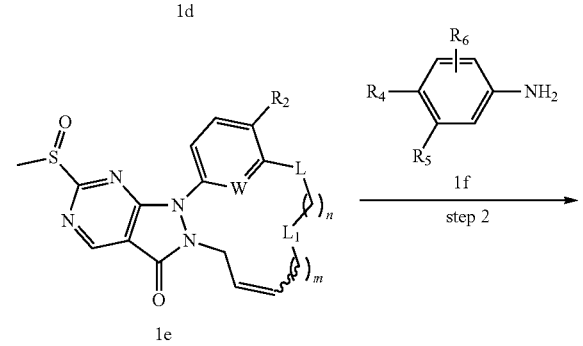

1e

-continued

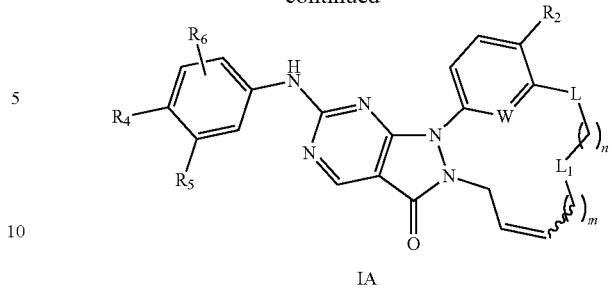

IA

In the method 1, $R_2$, $R_4$, $R_5$, $R_6$, L, $L_1$, m, n and W are as defined above; the method 1 comprises following steps: step (1) oxidizing the methylthio in compound 1d to sulfoxide with m-CPBA to obtain the compound 1e; step (2) carrying out the reaction between compound 1e and 1f under basic condition to obtain compound IA.

Method 2:

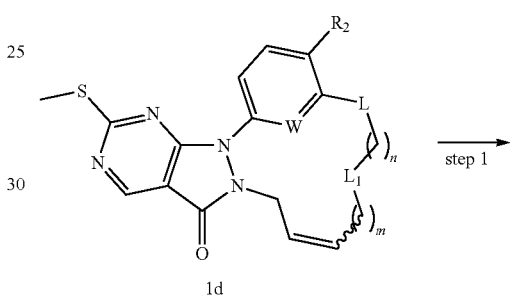

1d

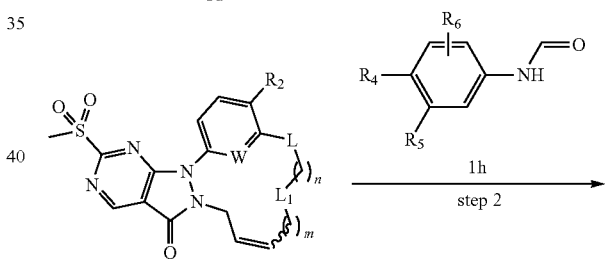

1g

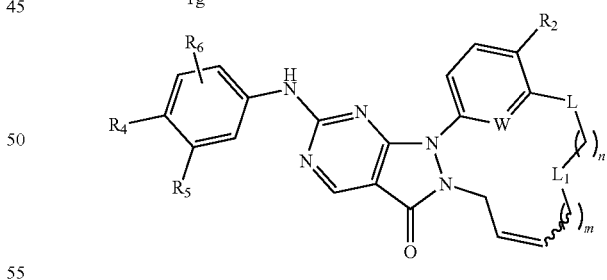

IA

In the method 2, $R_2$, $R_4$, $R_5$, $R_6$, L, $L_1$, m, n and W are as defined above; the method 2 comprises following steps: step (3) oxidizing the methylthio in compound 1d to sulfone with m-CPBA to obtain compound 1g; step (4) carrying out the reaction between compound 1g and 1h under basic condition to obtain compound IA.

Method 3:

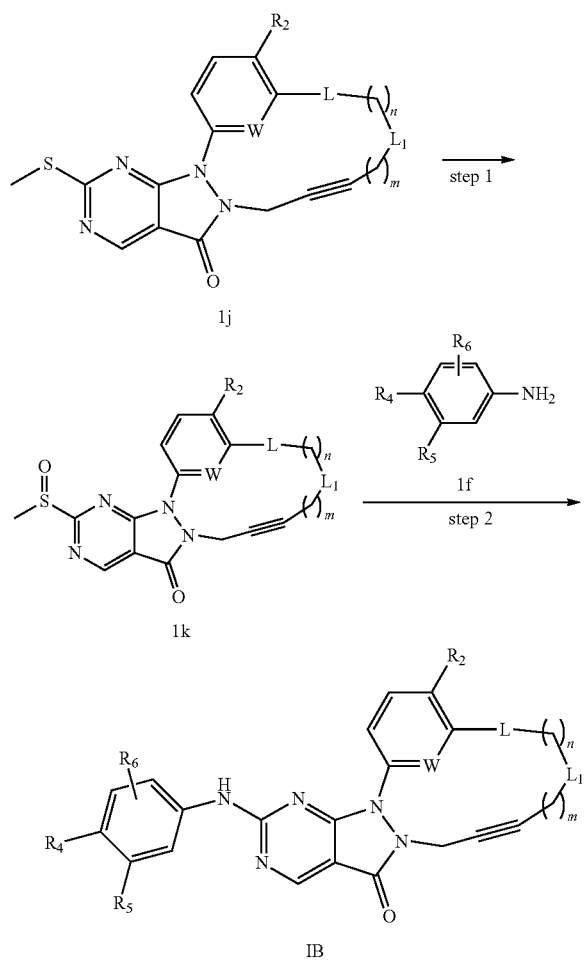

In the method 1, $R_2$, $R_4$, $R_5$, $R_6$, L, $L_1$, m, n and W are as defined above; the method 1 comprises following steps: step (1) oxidizing the methylthio in compound 1j to sulfoxide with m-CPBA to obtain the compound 1k; step (2) carrying out the reaction between compound 1k and 1f under basic condition to obtain compound IB.

In the method 1, the conditions and steps can be the conditions and steps for the reaction conventional in the art, and the following reaction conditions are particularly preferred in the present disclosure: for step (1), oxidizing compound 1d with m-CPBA in a dichloromethane solvent to obtain compound 1e; the amount of the reagent is preferably 1-50 mL/mmol compound 1d; the reaction time is preferably 0-24 hours, the temperature is preferably 0° C. to room temperature; the molar ratio of compound 1d to m-CPBA is preferably 1:0.95-1:1.05; for step (2), carrying out the reaction between compound 1e and 1f in toluene under basic condition (N,N-diisopropylethylamine or triethylamine) to obtain compound IA; the amount of the reagent is preferably 1-50 mL/mmol compound 1d; the reaction time is preferably 0-24 hours; the temperature is preferably room temperature to the reflux temperature of the solvent; the molar ratio of compound 1e, 1f to the base is preferably 1:0.9:1-1:2.5:2.5.

In the method 2, the conditions and steps can be the conditions and steps for the reaction conventional in the art, and the following reaction conditions are particularly preferred in the present disclosure: for step (1), oxidizing compound 1d with m-CPBA in a dichloromethane solvent to obtain compound 1g; the amount of the reagent is preferably 1-30 mL/mmol compound 1d; the reaction time is preferably 0-24 hours, the temperature is preferably 0° C. to room temperature; the molar ratio of compound 1d to m-CPBA is preferably 1:2-1:6; for step (2), carrying out the reaction between compound 1 g and 1h in tetrahydrofuran under basic condition (sodium hydride) to obtain compound IA; the amount of the reagent is preferably 1-50 mL/mmol compound 1g; the reaction time is preferably 0-24 hours; the temperature is preferably 0° C. to room temperature; the molar ratio of compound 1g, 1h to the base is preferably 1:0.9:1-1:2.5:2.5.

In the method 3, the conditions and steps can be the conditions and steps for the reaction conventional in the art, and the following reaction conditions are particularly preferred in the present disclosure: for step (1), oxidizing compound 1j with m-CPBA in a dichloromethane solvent to obtain compound 1k; the amount of the reagent is preferably 1-50 mL/mmol compound 1j; the reaction time is preferably 0-24 hours, the temperature is preferably 0° C. to room temperature; the molar ratio of compound 1j to m-CPBA is preferably 1:0.95-1:1.05; for step (2), carrying out the reaction between compound 1k and 1f in toluene under basic condition (N,N-diisopropylethylamine or triethylamine) to obtain compound IA; the amount of the reagent is preferably 1-50 mL/mmol compound 1k; the reaction time is preferably 0-24 hours; the temperature is preferably room temperature to the reflux temperature of the solvent; the molar ratio of compound 1k, 1f to the base is preferably 1:0.9:1-1:2.5:2.5.

In the method 1 or 2, compound 1d is obtained by the method shown by the reaction equation 1 below:

reaction equation 1

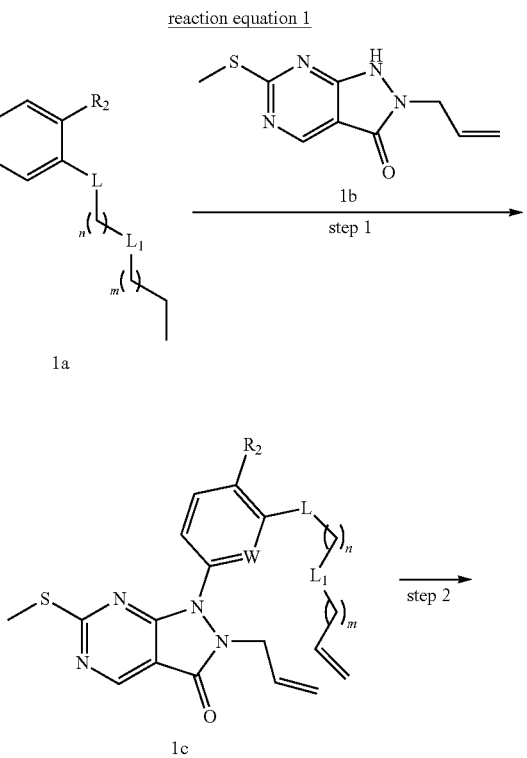

-continued

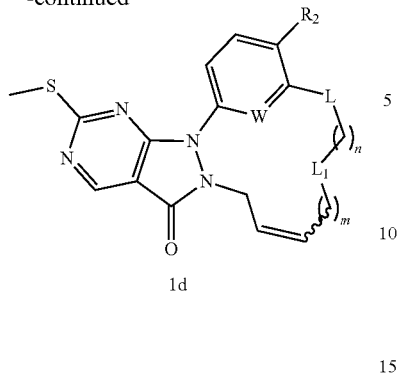

1d

-continued

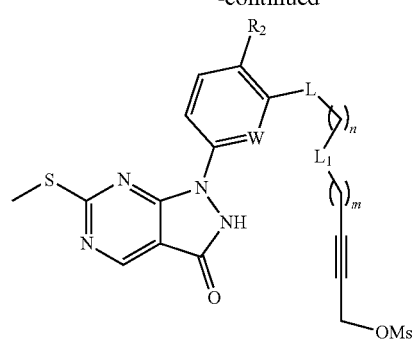

1i step 2 →

In the reaction equation 1, P is bromine, boric acid or borate, step (1) is carrying out Buchwald coupling reaction with 1a and 1b to obtain compound 1c; step (2) is carrying out RCM reaction with two alkenyls in compound 1c to obtain macrocyclic ring 1d.

When P is bromine, step (1) is carrying out the reaction under nitrogen protection, in 1,4-dioxane solvent and in the presence of base (1,2-N,N-dimethylethylenediamine, potassium carbonate) and cuprous chloride; the amount of the reagent is preferably 1-50 mL/mmol compound 1a; the reaction time is preferably 0-24 hours; the temperature is preferably room temperature to the reflux temperature of the solvent, more preferably 80-100° C.; the molar ratio of compound 1a to 1b is preferably 1:0.9 to 1:1.5. When P is boric acid or borate, step (1) is carrying out the reaction under nitrogen protection, in a mixed solvent of pyridine and chloroform and in the presence of copper acetate; the volume ratio of pyridine to chloroform is preferably 1:10, the amount of reagent is preferably 50 mL/mmol compound 1a; the reaction time is preferably 0-24 hours; the temperature is preferably room temperature to the reflux temperature of the solvent; the molar ratio of compound 1a to 1b is preferably 1:0.9 to 1:1.5. Step (2) is carrying out the reaction with Hoveyda-Grubbs catalyst under reflux in dichloromethane solvent to obtain compound 1d, and the amount of the catalyst is preferably 10 mol %;

In method 3, compound 1j is obtained by the method shown by the reaction equation 2 below:

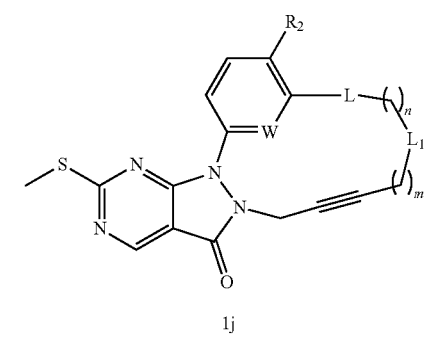

1j

In the reaction equation 2, step (1) is carrying out the reaction between methanesulfonyl and compound 1h in a solvent and in presence of base to obtain compound 1i, wherein the solvent is preferably dichloromethane and the base is preferably triethylamine or diisopropylethylamine; step (2) is carrying out reaction with compound 1i in a solvent under basic condition to obtain the compound 1j, wherein the solvent is preferably N,N-dimethylformamide, and the base is preferably potassium carbonate or sodium carbonate. 1h can be obtained by the method shown by the reaction equation 3 below:

reaction equation 2

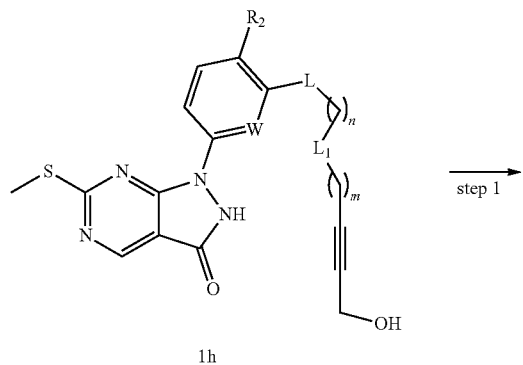

1h step 1 → reaction equation 3

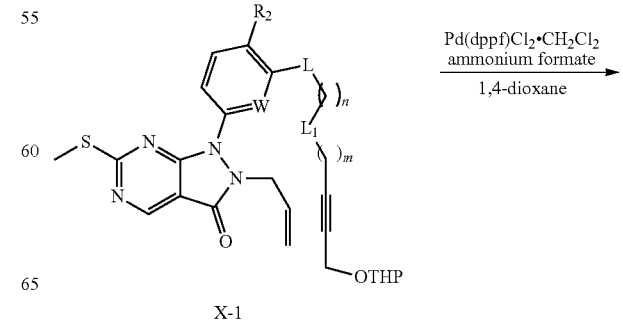

X-1

Pd(dppf)Cl$_2$·CH$_2$Cl$_2$
ammonium formate
───────────────→
1,4-dioxane

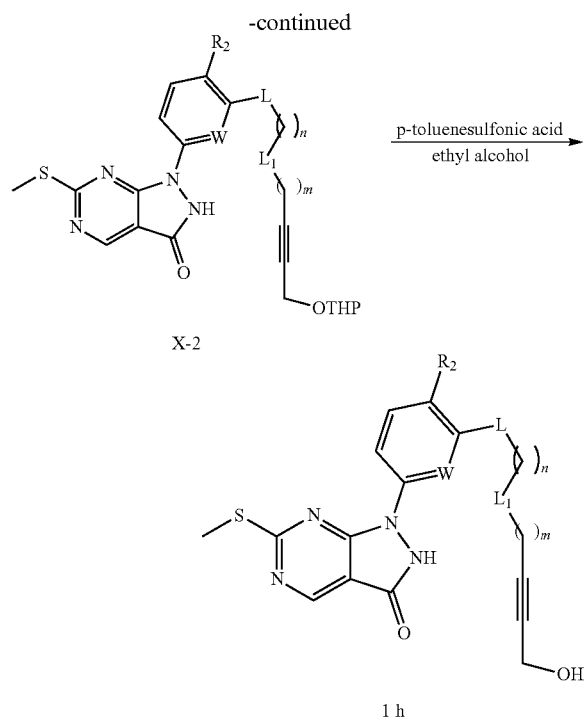

X-2

1h when an acidic system such as p-toluenesulfonic acid, hydrochloric acid, hydrogen chloride or trifluoroacetic acid is used in the final synthesis step of the above method 1, 2 or 3, or in the purification process, for example, the acidic system existing in the mobile phase of prep-HPLC, the compound IA would correspondingly be the p-toluenesulfonate, hydrochloride, trifluoroacetate etc.

In the above method, when an amino, a hydroxyl or a carboxyl is present in 1a, 1b, 1f or 1h, the amino, hydroxyl or carboxyl can be protected by a protective group to avoid any side reactions. If the amino protecting group or hydroxy protecting group is present, it is necessary to undergo a subsequent deprotection step to give compound IA. Any suitable amino protecting group, for example, a tert-butoxycarbonyl (Boc), can be used to protect the amino. If Boc is used as a protecting group, subsequent deprotection reactions can be carried out under standard conditions, for example, p-toluenesulfonic acid/methanol system, dichloromethane/trifluoroacetic acid system, saturated hydrogen chloride ether solution, or trim ethyl silyl trifluoromethanesulfonate/2,6-lutidine/dichloromethane system; any suitable hydroxyl protecting group, such as a benzyl, can be used to protect the amino group, and subsequent deprotection reactions can be carried out under standard conditions, for example, palladium on carbon/hydrogen; any suitable carboxyl protecting group, for example, to form a carboxylate group (such as, methyl carboxylate, ethyl carboxylate), can be used to protect the carboxyl group, and subsequent deprotection can be carried out under standard conditions, such as using sodium hydroxide, potassium hydroxide, lithium hydroxide to deprotect in tetrahydrofuran, water and/or methanol. The above deprotection is preferably carried out in the last step.

The compound of formula (I), the pharmaceutically acceptable salt thereof can be synthesized according to a general chemical synthesis method.

In general, the preparation of the salt can be carried out by reacting the free base or acid with an equivalent chemical equivalent or an excess of an acid (inorganic or organic acid) or a base (inorganic or organic base) in a suitable solvent or solvent composition.

The present disclosure also provides a pharmaceutical composition comprising a therapeutically effective amount of active ingredient and a pharmaceutically acceptable adjuvant; the active ingredient comprises a component selected from the group consisting of the compound of formula (I), the isomer, the prodrug, the stable isotope derivative and the pharmaceutically acceptable salt thereof.

In the pharmaceutical composition, the active ingredient can also comprise other therapeutic agents for cancer, viral infection or autoimmune diseases.

In the pharmaceutical composition, the pharmaceutically acceptable adjuvant can comprise a pharmaceutically acceptable carrier, diluent, and/or excipient.

According to the purpose of the treatment, the pharmaceutical composition can be formulated into various types of unit dosage, such as tablets, pills, powders, liquids, suspensions, emulsions, granules, capsules, suppositories, and injections (solutions and suspensions) and the like, and preferably liquids, suspensions, emulsions, suppositories and injections (solutions and suspensions), etc.

In order to shape the pharmaceutical composition in the form of a tablet, any excipient known and widely used in the art can be used. For Embodiment, carriers such as lactose, white sugar, sodium chloride, glucose, urea, starch, calcium carbonate, kaolin, crystalline cellulose, and silicic acid; binders such as water, ethanol, propanol, common syrup, dextrose solution, starch solution, gelatin solution, carboxymethyl cellulose, shellac, methyl cellulose and potassium phosphate, polyvinylpyrrolidone, etc.; disintegrating agents, such as dry starch, sodium alginate, agar powder, kelp powder, sodium bicarbonate, calcium carbonate, polyethylene sorbitan, sodium lauryl sulfate, monoglyceryl stearate, starch and lactose; disintegration inhibitors such as white sugar, glyceryl tristearate, coconut oil and hydrogenation oil; adsorption promoters such as quaternary ammonium bases and sodium lauryl sulfate; wetting agents such as glycerin, starch, etc.; adsorbents such as starch, lactose, kaolin, bentonite and colloidal silicic acid; such as pure talc, stearate, boric acid powder and polyethylene glycol. It is also possible to use a usual coating material to formulate a sugar-coated tablet, a gelatin film tablet, a casing tablet, a film-coated tablet, a two-layer film tablet, and a multilayer tablet.

In order to shape the pharmaceutical composition in the form of a pill, any excipient known and widely used in the art may be used, for Embodiment, carriers such as lactose, starch, coconut oil, hardened vegetable oil, kaolin and talc, etc.; binders such as gum arabic powder, tragacanth powder, gelatin and ethanol, etc.; disintegrating agents such as agar and kelp powder.

In order to shape the pharmaceutical composition in the form of a suppository, any excipient known and widely used in the art can be used, for Embodiment, polyethylene glycol, coconut oil, higher alcohols, esters of higher alcohols, gelatin and semi-synthetic glycerides, etc.

For the preparation of a pharmaceutical composition in the form of an injection, the solution or suspension may be sterilized (preferably by adding an appropriate amount of sodium chloride, glucose or glycerin, etc.) to prepare an injection which is isotonic with blood. Any of the commonly used carriers in the art can also be used. For example, water, ethanol, propylene glycol, ethoxylated isostearyl alcohol, polyoxylatedisostearyl alcohol, and fatty acid esters of polyethylene sorbitan. In addition, usual solubilizers, buffers, analgesics etc. can be added.

In the present disclosure, the content of the compound of formula (I), the isomer, the prodrug, the stable isotope derivative and the pharmaceutically acceptable salt thereof, and/or the other therapeutic agent comprised in the pharmaceutical composition does not have specific limitation, which can be selected within a wide range, typically 5 wt. %-95 wt. %, preferably 30 wt. % to 80 wt. %.

In the present disclosure, the administration method of the pharmaceutical composition is not particularly limited. Formulations of various dosage forms can be selected depending on the age, sex and other conditions and symptoms of the patient. For Embodiment, tablets, pills, solutions, suspensions, emulsions, granules or capsules are administered orally; injections can be administered alone or in combination with injectable solutions (e.g., glucose solution and amino acid solution); suppositories are given to the rectum.

The present disclosure also provides a use of the compound of formula (I), the isomer, the prodrug, the stable isotope derivative or the pharmaceutically acceptable salt thereof, or the pharmaceutical composition in manufacturing Wee1 inhibitor.

The present disclosure also provides a use of the compound of formula (I), the isomer, the prodrug, the stable isotope derivative or the pharmaceutically acceptable salt thereof, or the pharmaceutical composition in manufacturing chemotherapeutic or radioactive therapy sensitizers for treating cancer. Wherein the sensitizer of chemotherapeutic or radiotherapy refers to the medicament in the field of cancer therapy that used in combination with radiation therapy and/or chemotherapy using an anticancer agent to additively or synergistically improve the therapeutic effect of these radiotherapy and/or chemotherapy.

The present disclosure also provides a use of the compound of formula (I), the isomer thereof, the prodrug, the stable isotope derivative or the pharmaceutically acceptable salt thereof, or the pharmaceutical composition in manufacturing a medicament for treating and/or alleviating Wee1-mediated disease; the present disclosure preferably provides a use of the compound of represented by formula (I), the isomer thereof, the prodrug, the stable isotope derivative or the pharmaceutically acceptable salt thereof, or the pharmaceutical composition in manufacturing a medicament for treating and/or preventing Wee1-mediated disease; wherein the disease includes tumor and non-neoplastic disease. The disease is preferably cancer.

The present disclosure also provides a use of the compound of formula (I), the isomer thereof, the prodrug, the stable isotope derivative or the pharmaceutically acceptable salt thereof, or the pharmaceutical composition in manufacturing the medicament for treating and/or alleviating cancer.

The present disclosure further provides a method for treating cancers, virus and other infections, autoimmune diseases by using the compound of formula (I), the isomer, the prodrug, the stable isotope derivative or the pharmaceutically acceptable salt thereof, which comprises administering a therapeutically required amount of the compound of formula (I), the isomer, the prodrug, the stable isotope derivative or the pharmaceutically acceptable salt thereof, or the pharmaceutical composition, to a mammal.

The mammal is preferably a human.

The present disclosure further provides a use of the compound of formula (I), the isomer thereof, the prodrug, the stable isotope derivative or the pharmaceutically acceptable salt thereof, or the pharmaceutical composition in combination with one or more than one other therapeutic agents and/or therapeutic methods for treating and/or alleviating Wee1-mediated disease; the disease is preferably cancer.

The other therapeutic agent (such as, other therapeutic agents for treating cancers) may be formulated to a single dosage form with the compound of formula (I), or to be administered sequentially.

The cancers include metastatic and non-metastatic cancers, as well as familial hereditary and sporadic cancers, and may also include solid tumors and non-solid tumors.

Specific examples of said solid tumor may include, but are not limited to, eyes, bone, lung, stomach, pancreas, breast, prostate, brain (including glioblastoma and medulloblastoma), ovaries (including matrix cells produced by epithelial cells, generative cells and leydig cells), bladder, testis, spinal cord, kidney (including adenocarcinoma, nephroblastoma), mouth, lips, throat, oral cavity (including squamous-cell carcinoma), nasal cavity, small intestine, colon, rectum, parathyroid gland, gallbladder, bile duct, cervix, heart, inferior gland, bronchus, liver, ureter, vagina, anus, larynx, thyroid (including thyroid cancer and medullary carcinoma), esophagus, nasopharyngeal gland, salivary gland, adrenal gland, head and neck intraepithelial neoplasia (including Bowen's disease and Paget's disease), sarcoma (including leiomyosarcoma, rhabdomyosarcoma, liposarcoma, fibrosarcoma, osteosarcoma), skin (including melanoma, Kaposi's sarcoma, basocellular carcinoma and squamous-cell carcinoma) and other related tumor.

Specific examples of the solid tumor may include cancers selected from the group consisting of eye cancer, bone cancer, lung cancer, stomach cancer, pancreatic cancer, breast cancer, prostate cancer, brain cancer (including, but are not limited to, malignant glioma, medulloblastoma), ovary cancer, bladder cancer, cervical cancer, testicular cancer, kidney cancer (including, but are not limited to, adenocarcinoma and nephroblast cancer), oral cancer (including squamous cell carcinoma), tongue cancer, laryngeal cancer, nasopharyngeal cancer, head and neck cancer, colon cancer, small bowel cancer, rectal cancer, parathyroid cancer, thyroid cancer, esophageal cancer, gallbladder cancer, cholangiocarcinoma, cervical cancer, liver cancer, lung cancer (including, but not limited to small cell lung cancer, non-small cell lung cancer), villus epithelial cancer, osteosarcoma, Ewing's tumor, soft tissue sarcoma and skin cancer.

Specific examples of the non-solid tumors (including hematological tumors) may include, but are not limited to, one or more of lymphocytic leukemia (including acute lymphocytic leukemia, lymphoma, myeloma, chronic lymphocytic leukemia, Hodgkin's lymphoma, non-Hodgkin lymphoma, T cell chronic lymphocytic leukemia, B cell chronic lymphocytic leukemia), myeloid associated leukemia (including acute myeloid leukemia, chronic myeloid leukemia), and AIDs associated leukemia.

In the present disclosure, unless otherwise indicated, the term "optionally substituted at any position by a substituent selected from the group consisting of" refers to that one or more than one hydrogen atoms attached to one or more than one indicated atom is substituted by a indicated substituent, provided that the bond attached to the atom does not exceed the valence of the indicated atom, the position of substitution is any reasonable position in the art.

In the present disclosure, when a bond of a substituent is intersected with a bond formed by two ring atoms, such substituent may be bonded to any bondable ring atom.

Unless otherwise indicated, the following terms when used in the descriptions and the claims of the present disclosure have the following meanings:

The term "alkyl" refers to saturated branched or straight-chain hydrocarbon groups comprising 1 to 20 carbon atoms, preferably 1 to 10 carbon atoms, more preferably 1 to 8, 1 to 6, 1 to 4, 1 to 3 carbon atoms, such as methyl, ethyl, n-propyl, isopropyl, n-butyl, sec-butyl, t-butyl, isobutyl, pentyl, hexyl, heptyl, octyl, nonyl, decyl, 4,4-dimethylpentyl, 2,2,4-trimethylpentyl, undecyl, dodecyl and various isomers thereof.

The term "cycloalkyl" refers to saturated or partially unsaturated (comprising 1 or 2 double bonds) monocyclic or polycyclic group containing 3-20 carbon atoms. "monocyclic cycloalkyl" is preferably a 3-10 membered monocycloalkyl group, more preferably a 3-8 membered monocycloalkyl group, for example: cyclopropyl, cyclobutyl, cyclopentyl, cyclohexyl, cycloheptyl, cyclo-octyl, cyclodecyl, cyclododecyl, cyclohexenyl. "polycyclic cycloalkyl" includes "bridged cycloalkyl", "fused cycloalkyl" and "spirocycloalkyl", and representative examples of "bridged cycloalkyl" include, but are not limited to, borneol, bicyclo [2.2.1] heptenyl, bicyclo [3.1.1] heptyl, bicyclo[2.2.1]heptyl, bicyclo[2.2.2]octyl, bicyclo[3.2.2]nonyl, bicyclo[3.3.1] nonylalkyl, bicycle[4.2.1]nonanyl and adamantyl, and the like. "fused cycloalkyl" includes a cycloalkyl ring fused to a phenyl, cycloalkyl, or heteroaryl group, including but not limited to: benzocyclobutene, 2,3-dihydro-/H-indole, 2,3-cyclopentenopyridine, 5,6-dihydro-4H-cyclopentyl[B]thiophene, decalin and the like. "spirocycloalkyl" represents for a bicyclic group formed by the sharing of one carbon atom by two monocyclic cycloalkyl groups, including but not limited to: spiro[2,5]octyl, spiro[2,4]heptyl, spiro[4,5]decyl and the like. The polycyclic cycloalkyl group preferably contains 7-12 carbon atoms. The monocyclic cycloalkyl or polycyclic cycloalkyl group can be attached to the parent molecule moiety through any one or two carbon atoms of the ring.

The term "heterocycloalkyl" refers to saturated or partially unsaturated non-aromatic cyclic groups comprising carbon atoms and hetero atoms selected from nitrogen, oxygen or sulfur etc. The cyclic group can be monocyclic or polycyclic. In the present disclosure, the number of hetero atoms in the heterocycloalkyl is preferably 1, 2, 3 or 4, and the nitrogen, carbon or sulfur atom in the heterocycloalkyl group may be optionally oxidized. The nitrogen atom can be optionally further substituted with other groups to form a tertiary amine or a quaternary ammonium salt. The "monocyclic heterocycloalkyl" is preferably a 3 to 10 membered monocyclic heterocycloalkyl, more preferably a 3 to 8 membered monocyclic heterocycloalkyl. Such as: aziridinyl, tetrahydrofuran-2-yl, morpholin-4-yl, thiomorpholin-4-yl, thiomorpholine-S-oxide-4-yl, piperidin-1-yl, N-alkylpiperidin-4-yl, pyrrolidin-1-yl, N-alkylpyrrolidin-2-yl, piperazin-1-yl, 4-alkylpiperazin-1-yl and the like. "polycyclohetero-cycloalkyl" includes "fused heterocycloalkyl", "spiroheterocyclyl" and "bridgedheterocycloalkyl". "fused heterocycloalkyl" includes a monocyclic heterocycloalkyl ring fused to a phenyl, cycloalkyl, heterocycloalkyl or heteroaryl, including but not limited to: 2,3-dihydrobenzofuranyl, 1,3-dihydroisobenzofuranyl, indanyl, 2,3-dihydrobenzo[b]thienyl, dihydrobenzopyranyl, 1,2,3,4-tetrahydroquinolyl and the like. "spiroheterocyclyl" refers to a bicyclic group formed by two heterocycloalkyl groups or a cycloalkyl group and a heterocycloalkyl group sharing one carbon atom, and spiroheterocyclyl include, but are not limited to, 5-aza[2.5]octyl, 4-aza[2.5]octyl, 4-aza[2.4]heptyl or the like, the polycyclic heterocycloalkyl group is preferably 7-15 membered, more preferably 7-12 membered. Monocyclic heterocycloalkyl and polycyclic heterocycloalkyl can be attached to the parent molecular moiety through any atom on the ring. The above ring atoms specifically refer to carbon atoms and/or nitrogen atoms constituting the ring.

The term "cycloalkylalkyl" refers to an alkyl linkage between a cycloalkyl and a parent molecular moiety. Thus, "cycloalkylalkyl" includes the definition of alkyl and cycloalkyl as described above.

The term "heterocycloalkylalkyl" refers to an alkyl linkage between a heterocycloalkyl group and a parent molecular moiety. Thus, "heterocycloalkylalkyl" includes the definitions of alkyl and heterocycloalkyl as described above.

The term "alkoxy" refers to a cyclic or acyclic alkyl having indicated carbon atoms attached through an oxygen bridge, and includes alkyloxy, cycloalkyloxy, and heterocycloalkyloxy. Thus, "alkoxy" includes the definitions of alkyl, heterocycloalkyl and cycloalkyl as described above.

The term "hydroxyl" refers —OH. The term "hydroxyalkyl" refers to any one of the hydrogen atoms on the alkyl is substituted by a hydroxyl, including but not limited to, —CH$_2$OH, —CH$_2$CH$_2$OH, —CH$_2$CH$_2$C(CH$_3$)$_2$OH.

The term "alkylthio" refers to a cyclic or acyclic alkyl group having the number of carbon atoms attached through a sulfur bridge, the alkylthio group comprises alkylthio, cycloalkylthio and heterocycloalkylthio. Thus, "alkylthio" includes the definitions of alkyl, heterocycloalkyl and cycloalkyl as described above.

The term "alkenyl" refers to a straight, branched or cyclic non-aromatic hydrocarbon containing at least one carbon-carbon double bond. There may be 1 to 3 carbon-carbon double bonds, preferably one carbon-carbon double bond. The term "C$_{2-4}$ alkenyl" refers to an alkenyl having 2 to 4 carbon atoms, and the term "C$_{2-6}$ alkenyl" refers to an alkenyl group having 2 to 6 carbon atoms, including vinyl, propenyl, and butenyl, 2-methylbutenyl and cyclohexenyl. The alkenyl may be substituted.

The term "alkynyl" refers to a straight, branched or cyclic hydrocarbon containing at least one carbon to carbon triple bond. There may be 1 to 3 carbon-carbon triple bonds, preferably one carbon-carbon triple bond. The term "C$_{2-6}$ alkynyl" refers to an alkynyl having 2 to 6 carbon atoms and includes ethynyl, propynyl, butynyl and 3-methylbutynyl.

The term "aryl" refers to any stable 6 to 20 membered monocyclic or polycyclic aromatic groups such as phenyl, naphthyl, tetrahydronaphthyl, 2,3-dihydroindanyl or biphenyl.

The term "heteroaryl" refers to an aryl that at least one carbon atom is replaced by a heteroatom selected from nitrogen, oxygen or sulfur, which can be a 5-7 membered monocyclic structure or a 7-20 membered fused ring structure, preferably 5-6 membered monocyclic heteroaryl and 8-10 membered fused ring heteroaryl. In the present disclosure, the number of hetero atoms is preferably 1, 2 or 3, including: pyridyl, pyrimidinyl, piperazinyl, pyridazine-3 (2H)-one, furyl, thienyl, thiazolyl, pyrrolyl, imidazolyl, pyrazolyl, oxazolyl, isoxazolyl, 1,2,5-oxadiazolyl, 1,2,4-oxadiazolyl, 1,3,4-oxadiazolyl, 1,3,4-thiadiazole, 1,2,4-triazolyl, 1,2,3-triazolyl, tetrazolyl, indazoyl, isoindazolyl, indolyl, isosindolyl, benzofuranyl, benzothienyl, benzo[d][1,3]dioxolanyl, benzothiazolyl, benzoxazolyl, quinolyl, isoquinolinyl, isoquinolinone, quinazolinyl, 4-hydroxythieno[3,2-c]pyridyl, 4,5-dihydro-4-oxofuran[3,2] pyridinyl, 4-hydroxyl-5-azaindolyl, furan[2,3-c]pyridin-7 (6H)-one, thiophene[2,3-c]pyridin-7(6H)-one, 1,2,3,4-tetrahydropyrrolo[1,2-a]pyrazine and the like.

The term "arylalkyl" refers to an aryl attached to the parent molecular moiety through an alkyl. Thus, "arylalkyl" includes the definition of alkyl and aryl as defined above.

The term "heteroarylalkyl" refers to a heterocycloalkyl attached to the parent molecular moiety through an alkyl. Thus, "heteroarylalkyl" includes the definitions of alkyl and heteroaryl as defined above.

The term "halogen" refers to fluorine, chlorine, bromine or iodine.

The term "haloalkyl" refers to an alkyl optionally substituted by halogen. Thus, "haloalkyl" includes the definitions of the halogen and alkyl as defined above.

The term "haloalkoxy" refers to an alkoxy group optionally substituted by halogen. Thus, "haloalkoxy" includes the definitions of the halogen and alkoxy as defined above.

The term "amino" refers to —$NH_2$, and the term "alkylamino" refers to that at least one hydrogen atom on the amino group is substituted by an alkyl, including but not limited to —$NHCH_3$, —$N(CH_3)_2$, —$NHCH_2CH_3$, —$N(CH_2CH_3)_2$. The term "aminoalkyl" refers to that any one of the hydrogen atoms on the alkyl is substituted by an amino group, including but not limited to —$CH_2NH_2$, —$CH_2CH_2NH_2$. Thus, "aminoalkyl" and "alkylamino" include the definition of alkyl and amino as defined above.

The term "nitro" refers to —$NO_2$.

The term "cyano" refers to —CN.

The term "sulfydryl" refers to —SH.

"Room temperature" used herein refers to 15-30° C.

The " ⁓ " attached to the double bond in the present disclosure refers to Z-configuration, E-configuration, or a mixture thereof (cis-, trans-, or a mixture of cis- and trans-isomers). The " ⁓ " is preferably cis- or trans-.

The isotope-substituted derivative includes an isotope-substituted derivative that any hydrogen atom of the compound of formula I is replaced by 1 to 5 deuterium atoms, or any carbon atom of the compound of formula I is replaced by 1-3 $C^{14}$ atom, or any oxygen atom of the compound of formula I is replaced by 1 to 3 $O^{18}$ atom.

The term "prodrug" refers to the compound is capable of being converted to the original active compound after being subject to metabolism in the body. Typically, the prodrug is inactive or less active than the active parent compound, but can provide convenient preparation, administration or improve metabolic properties.

"Pharmaceutically acceptable salts" as described herein are discussed in Berge, et al., "*Pharmaceutically acceptable salts*", *J. Pharm. Sci.*, 66, 1-19 (1977), and it's apparent for pharmaceutical chemists that the salts are substantially non-toxic and can provide the desired pharmacokinetic properties, palatability, absorption, distribution, metabolism or excretion, and the like. The compounds of the present disclosure may have an acidic group, a basic group or an amphoteric group, and typical pharmaceutically acceptable salts include those prepared by reacting the compound of the present disclosure with an acid, for example, hydrochloride, hydrobromide, sulfate, pyrosulfate, bisulfate, sulfite, bisulfite, phosphate, monohydrogen phosphate, dihydrogen phosphate, metaphosphate, pyrophosphate, nitrate, acetate, propionate, citrate, octanoate, formate, acrylate, isobutyrate, hexanoate, heptanoate, oxalate, malonate, succinate, suberate, benzoate, methyl benzoate, phthalate, maleate, methanesulfonate, p-toluenesulfonate, (D,L)-tartaric acid, citric acid, maleic acid, (D,L)-malic acid, fumaric acid, succinic acid, succinate, lactate, triflate, naphthalene-1-sulfonate, mandelate, pyruvate, stearate, ascorbate, salicylate. When the compound of the present disclosure contains an acidic group, the pharmaceutically acceptable salt thereof may further include an alkali metal salt such as a sodium or potassium salt; an alkaline earth metal salt such as a calcium or magnesium salt; an organic base salt such as formed by ammonia, alkylamines, hydroxyalkylamines, amino acids (lysine, arginine) or N-methylglucamine and so on.

As used herein, "isomer" means that the compound of formula (I) of the present disclosure may have asymmetric centers and racemates, racemic mixtures and individual diastereomers, all of which including stereoisomers, geometric isomers are all included in the present disclosure. In the present disclosure, when the compound of formula I or a salt thereof is present in stereoisomeric form (for example, when it contains one or more asymmetric carbon atoms), individual stereoisomers (enantiomers and diastereomers) and mixtures thereof are included within the scope of the disclosure. The present disclosure also includes individual isomers of the compounds of formula I or salts, as well as mixtures with isomers in which one or more chiral centers are inverted. The scope of the disclosure includes mixtures of stereoisomers, as well as purified enantiomers or enantiomerically/diastereomerically enriched mixtures. The present disclosure includes mixtures of stereoisomers of all possible different combinations of all enantiomers and diastereomers. The present disclosure includes all combinations and subsets of stereoisomers of all the specific groups defined above. The present disclosure also includes geometric isomers of the compound of formula I or the salt thereof, including cis or trans isomers.

The above preferred conditions of the present disclosure may be arbitrarily combined without departing from the general knowledge in the art to obtain the preferred embodiments of the present disclosure.

The reagents and raw materials used in the present disclosure are commercially available.

DETAILED DESCRIPTION OF THE PREFERRED EMBODIMENT

The following embodiments serve to illustrate the present disclosure, but the embodiments should not be considered as limiting the scope of the disclosure. Some of the experimental methods of the following embodiments that are not indicated the specific conditions, can in according with the commonly used reaction conditions and procedures, or in accordance with the product specifications.

All the structures of the compounds in the present disclosure were confirmed by Nuclear Magnetic Resonance ($^1$H NMR) and/or Mass Spectra (MS).

$^1$H NMR chemical shifts (δ) were recorded in ppm ($10^{-6}$). NMR Spectra were recorded on Bruker AVANCE-400 spectrometer. The proper solvents are Chloroform-d ($CDCl_3$), Methanol-$D_4$ ($CD_3OD$), Dimethyl sulfoxide-$D_6$ (DMSO-$d_6$), tetramethylsilane as internal standard (TMS).

The analytical low-resolution mass spectra (MS) were recorded on Agilent 1200 HPLC/6120 using a XBridge C18, 4.6×50 mm, 3.5 μm, ESI source. The gradient elution method 1: 80-5% solvent $A_1$ and 20-95% solvent $B_1$ (1.8 min), and then 95% solvent $B_1$ and 5% solvent $A_1$ (over 3 min). "%" as used herein is volume percentage of the volume of a solvent in the total solvent volume. Solvent $A_1$: 0.01% aqueous solution of trifluoroacetic acid (TFA); Solvent $B_1$: 0.01% trifluoroacetic acid acetonitrile solution. "%" is the volume of a solvent in the total solvent volume. The gradient elution method 2: 80-5% solvent $A_2$ and 20-95% solvent $B_2$ (1.5 min), and then 95% solvent $B_2$ and 5% solvent $A_2$ (over 2 min), "%" is the volume of a solvent in the total solvent volume. Solvent A₂: 10 mM aqueous solution of ammonium bicarbonate; Solvent B₂: acetonitrile.

All the compounds in the present disclosure were separated by preparative high-performance liquid chromatography, column chromatography, flash column chromatography or TLC.

Preparative high-performance liquid chromatography purification (prep-HPLC) was performed on Shimadzu LC-20 HPLC, chromatographic column: waters xbridge Pre C18, 10 um, 19 mm×250 mm. Separation method 1: mobile phase A: 0.05% aqueous solution of trifluoroacetic acid, mobile phase B: acetonitrile; elution B is 40%, elution time: 20 min. Separation method 2: mobile phase A: 10 mmol/L aqueous solution of ammonium bicarbonate, mobile phase B: acetonitrile; the gradient elution B is from 25% to 80%, elution time: 30 min. Detection wavelength: 214 nm & 254 nm; the flow rate: 15.0 mL/min.

Flash column chromatography (flash system/Cheetah™) was performed on Agela Technologies MP200, the separation column was used Flash columm Silica-CS (80 g), Cat No. CS140080-0.

TLC was used Yantai xinnuo chemical, thickness of the coating is 0.2±0.03 mm, specification 20×20 cm. Column chromatography generally used Yantai Huanghai 200-300 mesh silica gel as carrier.

Embodiment 1: Synthesis of Compounds 1.1-1.4

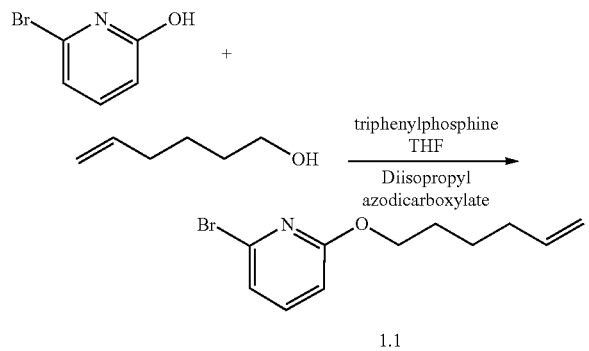

To a solution of triphenylphosphine (753 mg, 2.87 mmol) in tetrahydrofuran (THF) (6 mL) was added diisopropyl azodicarboxylate (580 mg, 2.87 mmol) under ice-bath, the reaction system was stirred for 5 min and then added 2-hydroxy 6-bromopyridine (500 mg, 2.87 mmol) and 5-hexen-1-ol (287 mg, 2.87 mmol) respectively, and then stirred for another 2 h, concentrated under reduced pressure to remove the solvent, the residue was triturated with petroleum ether for 0.5 h, filtered, the filtrate was concentrated, the residue was purified by column chromatography on silica gel (petroleum ether/ethyl acetate=30/1) to afford compound 1.1 (600 mg, yield: 82%) as a red liquid.

Compounds 1.2 (2-bromo-6-(4-penten-1-yloxy)pyridine), 1.3 (2-bromo-6-(3-buten-1-oxy)pyridine) and 1.4 (2-(2-(allyloxy)ethoxy)-6-bromopyridine) were synthesized following the synthetic method to the one used for compound 1.1, by replacing 5-hexen-1-ol to 4-penten-1-ol, 3-buten-1-ol or allyl hydroxyethyl ether.

Embodiment 2: Synthesis of Compounds 2.2-2.4

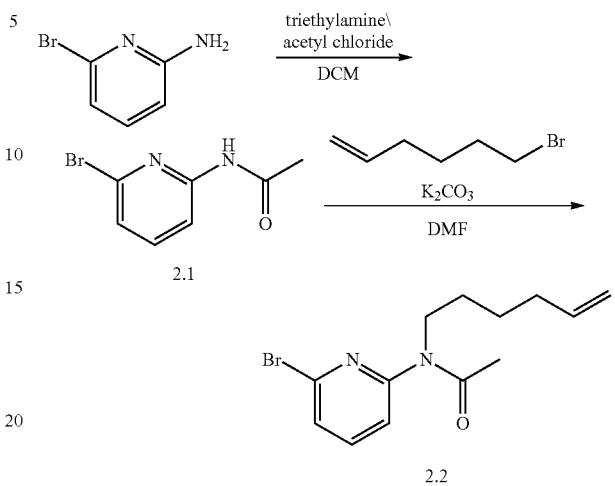

Step 1: To a solution of 6-bromopyridin-2-amine (3 g, 17.3 mmol) and triethylamine (4.8 mL, 34.6 mmol) in dichloromethane (DCM) (30 mL) was added acetyl chloride (2.03 g, 25.9 mmol) under ice-bath. The reaction system was stirred for 3 h. The reaction solution was poured into water, extracted with ethyl acetate, the organic layer was dried over anhydrous sodium sulfate, filtered and concentrated to afford compound 2.1 (2.5 g, yield: 68%) as a white solid.

Step 2: Compound 2.1 (1 g, 4.65 mmol), 6-bromo-1-hexene (1.14 g, 7.0 mmol), anhydrous potassium carbonate (K₂CO₃) (1.28 g, 9.3 mmol) were successively added into N,N-dimethylformamide (DMF) (20 mL), the reaction system was stirred at 60° C. for 16 h. The reaction solution was poured into water after cooled to room temperature, extracted with ethyl acetate, the organic layer was washed with brine, dried over anhydrous sodium sulfate, filtered and concentrated, the residue was purified by prep-TLC (petroleum ether/ethyl acetate=4/1) to afford compound 2.2 (700 mg, yield: 51%) as a colorless liquid.

m/z: [M+H]⁺ 297.1

Compounds 2.3 (N-(6-bromopyridin-2-yl)-N-(4-penten-1-yl)acetamide) or 2.4 (N-(6-bromopyridin-2-yl)-N-(3-buten-1-yl)acetamide) were synthesized following the synthetic method to the one used for compound 2.2, by replacing 6-bromo-1-hexene to 5-bromo-1-pentene or 4-bromo-1-butene.

Embodiment 3: Synthesis of Compound 2.6

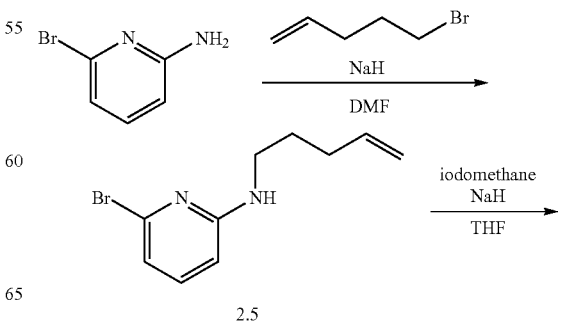

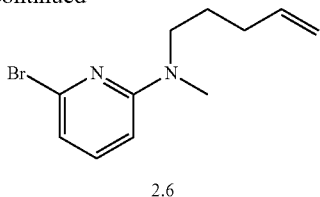

2.6

Step 1: The solution of 6-bromopyridin-2-amine (500 mg, 2.89 mmol) and sodium hydride (NaH) (139 mg, 3.5 mmol, 60%) in DMF (20 mL) was stirred at room temperature for 15 min, and then 5-bromopent-1-ene (517 mg, 3.47 mmol) was added to the reaction system, the reaction solution was stirred at room temperature for 16 h. The reaction solution was poured into water, extracted with ethyl acetate, dried over anhydrous sodium sulfate, concentrated under reduced pressure and purified by prep-TLC (petroleum ether/ethyl acetate=1/1) to afford compound 2.5 (270 mg, yield: 39%) as a colorless liquid.

Step 2: The solution of compound 2.5 (270 mg, 1.12 mmol) and NaH (45 mg, 1.12 mmol, 60%) in THF (10 mL) was heated to reflux for 2 h, and then iodomethane (159 mg, 1.12 mmol) was added to the above reaction system, the reaction solution was heated to reflux for 16 h. The reaction solution was poured into water, extracted with ethyl acetate, dried over anhydrous sodium sulfate, concentrated under reduced pressure and purified by prep-TLC (petroleum ether/ethyl acetate=1/1) to afford compound 2.6 (100 mg, yield: 35%) as a colorless liquid.

Embodiment 4: Synthesis of Compounds 3.2-3.5

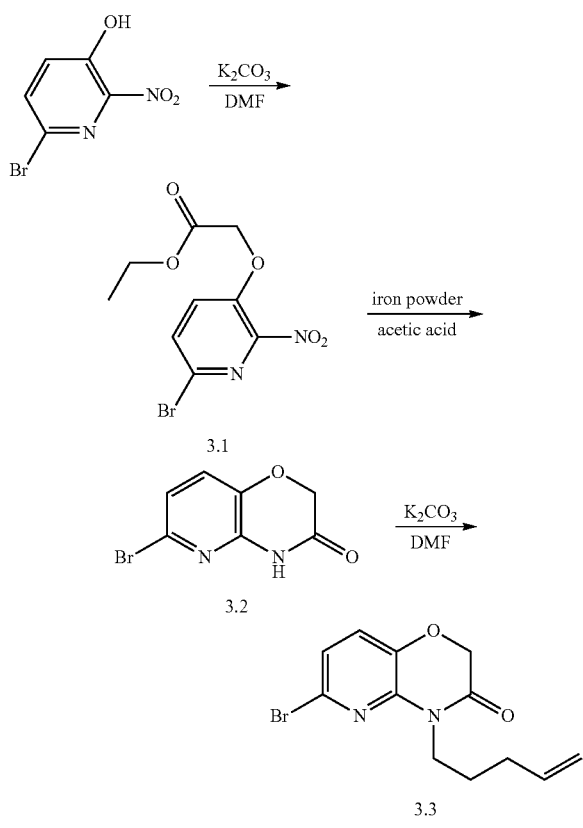

Step 1: To a solution of 6-bromo-2-nitropyridin-3-ol (2.18 g, 10 mmol) in DMF (20 mL) was added ethyl bromoacetate (1.66 g, 10 mmol), the reaction system was stirred at room temperature for 5 min, and then $K_2CO_3$ was added and stirred for another 2 h, the reaction was quenched by addition of water (100 mL), extracted with DCM (20 mL×3), the combined organic layers were dried over anhydrous sodium sulfate, concentrated, the residue was purified by column chromatography on silica gel (petroleum ether/ethyl acetate=5/1) to afford compound 3.1 (2.7 g, yield: 89%) as a light-yellow liquid.

m/z: $[M+H]^+$ 305.0

Step 2: Compound 3.1 (2.7 g, 8.85 mmol) and iron powder (2.48 g, 44.3 mmol) were added into acetic acid (40 nit), the reaction system was stirred at 100° C. for 2 h and then cooled down to room temperature, the reaction solution was filtered through a celite pad, $H_2O$ (100 mL) was added into the filtrate, extracted with dichloromethane (20 mL×3). The combined organic layers were dried over anhydrous sodium sulfate, concentrated, the residue was purified by column chromatography on silica gel (petroleum ether/ethyl acetate=3/1) to afford compound 3.2 (1.9 g, yield: 95%) as a light-yellow liquid.

m/z: $[M+H]^+$ 229.0

Step 3: Compound 3.2 (0.5 g, 2.2 mmol) and 5-bromo-1-pentene (0.36 g, 2.4 mmol) were dissolved in DMF (10 mL), and then $K_2CO_3$ was added. The mixture was stirred at room temperature for 2 h. The reaction system was diluted with ethyl acetate (30 mL), and washed with brine. Separation of organic layer and dried over anhydrous sodium sulfate, filtered and concentrated. The residue was purified by column chromatography on silica gel (petroleum ether/ethyl acetate=4/1) to afford compound 3.3 (0.51 g, yield: 79%) as a colorless oil.

Compounds 3.4 (6-bromo-4-(pent-4-en-1-yl)-2H-benzo[b][1,4]oxazin-3(4H)-one) was synthesized following the synthetic method to the one used for compound 3.3, by replacing 6-bromo-2-nitropyridin-3-ol to 4-bromo-2-nitrophenol.

Compounds 3.5 (6-bromo-4-(but-3-en-1-yl)-2H-pyrido[3,2-b][1,4]oxazin-3(4H)-one) was synthesized following the synthetic method to the one used for compound 3.3, by replacing 5-bromo-1-pentene to 4-bromo-1-butene.

Embodiment 5: Synthesis of Compound 4.2

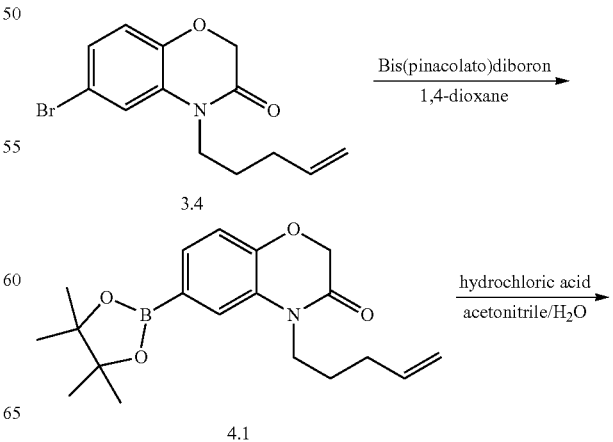

4.1

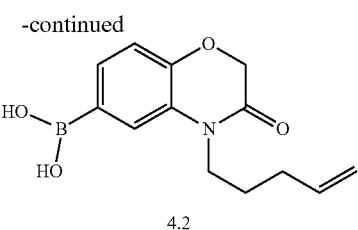

4.2

Step 1: Compound 3.4 (600 mg, 2.03 mmol); bis(pinacolato)diboron (774 mg, 3.05 mmol), potassium acetate (396 mg, 4.03 mmol) and [1,1'-bis(diphenylphosphino)ferrocene] dichloropalladium (148 mg, 0.20 mmol) were added into 1,4-dioxane (20 mL). The reaction system was stirred at 80° C. for 16 h under nitrogen. The reaction solution was poured into water, and extracted with ethyl acetate, dried over anhydrous sodium sulfate, concentrated under reduced pressure and purified by column chromatography on silica gel (petroleum ether/ethyl acetate=8/1) to afford compound 4.1 (600 mg, yield: 86%) as a colorless liquid.

Step 2: Compound 4.1 (500 mg, 1.46 mmol) and concentrated hydrochloric acid (5 mL) were added into a mixed solution of acetonitrile (10 mL) and H$_2$O (5 mL). The reaction system was heated to reflux for 16 h. The reaction solution was poured into water, extracted with ethyl acetate, dried over anhydrous sodium sulfate, concentrated under reduced pressure to afford compound 4.2 (400 mg, crude) as a yellow liquid.

Embodiment 6: Synthesis of Compound 5.4

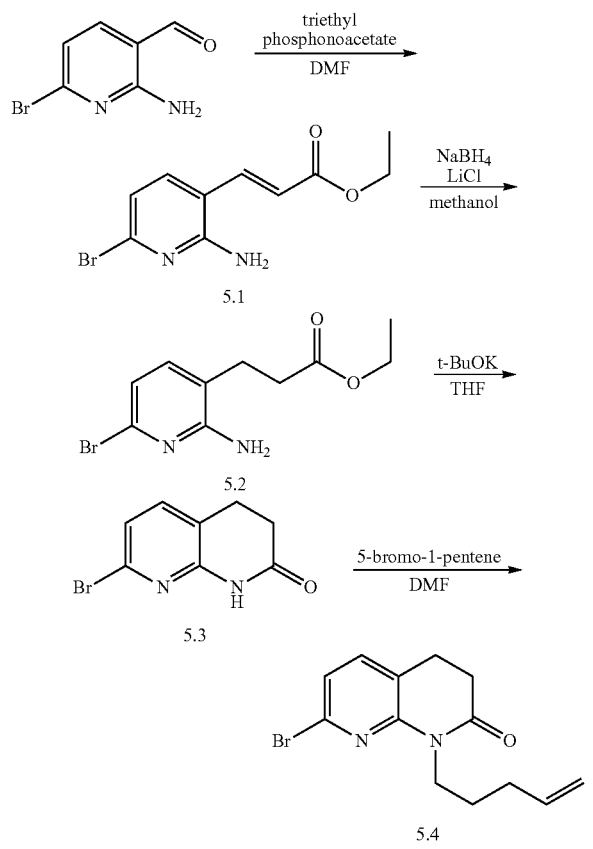

Step 1: To a solution of triethyl phosphonoacetate (1.5 g, 6.69 mmol) in DMF (30 mL) was added NaH (270 mg, 6.75 mmol, 60%) at 0° C., the reaction system was stirred for 0.5 h, and then 2-amino-6-bromonicotinaldehyde (900 mg, 4.48 mmol) was added into the above reaction system, and stirred at room temperature for 1 h. The reaction solution was poured into water, extracted with ethyl acetate, dried over anhydrous sodium sulfate, filtered, concentrated, the residue was purified by column chromatography on silica gel (petroleum ether/ethyl acetate=8/1) to afford compound 5.1 (400 mg, yield: 33%) as a yellow solid.

Step 2: To a solution of compound 5.1 (400 mg, 1.48 mmol) and lithium chloride (LiCl) (13 mg, 0.30 mmol) in methanol (15 mL) was added sodium borohydride (NaBH$_4$) (112 mg, 2.95 mmol), the reaction system was stirred at room temperature for 2 h, and then the reaction solution was poured into water, extracted with ethyl acetate, dried over anhydrous sodium sulfate, filtered, concentrated to afford compound 5.2 (400 mg, yield: 99%) as a colorless liquid.

Step 3: To a solution of compound 5.2 (400 mg, 1.46 mmol) in THF (15 mL) was added potassium tert-butoxide (t-BuOK) (246 mg, 2.2 mmol), the reaction system was stirred at room temperature for 2 h, the reaction solution was poured into water, extracted with ethyl acetate, dried over anhydrous sodium sulfate, filtered, concentrated to afford compound 5.3 (300 mg, yield: 90%) as an off-white solid.

Step 4: Compound 5.3 (300 mg, 1.32 mmol), 5-bromo-1-pentene (525 mg, 3.52 mmol) and K$_2$CO$_3$ (486 mg, 352 mmol) was added into DMF (15 mL), the reaction system was stirred at 100° C. for 16 h, and then the reaction solution was poured into water, extracted with ethyl acetate, dried over anhydrous sodium sulfate, filtered, concentrated under reduced pressure, the residue was purified by column chromatography on silica gel (petroleum ether/ethyl acetate=4/1) to afford compound 5.4 (300 mg, yield: 77%) as a colorless liquid.

Embodiment 7: Synthesis of Compound 6.1

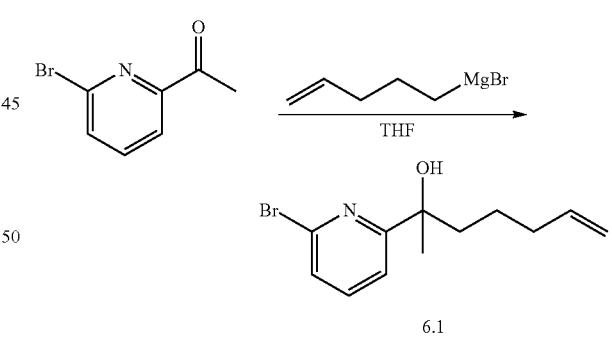

5-bromo-1-pentene (1.0 g, 6.71 mmol) and magnesium granules (179 mg, 7.38 mmol) was added into THF (10 mL), and then added iodine (20 mg, 0.08 mmol), after the reaction is triggered, the reaction system was heated to reflux for 45 min, after the magnesium granules were completely dissolved, the reaction solution was cooled to 0° C., and then to a solution of 1-(6-bromopyridin-2-yl)ethanone (1.48 g, 7.38 mmol) in THF (10 mL) was added the above reaction solution under ice-bath, the resulting mixture was stirred at room temperature for 3 h, the reaction solution was poured into saturated aqueous solution of ammonium chloride, extracted with ethyl acetate, dried over anhydrous sodium sulfate, filtered, concentrated, the residue was purified by column chromatography on silica gel (petroleum ether/ethyl acetate=20/1) to afford compound 6.1 (520 mg, yield: 30%) as a yellow liquid.

Embodiment 8: Synthesis of Compound 7.2

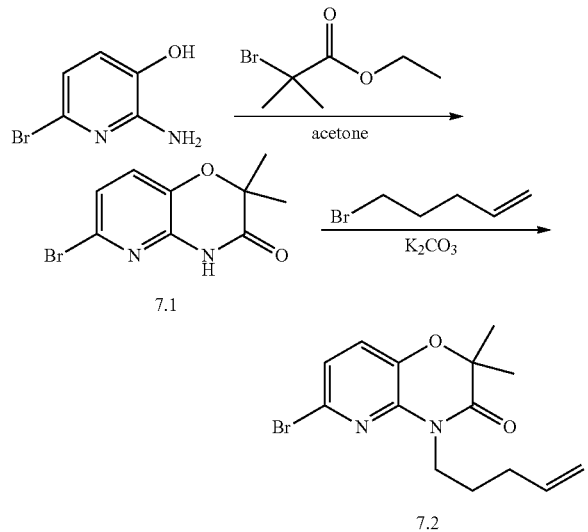

Step 1: To a solution of 2-amino-6-bromopyridin-3-ol (2.83 g, 9.17 mmol) and ethyl 2-bromoisobutyrate (2.7 g, 13.8 mmol) in acetone (30 mL) was added $K_2CO_3$ (6.33 g, 45.9 mmol), the reaction solution heated to reflux and stirred for overnight, concentrated under reduced pressure to remove the acetone, the resulting solid was dissolved in DCM, washed successively with $H_2O$ and brine, the organic layer was concentrated under reduced pressure, the residue was purified by column chromatography on silica gel (petroleum ether/ethyl acetate=3/1) to afford compound 7.1 (690 mg, yield: 23%) as a white solid.

Step 2: To a solution of compound 7.1 (690 mg, 2.68 mmol) and $K_2CO_3$ (740 mg, 5.36 mmol) in DMF (5 mL) was added 5-bromo-1-pentene (600 mg, 4.0 mmol), the reaction system was stirred at room temperature for overnight, the reaction was quenched by addition of $H_2O$ (20 mL), the aqueous layer was extracted with ethyl acetate (15 mL×3), the organic layers were combined and washed successively with $H_2O$ and brine, filtered, concentrated, the residue was purified by column chromatography on silica gel (petroleum ether/ethyl acetate=3/1) to afford compound 7.2 (790 mg, yield: 91%) as a white solid.

Embodiment 9: Synthesis of Compound 23.2

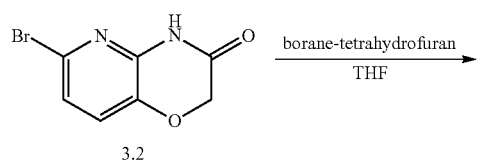

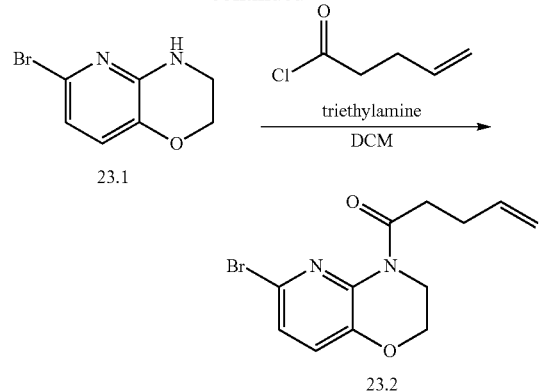

Step 1: To a solution of compound 3.2 (500 mg, 2.19 mmol) in THF (25 mL) was added borane tetrahydrofuran solution (5.5 mL, 5.5 mmol, 1.0 M) dropwise under ice-bath, the reaction system was heated to reflux and stirred for 1 h. The reaction was quenched by addition of methanol (10 drops) in reflux, the mixture was cooled to room temperature and then concentrated under reduced pressure to remove the solvent, the residue was purified by column chromatography on silica gel (petroleum ether/ethyl acetate=5/1) to afford compound 23.1 (470 mg, yield: 99%) as a white solid.

m/z: $[M+H]^+$ 215.1

To a solution of compound 23.1 (290 mg, 1.35 mmol) and triethylamine (410 mg, 4.1 mmol) in DCM (20 mL) was added 4-pentenoyl chloride (160 mg, 1.35 mmol) dropwise under ice-bath, the reaction system was stirred at room temperature for 1 h and then concentrated under reduced pressure to remove the solvent, the residue was purified by column chromatography on silica gel (petroleum ether/ethyl acetate=3/1) to afford compound 23.2 (380 mg, yield: 95%) as a colorless liquid.

m/z: $[M+H]^+$ 297.1

Embodiment 10: Synthesis of Compound 23.3

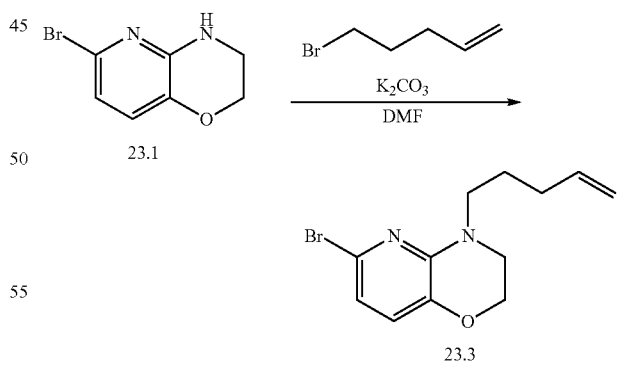

To a solution of compound 23.1 (500 mg, 2.33 mmol) in DMF (20 mL) was added NaH (186 mg, 4.66 mmol, 60%), the reaction system was stirred at room temperature for 0.5 h and then 5-bromo-1-pentene (381 mg, 2.56 mmol) was added into the above reaction system, stirred for another 16 h at 120° C. The reaction solution was poured into $H_2O$, extracted with ethyl acetate, dried over anhydrous sodium sulfate, filtered, concentrated under reduced pressure, the residue was purified by column chromatography on silica gel (petroleum ether/ethyl acetate=3/1) to afford compound 23.3 (450 mg, yield: 68%) as a colorless liquid.

m/z: [M+H]$^+$ 283.0

Embodiment 11: Synthesis of Compound 23.4

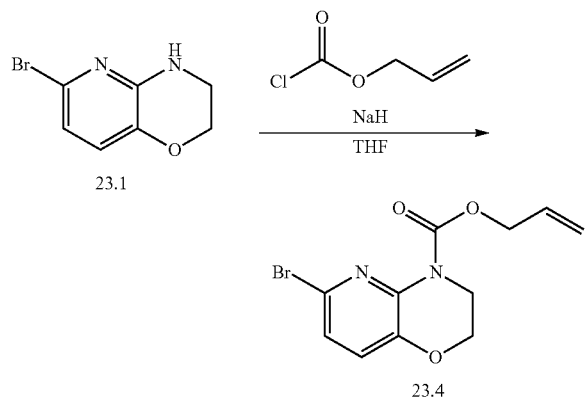

The solution of compound 23.1 (320 mg, 1.49 mmol) and NaH (179 mg, 4.48 mmol, 60%) in THF (20 mL) was heated to reflux for 2 h and then allyl carbonochloridate (540 mg, 4.48 mmol) was added into the above reaction system, the reaction solution was stirred for another 16 h at reflux. The reaction solution was poured into H$_2$O, extracted with ethyl acetate, the organic layers were separated and dried over anhydrous sodium sulfate, filtered, concentrated, the residue was purified by prep-TLC (petroleum ether/ethyl acetate=1/1) to afford compound 23.4 (440 mg, yield: 67%) as a colorless liquid.

Embodiment 12: Synthesis of Compound 8.3

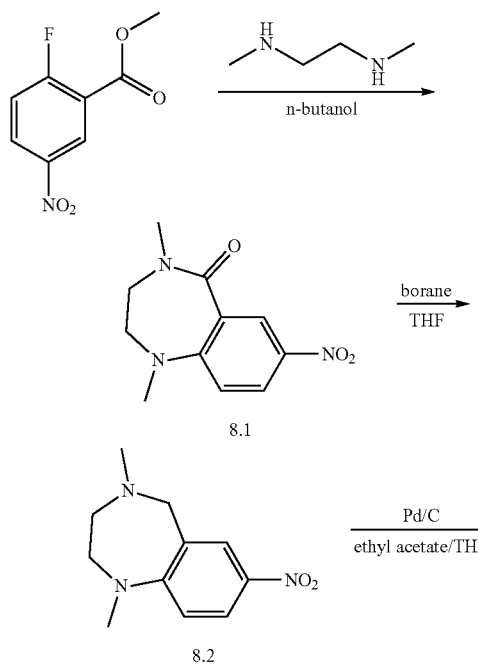

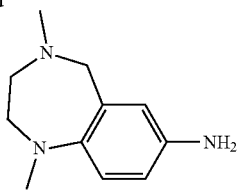

Step 1: To a solution of methyl 2-fluoro-5-nitrobenzoate (2.0 g, 10 mmol) and N,N'-dimethylethane-1,2-diamine (890 mg, 10 mmol) in n-butanol (30 mL) was added sodium carbonate (2.1 g, 20.1 mmol). The reaction system was stirred at 110° C. for 12 h. The reaction system was cooled to room temperature, concentrated under reduced pressure. The residue was purified by column chromatography on silica gel (DCM/methanol=20/1) to afford compound 8.1 (2.0 g, yield: 85%) as a yellow solid.

m/z: [M+H]$^+$ 236.0

Step 2: To a solution of compound 8.1 (1.0 g, 4.3 mmol) in THF (20 mL) was slowly added borane tetrahydrofuran solution (1.0 M, 8.5 mL) dropwise. After addition, the reaction system was stirred at 66° C. for overnight. The reaction system was cooled to room temperature, concentrated under reduced pressure. The residue was dissolved in DCM (20 mL) and washed with brine, dried over anhydrous sodium sulfate, filtered, concentrated under reduced pressure to afford compound 8.2 (850 mg, yield: 90%) as a yellow solid.

m/z: [M+H]$^+$ 222.1

Step 3: Compound 8.2 (850 mg, 3.84 mmol) was dissolved in a mixed solvent of THF (10 mL) and ethyl acetate (10 mL), Pd/C (50 mg, 10%) was added. The reaction system was replaced with hydrogen for 3 times and then stirred at room temperature for overnight under hydrogen. The reaction system was filtered through a celite pad. The filtrated was concentrated under reduced pressure to afford compound 8.3 (650 mg, yield: 88%) as a yellow solid.

Embodiment 13: Synthesis of Compound 9.2

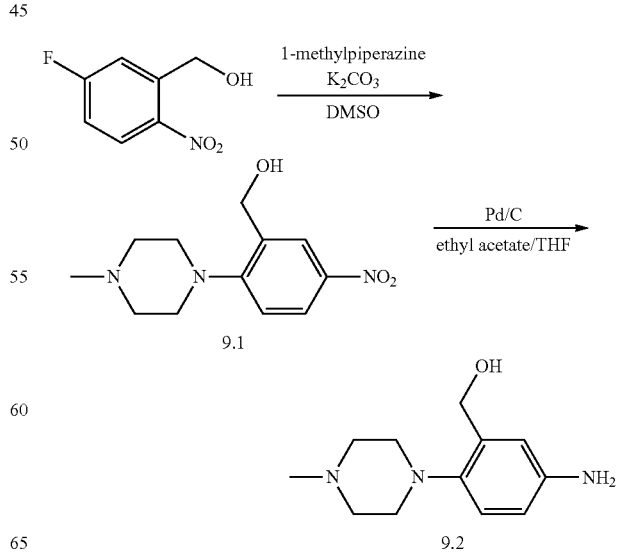

Step 1: To a solution of (5-fluoro-2-nitrophenyl)methanol (1.0 g, 5.8 mmol) and N-methylpiperazine (0.7 g, 6.4 mmol) in dimethyl sulfoxide (DMSO) (20 mL) was added $K_2CO_3$ (1.2 g, 8.8 mmol) in small portions. After addition, the reaction system was stirred at room temperature for overnight and then diluted with ethyl acetate (50 mL), washed with brine (50 mL×3), dried over anhydrous sodium sulfate, filtered, concentrated under reduced pressure to afford compound 9.1 (1.4 g, yield: 92%) as a yellow solid.

m/z: $[M+H]^+$ 252.0

Step 2: To a solution of compound 9.1 (1.3 g, 5.3 mmol) in a mixed solvent of THF (10 mL) and ethyl acetate (10 mL) was added Pd/C (100 mg, 5%). The reaction system was replaced with hydrogen for 3 times and then stirred at room temperature for 16 h under hydrogen. The reaction solution was filtered through a celite pad, the filtrated was concentrated under reduced pressure to afford compound 9.2 (1.0 g, yield: 84%) as a yellow solid.

m/z: $[M+H]^+$ 221.9

Embodiment 14: Synthesis of Compounds 10.8~40.11

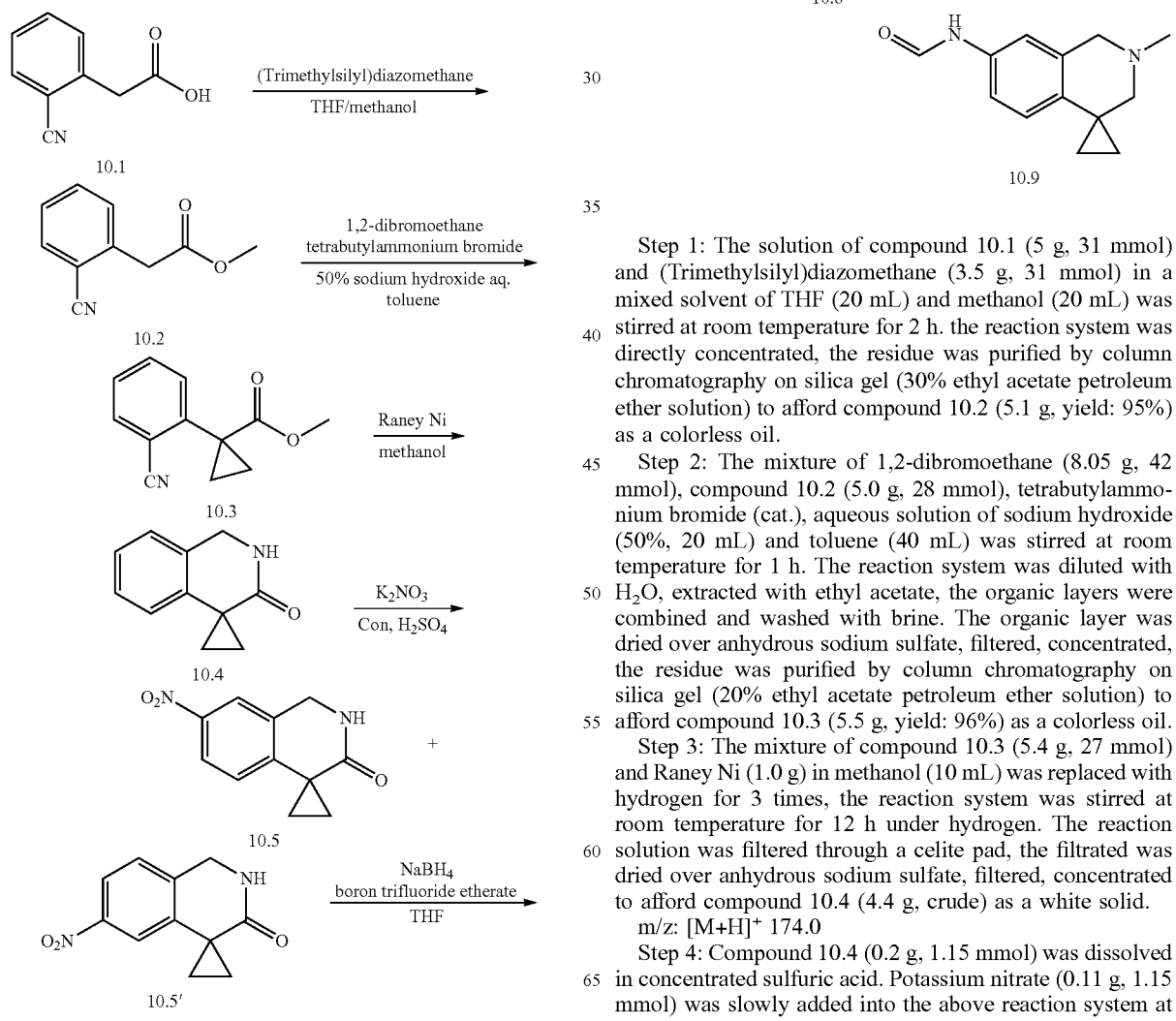

Step 1: The solution of compound 10.1 (5 g, 31 mmol) and (Trimethylsilyl)diazomethane (3.5 g, 31 mmol) in a mixed solvent of THF (20 mL) and methanol (20 mL) was stirred at room temperature for 2 h. the reaction system was directly concentrated, the residue was purified by column chromatography on silica gel (30% ethyl acetate petroleum ether solution) to afford compound 10.2 (5.1 g, yield: 95%) as a colorless oil.

Step 2: The mixture of 1,2-dibromoethane (8.05 g, 42 mmol), compound 10.2 (5.0 g, 28 mmol), tetrabutylammonium bromide (cat.), aqueous solution of sodium hydroxide (50%, 20 mL) and toluene (40 mL) was stirred at room temperature for 1 h. The reaction system was diluted with $H_2O$, extracted with ethyl acetate, the organic layers were combined and washed with brine. The organic layer was dried over anhydrous sodium sulfate, filtered, concentrated, the residue was purified by column chromatography on silica gel (20% ethyl acetate petroleum ether solution) to afford compound 10.3 (5.5 g, yield: 96%) as a colorless oil.

Step 3: The mixture of compound 10.3 (5.4 g, 27 mmol) and Raney Ni (1.0 g) in methanol (10 mL) was replaced with hydrogen for 3 times, the reaction system was stirred at room temperature for 12 h under hydrogen. The reaction solution was filtered through a celite pad, the filtrated was dried over anhydrous sodium sulfate, filtered, concentrated to afford compound 10.4 (4.4 g, crude) as a white solid.

m/z: $[M+H]^+$ 174.0

Step 4: Compound 10.4 (0.2 g, 1.15 mmol) was dissolved in concentrated sulfuric acid. Potassium nitrate (0.11 g, 1.15 mmol) was slowly added into the above reaction system at room temperature and then stirred at room temperature for 15 min. The reaction mixture was slowly added into ice-water dropwise, filtered, the filter cake was washed with H₂O, dried under vacuum to afford a mixture of compound 10.5 and 10.5' (50/1, 0.24 g, yield: 96%) as a light-yellow solid.

Step 5: To a solution of NaBH₄ (52 mg, 1.37 mmol) in THF (2.0 mL) was slowly added boron trifluoride etherate (260 mg, 1.83 mmol) and stirred at room temperature for 1 h. A solution of a mixture of compound 10.5 and 10.5' (100 mg, 0.46 mmol) in THF was added into the above reaction system and refluxed for 2 h, cooled to room temperature, the reaction was quenched by addition of saturated aqueous solution of ammonium chloride, the mixture was extracted with ethyl acetate, the combined organic layers were washed with brine, the organic layer was separated and dried over anhydrous sodium sulfate, filtered, concentrated to afford a mixture of compound 10.6 and 10.6' (50/1, 68 mg, crude) as a light-yellow solid.

Step 6: The mixture of compound 10.6 and 10.6' (50 mg, 0.25 mmol), acetic acid (1 dorp), and 37% formaldehyde (0.1 mL) was dissolved in DCM (1.5 mL). The reaction system was stirred at room temperature for 0.5 h, sodium cyanoborohydride (NaCNBH₃) (104 mg, 0.5 mmol) was added into the above reaction system and stirred at room temperature for 2 h, the reaction was quenched by addition of H₂O, extracted with ethyl acetate. The combined organic layers were washed with brine, the organic layer was separated and dried over anhydrous sodium sulfate, filtered, concentrated, the residue was purified by column chromatography on silica gel (50% ethyl acetate petroleum ether solution) to afford compound 10.7 (50 mg, yield: 94%) as a white solid.

m/z: [M+H]⁺ 219.0

Step 7: The mixture of compound 10.7 (50 mg, 0.23 mmol), ammonium formate (144 mg, 2.3 mmol) and Pd/C (10 mg, 10%) in methanol (2.0 mL) was stirred at room temperature for 12 h. Filtered, the filterate was diluted with saturated aqueous solution of sodium carbonate, extracted with ethyl acetate, the organic layers were combined and washed with brine, the organic layer was separated and dried over anhydrous sodium sulfate, filtered, concentrated, the residue was purified by column chromatography on silica gel (10% methanol DCM solution) to afford compound 10.8 (30 mg, yield: 70%) as a white solid.

m/z: [M+H]⁺ 189.0

Step 8: Compound 10.8 (30 mg) was dissolved in formic acid (5 mL), the reaction system was stirred at 100° C. for 30 min. The solution was concentrated under reduced pressure to afford compound 10.9 (35 mg, crude) as a brown oil.

Compounds 10.10 (2'-ethyl-2',3'-dihydro-1'H-spiro[cyclopropane-1,4'-isoquinolin]-7'-amine) was synthesized following the synthetic method to the one used for compound 10.8, by replacing 37% formaldehyde to acetaldehyde.

Compounds 10.11 (a mixture of 2'-isopropyl-2',3'-dihydro-1'H-spiro[cyclopropane-1,4'-isoquinolin]-7'-amine (Primary) and 2'-isopropyl-2',3'-dihydro-1'H-spiro[cyclopropane-1,4'-isoquinolin]-6'-amine (secondary)) was synthesized following the synthetic method to the one used for compound 10.8, by replacing 37% formaldehyde to acetone.

Embodiment 15: Synthesis of Compound 10.15

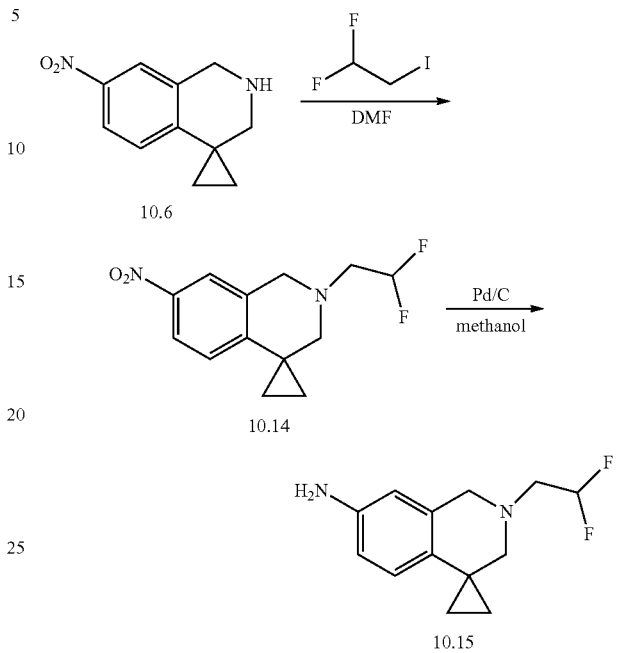

Step 1: To a solution of compound 10.6 (300 mg, 1.47 mmol) and 1,1-difluoro-2-iodoethane (564 mg, 2.94 mmol) in DMF (5 mL) was added K₂CO₃ (405 mg, 2.94 mmol), the reaction system was stirred at 100° C. for overnight. The reaction solution was cooled to room temperature and quenched by addition of H₂O, the aqueous layer was extracted with ethyl acetate (15 mL×3), the combined organic layers were washed successively with H₂O and brine, the organic layer was concentrated, the residue was purified by column chromatography on silica gel (petroleum ether/ethyl acetate=5/1) to afford compound 10.14 (330 mg, yield: 84%) as a white solid.

m/z: [M+H]⁺ 269.1

Step 2: The mixture of compound 10.14 (330 mg, 1.3 mmol) and Pd/C (150 mg, 5%) in methanol (20 mL) was replaced with hydrogen for 3 times and then stirred at room temperature for 16 h under hydrogen. The reaction was filtered through a celite pad. The filtrated was concentrated under reduced pressure to afford compound 10.15 (300 mg, crude), which was directly used for next step.

Embodiment 16: Synthesis of Compound 11.5

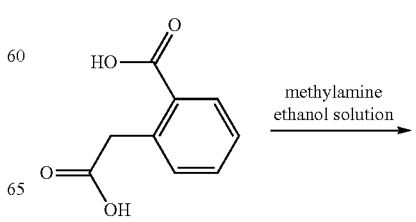

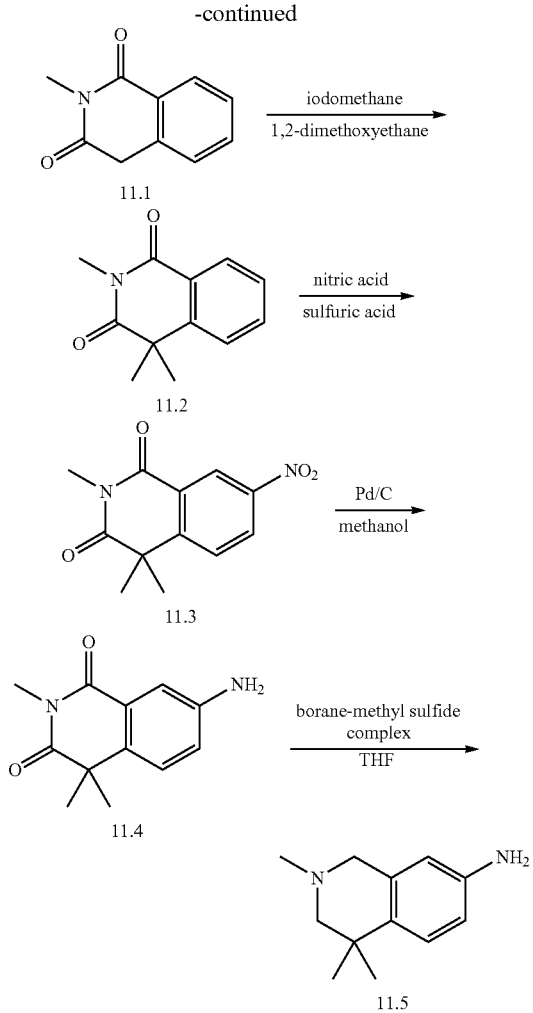

reaction solution was filtered through a celite pad, the filtrated was concentrated under reduced pressure to afford compound 11.4 (8 g, yield: 91%) as a brown solid.

Step 5: To a solution of compound 11.4 (4.0 g, 18.3 mmol) in THF (50 mL) was slowly added borane-methyl sulfide complex (8 mL, 82.4 mmol), the reaction solution was heated to reflux for 3 h and then cooled to 0° C., added methanol (20 mL), the mixture was stirred for 0.5 h and then concentrated under reduced pressure, to the residue was added hydrochloric acid (6 M) and heated to reflux for 1 h, the mixture was neutralized with sodium hydroxide and then extracted with a mixed solvent of DCM and methanol (10/1), the organic layer was separated and dried over anhydrous sodium sulfate, filtered, concentrated under reduced pressure to afford compound 11.5 (3 g, yield: 86%) as a brown liquid.

Embodiment 17: Synthesis of Compound 12.2

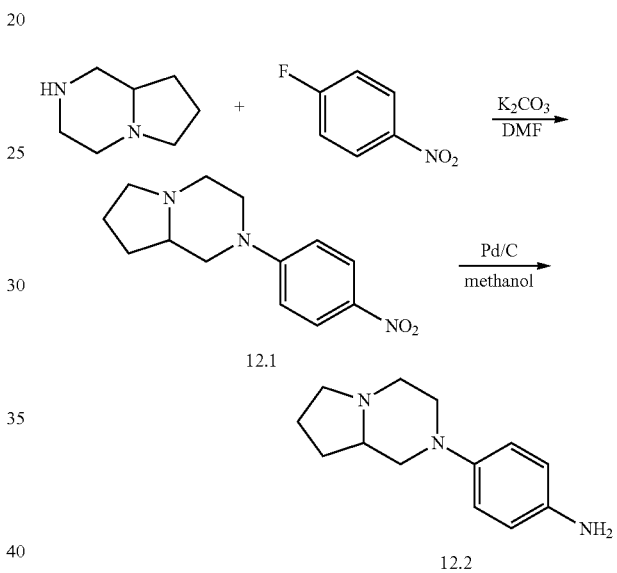

Step 1: A solution of 2-(carboxymethyl)benzoic acid (50.0 g, 278 mmol) in methylamine ethanol (150 mL) was stirred at room temperature for 15 h, dichlorobenzene (300 mL) was added into the above reaction system, the resulting mixture was stirred at 180° C. for 8 h. The reaction solution was poured into petroleum ether, filtered, the filter cake was dried under vacuum to afford compound 11.1 (45 g, yield: 92%) as an off-white solid.

Step 2: To a solution of compound 11.1 (20.0 g, 144 mmol) in 1,2-dimethoxyethane (250 mL) was added NaH (10.0 g, 251 mmol, 60%) and then stirred at room temperature for 0.5 h, iodomethane (35.6 g, 251 mmol) was added into the above reaction system and stirred for another 3 h. The reaction solution was poured into $H_2O$, the precipitation was filtered, the filter cake was dried under vacuum to afford compound 11.2 (16 g, yield: 55%) as a pink solid.

Step 3: To a solution of compound 11.2 (13.0 g, 64.0 mmol) in concentrated sulfuric acid (25 mL) was slowly dropped concentrated nitric acid (10 mL), the reaction system was stirred at 0° C. for 3 h, the reaction solution was poured into $H_2O$, the precipitation was filtered, the filter cake was dried under vacuum to afford compound 11.3 (10 g, yield: 63%) as a white solid.

Step 4: Compound 11.3 (10.0 g, 40.3 mmol) and Pd/C (2.0 g, 10%) was added into methanol (150 mL), the reaction system was replaced with hydrogen for 3 times and then stirred at room temperature for 16 h under hydrogen. The Step 1: To a solution of $K_2CO_3$ (978 mg, 7.1 mmol) and 4-fluoronitrobenzene (500 mg, 3.55 mmol) in DMF (5 mL) was added octahydropyrrolo[1,2-a]pyrazine (447 mg, 3.55 mmol). $K_2CO_3$ (1.2 g, 8.8 mmol) was added to the above mixture in small portions at room temperature. After addition, the reaction system was stirred at room temperature for overnight. The reaction solution was poured into ice water, the aqueous layer was extracted with ethyl acetate (10 mL×3), the combined organic layers were washed successively with $H_2O$ and brine, dried over anhydrous sodium sulfate, filtered, concentrated. The residue was purified by column chromatography on silica gel (DCM/methanol=20/1) to afford compound 12.1 (580 mg, yield: 66%) as a yellow oil.

m/z: $[M+H]^+$ 248.1

Step 2: To a solution of compound 12.1 (580 mg, 2.3 mmol) in methanol (20 mL) was added Pd/C (200 mg, 5%). The system was replaced with hydrogen for 3 times and then stirred at room temperature for 16 h under hydrogen (hydrogen balloon). The reaction solution was filtered through a celite pad. The filtrated was concentrated, the residue was purified by column chromatography on silica gel (DCM/methanol=15/1) to afford compound 12.2 (424 mg, yield: 85%) as a brown solid.

m/z: $[M+H]^+$ 218.0

Embodiment 18: Synthesis of Compound 13.2

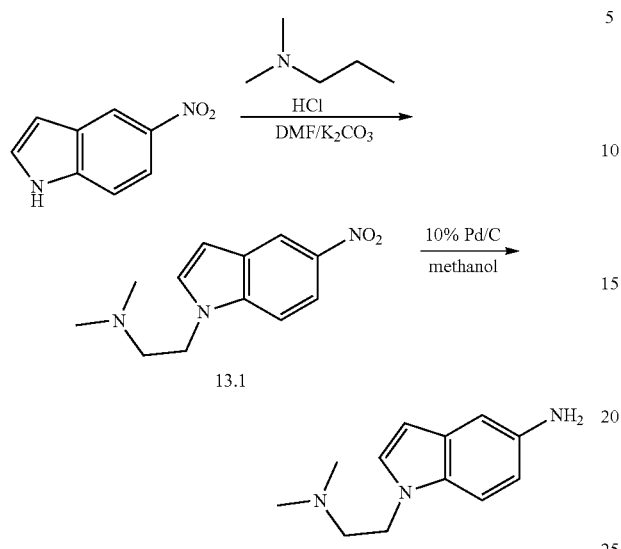

Step 1: The mixture of 5-nitroindole (1.0 g, 6.2 mmol), 2-chloroethyldimethylamine hydrochloride (1.3 g, 9.3 mmol) and anhydrous $K_2CO_3$ (3.4 g, 25 mmol) in DMF (15 mL) was stirred at 70° C. for 3 h. The reaction solution was cooled to room temperature, poured into ice-water (50 mL) and stirred, the solution was extracted with ethyl acetate (20 mL×3), the combined organic layers were washed successively with $H_2O$ and brine, the organic layer was dried over anhydrous sodium sulfate, filtered, concentrated, the residue was purified by column chromatography on silica gel (DCM/methanol=20/1) to afford compound 13.1 (700 mg, yield: 32%) as a colorless oil.

Step 2: To a solution of compound 13.1 (700 mg, 3 mmol) in methanol (20 mL) was added Pd/C (100 mg, 10%), the system was replaced with hydrogen for 3 times and then stirred for overnight under hydrogen (hydrogen balloon). The reaction was filtered through a celite pad, the filtrated was concentrated to afford compound 13.2 (600 mg, yield: 98%) as a brown oil.

m/z: $[M+H]^+$ 204.1

Embodiment 19: Synthesis of Compounds 14.4-14.9

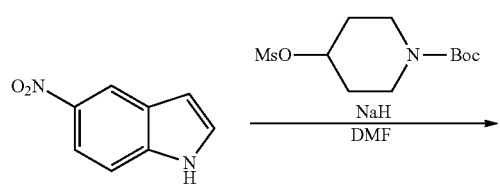

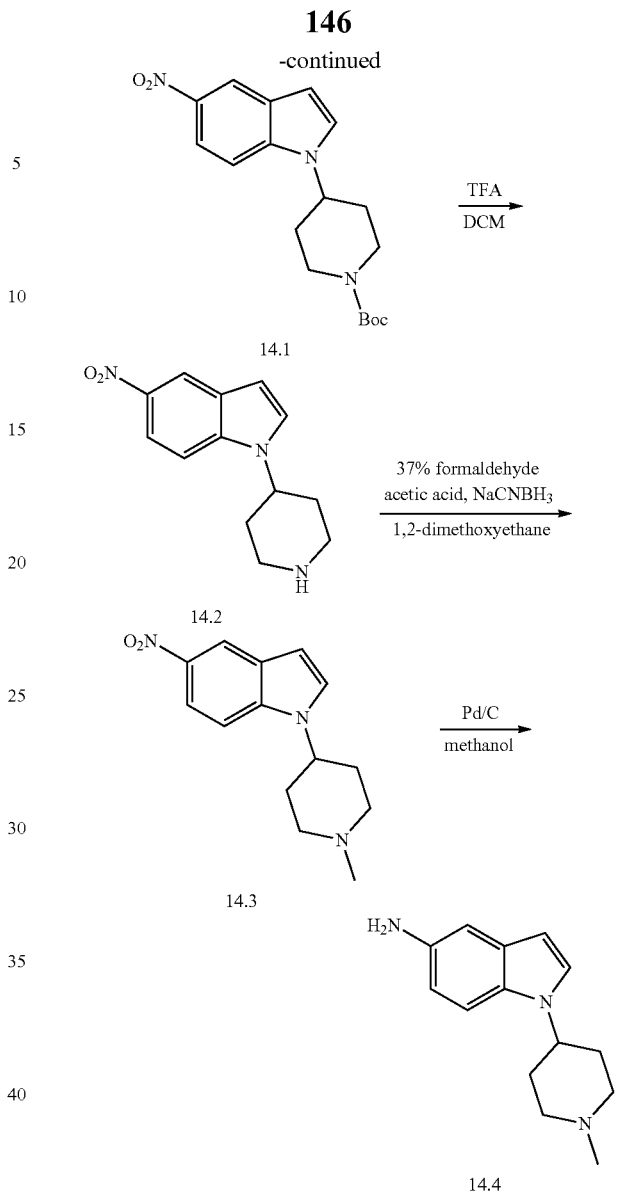

Step 1: 5-nitroindole (1.0 g, 6.2 mmol) was dissolved in DMF (10.0 mL) and then NaH (0.5 g, 12.4 mmol, 60%) was slowly added into the above system. The reaction system was stirred at 20° C. for 30 min and then 1-Boc-4-((methylsulfonyl)oxy)piperidine (1.72 g, 6.2 mmol) was added into the above reaction system, stirred at 100° C. for 12 h and then quenched by addition of $H_2O$, extracted with ethyl acetate (20 mL×3), the combined organic layers were washed successively with brine, the organic layer was separated and dried over anhydrous sodium sulfate, filtered, concentrated. The residue was purified by column chromatography on silica gel (35% ethyl acetate petroleum ether solution) to afford compound 14.1 (0.85 g, yield: 75%) as a yellow oil.

Step 2: The solution of compound 14.1 (0.85 g, 2.4 mmol) in a mixed solvent of TFA (2.0 mL) and DCM (4.0 mL) was stirred at room temperature for 1 h and then concentrated directly to afford compound 14.2 (0.55 g, crude) as a yellow oil.

Step 3: The solution of compound 14.2 (0.50 g, 2.0 mmol), 37% formaldehyde (0.33 g, 4.0 mmol), triethylamine (0.1 mL) and acetic acid (2 drop) in 1,2-dimethoxyethane (10 mL) was stirred at room temperature for 1 h. NaCNBH₃ (0.39 g, 6.0 mmol) was added into the above reaction system, the reaction system was stirred at room temperature for another 2 h. The reaction was quenched by addition of aqueous solution of sodium hydroxide (1.0 M), diluted with H₂O and extracted with ethyl acetate. The combined organic layers were washed with brine, the organic layer was separated and dried over anhydrous sodium sulfate, filtered, concentrated, the residue was purified by column chromatography on silica gel (5% methanol DCM solution) to afford compound 14.3 (0.35 g, yield: 66%) as a yellow solid.

Step 4: To a solution of compound 14.3 (0.35 g, 1.3 mmol) in methanol (10 mL) was added Pd/C (0.05 g, 5%). The system was replaced with hydrogen for 3 times and then stirred at room temperature for 12 h under hydrogen (hydrogen balloon). The reaction was filtered through a celite pad. The filtrated was concentrated to afford compound 14.4 (100 mg, crude) as a light-yellow solid.

m/z: [M+H]⁺ 230.1

Compounds 14.5 (1-(1-methylpiperidin-3-yl)-1H-indol-5-amine) was synthesized following the synthetic method to the one used for compound 14.4, by replacing 1-Boc-4-((methyl sulfonyl) oxy)piperidine to 1-Boc-3-((methylsulfonyl)oxy)piperidine in step 1.

Compounds 14.6 (1-(1-methylpyrrolidin-3-yl)-1H-indol-5-amine) was synthesized following the synthetic method to the one used for compound 14.4, by replacing 1-Boc-4-((methyl sulfonyl) oxy)piperidine to 1-Boc-3-((methyl sulfonyl)oxy)pyrrolidine in step 1.

Compounds 14.7 (1-(1-isopropylpiperidin-4-yl)-1H-indol-5-amine) was synthesized following the synthetic method to the one used for compound 14.4, by replacing 37% formaldehyde to acetone in step 3.

Compounds 14.8 (1-(1-isopropylpiperidin-4-yl)-1H-pyrrolo[2,3-b]pyridine-5-amine) was synthesized following the synthetic method to the one used for compound 14.4, by replacing 5-nitroindole to 5-nitro-1H-pyrrolo[2,3-b]pyridine in step 1 and 37% formaldehyde to acetone in step 3.

Compounds 14.9 (1-(1-isopropylpiperidin-4-yl)-1H-indazol-5-amine) was synthesized following the synthetic method to the one used for compound 14.4, by replacing 5-nitroindole to 5-nitro-1H-indazole in step 1 and 37% formaldehyde to acetone in step 3.

Embodiment 20: Synthesis of Compound 15.1

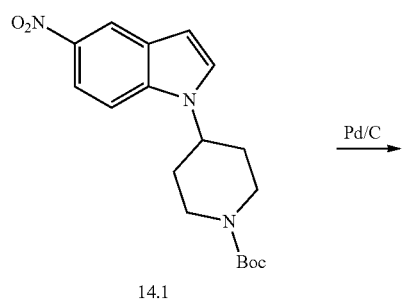

14.1

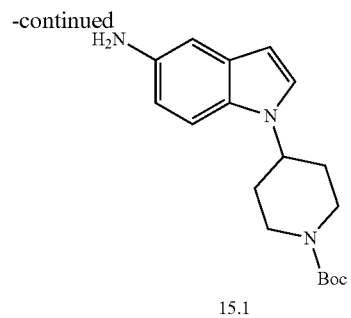

15.1

To a solution of Pd/C (100 mg, 5%) in methanol was added compound 14.1 (287 mg, 0.83 mmol), the system was replaced with hydrogen for 3 times and then stirred at room temperature for 12 h under hydrogen (hydrogen balloon). The reaction was filtered through a celite pad, the filtrated was concentrated to afford compound 15.1 (197 mg, yield: 75%) as a brown solid.

Embodiment 21: Synthesis of Compound 16.2

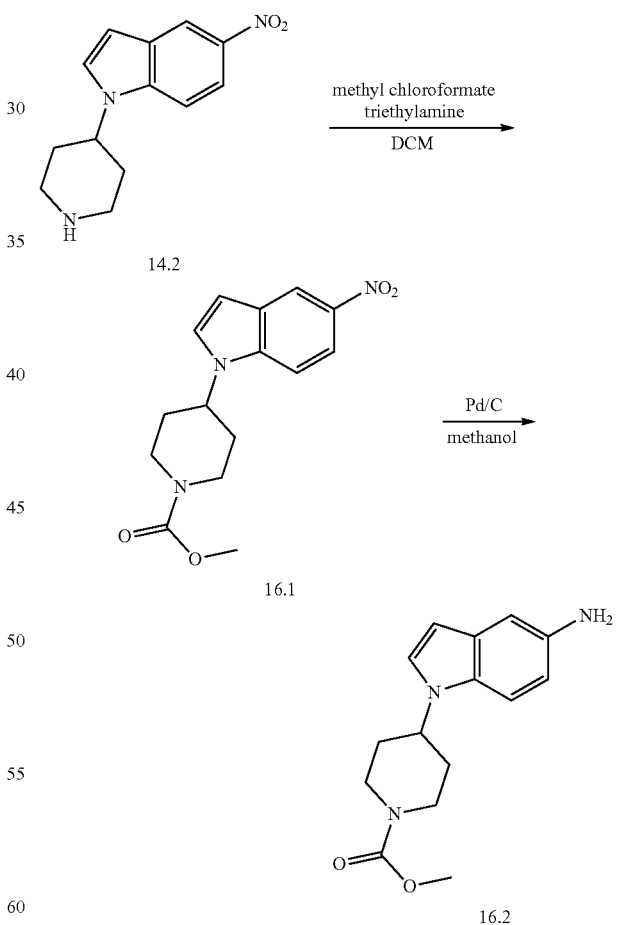

Step 1: To a solution of compound 14.2 (100 mg, 0.41 mmol) and triethylamine (82.8 mg, 0.82 mmol) in DCM was added methyl chloroformate (57.8 mg, 0.61 mmol) and then stirred at room temperature for overnight. The reaction solution was concentrated, the residue was purified by column chromatography on silica gel (petroleum ether/ethyl acetate=1/1) to afford compound 16.1 (57 mg, yield: 46%) as a yellow solid.

Step 2: To a solution of Pd/C (20 mg, 5%) in methanol was added compound 16.1 (57 mg, 0.19 mmol). The system was replaced with hydrogen for 3 times and then stirred at room temperature for 12 h under hydrogen (hydrogen balloon). The reaction was filtered through a celite pad, the filtrated was concentrated to afford compound 16.2 (43 mg, crude) as a brown solid.

Embodiment 22: Synthesis of Compound 16.4

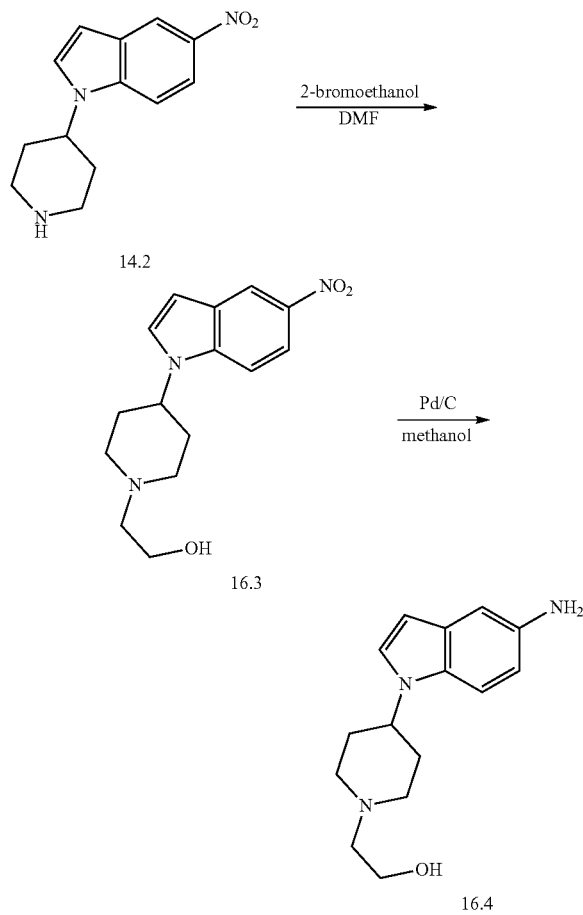

Step 1: The solution of compound 14.2 (110 mg, 0.45 mmol), 2-bromoethanol (168 mg, 1.35 mmol) and K$_2$CO$_3$ (186 mg, 1.35 mmol) in DMF (5 mL) was stirred at 100° C. for overnight. The reaction solution was cooled to room temperature and quenched by addition of H$_2$O, the aqueous layer was extracted with ethyl acetate (15 mL×3), the combined organic layers were washed successively with H$_2$O and brine, the organic layer was dried over anhydrous sodium sulfate, filtered, concentrated, the residue was purified by prep-TLC (DCM/methanol=10/1) to afford compound 16.3 (82 mg, yield: 60%) as a brown oil.

m/z: [M+H]$^+$ 290.2

Step 2: Compound 16.3 (82 mg, 0.28 mmol) and Pd/C (40 mg, 10%) were mixed with methanol (10 mL). The system was replaced with hydrogen for 3 times and then stirred at room temperature for 2 h under hydrogen (hydrogen balloon). The reaction was filtered through a celite pad, the filtrated was concentrated to afford compound 16.4 (74 mg, yield: 100%) as a brown solid.

Embodiment 23: Synthesis of Compound 16.6

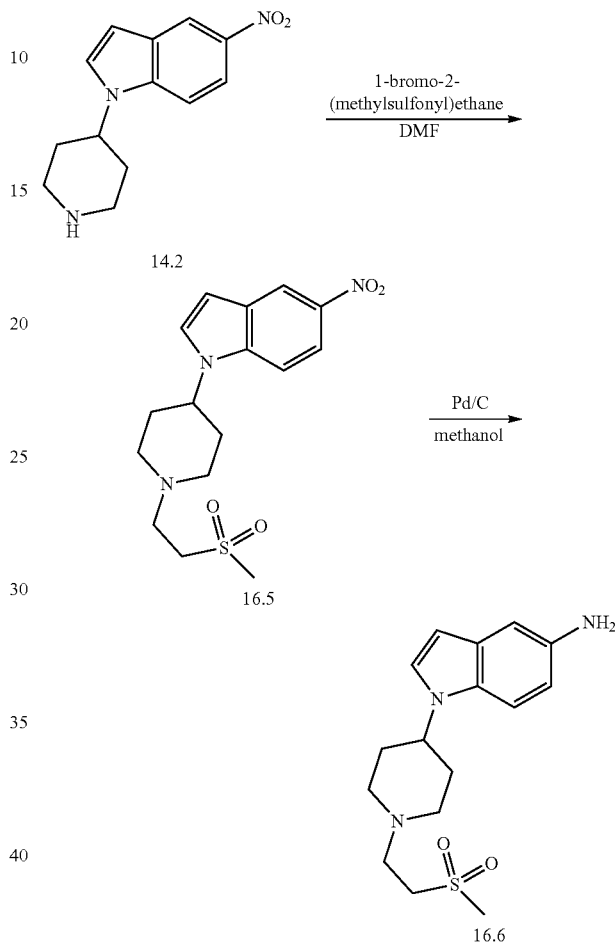

Step 1: To a solution of compound 14.2 (150 mg, 0.61 mmol) in anhydrous DMF (5 mL) was added NaH (73.4 mg, 1.83 mmol, 60%) under ice-bath, the reaction system was stirred at room temperature for 0.5 h, and then 1-bromo-2-(methylsulfonyl)ethane (343 mg, 1.83 mmol) was added into the above reaction system, and stirred at room temperature for overnight. The reaction system was heated to 50° C. and stirred for another 2 h, the reaction solution was poured into ice water, and extracted with ethyl acetate (10 mL×3), the combined organic layers were washed with H$_2$O and brine, dried over anhydrous sodium sulfate, filtered, concentrated, the residue was purified by prep-TLC (DCM/methanol=10/1) to afford compound 16.5 (200 mg, yield: 93%) as a yellow solid.

m/z: [M+H]$^+$ 352.2

Step 2: Compound 16.5 (200 mg, 0.57 mmol) and Pd/C (100 mg, 10%) were mixed with methanol (10.0 mL). The system was replaced with hydrogen for 3 times and then stirred at room temperature for 2 h under hydrogen (hydrogen balloon). The reaction was filtered through a celite pad, the filtrated was concentrated to afford compound 16.6 (130 mg, yield: 74%) as a yellow solid.

m/z: [M+H]$^+$ 322.2

Embodiment 24: Synthesis of Compound 17.3

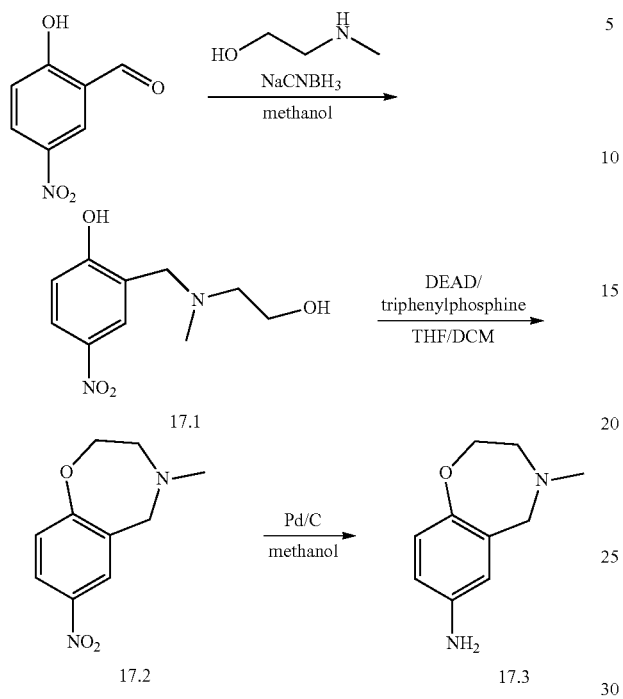

Step 1: To a solution of 2-hydroxy-5-nitrobenzaldehyde (1.67 g, 10.0 mmol) and N-methyl-2-hydroxyethylamine (1.13 g, 15.0 mmol) in methanol (60 mL) was added zinc chloride (1.36 g, 10.0 mmol) under ice-bath, the reaction system was stirred at room temperature for 2 h, and then NaCNBH$_3$ (1.24 g, 20.0 mmol) was added into the above reaction system, and stirred at room temperature for 1 h. The reaction was quenched by addition of H$_2$O, the aqueous layer was extracted with DCM (200 mL), the organic layer was washed with brine, dried over anhydrous sodium sulfate, filtered, concentrated under reduced pressure to afford compound 17.1 (1.2 g, yield: 53%) as a light yellow solid.

m/z: [M+H]$^+$ 227.1

Step 2: To a solution of compound 17.1 (732 mg, 3.2 mmol) and triphenylphosphine (1.27 g, 4.9 mmol) in a mixed solvent of THF (20 mL) and DCM (8 mL) was added diethyl azodicarboxylate (DEAD) (845 mg, 4.9 mmol) under ice-bath, the reaction system was stirred at room temperature for 2 h. The reaction solution was concentrated under reduced pressure, the residue was purified by column chromatography on silica gel (petroleum ether/ethyl acetate=1/1) to afford compound 17.2 (569 mg, contains a small amount of triphenylphosphine oxide) as a light-yellow solid.

m/z: [M+H]$^+$ 209.1

Step 3: Compound 17.2 (569 mg, 2.7 mmol) was dissolved in methanol (10.0 mL) and then added Pd/C (171 mg), The system was replaced with hydrogen for 3 times and then stirred at room temperature for 12 h under hydrogen (hydrogen balloon). The reaction solution was filtered through a celite pad, the filtrated was concentrated, the residue was purified by column chromatography on silica gel (DCM/methanol=10/1) to afford compound 17.3 (199 mg, two steps yield: 34%) as a red brown solid.

m/z: [M+H]$^+$ 179.1

Embodiment 25: Synthesis of Compound 18.6

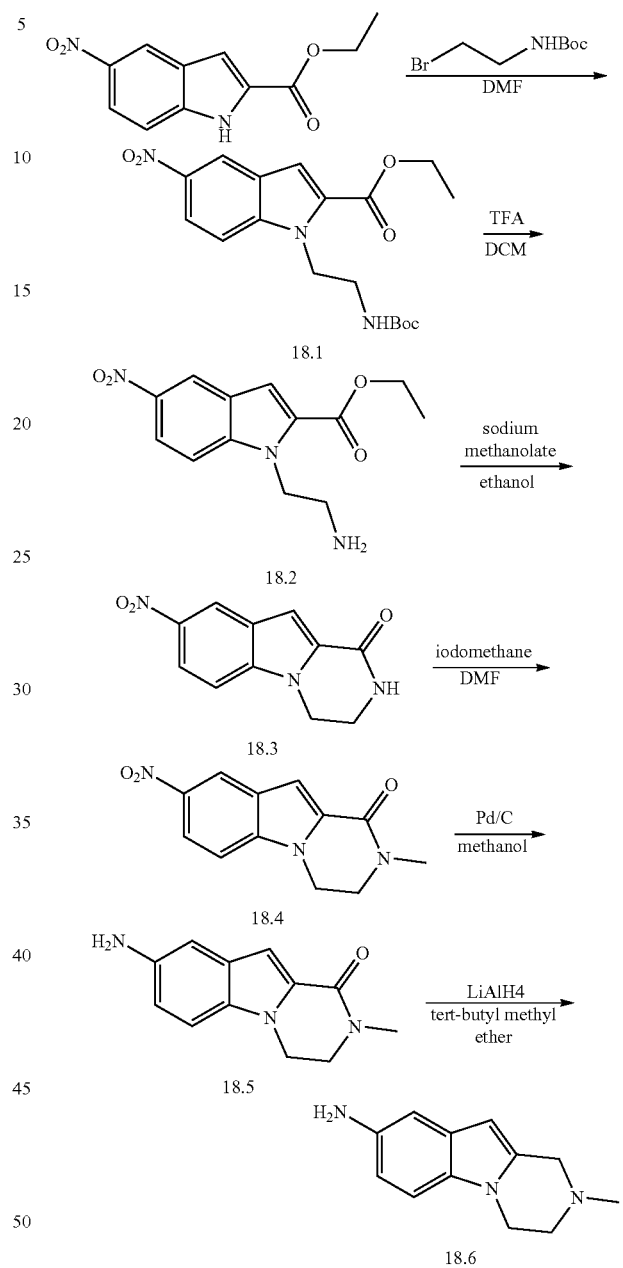

Step 1: To a solution of ethyl 5-nitroindole-2-carboxylate (2.34 g, 10.0 mmol) in DMF (50 mL) was added NaH (600 mg, 15.0 mmol, 60%) under ice-bath, the reaction system was stirred at room temperature for 0.5 h, and then N-Boc-bromoethylamine (2.92 g, 13.0 mmol) was added, the reaction system was stirred at 70° C. for overnight, and then diluted with ethyl acetate (100 mL), washed with brine. The organic layer was separated and dried over anhydrous sodium sulfate, filtered and concentrated. The residue was purified by column chromatography on silica gel (petroleum ether/ethyl acetate=4/1) to afford compound 18.1 (3.05 g, yield: 81%) as a light yellow solid.

Step 2: The solution of compound 18.1 (3.05 g, 8.1 mmol) in a mixed solvent of TFA (4 mL) and DCM (20 mL) was stirred at room temperature for 2 h and then the reaction was quenched by addition of saturated aqueous solution of sodium bicarbonate, the aqueous layer was extracted with DCM. The combined organic layers were washed with brine, the organic layer was separated and dried over anhydrous sodium sulfate, filtered, concentrated, the residue was purified by column chromatography on silica gel (DCM/methanol=10/1) to afford compound 18.2 (1.1 g, yield: 49%) as a light-yellow solid.

m/z: [M+H]$^+$ 278.4

Step 3: The solution of compound 18.2 (1.1 g, 4.0 mmol) and sodium methanolate (643 mg, 11.9 mmol) in ethanol (20 mL) was stirred at 55° C. for 2 h. The reaction system was diluted with brine and extracted with DCM. The combined organic layers were dried over anhydrous sodium sulfate, filtered, concentrated to afford compound 18.3 (361 mg, yield: 39%) as a yellow solid.

m/z: [M+H]$^+$ 232.4

Step 4: To a solution of compound 18.3 (310 mg, 1.3 mmol) in DMF (20 mL) was added NaH (81 mg, 2.0 mmol, 60%) under ice-bath, the reaction system was stirred at room temperature for 15 min, and then iodomethane (285 mg, 2.0 mmol) was added, the reaction system was stirred at room temperature for another 30 min and then diluted with ethyl acetate (100 mL), washed with brine. The organic layer was separated and dried over anhydrous sodium sulfate, filtered and concentrated to afford compound 18.4 (385 g, crude) as a yellow solid.

m/z: [M+H]$^+$ 246.0

Step 5: Compound 18.4 (358 mg, 1.5 mmol) was dissolved in methanol (15 mL) and then added Pd/C (180 mg), The system was replaced with hydrogen for 3 times and then stirred at room temperature for 0.5 h under hydrogen (hydrogen balloon). The reaction was filtered through a celite pad, the filtrated was concentrated to afford compound 18.5 (277 mg, yield: 109%) as a red solid.

m/z: [M+H]$^+$ 216.1

Step 6: To a solution of compound 18.5 (275 mg, 1.3 mmol) in tert-butyl methyl ether (30 mL) was added a solution of lithium aluminum hydride (LiAlH$_4$) in THF (1.95 mL, 4.9 mmol, 2.5 M) under ice-bath, the reaction system was stirred at 60° C. for 5 h. The reaction was quenched by addition of saturated aqueous solution of potassium sodium tartrate, diluted with ethyl acetate (100 mL) and washed with brine. The organic layer was separated and dried over anhydrous sodium sulfate, filtered and concentrated to afford compound 18.6 (248 mg, yield: 96%) as a red solid.

m/z: [M+H]$^+$ 202.3

Embodiment 26: Synthesis of Compound 19.6

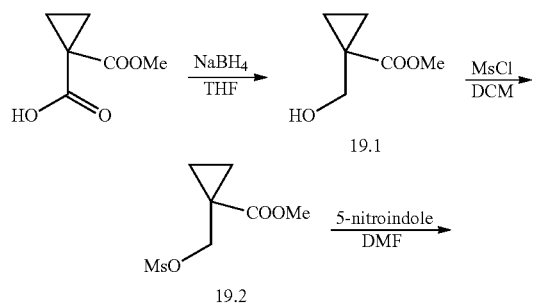

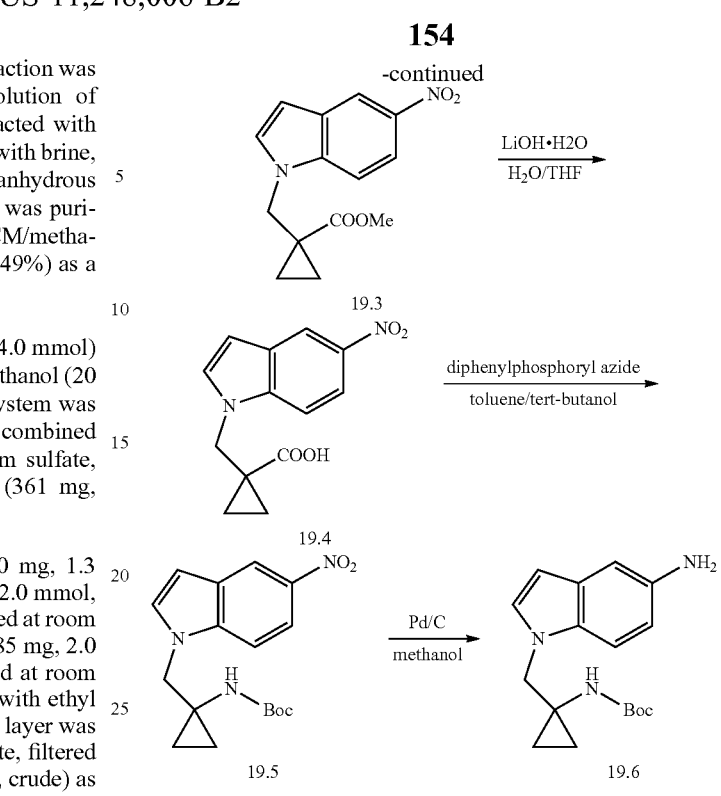

Step 1: To a solution of 1-(methoxycarbonyl)cyclopropanecarboxylic acid (10.0 g, 69.4 mmol) and triethylamine (10.8 mL, 78 mmol) in THF (200 mL) was added isobutyl chloroformate (10.2 mL, 78 mmol) dropwise at −10° C., and stirred at this temperature for 1 h, the reaction system was warmed up to 0° C., the solid of the reaction solution was filtered, the filtrate was on standby. The solution of NaBH$_4$ (7.87 g, 208 mmol) in a mixed solvent of THF (100 mL) and H$_2$O (25 mL) was added into the above filtrate dropwise during 1 h, after the addition, the resulting solution was stirred for another 1 h under ice-bath. The reaction solution was poured into cold aqueous solution of citric acid (20%) and stirred for 5 min, concentrated to remove the organic solvent, the aqueous layer was extracted with ethyl acetate, the combined organic layers were washed successively with H$_2$O and brine, dried over anhydrous sodium sulfate, filtered and concentrated to afford compound 19.1 (6.9 g, yield: 77%) as an oil.

Step 2: To a solution of compound 19.1 (5.6 g, 43 mmol) and triethylamine (8.7 mL, 86 mmol) in DCM (100 mL) was added methanesulfonyl chloride (MsCl) (7.4 g, 64.5 mmol) dropwise under ice-bath and stirred at room temperature for 3 h. The reaction solution was diluted with DCM and washed successively with hydrochloric acid (1.0 M), H$_2$O and brine, the organic layer was dried over anhydrous sodium sulfate, filtered and concentrated to afford compound 19.2 (8.9 g, yield: 100%) as a white solid.

Step 3: To a solution of 5-nitroindole (5.56 g, 34.3 mmol) and cesium carbonate (33.5 g, 103 mmol) in DMF (60 mL) was added compound 19.2 (10.7 g, 51.5 mmol), the reaction system was heated to 100° C. and stirred for overnight, the reaction solution was cooled to room temperature and poured into H$_2$O, the aqueous layer was extracted with ethyl acetate (20 mL×3), the combined organic layers were washed successively with H$_2$O and brine and then concentrated, the residue was purified by column chromatography on silica gel (petroleum ether/ethyl acetate=5/1) to afford compound 19.3 (8 g, yield: 72%) as a yellow solid.

m/z: [M+H]$^+$ 275.2

Step 4: To a solution of compound 19.3 (1.24 g, 4.5 mmol) in THF (30 mL) was added an aqueous solution (10 mL) of lithium hydroxide monohydrate (LiOH.H$_2$O) (475 mg, 11.3 mmol) dropwise and stirred at room temperature for overnight, concentrated under reduced pressure to remove THF, the aqueous layer was washed with a mixed solvent of petroleum ether/ethyl acetate (1/1) and then adjusted pH=3 with saturated aqueous solution of citric acid, extracted with ethyl acetate (10 mL×3), the combined organic layers were washed with H$_2$O and brine, dried over anhydrous sodium sulfate, filtered and concentrated to afford compound 19.4 (920 mg, yield: 79%) as a yellow solid.

Step 5: To a solution of compound 19.4 (520 mg) and triethylamine (607 mg, 6.0 mmol) in toluene (15 mL) was added diphenylphosphorylazide (605 mg, 2.2 mmol) dropwise under ice-bath, the reaction system was stirred at this temperature for 2 h and then warmed up to room temperature and stirred for another 4 h, to the reaction system was added tert-butanol (10 mL), the resulting mixture was stirred at reflux for overnight and then cooled to room temperature, concentrated under reduced pressure, to the residue was added DCM (20 mL) and washed successively with saturated aqueous solution of sodium bicarbonate, H$_2$O and brine, the organic layer was concentrated, the residue was purified by column chromatography on silica gel (petroleum ether/ethyl acetate=5/1) to afford compound 19.5 (460 mg, yield: 69%) as a yellow solid.

Step 6: Compound 19.5 (460 mg, 1.39 mmol) and Pd/C (100 mg, 10%) was mixed with methanol (30.0 mL). The system was replaced with hydrogen for 3 times and then stirred at room temperature for 2 h under hydrogen (hydrogen balloon). The reaction was filtered through a celite pad, the filtrate was concentrated to afford compound 19.6 (308 mg, yield: 74%) as a brown solid.

m/z: [M+H]$^+$ 302.2

Embodiment 27: Synthesis of Compound 19.8

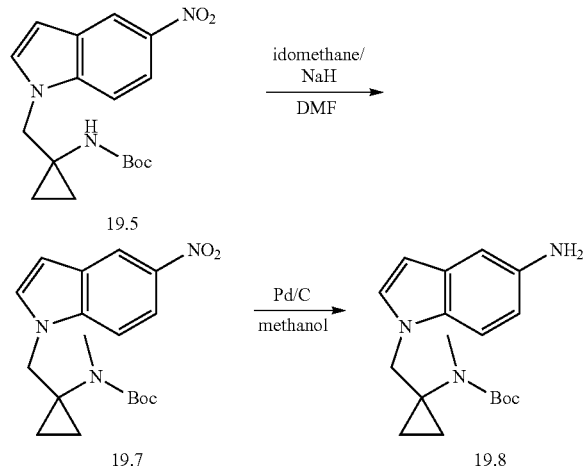

Step 1: To a solution of compound 19.5 (500 mg, 1.5 mmol) in DMF (10 mL) was added NaH (121 mg, 3.0 mmol, 60%) under ice-bath, the reaction system was stirred for 0.5 h, and then iodomethane (639 mg, 4.5 mmol) was added into the above reaction system and stirred at room temperature for 2 h, and then the reaction solution was poured into ice water, the aqeuous layer was extracted with ethyl acetate (20 mL×3), the combined organic layers were successively washed with H$_2$O and brine, the organic layer was concentrated, the residue was purified by column chromatography on silica gel (petroleum ether/ethyl acetate=5/1) to afford compound 19.7 (362 mg, yield: 70%) as an oil.

Step 2: Compound 19.7 (362 mg, 1.0 mmol) and Pd/C (100 mg, 10%) was mixed with methanol (15.0 mL). The system was replaced with hydrogen for 3 times and then stirred at room temperature for 2 h under hydrogen (hydrogen balloon), the reaction was filtered through a celite pad, the filtrated was concentrated to afford compound 19.8 (315 mg, yield: 100%) as a brown solid.

m/z: [M+H]$^+$ 316.2

Embodiment 28: Synthesis of Compound 20.2

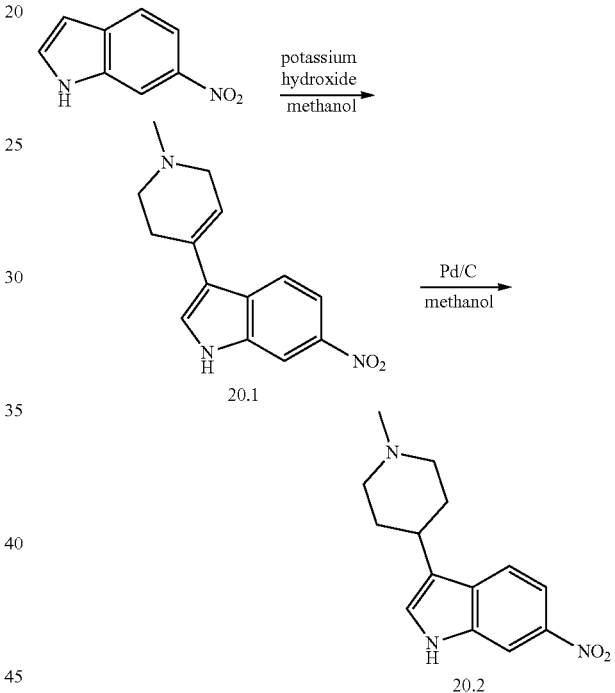

Step 1: 6-nitroindole (1.62 g, 10.0 mmol) and 1-methyl-4-piperidone (2.26 g, 20.0 mmol) was dissolved in methanol (20 mL) and then potassium hydroxide (1.12 g, 20.0 mmol) was added. The reaction system was heated to 90° C. and stirred for overnight, the reaction was cooled to room temperature and then quenched by addition of H$_2$O (100 mL), extracted with ethyl acetate, the organic layer was separated and dried over anhydrous sodium sulfate, filtered and concentrated, the residue was purified by column chromatography on silica gel (DCM/methanol=10/1) to afford compound 20.1 (760 mg, yield: 30%) as a light-yellow solid.

m/z: [M+H]$^+$ 258.1

Step 2: To a solution of compound 20.1 (760 mg, 2.9 mmol) in methanol (30 mL) was added Pd/C (50 mg), the reaction system was replaced with hydrogen for 3 times and then stirred for 30 min under hydrogen (hydrogen balloon). The mixture was filtered through a celite pad, the filtrate was concentrated to afford compound 20.2 (510 mg, yield: 77%) as a brown oil.

m/z: [M+H]$^+$ 230.1

Embodiment 29: Synthesis of Compound 21.1

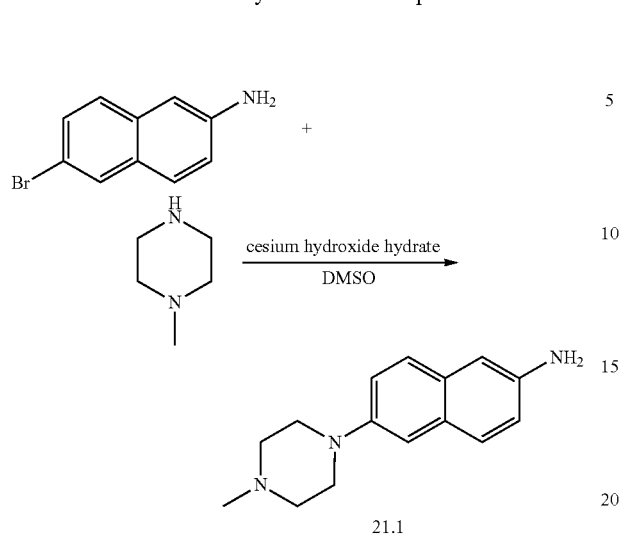

The solution of 6-bromonaphthalen-2-amine (500 mg, 2.25 mmol), N-methylpiperazine (270 mg, 2.7 mmol), cesium hydroxide hydrate (760 mg, 4.5 mmol) in DMSO (5.0 mL) was stirred at 120° C. for 20 h, the reaction system was cooled to room temperature and diluted with ice water (10 mL), the aqueous layer was extracted with DCM (20 mL×2), the combined organic layers were successively washed with H₂O and brine, dried over anhydrous sodium sulfate, filtered and concentrated, the residue was purified by flash column chromatography (petroleum ether/ethyl acetate=1/3) to afford compound 21.1 (70 mg, yield: 13%) as a brown solid.

Embodiment 30: Synthesis of Compound 22.5

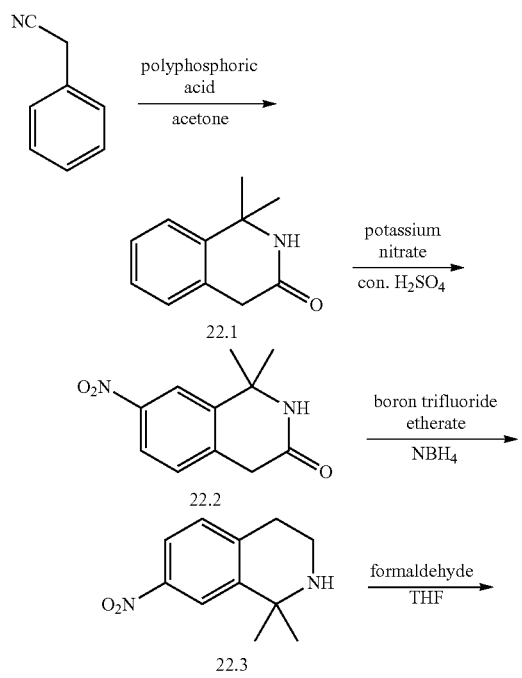

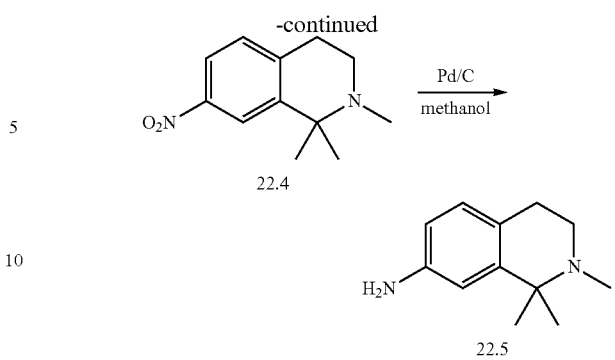

Step 1: The solution of phenylacetonitrile (10 g, 96.9 mmol) in polyphosphoric acid (120 g) was heated to 140° C., acetone (14.9 g, 257 mmol) was added at this temperature during 1 h and then kept the temperature and stirred for another 1 h. The reaction was cooled down and quenched by poured into ice water, petroleum ether was added and stirred, layered and discarded the organic layer, the aqueous layer was extracted with chloroform, the organic layers were separated and washed with saturated aqueous solution of sodium bicarbonate, dried over anhydrous sodium sulfate, filtered, the filtrate was concentrated to afford compound 22.1 (6.7 g, yield: 40%) as an oil.

Step 2: To a solution of compound 22.1 (6.7 g, 40.0 mmol) in sulfuric acid (80.0 mL) was added potassium nitrate (4.30 g, 42.0 mmol), the reaction system was stirred at room temperature for 1 h. The reaction solution was poured into ice-water (200 mL), extracted with DCM (200 mL×2), the combined organic layers were washed with brine, dried over anhydrous sodium sulfate, filtered and concentrated to afford compound 22.2 (5.0 g, yield: 56%) as a brown solid.

Step 3: Boron trifluoride etherate (772 g, 5.44 mmol) and NaBH₄ (155 mg, 4.08 mmol) were added into THF (10 mL) under ice-bath, the reaction system was stirred at 0° C. for 2 h, and then compound 22.2 (300 mg, 1.36 mmol) was added into the above reaction, the reaction was heated to reflux for 3 h. The reaction solution was concentrated under reduced pressure to remove the organic solvent, to the residue was added hydrochloric acid (20 mL, 5 M) and refluxed for 1 h, the resulting mixture was neutralized with saturated aqueous solution of sodium bicarbonate and then extracted with ethyl acetate, the organic layer was dried over anhydrous sodium sulfate, filtered and concentrated to afford compound 22.3 (250 mg, yield: 67%) as a yellow solid.

Step 4: The solution of compound 22.3 (250 mg, 1.21 mmol), aqueous solution of formaldehyde (2 mL) and acetic acid (0.3 mL) in methanol (10 mL) was stirred at room temperature for 2 h and then NaCNBH₃ (152 mg, 2.42 mmol) was added into the above system. The reaction system was stirred for another 2 h and then concentrated under reduced pressure to remove the solvent, to the residue was added H₂O, extracted with ethyl acetate, the organic layer was separated and dried over anhydrous sodium sulfate, filtered and concentrated to afford compound 22.4 (200 mg, yield: 75%) as a yellow solid.

Step 5: Compound 22.4 (200 mg, 0.91 mmol) and Pd/C (50 mg) was added into methanol (15 mL), the system was stirred under hydrogen (hydrogen balloon) for 0.5 h, the reaction solution was filtered through a celite pad, the filtered cake was rinsed with methanol, the filtrate was concentrated under reduced pressure to afford compound 22.5 (170 mg, yield: 98%) as a brown oil.

m/z: [M+H]⁺ 191.0

Embodiment 31: Synthesis of Compound 24.3

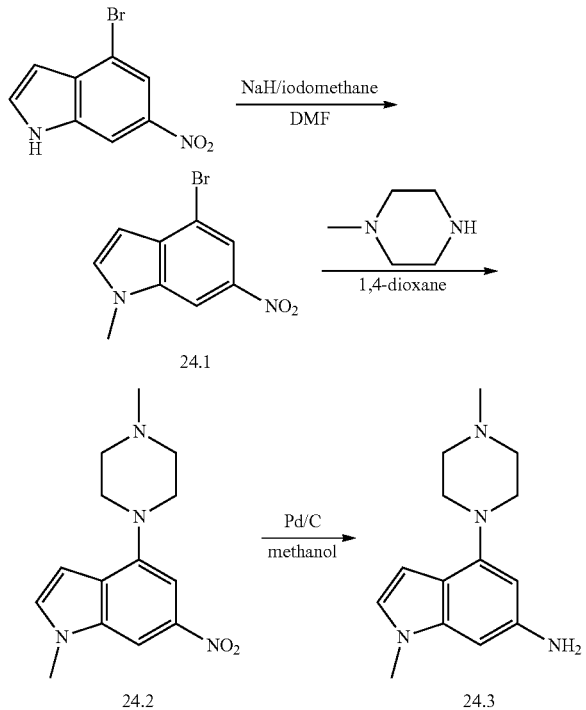

Embodiment 32: Synthesis of Compounds 25.2 and 25.3

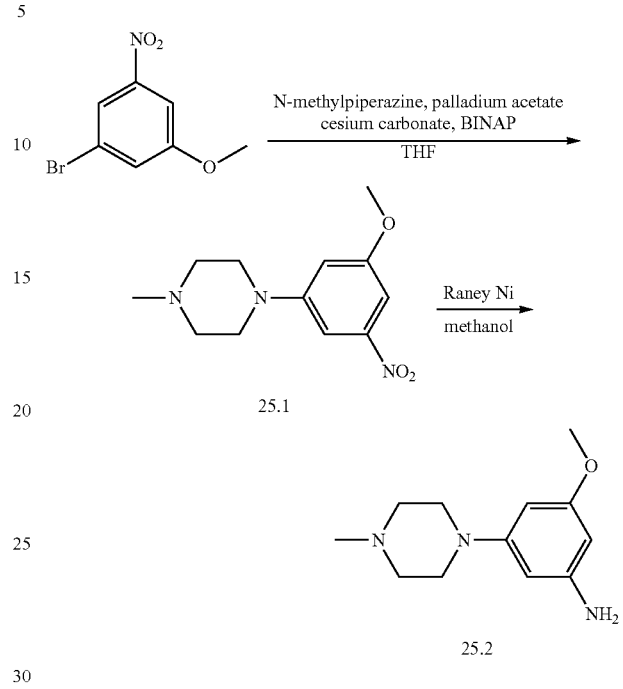

Step 1: To a solution of 4-bromo-6-nitro-1H-indole (690 mg, 2.86 mmol) in DMF (15 mL) was added NaH (229 mg, 5.73 mmol, 60%) under ice-bath, the resulting mixture was stirred at room temperature for 0.5 h and then iodomethane (1.22 g, 8.59 mmol) was added into the above mixture, the reaction system was stirred for another 2 h. The reaction solution was slowly poured into ice water, the aqueous layer was extracted with ethyl acetate (10 mL×2), the combined organic layers were successively washed with H$_2$O and brine and then concentrated, the residue was purified by column chromatography on silica gel (petroleum ether/ethyl acetate=5/1) to afford compound 24.1 (529 mg, yield: 73%) as a yellow solid.

Step 2: To a solution of compound 24.1 (200 mg, 0.78 mmol), N-methylpiperazine (78.4 mg, 0.78 mmol), cesium carbonate (767 mg, 2.35 mmol) and (±)-2,2'-Bis(diphenylphosphino)-1,1'-binaphthyl (BINAP) (14.7 mg, 24 μmol) in 1,4-dioxane (15 mL) was added tris(dibenzylideneacetone)dipalladium (7.2 mg, 7.8 μmol), the reaction system was replaced with nitrogen for 3 times and then stirred at 110° C. for overnight under nitrogen, cooled to room temperature, filtered through a celite pad, the filter caked was rinsed with ethyl acetate, the filtrate was concentrated, the residue was purified by prep-TLC (DCM/methanol=10/1) to afford compound 24.2 (210 mg, yield: 98%) as a yellow solid.

Step 3: The mixture of compound 24.2 (210 mg, 0.77 mmol) and Pd/C (60 mg, 5%) in methanol (15 mL) was replaced with hydrogen for 3 times and then stirred at room temperature for 1 h under hydrogen (hydrogen balloon). The solution was filtered, the filtrated was concentrated to afford compound 24.3 (205 mg, yield: 100%) as a brown solid.

Step 1: To a solution of 1-bromo-3-methoxy-5-nitrobenzene (1.00 g, 4.31 mmol) in THF (30.0 mL) was successively added palladium acetate (100 mg, 0.43 mmol), cesium carbonate (2.15 g, 6.60 mmol), BINAP (400 mg, 0.65 mmol), N-methylpiperazine (1.29 g, 12.9 mmol) under nitrogen, the reaction system stirred at 80° C. for 16 h. The reaction system was concentrate under reduced pressure and then purified by Flash column chromatography (petroleum ether/ethyl acetate=4/1) to afford compound 25.1 (1.15 g, yield: 106%) as a brown solid.

m/z: [M+H]$^+$ 252.2

Step 2: To a solution of compound 25.1 (150 mg, 0.60 mmol) in methanol (5.0 mL) was added Raney Ni (20 mg), the system was replaced with hydrogen for 3 times and then stirred at room temperature for 1 h under hydrogen. Filtered, the filtrate was concentrated under reduced pressure to afford compound 25.2 (90 mg, yield: 68%) as a yellow solid.

m/z: [M+H]$^+$ 222.2

Compounds 25.3 (4-methoxy-3-(4-methylpiperazin-1-yl) aniline) was synthesized following the synthetic method to the one used for compound 25.2, by replacing 1-bromo-3-methoxy-5-nitrobenzene to 2-bromo-1-methoxy-4-nitrobenzene in step 1.

Embodiment 33: Synthesis of Compound 26.6

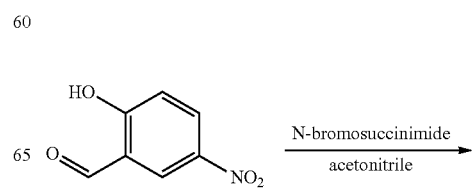

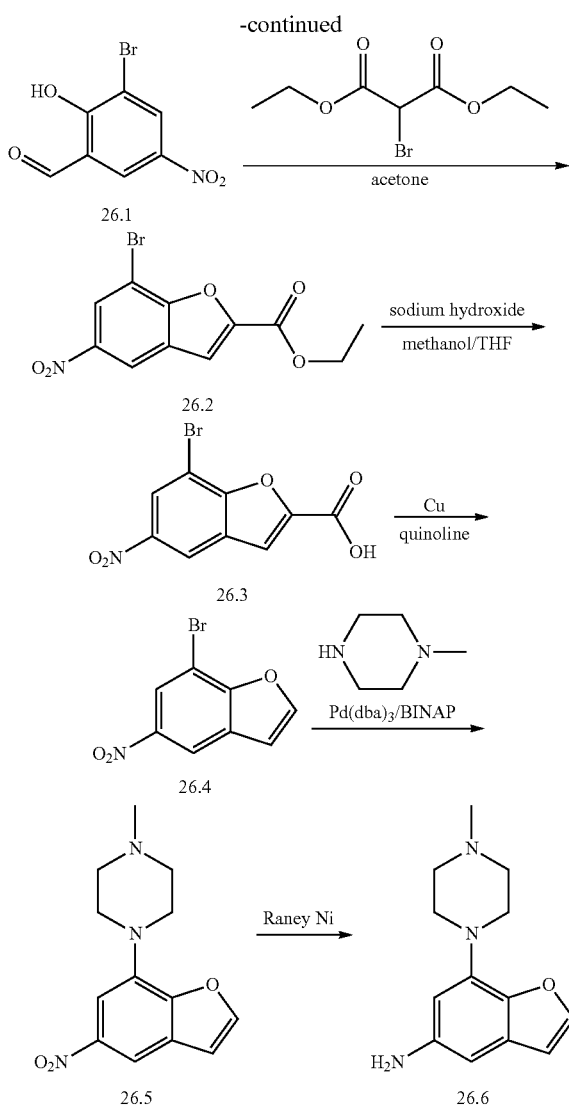

Step 1: To a solution of 2-hydroxy-5-nitrobenzaldehyde (2.0 g, 11.9 mmol) in acetonitrile (60 mL) was added N-bromosuccinimide (2.12 g, 12.0 mmol), the reaction system was stirred at room temperature for overnight and then added ethyl acetate, the organic layer was successively washed with $H_2O$, brine and $H_2O$, the organic layer was separated and dried over anhydrous sodium sulfate, filtered and concentrated, to the residue was added methanol and heated to reflux, and then water was added dropwise to the reaction system to precipitate a solid, and the mixture was cooled to 0° C. and stirred for 0.5 h, filtered, the filter cake was dried under vacuum to afford compound 26.1 (2.4 g, yield: 82%) as a yellow solid.

Step 2: To a solution of compound 26.1 (1 g, 4.06 mmol) and diethyl bromomalonate (1.16 g, 4.87 mmol) in acetone (15 mL) was added $K_2CO_3$ (1.12 g, 8.12 mmol), the reaction system was heated to reflux for 6 h, the reaction solution was cooled to room temperature and poured into ice water and stirred, filtered, the filter cake was dried under vacuum to afford compound 26.2 (945 mg, yield: 74%) as a yellow solid.

Step 3: To a solution of compound 26.2 (945 mg, 3.0 mmol) in a mixed solvent of methanol and THF (10 mL, 1/1) was added an aqueous solution (5 mL) of sodium hydroxide (361 mg, 9.0 mmol), the reaction system was stirred at room temperature for overnight. The reaction was quenched by addition of $H_2O$, concentrated under reduced pressure to remove the solvent, the aqueous layer was acidified with citric acid and extracted with ethyl acetate (20 mL), the organic layer was successively washed with $H_2O$ and brine, the organic layer was separated and dried over anhydrous sodium sulfate, filtered and concentrated to afford compound 26.3 (858 mg, yield: 100%) as a brown solid.

m/z: $[M+H]^+$ 286.0

Step 4: To a solution of compound 26.3 (200 mg, 0.7 mmol) in quinoline (2 mL) was added Cu powder (44.8 mg, 1.4 mmol) and heated to 200° C. and stirred for 0.5 h in a sealed tube. The reaction system was cooled to room temperature and poured into concentrated hydrochloric acid (15 mL), the aqueous layer was extracted with ethyl acetate (5 mL×3), the combined organic layers were successively washed with $H_2O$ and brine, the organic layer was dried over anhydrous sodium sulfate, filtered and concentrated, the residue was by column chromatography on silica gel (petroleum ether/ethyl acetate=10/1) to afford compound 26.4 (130 mg, yield: 71%) as a white solid.

Step 5: To a solution of compound 26.4 (130 mg, 0.50 mmol), 2,2'-Bis(diphenylphosphino)-1,1'-binaphthyl (BINAP) (9.3 mg, 15 μmol), cesium carbonate (488 mg, 1.5 mmol) and N-methylpiperazine (49.9 mg, 0.50 mmol) in 1,4-dioxane (15 mL) was added tris(dibenzylideneacetone)dipalladium $(Pd(dba)_3)$ (4.6 mg, 5.0 μmol), the reaction system was replaced with nitrogen for 3 times and then heated to 110° C. and stirred for overnight under nitrogen. The reaction solution was cooled to room temperature, filtered through a celite pad, the filtrate was concentrated, the residue was purified by prep-TLC (DCM/methanol=10/1) to afford compound 26.5 (68 mg, yield: 52%) as a brown solid.

m/z: $[M+H]^+$ 262.2

Step 6: To a solution of compound 26.5 (68 mg, 0.26 mmol) and hydrazine hydrate (65 mg, 1.3 mmol) in a mixed solvent of ethanol and THF (15 mL, 3/1) was added Raney Ni (30 mg), the system was stirred at room temperature for overnight and then filtered, the filtrate was concentrated, the residue was purified by prep-TLC (DCM/methanol=8/1) to afford compound 26.6 (28 mg, yield: 47%) as a brown solid.

m/z: $[M+H]^+$ 232.1

Embodiment 34: Synthesis of Compound 27.6

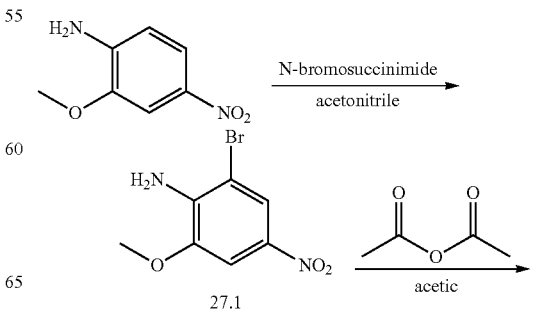

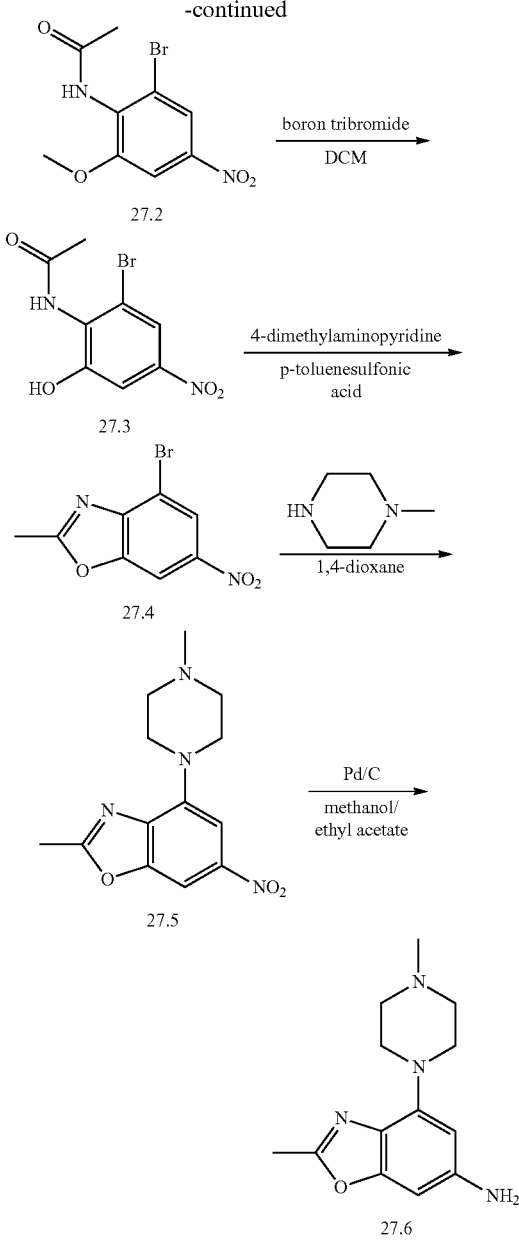

Step 1: To a solution of 2-methoxy-4-nitroaniline (1.68 g, 10.0 mmol) in acetonitrile (20 mL) was added N-bromosuccinimide (1.96 g, 11.0 mmol), the reaction system was stirred at room temperature for 2 h and then diluted with ethyl acetate, the organic layer was successively washed with H₂O and brine and dried over anhydrous sodium sulfate, filtered and concentrated, the residue was dissolved in a refluxed solution of methanol, H₂O was added dropwise to precipitate a solid and then cooled to 0° C. and stirred for 0.5 h, filtered, the filter cake was dried under vacuum to afford compound 27.1 (2.2 g, yield: 89%) as a brown solid.

Step 2: To a solution of compound 27.1 (2.2 g, 8.9 mmol) in acetic acid (10 mL) was added acetic anhydride (10 mL), the reaction system was stirred at reflux for 3 h, the reaction solution was cooled to room temperature and poured into ice water and stirred, filtered, the filter cake was rinsed with H₂O, the residue was added into ethanol and stirred at reflux for 15 min until completely dissolved and then to the above clarified solution was added ammonium hydroxide (1 mL), stirred and cooled to room temperature, filtered, the filter cake was rinsed with ethanol, dried under vacuum to afford compound 27.2 (2.1 g, yield: 82%) as a white solid.

m/z: [M+H]$^+$ 289.0

Step 3: To a solution of compound 27.2 (1.0 g, 3.46 mmol) in DCM (60 mL) was added boron tribromide (4.33 g, 17.3 mmol) under ice-bath, the reaction system was slowly warmed up to room temperature and stirred for overnight. The reaction was quenched by addition of hydrochloric acid (1 M), the aqueous layer was extracted with DCM, the combined organic layer was successively washed with H₂O and brine, the organic layer was concentrated, the residue was purified by column chromatography on silica gel (DCM/methanol=50/1) to afford compound 27.3 (890 mg, yield: 93%) as a white solid.

m/z: [M+H]$^+$ 275.0

Step 4: To a solution of compound 27.3 (1.15 g, 4.18 mmol) and p-toluenesulfonic acid (79.5 mg, 0.418 mmol) in 1,3-dichlorobenzene (25 mL) was added 4-dimethylaminopyridine (26 mg, 0.21 mmol), the reaction system was heated up to 170° C. and stirred for 4 h. The reaction solution was cooled to room temperature, the organic solvent was removed by using the vacuum pump, the residue was purified by column chromatography on silica gel (petroleum ether/ethyl acetate=5/1) to afford compound 27.4 (700 mg, yield: 65%) as a brown solid.

m/z: [M+H]$^+$ 257.0

Step 5: To a solution of compound 27.4 (830 mg, 3.23 mmol), BINAP (60.4 mg, 0.097 mmol), cesium carbonate (3.16 g, 9.69 mmol) and N-methylpiperazine (323.0 mg, 3.23 mmol) in 1,4-dioxane (30 mL) was added Pd(dba)₃ (29.6 mg, 0.032 mmol), the reaction system was replaced with nitrogen for 3 times and then heated to 110° C. and stirred for 3 h under nitrogen. The reaction solution was cooled to room temperature, filtered, the filtrate was concentrated, the residue was purified by prep-TLC (DCM/methanol=10/1) to afford compound 27.5 (60 mg, yield: 7%) as a brown solid.

m/z: [M+H]$^+$ 277.2

Step 6: To a solution of compound 27.5 (60 mg, 0.22 mmol) in a mixed solvent of methanol and acetic acetate (10 mL, 1/1) was added Pd/C (30 mg, 10%), the system was replaced with hydrogen for 3 times and then stirred at room temperature for 2 h under hydrogen, the reaction solution was filtered through a celite pad, the filtrated was concentrated under reduced pressure, the residue was purified by prep-TLC (DCM/methanol=8/1) to afford compound 27.6 (23 mg, yield: 42%) as a brown solid.

m/z: [M+H]$^+$ 247.2

Embodiment 35: Synthesis of Compound 1-1-1

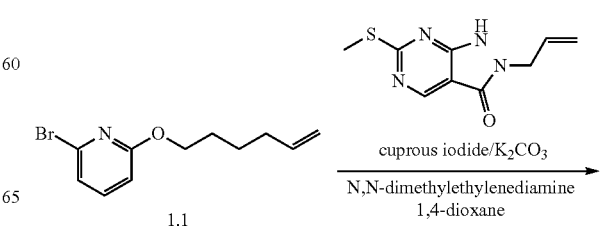

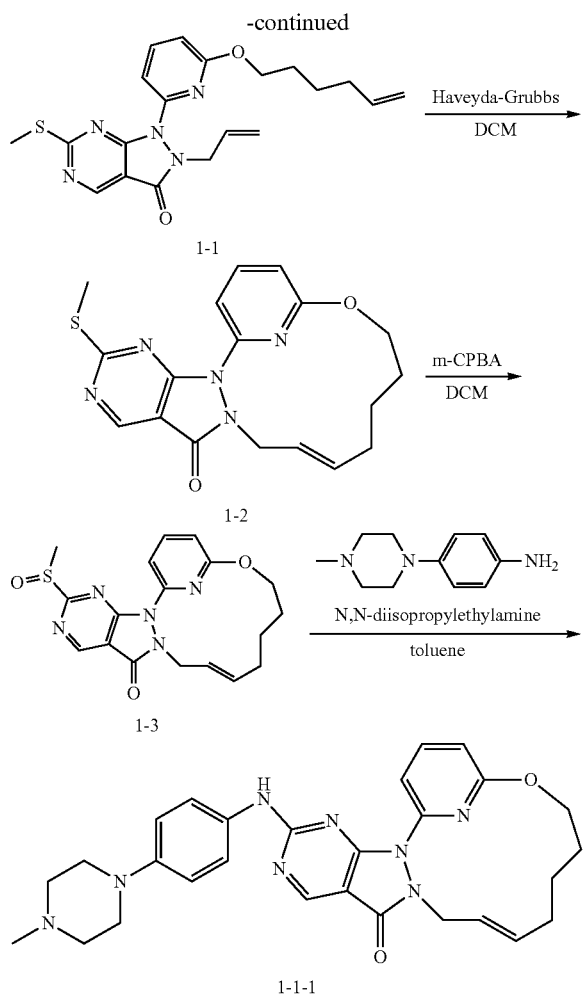

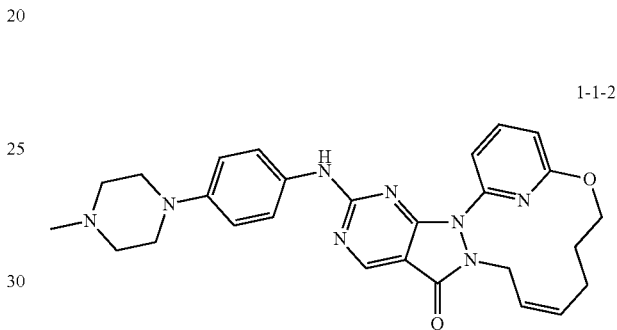

remove the organic solvent to afford compound 1-3 (59 mg, yield: 100%) as a white solid.

m/z: [M+H]⁺ 385.9

Step 4: The solution of compound 1-3 (59 mg, 0.154 mmol), N,N-diisopropylethylamine (40 mg, 0.308 mmol) and 4-(N-methylpiperazin)aniline (30 mg, 0.154 mmol) in toluene (10 mL) was stirred at 70° C. for overnight and then concentrated under reduced pressure to remove the organic solvent, the residue was purified by prep-HPLC to afford compound 1-1-1 (trans, 16.2 mg, yield: 21%) as a white solid.

m/z: [M+H]⁺ 512.9; ¹H NMR (400 MHz, CD₃OD): δ 8.78 (s, 1H), 7.88 (t, J=7.8 Hz, 1H), 7.57 (d, J=8.8 Hz, 2H), 7.39 (d, J=7.6 Hz, 1H), 6.95 (d, J=7.2 Hz, 2H), 6.73 (d, J=8.0 Hz, 1H), 5.75 (dt, J=8.0, 15.6 Hz, 1H), 5.39 (dt, J=8.0, 16.0 Hz, 1H), 4.59 (t, J=6.8 Hz, 2H), 4.30 (d, J=5.6 Hz, 2H), 3.19 (t, J=5.2 Hz, 4H), 2.65 (t, J=4.8 Hz, 4H), 2.38 (s, 3H), 2.22-2.19 (m, 2H), 1.85-1.82 (m, 2H), 1.58-1.56 (m, 2H).

Embodiment 36: Synthesis of Compound 1-1-2

1-1-2

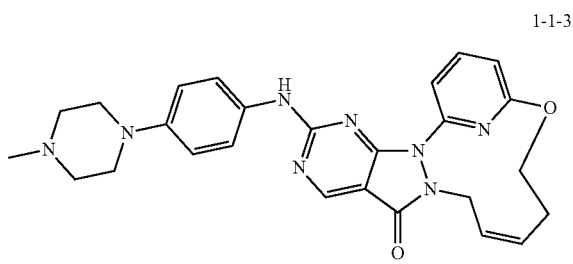 [SMILES: CN1CCN(c2ccc(Nc3ncc4c(=O)n5n(c4n3)-c3cccc(n3)OCC/C=C\C5)cc2)CC1]

Compound 1-1-2 (cis) was synthesized following the synthetic method to the one used for compound 1-1-1, by using compound 1.2 as a starting material.

m/z: [M+H]⁺ 498.8; ¹H NMR (400 MHz, CD₃OD): δ 8.79 (s, 1H), 7.86 (t, J=8.0 Hz, 1H), 7.64 (d, J=8.8 Hz, 2H), 7.50 (d, J=8.0 Hz, 1H), 7.02 (d, J=8.8 Hz, 2H), 6.70 (d, J=8.0 Hz, 1H), 6.07 (dt, J=7.6, 10.8 Hz, 1H), 5.55 (dt, J=7.2, 10.8 Hz, 1H), 4.57 (s, 2H), 4.34 (d, J=8.0 Hz, 2H), 3.82 (d, J=13.6 Hz, 2H), 3.63 (d, J=12.0 Hz, 2H), 3.30 (d, J=16.0 Hz, 2H), 3.07 (d, J=12.4 Hz, 2H), 3.00 (s, 3H), 2.20 (br. s, 2H), 1.91 (br. s, 2H).

Step 1: Compound 1.1 (255 mg, 1 mmol), 2-allyl-6-(methylthio)-1H-pyrazolo[3,4-d] pyrimidin-3(2H)-one (222 mg, 1 mmol), cuprous iodide (191 mg, 1 mmol), anhydrous K₂CO₃ (276 mg, 2 mmol) and N,N-dimethylethylenediamine (88 mg, 1 mmol) was successively added into 1,4-dioxane (20 mL), the reaction system was stirred at 100° C. for overnight. The reaction solution was cooled to room temperature, filtered, the filtrate was concentrated, the residue was purified by column chromatography on silica gel (petroleum ether/ethyl acetate=1/1) to afford compound 1-1 (205 mg, yield: 52%) as a red liquid.

m/z: [M+H]⁺ 398.1

Step 2: To a solution f of compound 1-1 (205 mg, 0.52 mmol) in DCM (20 mL) was added Hoveyda-Grubbs reagent (2 mg), the reaction system was stirred at 40° C. for 16 h. The reaction solution was directly concentrated under reduced pressure to remove the organic solvent after cooled down, the residue was purified by column chromatography on silica gel (petroleum ether/ethyl acetate=5/1) to afford compound 1-2 (57 mg, yield: 30%) as a white solid.

m/z: [M+H]⁺ 370.1

Step 3: To a solution f of compound 1-2 (57 mg, 0.154 mmol) in DCM (10 mL) was added 3-chloroperoxybenzoic acid (m-CPBA) (31 mg, 0.154 mmol), the reaction system was stirred at room temperature for 1 h and then the reaction solution was directly concentrated under reduced pressure to Embodiment 37: Synthesis of Compound 1-1-3

1-1-3

Compound 1-1-3 (cis) was synthesized following the synthetic method to the one used for compound 1-1-1, by using compound 1.3 as a starting material.

m/z: [M+H]⁺ 484.9; ¹H NMR (400 MHz, CD₃OD): δ 8.82 (s, 1H), 7.89 (t, J=7.6 Hz, 1H), 7.71 (d, J=8.4 Hz, 1H), 7.66 (d, J=8.8 Hz, 2H), 7.07 (d, J=8.8 Hz, 2H), 6.75 (d, J=8.0 Hz, 1H), 6.10 (dt, J=8.0, 11.2 Hz, 1H), 5.86 (dt, J=8.8, 11.2 Hz, 1H), 4.46-4.31 (m, 4H), 3.85 (d, J=13.2 Hz, 2H), 3.64 (d,

J=10.4 Hz, 2H), 3.34-3.32 (m, 2H), 3.07 (d, J=11.6 Hz, 2H), 3.01 (s, 3H), 2.56-2.51 (m, 2H).

Embodiment 38: Synthesis of Compound 1-1-4

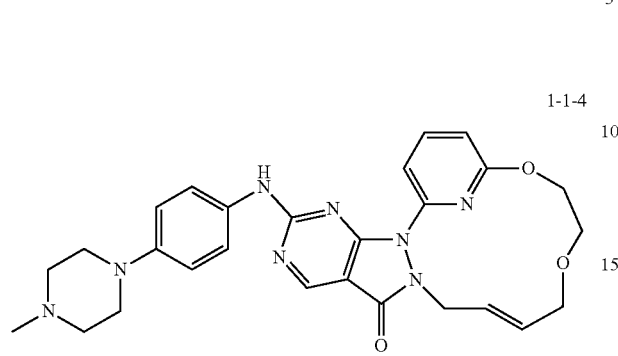

1-1-4

Compound 1-1-4 (trans) was synthesized following the synthetic method to the one used for compound 1-1-1, by using compound 1.4 as a starting material.

m/z: [M+H]⁺ 515.4; ¹H NMR (400 MHz, CDCl₃): δ 8.78 (s, 1H), 7.69 (d, J=8.0 Hz, 1H), 7.42-7.39 (m, 2H), 7.22 (d, J=7.6 Hz, 1H), 6.82 (d, J=6.8 Hz, 2H), 6.64 (d, J=7.6 Hz, 1H), 5.87 (dt, J=5.6, 15.6 Hz, 1H), 5.58 (dt, J=7.2, 15.2 Hz, 1H), 4.61 (t, J=5.6 Hz, 2H), 4.25 (d, J=5.2 Hz, 2H), 4.03 (d, J=7.2 Hz, 2H), 3.78 (t, J=5.6 Hz, 2H), 3.13 (t, J=4.8 Hz, 4H), 2.54 (t, J=4.8 Hz, 4H), 2.30 (s, 3H).

Embodiment 39: Synthesis of Compound 1-1-5

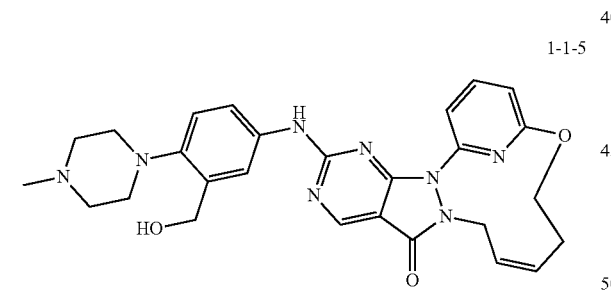

1-1-5

Compound 1-1-5 (cis) was synthesized following the synthetic method to the one used for compound 1-1-1, by replacing compound 1.1 to 1.3 in step 1 and 4-(N-methylpiperazin)aniline to compound 9.2 in step 4.

m/z: [M+H]⁺ 515.4; ¹H NMR (400 MHz, CD₃OD): δ 8.72 (s, 1H), 7.91 (s, 1H), 7.82 (t, J=8.0 Hz, 1H), 7.65 (d, J=8.0 Hz, 1H), 7.48 (dd, J=2.4, 8.4 Hz, 1H), 7.09 (d, J=8.8 Hz, 1H), 6.64 (d, J=8.0 Hz, 1H), 6.01-5.96 (m, 1H), 5.70 (dt, J=8.8, 10.8 Hz, 1H), 4.65 (s, 2H), 4.34 (br. s, 2H), 4.22 (s, 2H), 3.49 (d, J=11.2 Hz, 2H), 3.28-3.20 (m, 4H), 3.05-2.98 (m, 2H), 2.90 (s, 3H), 2.44-2.39 (m, 2H).

Embodiment 40: Synthesis of Compound 1-1-6

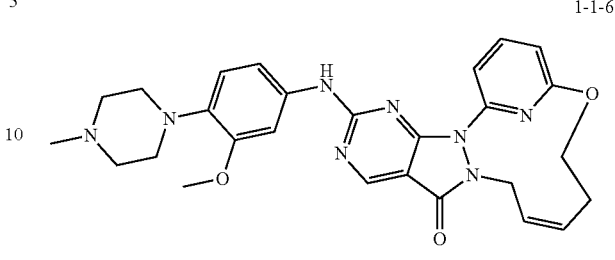

1-1-6

Compound 1-3-2 (trans) was synthesized following the synthetic method to the one used for compound 1-1-1, by replacing compound 1.1 to 1.4 in step 1 and 4-(N-methylpiperazin)aniline to compound 11.5 in step 4. Compound 3-3-10 (cis) was synthesized following the synthetic method to the one used for compound 3-3-1, by replacing compound 9.2 to 12.2 in step 2. Compound 8-3-1 (cis) was synthesized following the synthetic method to the one used for compound 1-1-1, by replacing compound 1.1 to 23.4 in step 1 and 4-(N-methylpiperazin)aniline to compound 10.8 in step 4.

m/z: [M+H]⁺ 514.9; ¹H NMR (400 MHz, DMSO-d₆): δ 10.10 (s, 1H), 8.84 (s, 1H), 7.94 (t, J=8.0 Hz, 1H), 7.69-7.67 (m, 1H), 7.34 (d, J=2.0 Hz, 1H), 7.29 (dd, J=2.0, 8.4 Hz, 1H), 6.88 (d, J=8.8 Hz, 1H), 6.77 (d, J=8.4 Hz, 1H), 5.95 (dt, J=8.0, 10.8 Hz, 1H), 5.76 (dt, J=8.8, 10.4 Hz, 1H), 4.30 (s, 2H), 4.26 (s, 2H), 3.72 (s, 3H), 2.94 (s, 4H), 2.46 (s, 6H), 2.22 (s, 3H).

Embodiment 41: Synthesis of Compound 1-2-1

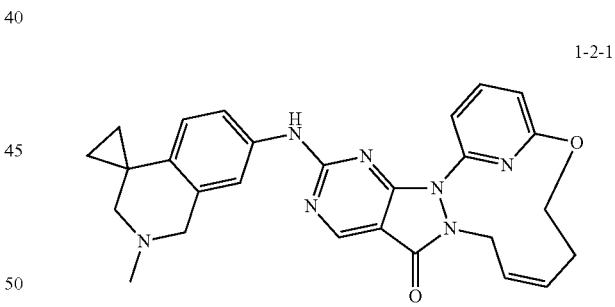

1-2-1

Compound 1-2-1 (cis) was synthesized following the synthetic method to the one used for compound 1-1-1, by replacing compound 1.1 to 1.3 in step 1 and 4-(N-methylpiperazin)aniline to compound 10.8 in step 4.

m/z: [M+H]⁺ 482.4; ¹H NMR (400 MHz, CDCl₃): δ 8.87 (s, 1H), 7.79 (t, J=8.0 Hz, 1H), 7.69 (d, J=7.6 Hz, 1H), 7.52 (s, 1H), 7.49 (s, 1H), 7.26 (d, J=2.0 Hz, 1H), 6.70 (t, J=8.4 Hz, 2H), 6.24 (dt, J=8.0, 10.8 Hz, 1H), 5.81 (dt, J=9.2, 10.4 Hz, 1H), 4.45 (s, 2H), 4.36 (s, 2H), 3.77 (s, 2H), 2.61 (s, 2H), 2.56-2.51 (m, 5H), 1.07-0.90 (m, 4H).

Embodiment 42: Synthesis of Compound 1-2-2

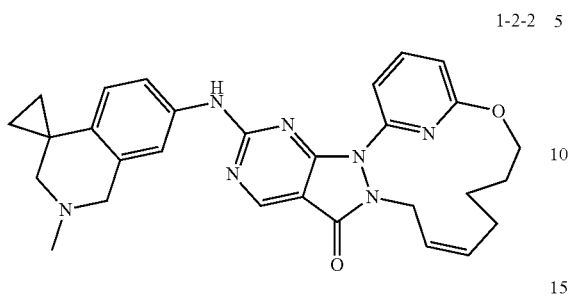

1-2-2

Compound 1-2-2 (cis) was synthesized following the synthetic method to the one used for compound 1-1-1, by replacing 4-(N-methylpiperazin)aniline to compound 10.8 in step 4.

m/z: [M+H]$^+$ 510.4; $^1$H NMR (400 MHz, DMSO-d$_6$): δ 10.17 (s, 1H), 8.85 (s, 1H), 7.95 (t, J=8.0 Hz, 1H), 7.59 (s, 1H), 7.41 (d, J=7.6 Hz, 1H), 7.34 (dd, J=1.6, 8.4 Hz, 1H), 6.79 (d, J=8.4 Hz, 1H), 6.65 (d, J=8.8 Hz, 1H), 5.67 (dt, J=5.2, 15.2 Hz, 1H), 5.37 (dt, J=7.2, 15.2 Hz, 1H), 4.51 (t, J=6.8 Hz, 2H), 4.21 (d, J=8.0 Hz, 2H), 3.53 (s, 2H), 2.43 (s, 2H), 2.33 (s, 3H), 2.13 (s, 2H), 1.74 (dd, J=6.0, 12.0 Hz, 2H), 1.47 (t, J=3.2 Hz, 2H), 0.91-0.81 (m, 4H).

Embodiment 43: Synthesis of Compound 1-3-1

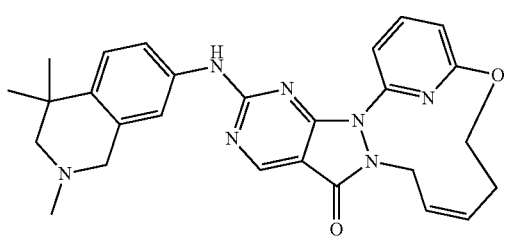

1-3-1

Compound 1-3-1 (cis) was synthesized following the synthetic method to the one used for compound 1-1-1, by replacing compound 1.1 to 1.3 in step 1 and 4-(N-methylpiperazin)aniline to compound 11.5 in step 4.

m/z: [M+H]$^+$ 484.4; $^1$H NMR (400 MHz, CDCl$_3$): δ 8.88 (s, 1H), 7.80 (t, J=8.0 Hz, 1H), 7.71 (d, J=7.6 Hz, 1H), 7.51 (s, 1H), 7.48 (s, 1H), 7.35-7.29 (m, 1H), 6.71 (d, J=8.0 Hz, 1H), 6.23 (ddd, J=8.0, 12.4, 20.0 Hz, 1H), 5.81 (dd, J=8.8, 20.0 Hz, 1H), 4.45 (s, 2H), 4.36 (s, 2H), 3.58 (s, 2H), 2.56-2.51 (m, 2H), 2.47 (s, 3H), 2.45 (s, 2H), 1.35 (s, 6H).

Embodiment 44: Synthesis of Compound 1-3-2

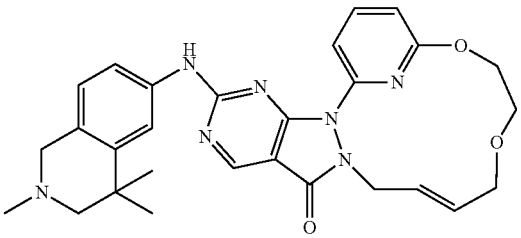

1-3-2

Compound 1-3-2 (trans) was synthesized following the synthetic method to the one used for compound 1-1-1, by replacing compound 1.1 to 1.4 in step 1 and 4-(N-methylpiperazin)aniline to compound 11.5 in step 4.

m/z: [M+H]$^+$ 514.4; $^1$H NMR (400 MHz, DMSO-d$_6$): δ 10.33 (s, 1H), 9.72 (t, J=2.0 Hz, 1H), 8.91 (s, 1H), 8.05 (t, J=8.0 Hz, 1H), 7.69 (s, 1H), 7.58 (dd, J=2.0, 8.8 Hz, 1H), 7.44 (d, J=8.8 Hz, 1H), 7.41 (d, J=7.2 Hz, 1H), 6.85 (d, J=8.0 Hz, 1H), 5.89-5.83 (m, 1H), 5.52-5.48 (m, 1H), 4.63-4.56 (m, 2H), 4.32 (s, 2H), 4.28 (s, 2H), 4.03 (d, J=6.8 Hz, 2H), 3.74 (t, J=5.2 Hz, 2H), 3.50-3.5 (m, 1H), 3.27-3.21 (m, 1H), 3.01 (s, 3H), 1.38 (s, 3H), 1.33 (s, 3H).

Embodiment 45: Synthesis of Compounds 2-1-1 and 2-1-2

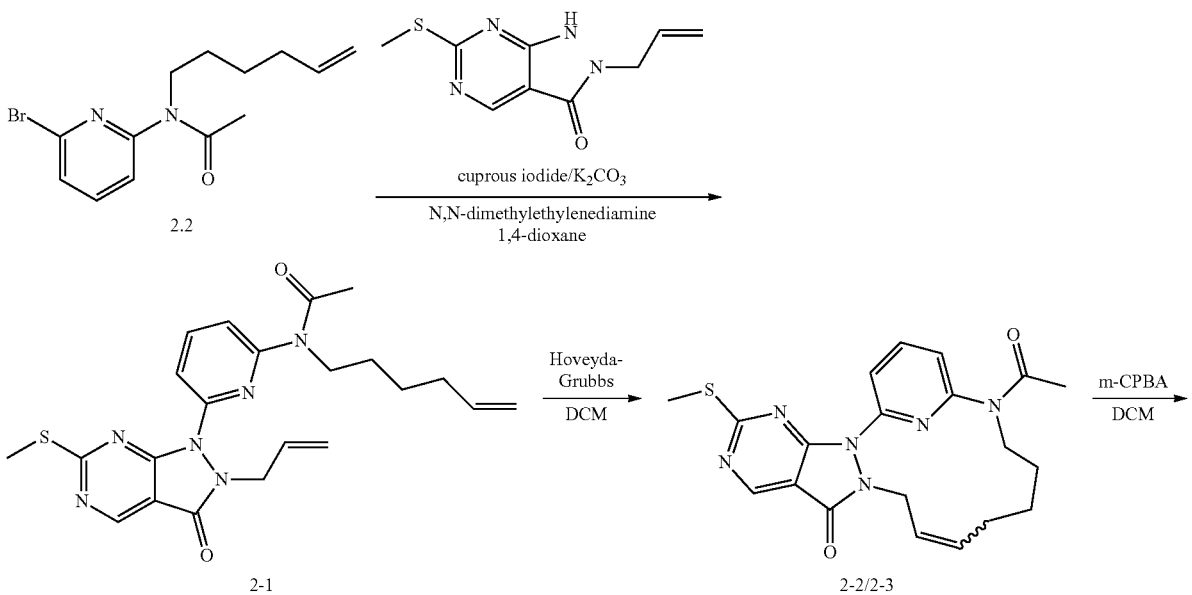

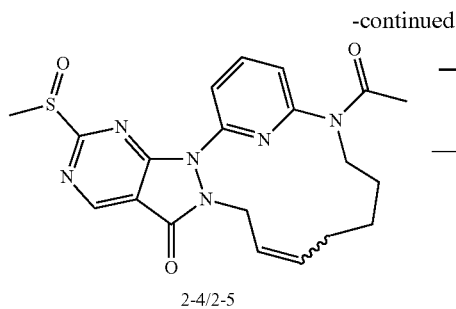

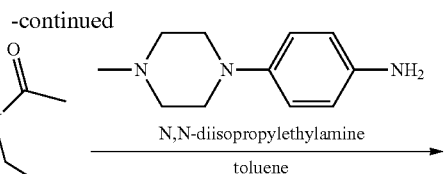

2-4/2-5

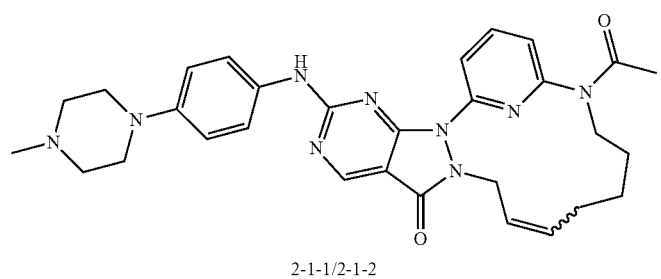

2-1-1/2-1-2

Step 1: Compound 2.2 (200 mg, 0.67 mmol), 2-allyl-6-(methylthio)-1H-pyrazolo[3,4-d] pyrimidin-3(2H)-one (179 mg, 0.81 mmol), anhydrous $K_2CO_3$ (186 mg, 1.35 mmol), cuprous iodide (128 mg, 0.67 mmol) and N,N-dimethylethylenediamine (59 mg, 0.67 mmol) was successively added into 1,4-dioxane (20 mL), the reaction system was stirred at 100° C. for 16 h. The reaction solution was cooled to room temperature and concentrated, the residue was purified by prep-TLC (petroleum ether/ethyl acetate=1/1) to afford compound 2-1 (160 mg, yield: 54%) as a brown solid.

m/z: $[M+H]^+$ 439.0

Step 2: To a solution of compound 2-1 (160 mg, 0.365 mmol) in DCM (30 mL) was added Hoveyda-Grubbs reagent (30 mg), the reaction system was stirred at 45° C. for 4 h. The reaction solution was cooled down and concentrated under reduced pressure to remove DCM, the residue was purified by prep-TLC (petroleum ether/ethyl acetate=1/1) to afford compound 2-2 (cis, 40 mg, yield: 27%, more polar) and 2-3 (trans, 60 mg, yield: 40%, less polar), as white solids.

m/z: $[M+H]^+$ 410.9

Step 3: To a solution f of compound 2-2 (40 mg, 0.097 mmol) in DCM (10 mL) was added m-CPBA (17 mg, 0.097 mmol), the reaction system was stirred at room temperature for 1 h and then concentrated under reduced pressure to remove DCM to afford compound 2-4 (43 mg, yield: 100%) as a white solid.

m/z: $[M+H]^+$ 427.0

Step 4: Compound 2-4 (43 mg, 0.097 mmol), N,N-diisopropylethylamine (0.3 mL) and 4-(N-methylpiperazin)aniline (19 mg, 0.097 mmol) was dissolved in toluene (10 mL), the reaction system was stirred at 90° C. for overnight and then concentrated under reduced pressure to remove the solvent, the residue was purified by prep-HPLC to afford compound 2-1-1 (cis, 29 mg, yield: 54%) as a white solid.

m/z: $[M+H]^+$ 553.8; $^1$H NMR (400 MHz, CD$_3$OD): δ 8.85 (s, 1H), 8.00-8.25 (m, 2H), 7.65 (dd, J=2.4, 6.8 Hz, 2H), 7.35-7.40 (m, 1H), 7.06 (dd, J=2.4, 6.8 Hz, 2H), 5.25-5.50 (m, 2H), 5.05-5.15 (m, 1H), 4.09 (t, J=7.6 Hz, 2H), 3.86 (d, J=13.2 Hz, 2H), 3.65 (d, J=12.4 Hz, 2H), 2.95-3.20 (m, 5H), 2.05-2.25 (m, 5H), 1.30-1.75 (m, 6H).

Compound 2-1-2 (trans, 57 mg) was synthesized as a white solid following the synthetic method to the one used for compound 2-1-1, by using compound 2-2 as a starting material.

m/z: $[M+H]^+$ 553.8; $^1$H NMR (400 MHz, CD$_3$OD): δ 8.83 (s, 1H), 8.15 (t, J=8.0 Hz, 1H), 7.71 (d, J=8.0 Hz, 1H), 7.51-7.60 (m, 3H), 6.97 (d, J=8.4 Hz, 2H), 5.45-5.50 (m, 1H), 5.30-5.48 (m, 1H), 4.43 (d, J=5.6 Hz, 2H), 3.85-4.00 (m, 2H), 3.80 (d, J=13.6 Hz, 2H), 3.63 (d, J=12.4 Hz, 2H), 2.80-3.20 (m, 5H), 1.85-2.25 (m, 5H), 1.25-1.75 (m, 6H).

Embodiment 46: Synthesis of Compound 2-2-1

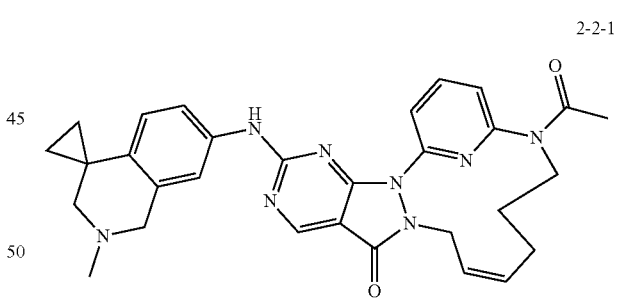

2-2-1

Compound 2-2-1 (cis) was synthesized following the synthetic method to the one used for compound 2-1-1, by replacing compound 2.2 to 2.3 in step 1 and 4-(N-methylpiperazin)aniline to compound 10.8 in step 4.

m/z: $[M+H]^+$ 536.6; $^1$H NMR (400 MHz, CDCl$_3$): δ 8.82 (s, 1H), 7.94 (d, J=8.0 Hz, 1H), 7.77 (t, J=8.0 Hz, 1H), 7.38 (s, 1H), 7.32 (s, 1H), 7.20 (d, J=6.4 Hz, 1H), 6.59 (d, J=8.4 Hz, 1H), 5.47-5.32 (m, 2H), 4.86 (d, J=6.8 Hz, 2H), 3.86 (t, J=5.2 Hz, 2H), 3.64 (s, 2H), 2.50 (s, 2H), 2.41 (s, 3H), 2.20 (dd, J=6.4, 13.2 Hz, 2H), 2.11 (s, 3H), 1.56-1.45 (m, 2H), 0.95-0.85 (m, 4H).

Embodiment 47: Synthesis of Compound 2-3-1

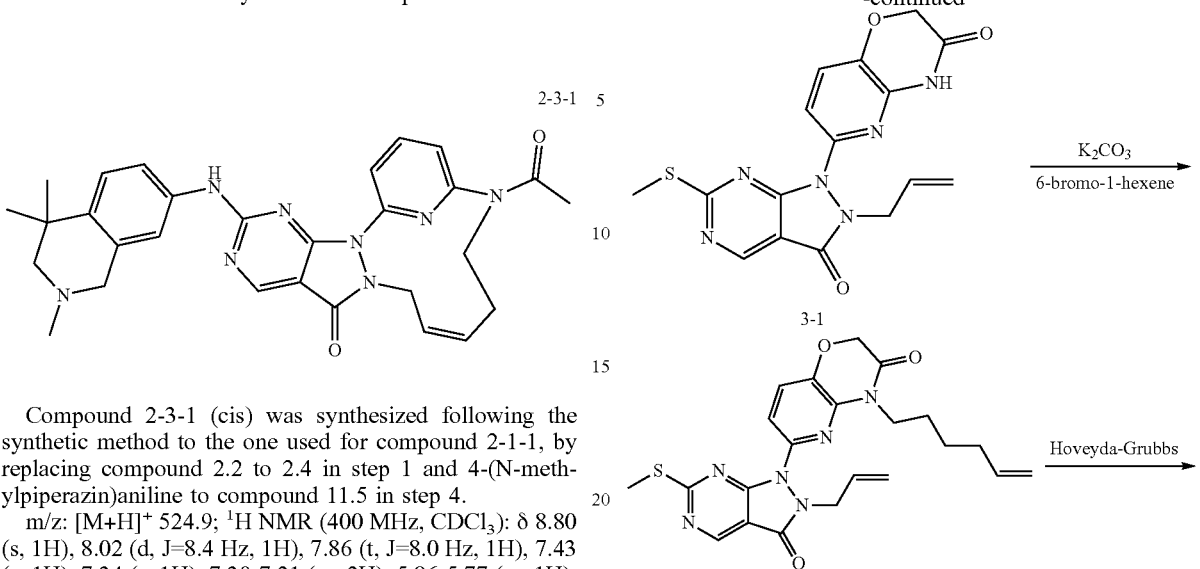

Compound 2-3-1 (cis) was synthesized following the synthetic method to the one used for compound 2-1-1, by replacing compound 2.2 to 2.4 in step 1 and 4-(N-methylpiperazin)aniline to compound 11.5 in step 4.

m/z: [M+H]$^+$ 524.9; $^1$H NMR (400 MHz, CDCl$_3$): δ 8.80 (s, 1H), 8.02 (d, J=8.4 Hz, 1H), 7.86 (t, J=8.0 Hz, 1H), 7.43 (s, 1H), 7.34 (s, 1H), 7.30-7.21 (m, 2H), 5.86-5.77 (m, 1H), 5.61-5.52 (m, 1H), 4.47 (d, J=7.6 Hz, 2H), 3.90 (s, 2H), 3.58 (s, 2H), 2.45-2.32 (m, 7H), 2.00 (s, 3H), 1.28 (s, 6H).

Embodiment 48: Synthesis of Compound 2-3-2

Compound 2-3-2 (cis) was synthesized following the synthetic method to the one used for compound 2-1-1, by replacing compound 2.2 to 2.3 in step 1 and 4-(N-methylpiperazin)aniline to compound 11.5 in step 4.

m/z: [M+H]$^+$ 538.9; $^1$H NMR (400 MHz, CDCl$_3$): δ 8.81 (s, 1H), 7.95 (d, J=8.0 Hz, 1H), 7.77 (t, J=7.6 Hz, 1H), 7.40 (t, J=8.0 Hz, 1H), 7.27-7.19 (m, 3H), 5.45-5.33 (m, 2H), 4.86 (d, J=6.8 Hz, 2H), 3.86 (t, J=5.6 Hz, 2H), 3.46 (s, 3H), 2.36 (s, 3H), 2.35 (d, J=2.0 Hz, 2H), 2.23-2.18 (m, 2H), 2.11 (s, 3H), 1.59-1.55 (m, 2H), 1.25 (s, 6H).

Embodiment 49: Synthesis of Compound 3-1-1

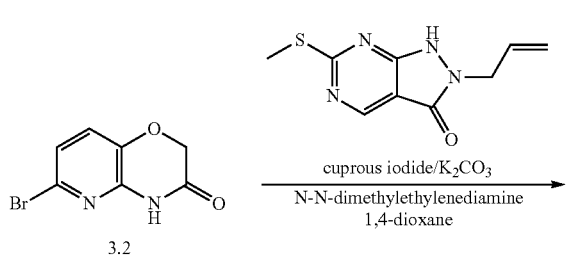

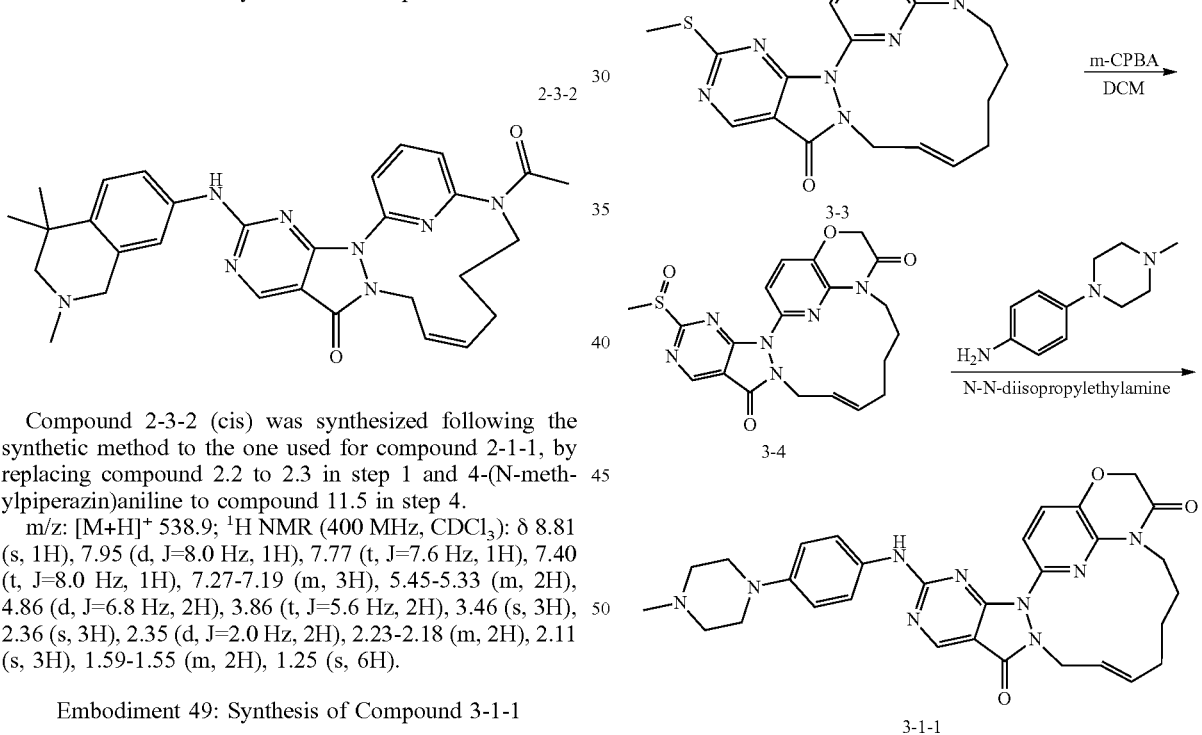

Step 1: Compound 3.2 (1.9 g, 8.29 mmol), 2-allyl-6-(methylthio)-1H-pyrazolo[3,4-d] pyrimidin-3(2H)-one (1.84 g, 8.29 mmol), cuprous iodide (1.5 g, 8.29 mmol), anhydrous K$_2$CO$_3$ (2.35 g, 17 mmol) and N,N-dimethylethylenediamine (0.73 g, 8.29 mmol) was successively added into 1,4-dioxane (30 mL), the reaction system was stirred at 100° C. for overnight. The reaction solution was cooled to room temperature, filtered, the filtrate was concentrated, the residue was purified by column chromatography on silica gel (petroleum ether/ethyl acetate=1/1) to afford compound 3-1 (1.56 g, yield: 51%) as a yellow solid.

Step 2: To a solution of compound 3-1 (0.37 g, 1 mmol) in DMF (8 mL) was added 6-bromo-1-hexene (0.25 g, 1.5 mmol) and stirred at room temperature for 5 min, added K₂CO₃ (0.28 g, 2 mmol), the reaction system was stirred at 50° C. for another 3 h, cooled to room temperature and the reaction was quenched by addition of H₂O, extracted with DCM (100 mL×3), the combined organic layers were dried over anhydrous sodium sulfate, filtered and concentrated. The residue was purified by column chromatography on silica gel (petroleum ether/ethyl acetate=2/1) to afford compound 3-2 (0.35 g, yield: 77%) as a light-yellow solid.

Step 3: To a solution of compound 3-2 (0.35 g, 0.77 mmol) in DCM (10 mL) was added Hoveyda-Grubbs reagent (20 mg, 0.032 mmol), the reaction system was stirred at room temperature for overnight and then concentrated under reduced pressure to remove the solvent, the residue was purified by prep-TLC (petroleum ether/ethyl acetate=2/1) to afford compound 3-3 (110 mg, yield: 33%) as a yellow oil.

m/z: [M+H]⁺ 424.8

Step 4: To a solution of compound 3-3 (0.11 g, 0.26 mmol) in DCM (10 mL) was added m-CPBA (47 mg, 0.30 mmol), the reaction system was stirred at room temperature for 30 min and then concentrated under reduced pressure to afford compound 3-4 (0.155 g, crude), which was used directly for next step.

m/z: [M+H]⁺ 440.9

Step 5: Compound 3-4 obtained in step 4 (0.155 g, crude), N,N-diisopropylethylamine (34 mg, 0.26 mmol) and 4-(N-methylpiperazin)aniline (38 mg, 0.2 mmol) was dissolved in toluene (5 mL), the reaction system was stirred at 70° C. for 1 h and then concentrated under reduced pressure to remove the solvent, the residue was purified by prep-HPLC to afford compound 3-1-1 (trans, 13.5 mg, two steps yield: 9.1%) as a yellow solid.

m/z: [M+H]⁺ 567.9; ¹H NMR (400 MHz, CD₃OD): δ 8.81 (s, 1H), 7.62 (d, J=8.0 Hz, 2H), 7.59 (d, J=8.0 Hz, 1H), 7.50 (d, J=8.0 Hz, 1H), 7.02 (d, J=8.0 Hz, 2H), 5.72-5.61 (m, 2H), 4.73 (s, 2H), 4.39 (s, 2H), 4.04 (t, J=8.0 Hz, 2H), 3.81 (br. s, 2H), 3.62 (br. s, 2H), 3.10-3.03 (m, 2H), 3.00 (s, 3H), 2.24-2.19 (m, 3H), 2.08-2.03 (m, 1H), 1.69-1.65 (m, 2H), 1.55-1.51 (m, 2H).

Embodiment 50: Synthesis of Compound 3-2-1

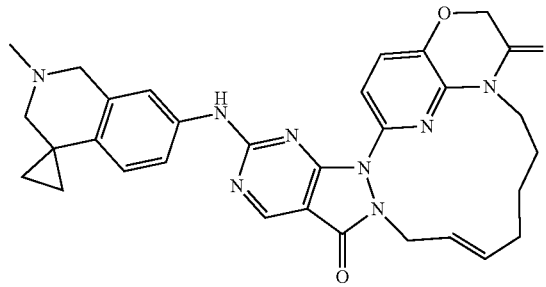

3-2-1

Compound 3-2-1 (trans) was synthesized following the synthetic method to the one used for compound 3-1-1, by replacing 4-(N-methylpiperazin)aniline to compound 10.8 in step 5.

m/z: [M+H]⁺ 565.1; ¹H NMR (400 MHz, CD₃OD): δ 8.81 (s, 1H), 7.66 (d, J=1.6 Hz, 1H), 7.64 (d, J=8.4 Hz, 1H), 7.59 (dd, J=2.0, 8.4 Hz, 1H), 7.49 (d, J=8.4 Hz, 1H), 6.85 (d, J=8.4 Hz, 1H), 5.72-5.58 (m, 2H), 4.74 (s, 2H), 4.60, 4.48 (two q, J=14.8 Hz, 2H), 4.36 (s, 2H), 3.99 (dd, J=8.0, 8.4 Hz, 2H), 3.64, 3.28 (two q, J=12.4 Hz, 2H), 3.10 (s, 3H), 2.20 (dt, J=6.4, 12.8 Hz, 2H), 1.70-1.66 (m, 2H), 1.54-1.49 (m, 2H), 1.30-1.05 (m, 4H).

Embodiment 51: Synthesis of Compound 3-2-2

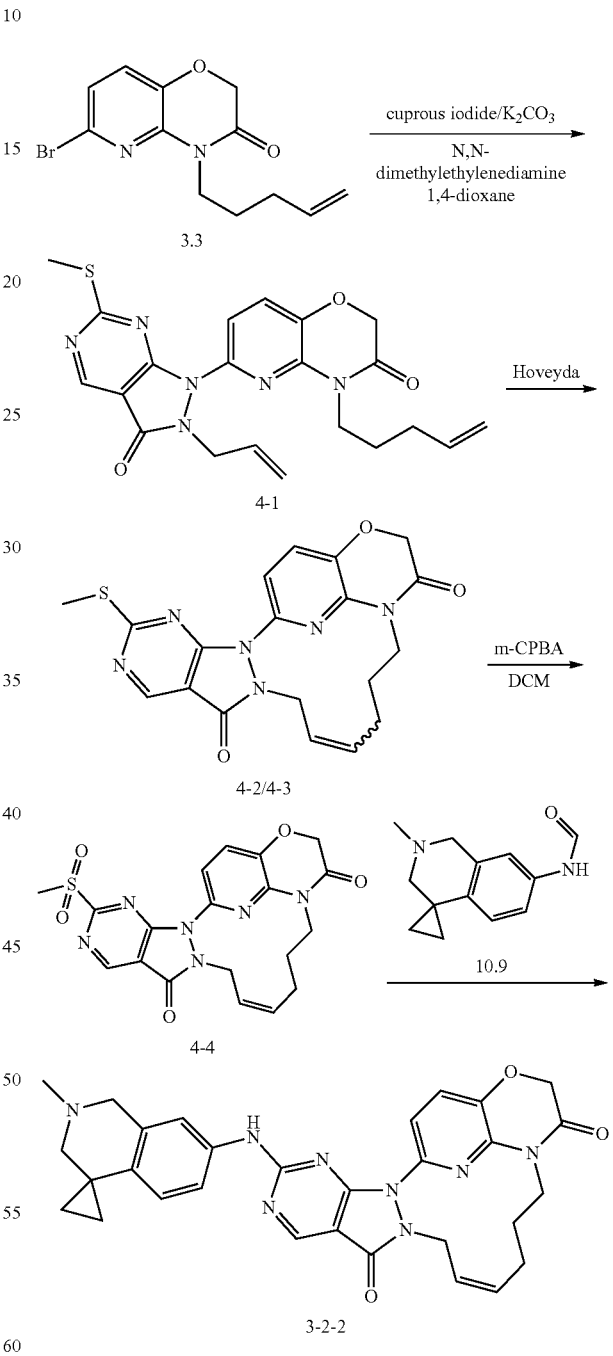

Step 1: Compound 3.3 (53 g, 0.18 mol) and 2-allyl-6-(methylthio)-1H-pyrazolo[3,4-d] pyrimidin-3(2H)-one (35.7 g, 0.61 mol) was dissolved in 1,4-dioxane (530 mL) and DMF (53 mL), to the above solution was added cuprous iodide (34 g, 178 mmol) and cesium carbonate (116 g, 356 mmol), after 5 min was added N,N-dimethylethylenediamine (15.7 g, 178 mmol). The mixture was stirred at 100° C. for overnight under nitrogen. The mixture was diluted with ethyl acetate and washed with $H_2O$, the organic layer was separated and dried over anhydrous sodium sulfate, filtered and concentrated. The residue was purified by column chromatography on silica gel (petroleum ether/ethyl acetate=1/1) to afford compound 4-1 (42 g, yield: 54%) as an off-white solid.

m/z: $[M+H]^+$ 438.9

Step 2: To a solution of compound 4-1 (42.0 g, 950 mmol) in DCM (420 mL) was added Hoveyda-Grubbs reagent (2.3 g) in 4 batches during 4 h, the reaction system was stirred at 40° C. for overnight and then the reaction solution was concentrated, the residue was purified by column chromatography on silica gel, eluted with the eluent petroleum ether/ethyl acetate=5/1~1/1 for 45 minutes to afford compound 4-3 (600 mg, yield: 1.5%) and then eluted with the the eluent petroleum ether/ethyl acetate=1/1 for 45 minutes to afford compound 4-2 (25.2 g, yield: 64%), as white solids.

m/z: $[M+H]^+$ 411.2

Step 3: To a solution of compound 4-2 (700 mg, 1.7 mmol) in DCM (20 mL) was added m-CPBA (355 mg, 1.8 mmol) in small portions under ice-water bath. After the addition, the reaction system was stirred at 0° C. for 30 min. The reaction solution was successively washed with saturated aqueous solution of sodium bicarbonate (10 mL) and brine (20 mL). The organic layer was dried over anhydrous sodium sulfate, filtered and concentrated to afford compound 4-4 (730 mg, yield: 100%) as a yellow solid.

Step 4: Compound 4-4 (300 mg, 0.7 mmol), compound 10.8 (146 mg, 0.77 mmol) and N,N-diisopropylethylamine (136 mg, 1.1 mmol) was dissolved in toluene (20 mL), the reaction system was stirred at 70° C. for overnight and then the mixture was washed with brine (20 mL×2), dried over anhydrous sodium sulfate, filtered and concentrated. The residue was purified by column chromatography on silica gel (DCM/methanol=10/1), the obtained compound was recrystallized from methanol to afford compound 3-2-2 (137 mg, yield: 35%) as a yellow solid.

m/z: $[M+H]^+$ 550.9; $^1H$ NMR (400 MHz, $CD_3OD$): δ 8.81 (s, 1H), 7.65 (d, J=2.0 Hz, 1H), 7.60-7.56 (m, 2H), 7.48 (d, J=8.4 Hz, 1H), 6.84 (d, J=8.8 Hz, 1H), 5.91 (dt, J=7.2, 11.2 Hz, 1H), 5.55 (dt, J=7.2, 11.2 Hz, 1H), 4.82 (s, 2H), 4.60, 4.47 (two q, J=16.0 Hz, 2H), 4.37 (d, J=7.2 Hz, 2H), 4.09 (t, J=4.4 Hz, 2H), 3.63, 3.27 (two q, J=12.4 Hz, 2H), 3.09 (s, 3H), 2.14 (br. s, 2H), 1.87 (br. s, 2H), 1.31-1.05 (m, 4H).

Embodiment 52: Synthesis of Compound 3-3-1

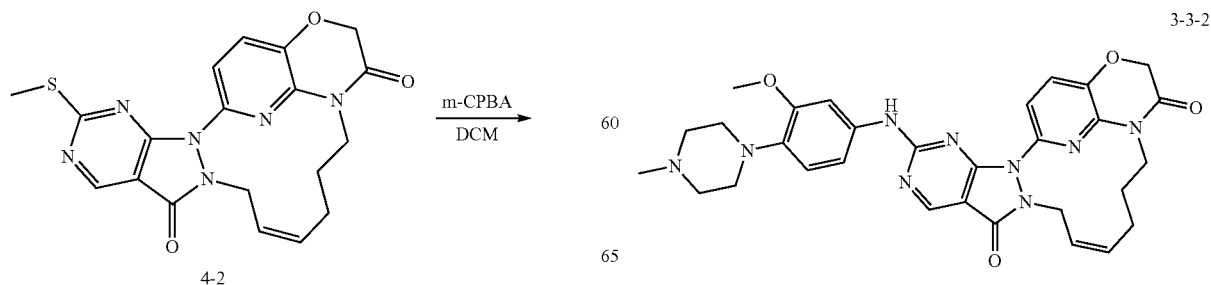

4-2

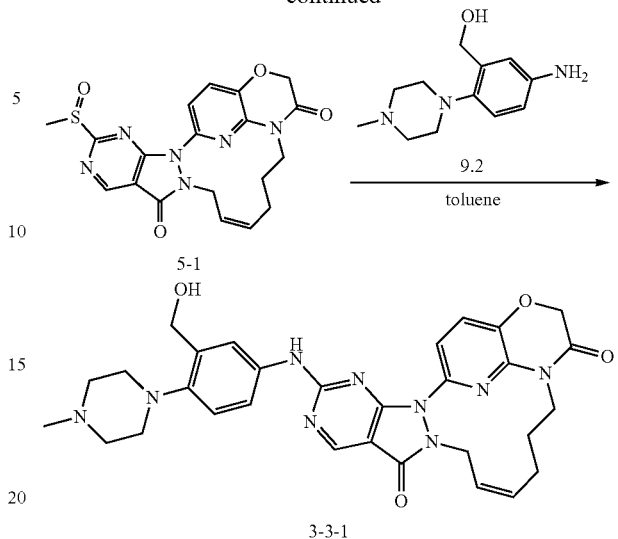

Step 1: To a solution of compound 4-2 (700 mg, 1.7 mmol) in DCM (20 mL) was added m-CPBA (355 mg, 1.8 mmol) in small portions under ice-water bath. After the addition, the reaction system was stirred at 0° C. for 30 min. The mixture was successively washed with saturated aqueous solution of sodium bicarbonate (10 mL) and brine (20 mL). The organic layer was dried over anhydrous sodium sulfate, filtered and concentrated to afford compound 5-1 (730 mg, yield: 100%) as a yellow solid.

m/z: $[M+H]^+$ 427.0

Step 2: Compound 5-1 (250 mg, 0.59 mmol), compound 9.2 (143 mg, 0.64 mmol) and N,N-diisopropylethylamine (114 mg, 0.88 mmol) was dissolved in toluene (10 mL), the reaction system was stirred at 70° C. for 16 h. The reaction system was concentrated under reduced pressure, the residue was dissolved in DCM (30 mL) and washed with brine (30 mL), dried over anhydrous sodium sulfate, filtered and concentrated. The residue was purified by column chromatography on silica gel (DCM/methanol=10/1), the obtained product was recrystallized from methanol to afford compound 3-3-1 (50 mg, yield: 15%) as a yellow solid.

m/z: $[M+H]^+$ 583.9; $^1H$ NMR (400 MHz, $CDCl_3$): δ 8.78 (s, 1H), 7.50 (br. s, 1H), 7.42 (d, J=7.2 Hz, 1H), 7.40 (s, 1H), 7.30 (d, J=6.8 Hz, 1H), 7.12 (d, J=8.8 Hz, 1H), 5.98-6.07 (m, 1H), 5.47 (dt, J=10.8, 7.2 Hz, 1H), 4.68 (s, 4H), 4.27 (d, J=7.6 Hz, 2H), 4.08-4.11 (m, 2H), 2.95 (t, J=4.8 Hz, 4H), 2.57 (br. s, 4H), 2.32 (s, 3H), 2.05 (br. s, 2H), 1.85 (br. s, 2H), 1.58 (br. s, 2H).

Embodiment 53: Synthesis of Compound 3-3-2

Compound 3-3-2 (cis) was synthesized following the synthetic method to the one used for compound 3-3-1, by replacing compound 9.2 to 3-methoxy-4-(4-methylpiperazin-1-yl)aniline in step 2.

m/z: [M+H]$^+$ 583.9; $^1$H NMR (400 MHz, CD$_3$OD): δ 8.76 (s, 1H), 7.42 (d, J=8.4 Hz, 1H), 7.34 (d, J=8.4 Hz, 1H), 7.27 (d, J=2.4 Hz, 1H), 7.06 (dd, J=8.4, 2.4 Hz, 1H), 6.88 (d, J=8.8 Hz, 1H), 5.70-5.77 (m, 1H), 5.44-5.55 (m, 1H), 4.73 (s, 2H), 4.32 (d, J=7.2 Hz, 2H), 4.05 (t, J=4.8 Hz, 2H), 3.69 (s, 3H), 3.47 (d, J=10.4 Hz, 4H), 3.22-3.26 (m, 2H), 2.92-2.98 m, 2H), 2.87 (s, 3H), 2.05 (br. s, 2H), 1.81 (br. s, 2H).

Embodiment 54: Synthesis of Compound 3-3-3

3-3-3

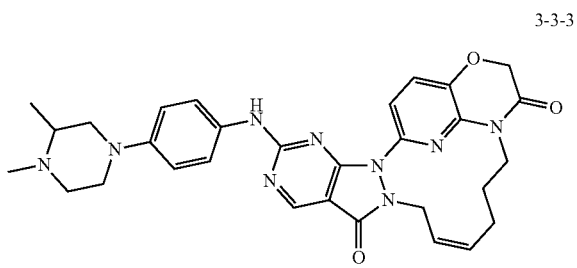 [SMILES: CC1CN(c2ccc(Nc3ncc4c(=O)n5n(c4n3)-c3ccc4c(n3)N(CCC/C=C\C5)C(=O)CO4)cc2)CCN1C]

Compound 3-3-3 (cis) was synthesized following the synthetic method to the one used for compound 3-3-1, by replacing compound 9.2 to 3-methyl-4-(4-methylpiperazin-1-yl)aniline in step 2.

m/z: [M+H]$^+$ 567.9; $^1$H NMR (400 MHz, CDCl$_3$): δ 8.70 (s, 1H), 7.50 (d, J=9.2 Hz, 2H), 7.44 (d, J=8.8 Hz, 1H), 7.38 (d, J=8.8 Hz, 1H), 6.89 (d, J=9.2 Hz, 2H), 5.79-5.87 (m, 1H), 5.44-5.51 (m, 1H), 4.70 (s, 2H), 4.29 (d, J=7.6 Hz, 2H), 4.00-4.07 (m, 2H), 3.72 (t, J=14.8 Hz, 2H), 3.53 (d, J=12.8 Hz, 1H), 3.24-3.40 (m, 2H), 2.86-2.97 (m, 4H), 2.67 (dd, J=13.2, 10.8 Hz, 1H), 2.05 (d, J=4.4 Hz, 2H), 1.75-1.84 (m, 2H), 1.36 (d, J=6.4 Hz, 3H).

Embodiment 55: Synthesis of Compound 3-3-4

3-3-4

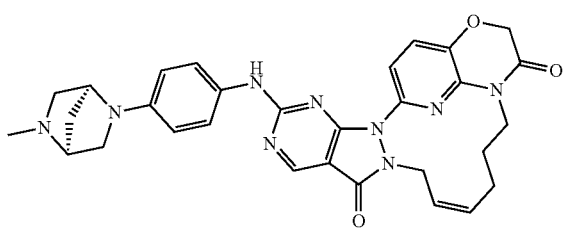

Compound 3-3-4 (cis) was synthesized following the synthetic method to the one used for compound 3-3-1, by replacing compound 9.2 to 4-((1S,4S)-5-methyl-2,5-diazabicyclo[2.2.1] heptan-2-yl)aniline in step 2.

m/z: [M+H]$^+$ 565.8; $^1$H NMR (400 MHz, DMSO-d$_6$): δ 10.47 (br. s, 1H), 8.81 (s, 1H), 7.69 (br. s, 1H), 7.53 (d, J=8.0 Hz, 2H), 7.47 (d, J=8.4 Hz, 1H), 6.65 (dd, J=12.0, 9.2 Hz, 2H), 5.86 (s, 1H), 5.47-5.57 (m, 1H), 4.85 (s, 2H), 4.52-4.64 (m, 1H), 4.31-4.43 (m, 1H), 4.22 (d, J=7.4 Hz, 2H), 3.96-4.03 (m, 2H), 3.45-3.63 (m, 3H), 3.04 (d, J=11.6 Hz, 1H), 2.67-2.86 (m, 3H), 2.37 (d, J=11.2 Hz, 1H), 2.03-2.21 (m, 3H), 1.81 (br. s, 2H).

Embodiment 56: Synthesis of Compound 3-3-5

3-3-5

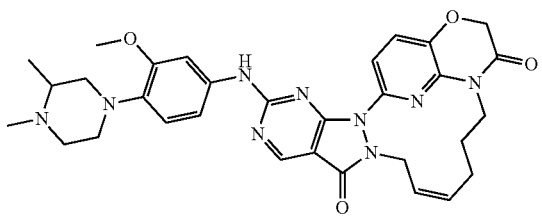

Compound 3-3-5 (cis) was synthesized following the synthetic method to the one used for compound 3-3-1, by replacing compound 9.2 to 4-(3,4-dimethylpiperazin-1-yl)-3-methoxyaniline in step 2.

m/z: [M+H]$^+$ 598.0; $^1$H NMR (400 MHz, DMSO-d$_6$): δ 10.85 (s, 1H), 10.12 (br. s, 1H), 8.85 (s, 1H), 7.64 (dd, J=8.4, 2.8 Hz, 1H), (m, 1H), 7.43 (d, J=8.0 Hz, 2H), 7.25 (d, J=6.8 Hz, 1H), 6.88 (d, J=8.8 Hz, 1H), 5.68-5.80 (m, 1H), 5.47-5.57 (m, 1H), 4.86 (m, 2H), 4.23 (d, J=7.2 Hz, 2H), 3.96-4.00 (m, 3H), 3.63 (br. s, 3H), 3.34-3.49 (m, 3H), 3.17-3.29 (m, 1H), 2.97-3.07 (m, 1H), 2.80 (d, J=4.4 Hz, 4H), 2.07 (br. s, 2H), 1.80 (br. s, 2H), 1.33 (d, J=6.4 Hz, 3H).

Embodiment 57: Synthesis of Compound 3-3-6

3-3-6

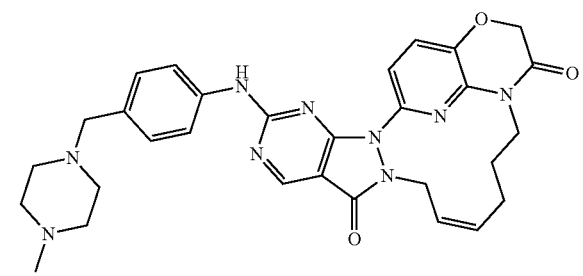

Compound 3-3-6 (cis) was synthesized following the synthetic method to the one used for compound 3-3-1, by replacing compound 9.2 to 4-((4-methylpiperazin-1-yl)methyl)aniline in step 2.

m/z: [M+H]$^+$ 567.9; $^1$H NMR (400 MHz, CDCl$_3$): δ 8.79 (s, 1H), 7.46 (d, J=8.4 Hz, 2H), 7.40 (d, J=3.2 Hz, 1H), 7.37 (dd, J=8.4, 2.8 Hz, 2H), 7.21 (s, 1H), 5.95-6.03 (m, 1H), 5.46 (dt, J=10.8, 7.2 Hz, 1H), 4.70 (s, 2H), 4.27 (d, J=7.2 Hz, 2H), 4.08 (dd, J=5.2, 4.4 Hz, 2H), 3.42 (s, 2H), 2.44 (br. s, 4H), 2.25 (s, 3H), 2.05 (br. s, 2H), 1.84 (br. s, 2H), 1.60 (br. s, 4H).

Embodiment 58: Synthesis of Compound 3-3-7

3-3-7

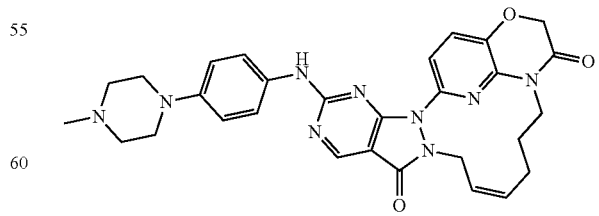

Compound 3-3-7 (cis) was synthesized following the synthetic method to the one used for compound 3-3-1, by replacing compound 9.2 to 4-(N-methylpiperazin)aniline in step 2.

m/z: [M+H]+ 553.7; 1H NMR (400 MHz, DMSO-d6): δ 10.76 (s, 1H), 8.83 (s, 1H), 7.69 (d, J=8.0 Hz, 1H), 7.61 (d, J=8.8 Hz, 2H), 7.48 (d, J=8.4 Hz, 1H), 6.98 (d, J=9.2 Hz, 2H), 5.90-5.79 (m, 1H), 5.51-5.55 (m, 1H), 4.85 (s, 2H), 4.23 (d, J=7.2 Hz, 2H), 4.00 (t, J=4.0 Hz, 2H), 3.76 (d, J=12.8 Hz, 2H), 3.49 (d, J=11.6 Hz, 2H), 3.05-3.16 (m, 4H), 2.81 (d, J=4.4 Hz, 3H), 2.15 (br. s, 2H), 1.94 (br. s, 2H).

Embodiment 59: Synthesis of Compound 3-3-8

3-3-8

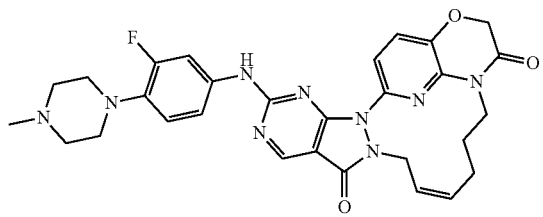

Compound 3-3-8 (cis) was synthesized following the synthetic method to the one used for compound 3-3-1, by replacing compound 9.2 to 3-fluoro-4-methylpiperazin-1-aniline in step 2.

m/z: [M+H]+ 571.9; 1H NMR (400 MHz, CDCl3): δ 8.78 (s, 1H), 7.66 (d, J=10.8 Hz, 1H), 7.45-7.37 (m, 3H), 6.96-6.93 (m, 1H), 6.84 (t, J=8.8 Hz, 1H), 6.03 (dd, J=8.0, 10.0 Hz, 1H), 5.47 (dt, J=7.2, 11.2 Hz, 1H), 4.69 (s, 2H), 4.28 (d, J=7.6 Hz, 2H), 4.09 (t, J=4.8 Hz, 2H), 3.05 (t, J=4.8 Hz, 4H), 2.60 (s, 4H), 2.33 (s, 3H), 2.06 (s, 2H), 1.85 (s, 2H).

Embodiment 60: Synthesis of Compound 3-3-9

3-3-9

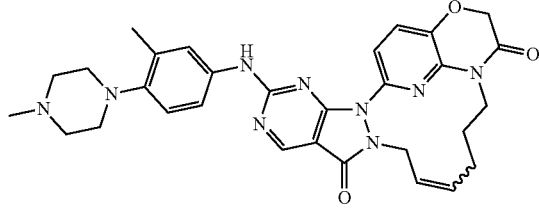

Compound 3-3-9 (a mixture of cis and trans) was synthesized following the synthetic method to the one used for compound 3-3-1, by replacing compound 4-2 to a mixture of compound 4-2 and 4-3 in step 1 and compound 9.2 to 3-methyl-4-methylpiperazin-1-aniline in step 2.

m/z: [M+H]+ 567.9; 1H NMR (400 MHz, CDCl3): δ 8.76 (s, 1H), 7.55 (s, 1H), 7.43-7.25 (m, 2H), 7.23 (d, J=2.8 Hz, 1H), 6.92 (d, J=8.4 Hz, 1H), 6.07-5.95 (m, 1H), 5.49-5.43 (m, 1H), 4.70 (s, 2H), 4.27 (d, J=1.2 Hz, 2H), 4.10-4.07 (m, 2H), 2.88-2.85 (m, 4H), 2.55-2.46 (m, 4H), 2.31 (s, 3H), 2.23 (s, 3H), 2.07 (s, 2H), 1.82 (s, 2H) (major rotamer 4:1).

Embodiment 61: Synthesis of Compound 3-3-10

3-3-10

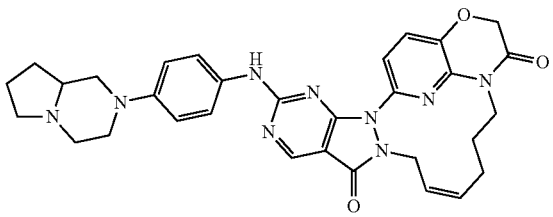

Compound 3-3-10 (cis) was synthesized following the synthetic method to the one used for compound 3-3-1, by replacing compound 9.2 to 12.2 in step 2.

m/z: [M+H]+ 580.0; 1H NMR (400 MHz, DMSO-d6): δ 10.03 (d, J=3.6 Hz, 1H), 8.80 (s, 1H), 7.72-7.71 (m, 1H), 7.54 (d, J=9.2 Hz, 2H), 7.47 (d, J=8.4 Hz, 1H), 6.91 (d, J=8.8 Hz, 2H), 5.88-5.83 (m, 1H), 5.55-5.48 (m, 1H), 4.84 (s, 2H), 4.21 (d, J=7.2 Hz, 2H), 3.99 (s, 2H), 3.72 (d, J=10.4 Hz, 1H), 3.43 (d, J=3.6 Hz, 1H), 3.06-2.99 (m, 2H), 2.71-2.65 (m, 1H), 2.35 (t, J=10.4 Hz, 1H), 2.25-2.20 (m, 1H), 2.09-1.99 (m, 4H), 1.85-1.72 (m, 5H), 1.40-1.32 (m, 1H).

Embodiment 62: Synthesis of Compound 3-3-11

3-3-11

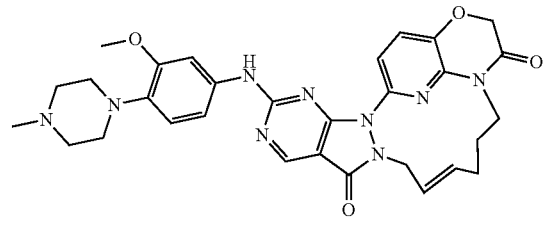

Compound 3-3-11 (trans) was synthesized following the synthetic method to the one used for compound 3-3-1, by replacing compound 4.2 to 4.3 in step 1 and compound 9.2 to 3-methoxy-4-(4-methylpiperazin-1-yl)aniline in step 2.

m/z: [M+H]+ 584.3; 1H NMR (400 MHz, CDCl3): δ 8.76 (s, 1H), 7.37 (s, 1H), 7.36 (d, J=8.4 Hz, 1H), 7.29 (d, J=8.0 Hz, 1H), 7.07 (s, 1H), 6.99 (d, J=9.2 Hz, 1H), 6.81 (d, J=8.8 Hz, 1H), 5.43-5.31 (m, 2H), 4.61 (s, 2H), 4.30 (s, 2H), 4.12 (s, 2H), 3.73 (s, 3H), 3.01 (s, 4H), 2.56 (s, 4H), 2.29 (s, 3H), 1.98 (dd, J=6.0, 11.6 Hz, 2H), 1.82 (s, 2H).

Embodiment 63: Synthesis of Compound 3-3-12

3-3-12

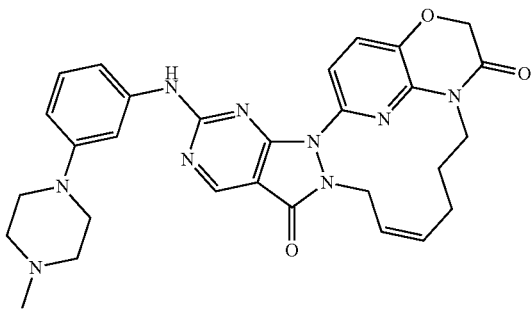

Compound 3-3-12 (cis) was synthesized following the synthetic method to the one used for compound 3-3-1, by replacing compound 9.2 to 3-(4-methylpiperazin-1-yl)aniline in step 2.

m/z: [M+H]$^+$ 554.2; $^1$H NMR (400 MHz, DMSO-d$_6$): δ 10.13 (s, 1H), 9.66 (s, 1H), 8.89 (s, 1H), 7.65 (d, J=8.0 Hz, 1H), 7.48-7.37 (m, 2H), 7.25-7.15 (m, 2H), 6.74-6.64 (m, 1H), 5.79-5.69 (m, 1H), 5.58-5.48 (m, 1H), 4.89 (s, 2H), 4.29-4.19 (m, 2H), 4.41-3.97 (m, 2H), 3.66 (d, J=12.4 Hz, 2H), 3.59-3.45 (m, 2H), 3.19-3.07 (m, 2H), 2.95-2.78 (m, 5H), 2.08 (s, 2H), 1.82 (s. 2H).

Embodiment 64: Synthesis of Compound 3-3-13

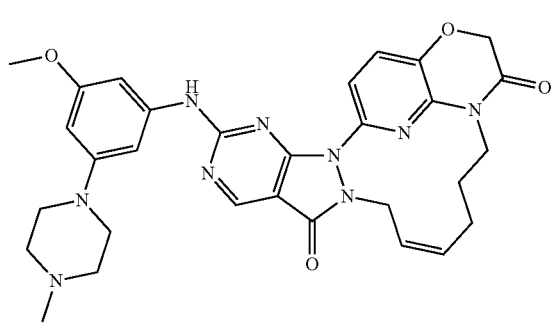

3-3-13

Compound 3-3-13 (cis) was synthesized following the synthetic method to the one used for compound 3-3-1, by replacing compound 9.2 to 25.2 in step 2.

m/z: [M+H]$^+$ 584.3; $^1$H NMR (400 MHz, CDCl$_3$): δ 8.86 (s, 1H), 7.45-7.38 (m, 2H), 6.79 (s, 1H), 6.74 (s, 1H), 6.21 (t, J=2.0 Hz, 1H), 6.05-5.99 (m, 1H), 5.58-5.51 (m, 1H), 4.76 (s, 2H), 4.35 (d, J=7.2 Hz, 2H), 4.19-4.14 (m, 2H), 3.74 (s, 3H), 3.21-3.13 (m, 4H), 2.66-2.58 (s, 4H), 2.40 (s, 3H), 2.15-2.07 (m, 2H), 1.96-1.88 (m, 2H).

Embodiment 65: Synthesis of Compound 3-3-14

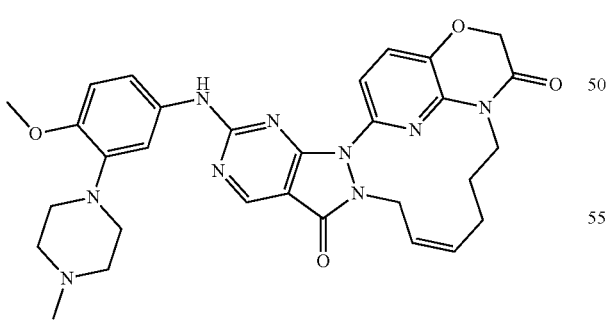

3-3-14

Compound 3-3-14 (cis) was synthesized following the synthetic method to the one used for compound 3-3-1, by replacing compound 9.2 to 25.3 in step 2.

m/z: [M+H]$^+$ 584.3; $^1$H NMR (400 MHz, DMSO-d$_6$): δ 10.01 (br. s, 1H), 8.82 (s, 1H), 7.65-7.61 (m, 1H), 7.35-7.29 (m, 2H), 7.17 (s, 1H), 6.85 (d, J=8.8 Hz, 1H), 5.73-5.68 (m, 1H), 5.57-5.52 (m, 1H), 4.86 (s, 2H), 4.21 (d, J=7.2 Hz, 2H), 4.02-4.01 (m, 2H), 3.73 (s, 3H), 2.80-2.70 (m, 4H), 2.39-2.36 (m, 4H), 2.19 (s, 3H), 2.20-2.10 (m, 2H), 1.83-1.79 (m, 2H).

Embodiment 66: Synthesis of Compound 3-4-1

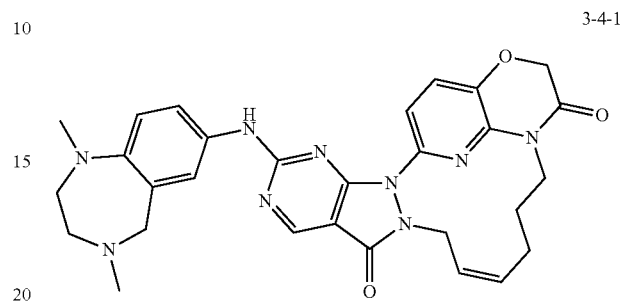

3-4-1

Compound 3-4-1 (cis) was synthesized following the synthetic method to the one used for compound 3-3-1, by replacing compound 9.2 to 8.3 in step 2.

m/z: [M+H]$^+$ 554.1; $^1$H NMR (400 MHz, DMSO-d$_6$): δ 11.11 (br. s, 1H), 10.23 (br. s, 1H), 8.85 (s, 1H), 7.70-7.75 (m, 2H), 7.60 (dd, J=8.8, 2.8 Hz, 1H), 7.48 (d, J=8.0 Hz, 1H), 6.99 (d, J=8.8 Hz, 1H), 5.83-5.80 (m, 1H), 5.48-5.52 (m, 1H), 4.91 (s, 2H), 4.23 (d, J=7.3 Hz, 4H), 3.98 (t, J=4.4 Hz, 2H), 3.34-3.45 (m, 1H), 3.08-3.31 (m, 3H), 2.86 (s, 3H), 2.75 (d, J=4.0 Hz, 3H), 2.06 (br. s, 2H), 1.79 (br. s, 2H).

Embodiment 67: Synthesis of Compound 3-4-2

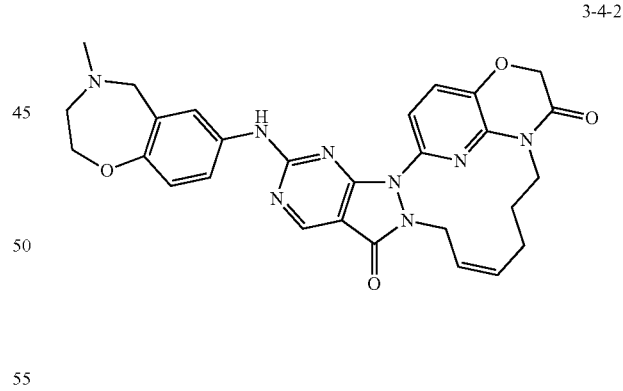

3-4-2

Compound 3-4-2 (cis) was synthesized following the synthetic method to the one used for compound 3-3-1, by replacing compound 9.2 to 17.3 in step 2.

m/z: [M+H]$^+$ 540.9; $^1$H NMR (400 MHz, CDCl$_3$): δ 8.87 (s, 1H), 7.50-7.41 (m, 4H), 7.35 (dd, J=2.8, 8.8 Hz, 1H), 6.98 (d, J=8.8 Hz, 1H), 6.12 (dd, J=7.2, 18.4 Hz, 1H), 5.54 (dt, J=7.2, 11.2 Hz, 1H), 4.78 (s, 2H), 4.36 (d, J=7.6 Hz, 2H), 4.22-4.15 (m, 2H), 4.11-4.06 (m, 2H), 3.72 (s, 2H), 3.06-2.98 (m, 2H), 2.43 (s, 3H), 2.19-2.11 (m, 2H), 1.98-1.89 (m, 2H).

Embodiment 68: Synthesis of Compound 3-2-3

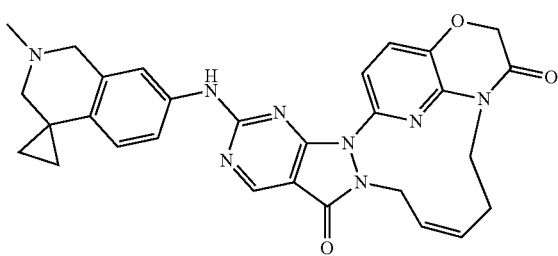

3-2-3

Compound 3-2-3 (cis) was synthesized following the synthetic method to the one used for compound 1-1-1, by replacing compound 1.1 to 3.5 in step 1 and 4-(N-methylpiperazin)aniline to compound 10.8 in step 4.

m/z: [M+H]$^+$ 536.6; $^1$H NMR (400 MHz, CDCl$_3$): δ 8.87 (s, 1H), 7.73 (d, J=8.8 Hz, 1H), 7.43 (d, J=8.8 Hz, 2H), 7.30 (d, J=2.0 Hz, 1H), 6.69 (d, J=8.4 Hz, 1H), 6.22 (dt, J=8.0, 11.2 Hz, 1H), 5.88 (dd, J=8.8, 20 Hz, 1H), 4.80 (s, 2H), 4.44 (d, J=8.0 Hz, 2H), 4.15-4.02 (m, 2H), 3.77 (s, 2H), 2.62 (s, 2H), 2.53 (s, 3H), 2.44 (dd, J=6.4, 10.8 Hz, 2H), 1.07-0.83 (m, 4H).

Embodiment 69: Synthesis of Compound 3-2-5

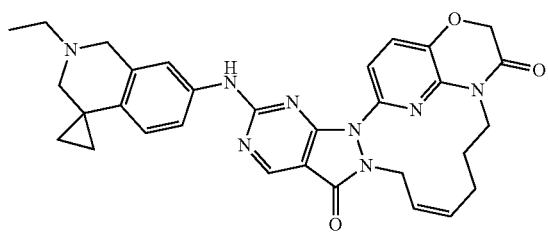

3-2-5

Compound 3-2-5 (cis) was synthesized following the synthetic method to the one used for compound 3-3-1, by replacing compound 9.2 to 10.10 in step 2.

m/z: [M+H]$^+$ 565.4; $^1$H NMR (400 MHz, CD$_3$OD): δ 8.74 (s, 1H), 7.61 (s, 1H), 7.49 (d, J=8.4 Hz, 1H), 7.43 (dd, J=2.4, 8.8 Hz, 1H), 7.39 (d, J=8.4 Hz, 1H), 6.73 (d, J=8.8 Hz, 1H), 5.81 (dt, J=7.2, 10.8 Hz, 1H), 5.50-5.44 (m, 1H), 4.71 (s, 2H), 4.47 (d, J=14.8 Hz, 1H), 4.33 (d, J=14.8 Hz, 1H), 4.30 (d, J=7.2 Hz, 2H), 4.01 (d, J=4.4 Hz, 2H), 3.51 (d, J=12.4 Hz, 1H), 3.30-3.22 (m, 2H), 3.15 (d, J=12.4 Hz, 1H), 2.05 (s, 2H), 1.79 (s, 2H), 1.35 (t, J=7.2 Hz, 3H), 1.19-1.04 (m, 4H).

Embodiment 70: Synthesis of Compounds 3-2-6 and 3-2-7

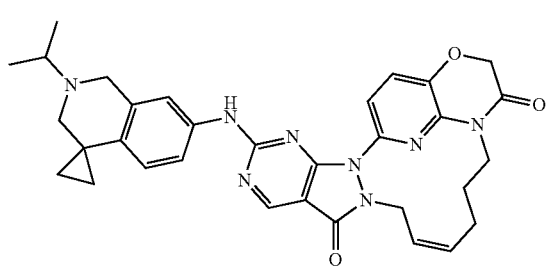

3-2-6

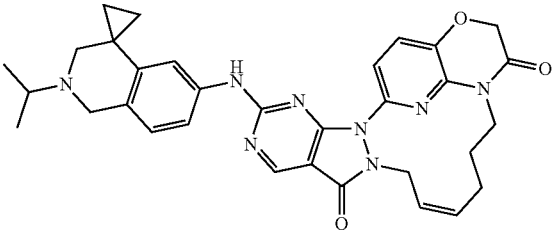

3-2-7

Compounds 3-2-6 (cis) and 3-2-7 (cis) were synthesized following the synthetic method to the one used for compound 3-3-1, by replacing compound 9.2 to 10.11 in step 2, and the final step was purified by prep-HPLC.

3-2-6: m/z: [M+H]$^+$ 579.4; $^1$H NMR (400 MHz, CD$_3$OD): δ 8.74 (d, J=3.2 Hz, 1H), 7.64 (s, 1H), 7.49 (d, J=8.4 Hz, 1H), 7.42 (dd, J=2.0, 8.8 Hz, 1H), 7.39 (d, J=8.4 Hz, 1H), 6.74 (d, J=8.8 Hz, 1H), 5.82-5.78 (m, 1H), 5.49-5.46 (m, 1H), 4.72 (s, 2H), 4.50 (d, J=15.2 Hz, 1H), 4.31 (d, J=7.2 Hz, 2H), 4.28 (d, J=15.6 Hz, 1H), 4.03 (d, J=4.4 Hz, 2H), 3.59 (dd, J=6.4, 12.8 Hz, 2H), 3.00 (d, J=12.0 Hz, 1H), 2.06 (br. s, 2H), 1.80 (br. s, 2H), 1.36 (d, J=6.4 Hz, 6H), 1.19-0.90 (m, 4H).

3-2-7: m/z: [M+H]$^+$ 579.4; $^1$H NMR (400 MHz, CD$_3$OD): δ 8.74 (d, J=3.2 Hz, 1H), 7.64 (s, 1H), 7.49 (d, J=8.4 Hz, 1H), 7.42 (dd, J=2.0, 8.8 Hz, 1H), 7.39 (d, J=8.4 Hz, 1H), 6.74 (d, J=8.8 Hz, 1H), 5.82-5.78 (m, 1H), 5.46-5.49 (m, 1H), 4.75 (s, 2H), 4.50 (d, J=15.2 Hz, 1H), 4.32-4.27 (m, 3H), 4.04-4.03 (m, 2H), 3.62-3.57 (m, 2H), 3.01 (d, J=12.0 Hz, 1H), 2.06 (br. s, 2H), 1.80 (br. s, 2H), 1.36 (d, J=6.4 Hz, 6H), 1.11-0.90 (m, 4H).

Embodiment 71: Synthesis of Compound 3-2-8

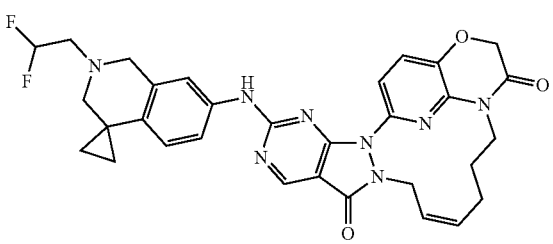

3-2-8

Compound 3-2-8 (cis) was synthesized following the synthetic method to the one used for compound 3-3-1, by replacing compound 9.2 to 10.15 in step 2.

m/z: [M+H]$^+$ 601.0; $^1$H NMR (400 MHz, CD$_3$OD): δ 8.90 (s, 1H), 7.71 (d, J=2.0 Hz, 1H), 7.67 (d, J=8.0 Hz, 1H), 7.57 (dd, J=2.4, 8.8 Hz, 1H), 7.50 (d, J=8.4 Hz, 1H), 6.89 (d, J=8.8 Hz, 1H), 6.54 (tt, J=3.6, 12.0 Hz, 1H), 5.93-5.90 (m, 1H), 5.63-5.59 (m, 1H), 4.86 (s, 2H), 4.69 (s, 2H), 4.44 (d, J=7.6 Hz, 2H), 4.16 (t, J=4.8 Hz, 2H), 3.96 (td, J=3.6, 14.8 Hz, 2H), 3.62 (s, 2H), 2.18 (s, 2H), 1.93 (s, 2H), 1.31-1.22 (m, 4H).

Embodiment 72: Synthesis of Compound 3-5-1

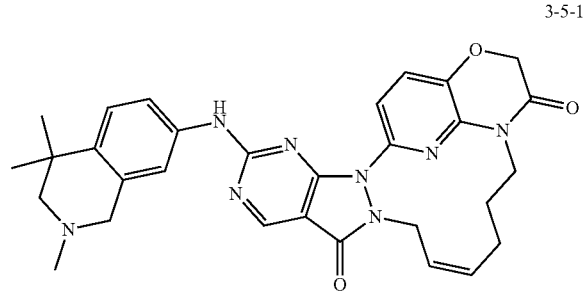 [SMILES: CN1Cc2cc(Nc3ncc4c(=O)n5n(c4n3)-c3ccc4c(n3)N(CCC/C=C\C5)C(=O)CO4)ccc2C(C)(C)C1]

Compound 3-5-1 (cis) was synthesized following the synthetic method to the one used for compound 3-3-1, by replacing compound 9.2 to 11.5 in step 2.

m/z: [M+H]$^+$ 552.9; $^1$H NMR (400 MHz, CDCl$_3$): δ 8.78 (s, 1H), 7.41 (s, J=8.4 Hz, 1H), 7.35 (s, J=8.4 Hz, 2H), 7.25 (d, J=8.4 Hz, 2H), 6.02 (dt, J=7.6, 10.4 Hz, 1H), 5.47 (dt, J=7.2, 11.2 Hz, 1H), 4.69 (s, 2H), 4.27 (d, J=7.2 Hz, 2H), 4.10 (t, J=4.8 Hz, 2H), 3.45 (s, 2H), 2.37 (s, 3H), 2.35 (s, 2H), 2.06 (br. s, 2H), 1.85 (br. s, 2H), 1.24 (s, 6H).

Embodiment 73: Synthesis of Compound 3-5-2

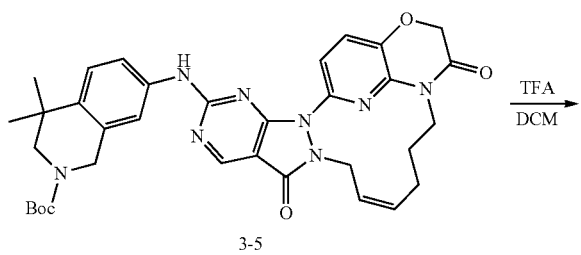

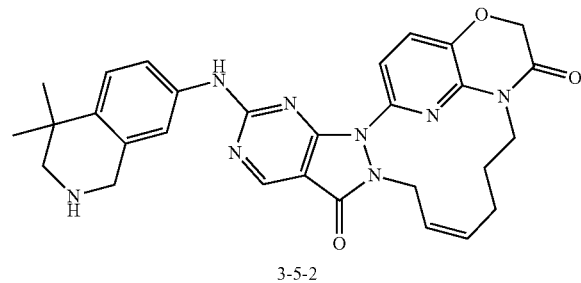

Compound 3-5 (cis) was synthesized following the synthetic method to the one used for compound 3-3-1, by replacing compound 9.2 to tert-butyl 7-amino-4,4-dimethyl-3,4-dihydroisoquinoline-2(1H)-carboxylate in step 2.

The mixture of compound 3-5 (150 mg, 0.235 mmol) in THF (1 mL) and DCM (5 mL) was stirred at room temperature for 1 h. The reaction solution was concentrated under reduced pressure, the residue was purified by prep-HPLC to afford compound 3-5-2 (cis) (44.6 mg, yield: 25%) as a white solid.

m/z: [M+H]$^+$ 539.4; $^1$H NMR (400 MHz, DMSO-d$_6$): δ 8.86 (s, 1H), 7.68 (d, J=2.4 Hz, 1H), 7.58 (d, J=8.0 Hz, 1H), 7.57 (d, J=8.8 Hz, 1H), 7.49 (d, J=8.0 Hz, 1H), 7.43 (d, J=8.8 Hz, 1H), 5.96-5.89 (m, 1H), 5.62-5.52 (m, 1H), 4.81 (s, 2H), 4.41 (d, J=7.6 Hz, 2H), 4.30 (s, 2H), 4.16-4.12 (m, 2H), 3.32 (s, 2H), 2.21-2.17 (m, 2H), 1.91 (br. s, 2H), 1.43 (s, 6H).

Embodiment 74: Synthesis of Compound 3-5-3

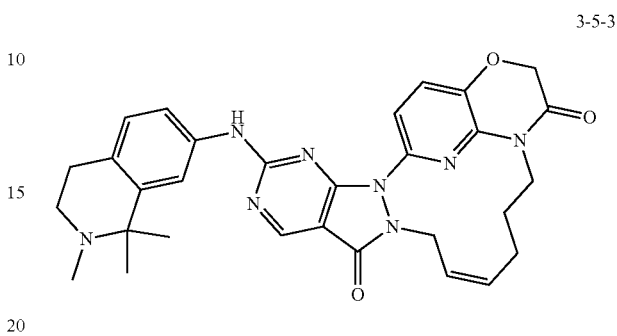

Compound 3-5-3 (cis) was synthesized following the synthetic method to the one used for compound 3-3-1, by replacing compound 9.2 to 22.5 in step 2.

m/z: [M+H]$^+$ 553.4; $^1$H NMR (400 MHz, DMSO-d$_6$): δ 10.18 (s, 1H), 9.81-9.79 (m, 1H), 8.84 (s, 1H), 7.78 (s, 1H), 7.61 (d, J=8.0 Hz, 1H), 7.54 (d, J=8.4 Hz, 1H), 7.41 (d, J=8.4 Hz, 1H), 7.14 (d, J=8.4 Hz, 1H), 5.72-5.69 (m, 1H), 5.56-5.52 (m, 1H), 4.97 (s, 2H), 4.24 (d, J=7.2 Hz, 2H), 4.01 (t, J=4.4 Hz, 2H), 3.56-3.31 (m, 2H), 3.08-2.91 (m, 2H), 2.85 (d, J=4.4 Hz, 3H), 2.09-2.01 (m, 2H), 1.89 (br. s, 2H), 1.52 (s, 3H), 1.47 (s, 3H).

Embodiment 75: Synthesis of Compound 3-6-1

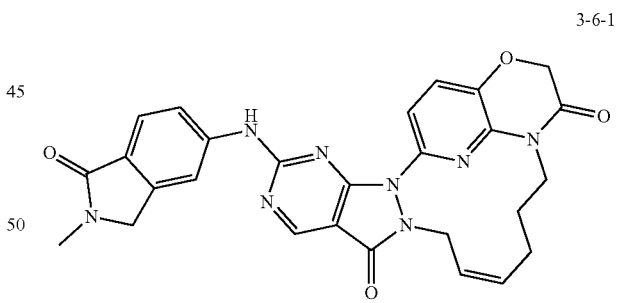

Compound 3-6-1 (cis) was synthesized following the synthetic method to the one used for compound 3-3-1, by replacing compound 9.2 to 5-amino-2-methylisoindolin-1-one in step 2.

m/z: [M+H]$^+$ 524.8; $^1$H NMR (400 MHz, DMSO-d$_6$): δ 8.93 (s, 1H), 8.10 (s, 1H), 7.74-7.71 (m, 2H), 7.59 (d, J=8.4 Hz, 1H), 7.50 (d, J=8.4 Hz, 1H), 5.80-5.91 (m, 1H), 5.49-5.60 (m, 1H), 4.83 (s, 2H), 4.43 (s, 2H), 4.27 (d, J=7.2 Hz, 2H), 3.98-4.01 (m, 2H), 3.06 (s, 3H), 2.08 (br. s, 2H), 1.81 (br. s, 2H).

Embodiment 76: Synthesis of Compound 3-7-1

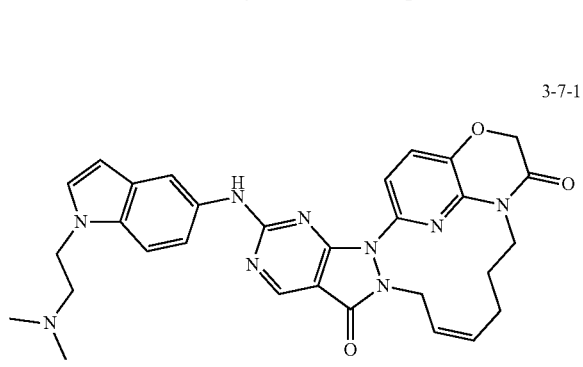 [SMILES: CN(C)CCn1ccc2cc(Nc3ncc4c(=O)n5n(c4n3)-c3ccc4c(n3)N(CCC/C=C\C5)C(=O)CO4)ccc21]

Compound 3-7-1 (cis) was synthesized following the synthetic method to the one used for compound 3-3-1, by replacing compound 9.2 to 13.2 in step 2.

m/z: [M+H]$^+$ 565.9; $^1$H NMR (400 MHz, CDCl$_3$): δ 8.86 (s, 1H), 7.96 (br. s, 1H), 7.56 (s, 1H), 7.39 (d, J=8.4 Hz, 1H), 7.32 (d, J=8.4 Hz, 1H), 7.23-7.27 (m, 1H), 7.19 (d, J=3.2 Hz, 1H), 6.45 (d, J=3.2 Hz, 1H), 6.16-6.14 (m, 1H), 5.55 (dt, J=10.8, 7.6 Hz, 1H), 4.76 (s, 2H), 4.35 (d, J=7.6 Hz, 2H), 4.26 (t, J=7.2 Hz, 2H), 4.14-4.21 (m, 2H), 2.74 (t, J=7.2 Hz, 2H), 2.34 (s, 6H), 2.15 (br. s, 2H), 1.93 (br. s, 2H).

Embodiment 77: Synthesis of Compound 3-7-2

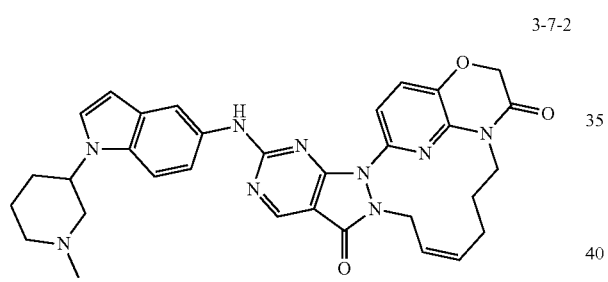

Compound 3-7-2 (cis) was synthesized following the synthetic method to the one used for compound 3-3-1, by replacing compound 9.2 to 14.5 in step 2.

m/z: [M+H]$^+$ 592.1; $^1$H NMR (400 MHz, CDCl$_3$): δ 8.78 (s, 1H), 7.84 (s, 1H), 7.48 (d, J=8.0 Hz, 1H), 7.43 (br. s, 1H), 7.40 (s, 1H), 7.32 (d, J=8.4 Hz, 1H), 7.29-7.19 (m, 1H), 6.38 (d, J=2.8 Hz, 1H), 6.07-6.05 (m, 1H), 5.47 (dt, J=7.6, 10.8 Hz, 1H), 4.68 (s, 2H), 4.44-4.39 (m, 1H), 4.26 (d, J=7.6 Hz, 2H), 4.09 (t, J=4.8 Hz, 2H), 3.06-3.02 (m, 1H), 2.81 (d, J=11.6 Hz, 1H), 2.27 (s, 3H), 2.13 (t, J=10.4 Hz, 1H), 2.06-1.97 (m, 4H), 1.86-1.69 (m, 5H).

Embodiment 78: Synthesis of Compound 3-7-3

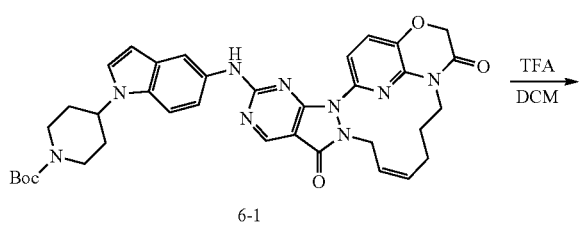

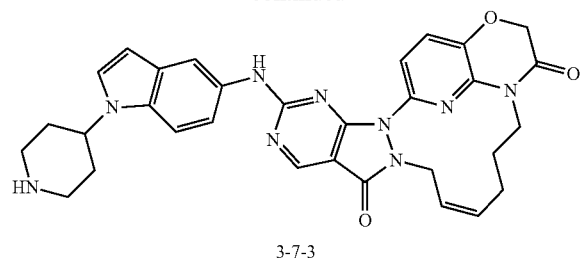

Compound 6-1 was synthesized following the synthetic method to the one used for compound 3-3-1, by replacing compound 9.2 to 15.1 in step 2.

To a solution of compound 6.1 (51 mg, 0.075 mmol) in DCM (10 mL) was added TFA (2 mL) dropwise, the reaction system was stirred at room temperature for 2 h, concentrated. The residue was purified by prep-HPLC to afford compound 3-7-3 (23.5 mg, yield: 39%) as a white solid.

m/z: [M+H]$^+$ 577.8; $^1$H NMR (400 MHz, DMSO-d$_6$): δ 10.11 (br. s, 1H), 8.83 (s, 1H), 8.67 (br. s, 1H), 8.43 (br. s, 1H), 7.97 (s, 1H), 7.64 (d, J=8.0 Hz, 1H), 7.54 (s, 1H), 7.50 (d, J=8.8 Hz, 1H), 7.41-7.37 (m, 2H), 6.45 (d, J=3.2 Hz, 1H), 5.84-5.83 (m, 1H), 5.51 (dt, J=7.2, 10.8 Hz, 1H), 4.84 (s, 1H), 4.69-4.66 (m, 1H), 4.23 (d, J=7.2 Hz, 2H), 4.00-3.98 (m, 2H), 3.49-3.40 (m, 2H), 3.23-3.15 (m, 2H), 2.14-2.09 (m, 6H), 1.80 (s, 2H).

Embodiment 79: Synthesis of Compound 3-7-4

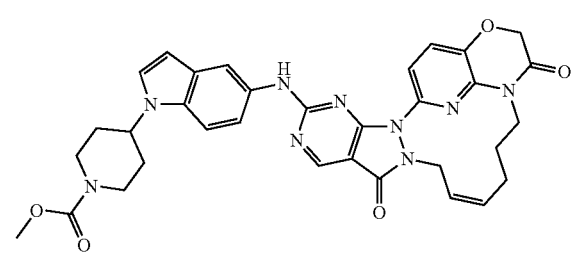

Compound 3-7-4 (cis) was synthesized following the synthetic method to the one used for compound 3-3-1, by replacing compound 9.2 to 16.2 in step 2.

m/z: [M+H]$^+$ 636.1; $^1$H NMR (400 MHz, CDCl$_3$): δ 8.87 (s, 1H), 7.97 (s, 1H), 7.57 (d, J=7.6 Hz, 1H), 7.41 (d, J=8.0 Hz, 1H), 7.34 (d, J=8.8 Hz, 1H), 7.25 (d, J=2.0 Hz, 1H), 7.22 (d, J=3.2 Hz, 1H), 6.50 (d, J=3.2 Hz, 1H), 6.25-6.15 (m, 1H), 5.58-5.51 (m, 1H), 4.77 (s, 2H), 4.44-4.39 (m, 3H), 4.36 (d, J=7.2 Hz, 2H), 4.18 (t, J=4.8 Hz, 2H), 3.77 (s, 3H), 3.05-2.99 (m, 2H), 2.16-2.12 (m, 4H), 2.01-1.94 (m, 4H).

Embodiment 80: Synthesis of Compound 3-7-5

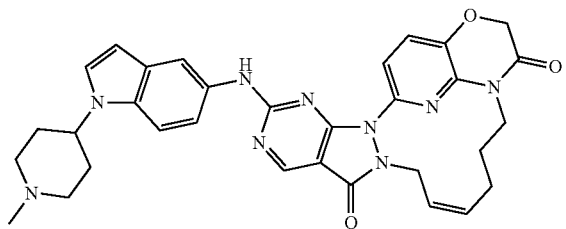

3-7-5

Compound 3-7-5 (cis) was synthesized following the synthetic method to the one used for compound 3-3-1, by replacing compound 9.2 to 14.4 in step 2.

m/z: [M+H]$^+$ 592.0; $^1$H NMR (400 MHz, DMSO-d$_6$): δ 11.21 (s, 1H), 10.21 (s, 1H), 8.85 (s, 1H), 7.97 (s, 1H), 7.69-7.35 (m, 5H), 6.44 (d, J=4.0 Hz, 1H), 5.75-5.67 (m, 1H), 5.51 (dt, J=7.2, 10.8 Hz, 1H), 4.85 (s, 2H), 4.69-4.63 (m, 1H), 4.23 (d, J=7.6 Hz, 2H), 3.99 (t, J=4.8 Hz, 2H), 3.64-3.54 (m, 2H), 3.27-3.21 (m, 2H), 2.79 (d, J=4.8 Hz, 3H), 2.52-47 (m, 2H), 2.15-2.08 (m, 4H), 1.80 (br. s, 2H).

Embodiment 81: Synthesis of Compound 3-7-6

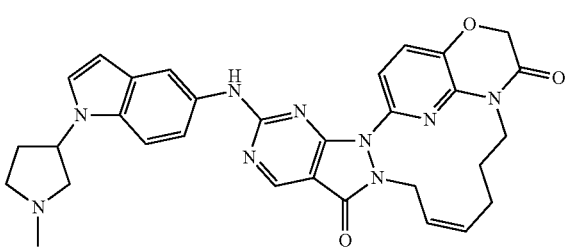

3-7-6

Compound 3-7-6 (cis) was synthesized following the synthetic method to the one used for compound 3-3-1, by replacing compound 9.2 to 14.6 in step 2.

m/z: [M+H]$^+$ 577.9; $^1$H NMR (400 MHz, CDCl$_3$): δ 8.84 (s, 1H), 7.93 (br. s, 1H), 7.56 (d, J=8.4 Hz, 2H), 7.44-7.36 (m, 3H), 7.22 (dd, J=2.0 Hz, 9.2 Hz, 1H), 6.45 (d, J=3.2 Hz, 1H), 6.14 (dd, J=7.6, 18.0 Hz, 1H), 5.54 (dt, J=7.6, 10.8 Hz, 1H), 5.04-4.96 (m, 1H), 4.74 (s, 2H), 4.33 (d, J=7.6 Hz, 2H), 4.21-4.12 (m, 2H), 3.02-2.83 (m, 3H), 2.58-2.46 (m, 2H), 2.43 (s, 3H), 2.18-2.05 (m, 3H), 1.95-1.87 (m, 2H).

Embodiment 82: Synthesis of Compound 3-7-7

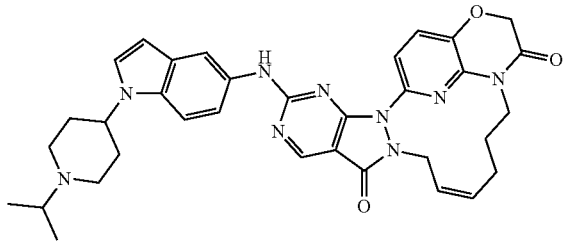

3-7-7

Compound 3-7-7 (cis) was synthesized following the synthetic method to the one used for compound 3-3-1, by replacing compound 9.2 to 14.7 in step 2.

m/z: [M+H]$^+$ 620.1; $^1$H NMR (400 MHz, CD$_3$OD): δ 8.68 (s, 1H), 7.85 (s, 1H), 7.43 (d, J=8.4 Hz, 1H), 7.37 (d, J=8.4 Hz, 1H), 7.33 (d, J=9.2 Hz, 1H), 7.26 (dd, J=2.4, 9.2 Hz, 1H), 7.21 (d, J=3.2 Hz, 1H), 6.37 (d, J=3.2 Hz, 1H), 5.87-5.83 (m, 1H), 5.47-5.44 (m, 1H), 4.67 (s, 2H), 4.63-4.62 (m, 1H), 4.26 (d, J=7.2 Hz, 2H), 4.00 (t, J=4.4 Hz, 2H), 3.56-3.53 (m, 3H), 3.30-3.22 (m, 2H), 2.29-2.04 (m, 4H), 2.04 (br. s, 2H), 1.77 (br. s, 2H), 1.34 (d, J=6.8 Hz, 6H).

Embodiment 83: Synthesis of Compound 3-7-8

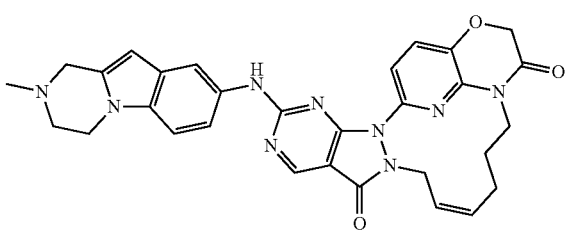

3-7-8

Compound 3-7-8 (cis) was synthesized following the synthetic method to the one used for compound 3-3-1, by replacing compound 9.2 to 18.6 in step 2.

m/z: [M+H]$^+$ 564.0; $^1$H NMR (400 MHz, DMSO-d$_6$): δ 10.51 (br. s, 1H), 10.14 (br. s, 1H), 8.84 (s, 1H), 8.01 (br. s, 1H), 7.65 (d, J=8.4 Hz, 1H), 7.53 (d, J=8.4 Hz, 1H), 7.49-7.38 (m, 3H), 6.42 (s, 1H), 5.94-5.77 (m, 1H), 5.57-5.47 (m, 1H), 4.85 (s, 2H), 4.65-4.37 (m, 2H), 4.23 (d, J=7.6 Hz, 4H), 4.04-3.89 (m, 4H), 3.02 (s, 3H), 2.14-2.02 (m, 2H), 1.86-1.73 (m, 2H).

Embodiment 84: Synthesis of Compound 3-7-9

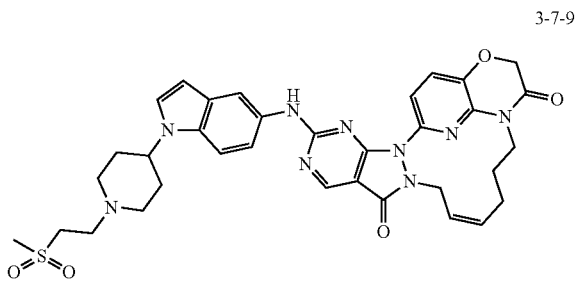 [SMILES: CS(=O)(=O)CCN1CCC(n2ccc3cc(Nc4ncc5c(=O)n6n(c5n4)-c4ccc5c(n4)N(CCC/C=C\C6)C(=O)CO5)ccc32)CC1]

3-7-9

Compound 3-7-9 (cis) was synthesized following the synthetic method to the one used for compound 3-3-1, by replacing compound 9.2 to 16.6 in step 2.

m/z: [M+H]$^+$ 683.9; $^1$H NMR (400 MHz, DMSO-d$_6$): δ 10.08 (dd, J=7.6, 9.6 Hz, 1H), 8.82 (s, 1H), 7.94 (s, 1H), 7.66 (d, J=8.4 Hz, 1H), 7.53 (d, J=8.0 Hz, 1H), 7.47 (d, J=3.2 Hz, 1H), 7.45 (s, 1H), 7.37 (d, J=8.8 Hz, 1H), 6.39 (d, J=3.2 Hz, 1H), 5.87-5.81 (m, 1H), 5.52 (dt, J=6.8, 11.2 Hz, 1H), 4.82 (s, 2H), 4.36-4.29 (m, 1H), 4.22 (d, J=7.2 Hz, 2H), 4.00-3.97 (m, 2H), 3.34-3.24 (m, 2H), 3.07 (s, 3 H), 3.02 (s, 2H), 2.79 (t, J=6.8 Hz, 2H), 2.33-2.22 (m, 2H), 2.08-2.02 (m, 2H), 1.92-1.84 (m, 4H), 1.75-1.81 (m, 2H).

Embodiment 85: Synthesis of Compound 3-7-10

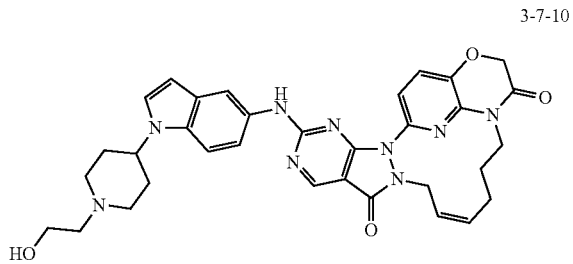 [SMILES: O=C1COc2ccc3nc2N1CCC/C=C\Cn1c(=O)c2cnc(Nc4ccc5c(ccn5C5CCN(CCO)CC5)c4)nc2n1-3]

3-7-10

Compound 3-7-10(cis) was synthesized following the synthetic method to the one used for compound 3-3-1, by replacing compound 9.2 to 16.4 in step 2.

m/z: [M+H]$^+$ 622.0; $^1$H NMR (400 MHz, CDCl$_3$): δ 8.81 (s, 1H), 7.95 (d, J=1.6 Hz, 1H), 7.55 (d, J=7.6 Hz, 1H), 7.39 (d, J=8.4 Hz, 1H), 7.32 (d, J=8.8 Hz, 1H), 7.26-7.21 (m, 2H), 6.47 (d, J=2.8 Hz, 1H), 6.14-6.10 (m, 1H), 5.53 (dt, J=7.2, 11.2 Hz, 1H), 4.75 (s, 2H), 4.33 (d, J=7.6 Hz, 2H), 4.27-4.21 (m, 1H), 4.16 (t, J=4.8 Hz, 2H), 3.68 (t, J=5.6 Hz, 2H), 3.13 (d, J=12.0 Hz, 2H), 2.64 (t, J=5.6 Hz, 2H), 2.40-2.31 (m, 2H), 2.06-2.01 (m, 6H), 1.92 (br. s 2H).

Embodiment 86: Synthesis of Compound 3-7-11

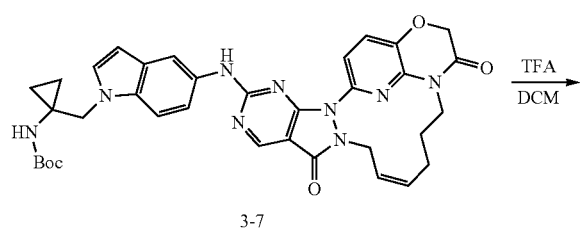

3-7

3-7-11

Compound 3-7 (cis) was synthesized following the synthetic method to the one used for compound 3-3-1, by replacing compound 9.2 to 19.6 in step 2.

The mixture of compound 3-7 (130 mg, 0.19 mmol) in DCM (10 mL) and TFA (2 mL) was stirred at room temperature for 2 h, the reaction system was directly concentrated, the residue was purified by prep-HPLC to afford compound 3-7-11 (cis) (46.7 mg, yield: 43%) as a yellow solid.

m/z: [M+H]$^+$ 563.9; $^1$H NMR (400 MHz, CD$_3$OD): δ 8.69 (s, 1H), 7.88 (d, J=2.0 Hz, 1H), 7.45 (d, J=8.4 Hz, 1H), 7.41 (d, J=8.4 Hz, 1H), 7.33 (d, J=8.8 Hz, 1H), 7.29 (dd, J=2.0, 8.8 Hz, 1H), 7.21 (d, J=2.8 Hz, 1H), 6.43 (d, J=2.8 Hz, 1H), 5.86 (dd, J=3.2, 7.2 Hz, 1H), 5.50-5.46 (m, 1H), 4.70 (s, 2H), 4.37 (s, 2H), 4.29 (d, J=7.6 Hz, 2H), 4.05-4.03 (m, 2H), 2.07 (br. s, 2H), 1.80 (br. s, 2H), 1.06-0.94 (m, 4H).

Embodiment 87: Synthesis of Compound 3-7-12

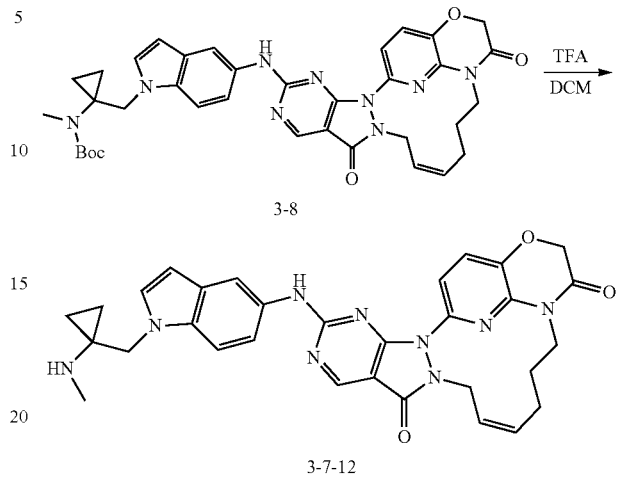

3-8

3-7-12

Compound 3-8(cis) was synthesized following the synthetic method to the one used for compound 3-3-1, by replacing compound 9.2 to 19.8 in step 2. Compound 3-7-12 (cis) was synthesized following the synthetic method to the one used for compound 3-7-11, by using compound 3-8 as a starting material.

m/z: [M+H]$^+$ 578.4; $^1$H NMR (400 MHz, DMSO-d$_6$): δ 10.12 (s, 1H), 8.85-8.84 (m, 3H), 8.01 (s, 1H), 7.64 (d, J=8.4 Hz, 1H), 7.53 (d, J=9.2 Hz, 2H), 7.42 (d, J=8.8 Hz, 1H), 7.41 (s, 1H), 6.50 (d, J=3.2 Hz, 1H), 5.84-5.82 (m, 1H), 5.55-5.49 (m, 1H), 4.85 (s, 2H), 4.55 (s, 2H), 4.23 (d, J=7.2 Hz, 2H), 3.99 (t, J=4.0 Hz, 2H), 2.51 (s, 3H), 2.09 (s, 2H), 1.80 (s, 2H), 1.11-0.85 (m, 4H).

Embodiment 88: Synthesis of Compound 3-7-13

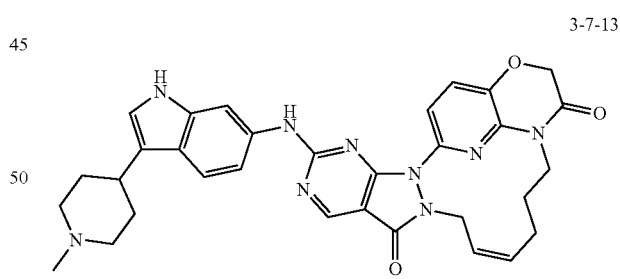

3-7-13

Compound 3-7-13 (cis) was synthesized following the synthetic method to the one used for compound 3-3-1, by replacing compound 9.2 to 20.2 in step 2.

m/z: [M+H]$^+$ 592.4; $^1$H NMR (400 MHz, DMSO-d$_6$): δ 10.81 (s, 1H), 10.12 (s, 1H), 9.40 (s, 1H), 8.84 (s, 1H), 7.86 (s, 1H), 7.70 (d, J=7.6 Hz, 1H), 7.52 (d, J=6.8 Hz, 1H), 7.49 (d, J=4.8 Hz, 1H), 7.25 (d, J=9.2 Hz, 1H), 7.08 (d, J=2.0 Hz, 1H), 5.88-5.80 (m, 1H), 5.55-5.49 (m, 1H), 4.84 (s, 2H), 4.23 (d, J=7.2 Hz, 2H), 4.00-3.98 (m, 2H), 3.52 (d, J=10.8 Hz, 2H), 3.17-3.09 (m, 2H), 3.02-2.97 (m, 1H), 2.83 (d, J=4.8 Hz, 3H), 2.15-2.05 (m, 4H), 1.93-1.81 (m, 4H).

Embodiment 89: Synthesis of Compound 3-7-14

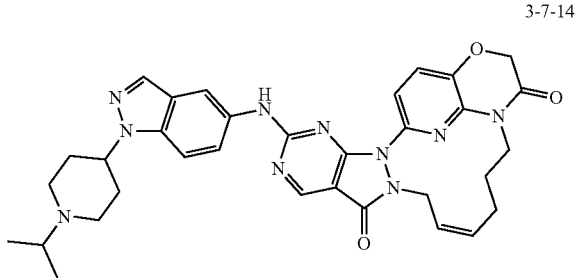 [SMILES: CC(C)N1CCC(n2ncc3cc(Nc4ncc5c(=O)n6n(c5n4)-c4ccc5c(n4)N(CCC/C=C\C6)C(=O)CO5)ccc32)CC1]

3-7-14

Compound 3-7-14 (cis) was synthesized following the synthetic method to the one used for compound 3-3-1, by replacing compound 9.2 to 14.9 in step 2.

m/z: [M+H]$^+$ 621.4; $^1$H NMR (400 MHz, CDCl$_3$): δ 8.80 (s, 1H), 7.99 (s, 1H), 7.85 (s, 1H), 7.45-7.32 (m, 4H), 6.05-6.02 (m, 1H), 5.51-5.44 (m, 1H), 4.69 (s, 2H), 4.34 (d, J=7.2 Hz, 1H), 4.28 (d, J=7.6 Hz, 2H), 4.10 (t, J=4.4 Hz, 2H), 3.00 (s, 2H), 2.77 (s, 1H), 2.35-2.28 (m, 4H), 2.06-2.00 (m, 4H), 1.85 (s, 2H), 1.04 (d, J=5.2 Hz, 6H).

Embodiment 90: Synthesis of Compound 3-7-15

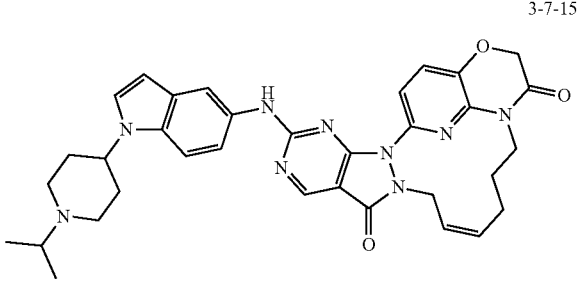 [SMILES: CC(C)N1CCC(n2ccc3cc(Nc4ncc5c(=O)n6n(c5n4)-c4ccc5c(n4)N(CCC/C=C\C6)C(=O)CO5)ccc32)CC1]

3-7-15

Compound 3-7-15 (cis) was synthesized following the synthetic method to the one used for compound 3-3-1, by replacing compound 9.2 to 14.8 in step 2.

m/z: [M+H]$^+$ 621.3; $^1$H NMR (400 MHz, CDCl$_3$): δ 8.86 (s, 1H), 8.33 (d, J=2.4 Hz, 1H), 8.23 (d, J=2.0 Hz, 1H), 7.44 (d, J=8.4 Hz, 1H), 7.39 (d, J=3.2 Hz, 1H), 7.35 (d, J=8.4 Hz, 1H), 6.43 (d, J=3.2 Hz, 1H), 6.13-6.06 (m, 1H), 5.57-5.50 (m, 1H), 4.84-4.74 (m, 1H), 4.74 (s, 2H), 4.33 (d, J=7.2 Hz, 2H), 4.18-4.12 (m, 2H), 3.09 (d, J=10.8 Hz, 2H), 2.93-2.84 (m, 1H), 2.53-2.49 (m, 2H), 2.17-2.08 (m, 6H), 1.94-1.87 (m, 2H), 1.13 (d, J=6.4 Hz, 6H).

Embodiment 90: Synthesis of Compound 3-7-16

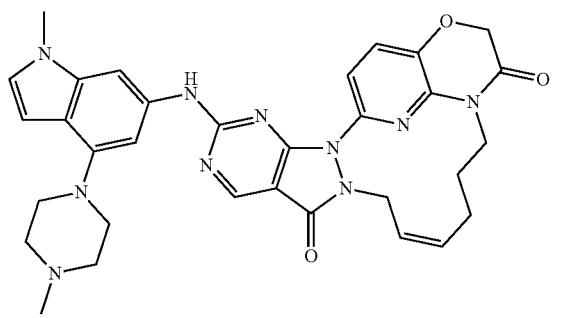

3-7-16

Compound 3-7-16 (cis) was synthesized following the synthetic method to the one used for compound 3-3-1, by replacing compound 9.2 to 24.3 in step 2.

m/z: [M+H]$^+$ 607.4; $^1$H NMR (400 MHz, CDCl$_3$): δ 8.89 (s, 1H), 7.54 (s, 1H), 7.48 (d, J=8.0 Hz, 1H), 7.46 (s, 1H), 7.37 (d, J=8.0 Hz, 1H), 6.98 (d, J=3.2 Hz, 1H), 6.56 (s, 1H), 6.45 (d, J=4.4 Hz, 1H), 6.08-6.05 (m, 1H), 5.58-5.55 (m, 1H), 4.77 (s, 2H), 4.36 (d, J=8.8 Hz, 2H), 4.19 (dd, J=4.4, 4.8 Hz, 2H), 3.70 (s, 3H), 3.25 (s, 4H), 2.67 (s, 4H), 2.41 (s, 3H), 2.14 (m, 2H), 1.94 (m, 2H).

Embodiment 92: Synthesis of Compound 3-7-17

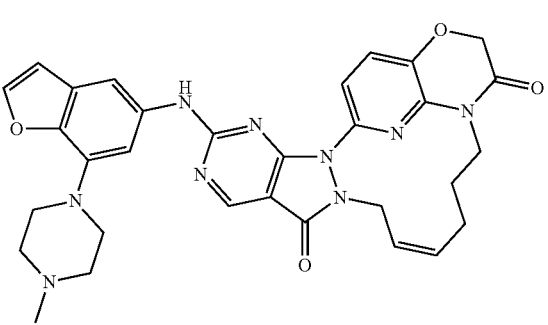

3-7-17

Compound 3-7-17 (cis) was synthesized following the synthetic method to the one used for compound 3-3-1, by replacing compound 9.2 to 26.6 in step 2.

m/z: [M+H]$^+$ 594.2; $^1$H NMR (400 MHz, DMSO-d$_6$): δ 10.12-10.13 (br. s, 1H), 9.86 (s, 1H), 8.87 (s, 1H), 7.97 (s, 1H), 7.76 (s, 1H), 7.65-7.70 (t, J=8.8 Hz, 1H), 7.47-7.49 (d, J=8.4 Hz, 1H), 7.10-7.12 (m, 1H), 6.94 (s, 1H), 5.77-5.80 (br. s, 1H), 5.51-5.55 (m, 1H), 4.86-4.88 (m, 2H), 4.39-4.41 (t, J=7.2 Hz, 2H), 3.99-4.01 (m, 2H), 3.81-3.84 (m, 2H), 3.35 (s, 2H), 3.27-3.32 (m, 2H), 2.98-3.04 (m, 2H), 2.87-2.89 (m, 3H), 2.07 (s, 2H), 1.80 (s, 2H).

Embodiment 93: Synthesis of Compound 3-7-18

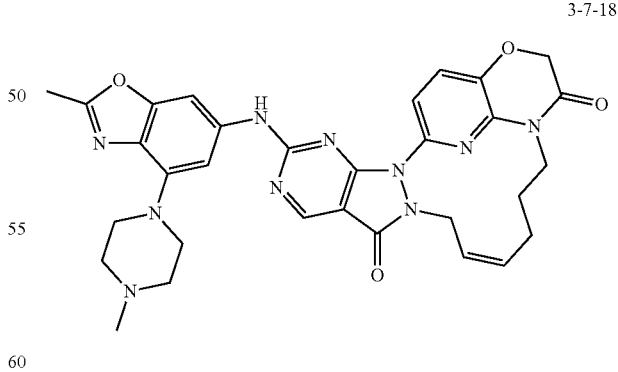

3-7-18

Compound 3-7-18 (cis) was synthesized following the synthetic method to the one used for compound 3-3-1, by replacing compound 9.2 to 27.6 in step 2.

m/z: [M+H]$^+$ 609.2; $^1$H NMR (400 MHz, CDCl$_3$): δ 8.90 (s, 1H), 7.74-7.80 (m, 2H), 7.54-7.56 (m, 1H), 7.45-7.47 (m, 1H), 6.68 (s, 1H), 6.05-6.08 (m, 1H), 5.55-5.58 (m, 1H), 4.81 (s, 2H), 4.37-4.39 (m, 2H), 4.17-4.19 (m, 2H), 3.58-

3.59 (m, 3H), 3.10-3.30 (br. s, 1H), 2.87 (s, 3H), 2.62 (s, 3H), 2.14 (s, 2H), 1.94 (s, 2H), 1.39-1.43 (m, 2H).

Embodiment 94: Synthesis of Compound 3-8-1

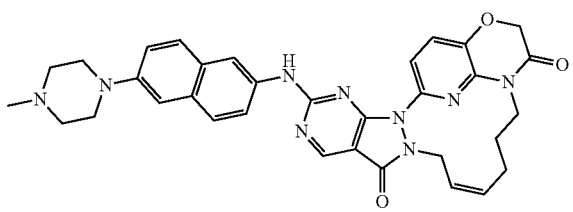

3-8-1

Compound 3-8-1 (cis) was synthesized following the synthetic method to the one used for compound 3-3-1, by replacing compound 9.2 to 21.1 in step 2.

m/z: [M+H]⁺ 604.4; ¹H NMR (400 MHz, CD$_3$OD): δ 8.86 (s, 1H), 8.29 (s, 1H), 7.69 (s, 1H), 7.57 (d, J=8.8 Hz, 1H), 7.52 (d, J=8.8 Hz, 1H), 7.47 (dd, J=1.6, 10.0 Hz, 1H), 7.43 (s, 1H), 7.21 (dd, J=2.4, 8.8 Hz, 1H), 7.12 (d, J=2.4 Hz, 1H), 5.89-5.86 (m, 1H), 5.51-5.47 (m, 1H), 4.71 (s, 2H), 4.30 (d, J=7.2 Hz, 2H), 4.05 (t, J=4.4 Hz, 2H), 3.87 (d, J=12.4 Hz, 2H), 3.57 (d, J=11.2 Hz, 2H), 3.28-3.23 (m, 2H), 3.04-2.91 (m, 2H), 2.89 (s, 3H), 2.06 (br. s, 2H), 1.81 (br. s, 2H).

Embodiment 95: Synthesis of Compound 4-1-1

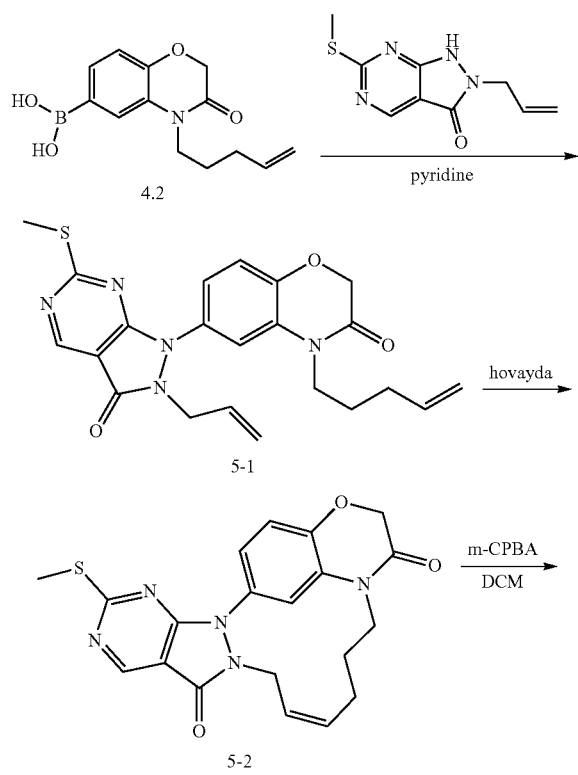

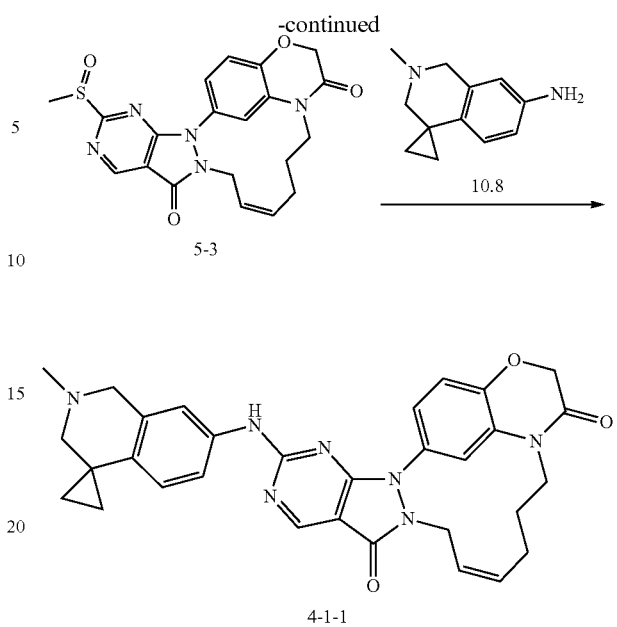

4-1-1

Step 1: 2-allyl-6-(methylthio)-1H-pyrazolo[3,4-d]pyrimidin-3(2H)-one (324 mg, 1.46 mmol), compound 4.2 (400 mg, crude), copper acetate (358 mg, 2.92 mmol) and pyridine (3 mL) was added into chloroform (30 mL). The reaction system was stirred at 60° C. for 16 h. The reaction solution was directly concentrated under reduced pressure and then purified by column chromatography on silica gel (petroleum ether/ethyl acetate=4/1) to afford compound 5-1 (150 mg, yield: 23%) as a colorless liquid.

Step 2: To a solution of compound 5-1 (150 mg, 0.343 mmol) in DCM (30 mL) was added Hoveyda-Grubbs reagent (30 mg), the reaction system was stirred at 40° C. for 16 h. The reaction solution was cooled down and concentrated to remove DCM, the residue was purified by column chromatography on silica gel (ether/ethyl acetate=5/1) to afford compound 5-2 (50 mg, yield: 33%) as a white solid.

Step 3: To a solution f of compound 5-2 (50 mg, 0.122 mmol) in DCM (10 mL) was added m-CPBA (25 mg, 0.122 mmol), the reaction system was stirred at room temperature for 1 h and then concentrated under reduced pressure to remove DCM to afford compound 5-3 (78 mg, crude) as a white solid.

m/z: [M+H]⁺ 426.0

Step 4: The solution of compound 5-3 (78 mg, crude), N,N-diisopropylethylamine (0.5 mL) and compound 10.8 (25 mg, 0.134 mmol) in toluene (10 mL) was stirred at 70° C. for overnight and then concentrated under reduced pressure to remove the solvent, the residue was purified by prep-HPLC to afford compound 4-1-1 (10 mg, two steps yield: 15%) as a white solid.

m/z: [M+H]⁺ 549.8; ¹H NMR (400 MHz, CD$_3$OD): δ 8.83 (s, 1H), 7.60 (s, 1H), 7.43-7.33 (m, 2H), 7.23 (d, J=8.4 Hz, 1H), 6.67 (d, J=8.8 Hz, 1H), 5.99-5.94 (m, 1H), 5.78-5.71 (m, 1H), 4.74 (s, 2H), 4.33-4.28 (m, 1H), 4.00-3.96 (m, 1H), 3.67 (s, 3H), 2.60 (s, 2H), 2.47 (s, 3H), 2.23-1.62 (m, 6H), 1.03-0.90 (m, 4H).

Embodiment 96: Synthesis of Compound 5-1-1

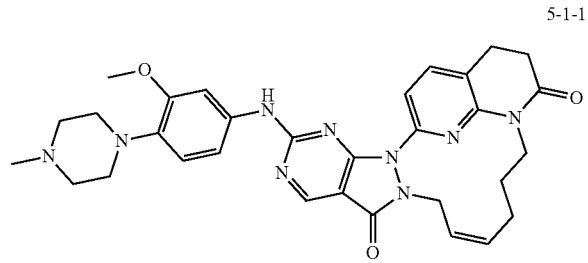 [SMILES: COc1cc(Nc2ncc3c(=O)n4n(c3n2)-c2ccc3c(n2)N(CCC/C=C\C4)C(=O)CC3)ccc1N1CCN(C)CC1]

5-1-1

Compound 5-1-1 (cis) was synthesized following the synthetic method to the one used for compound 1-1-1, by replacing compound 1.1 to 5.4 in step 1 and 4-(N-methylpiperazin)aniline to 3-methoxy-4-(4-methylpiperazin-1-yl)aniline in step 4.

m/z: [M+H]$^+$ 582.0; $^1$H NMR (400 MHz, CDCl$_3$): δ 8.78 (s, 1H), 7.65 (br.s, 1H), 7.51 (d, J=8.0 Hz, 1H), 7.36 (d, J=8.0 Hz, 1H), 7.12 (s, 1H), 7.02 (d, J=8.0 Hz, 1H), 6.82 (d, J=8.0 Hz, 1H), 6.00-5.97 (m, 1H), 5.49-5.46 (m, 1H), 4.29 (d, J=4.0 Hz, 2H), 4.08 (t, J=4.0 Hz, 2H), 3.68 (s, 3H), 3.03 (s, 4H), 2.91 (t, J=8.0 Hz, 2H), 2.70 (dd, J=4.0, 8.0 Hz, 2H), 2.59 (s, 4H), 2.31 (s, 3H), 2.02 (s, 2H), 1.82 (s, 2H).

Embodiment 97: Synthesis of Compound 6-1-1

6-1-1

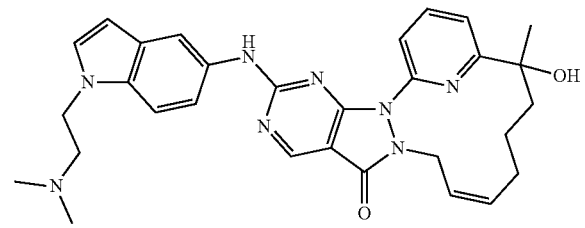

Compound 6-1-1 (cis) was synthesized following the synthetic method to the one used for compound 1-1-1, by replacing compound 1.1 to 6.1 in step 1 and 4-(N-methylpiperazin)aniline to compound 13.2 in step 4.

m/z: [M+H]$^+$ 538.8; $^1$H NMR (400 MHz, CD$_3$OD): δ 8.80 (s, 1H), 8.04 (t, J=8.0 Hz, 1H), 7.96-7.88 (m, 1H), 7.75 (d, J=7.6 Hz, 1H), 7.63 (d, J=8.0 Hz, 1H), 7.31-7.24 (m, 3H), 6.36 (s, 1H), 5.57-5.35 (m, 2H), 4.32-4.29 (m, 2H), 3.92-3.87 (m, 1H), 3.66 (s, 1H), 2.75 (t, J=6.8 Hz, 2H), 2.33 (s, 6H), 2.23-1.61 (m, 6H), 1.44 (s, 3H).

Embodiment 98: Synthesis of Compound 7-1-1

7-1-1

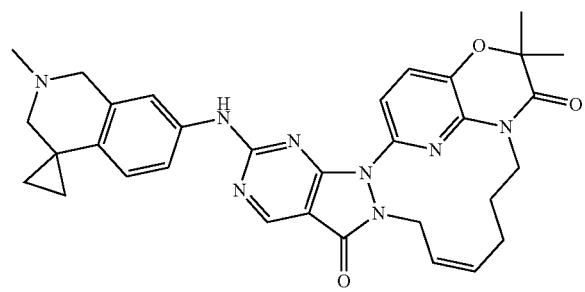

Compound 7-1-1 (cis) was synthesized following the synthetic method to the one used for compound 1-1-1, by replacing compound 1.1 to 7.2 in step 1 and 4-(N-methylpiperazin)aniline to compound 10.8 in step 4.

m/z: [M+H]$^+$ 578.9; $^1$H NMR (400 MHz, DMSO-d$_6$): δ 10.09 (s, 1H), 8.84 (s, 1H), 7.67 (d, J=8.4 Hz, 1H), 7.52 (d, J=8.4 Hz, 2H), 7.35 (dd, J=1.6, 8.4 Hz, 1H), 6.65 (d, J=8.4 Hz, 1H), 5.87-5.82 (m, 1H), 5.50 (dt, J=7.2, 11.2 Hz, 1H), 4.27 (d, J=7.2 Hz, 2H), 3.99 (t, J=4.0 Hz, 2H), 3.49 (s, 2H), 2.42 (s, 2H), 2.31 (s, 3H), 2.08 (s, 2H), 1.77 (s, 2H), 1.48 (s, 6H), 0.91-0.80 (m, 4H).

Embodiment 99: Synthesis of Compound 7-2-1

7-2-1

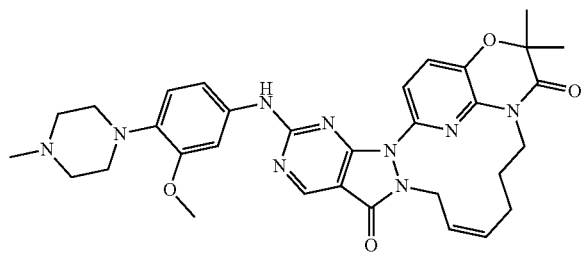

Compound 7-2-1 (cis) was synthesized following the synthetic method to the one used for compound 1-1-1, by replacing compound 1.1 to 7.2 in step 1 and 4-(N-methylpiperazin)aniline to 3-methoxy-4-(4-methylpiperazin-1-yl)aniline in step 4.

m/z: [M+H]$^+$ 612.0; $^1$H NMR (400 MHz, DMSO-d$_6$): δ 10.05 (s, 1H), 8.83 (s, 1H), 7.64 (d, J=8.4 Hz, 1H), 7.48 (d, J=8.4 Hz, 1H), 7.40 (s, 1H), 7.19 (d, J=8.4 Hz, 1H), 6.82 (d, J=8.8 Hz, 1H), 5.80-5.75 (m, 1H), 5.54-5.49 (m, 1H), 4.26 (d, J=7.2 Hz, 2H), 3.99 (s, 2H), 3.61 (s, 3H), 2.91 (s, 4H), 2.44 (s, 4H), 2.21 (s, 3H), 2.06 (s, 2H), 1.77 (s, 2H), 1.51 (s, 6H).

Embodiment 100: Synthesis of Compound 8-1-1

8-1-1

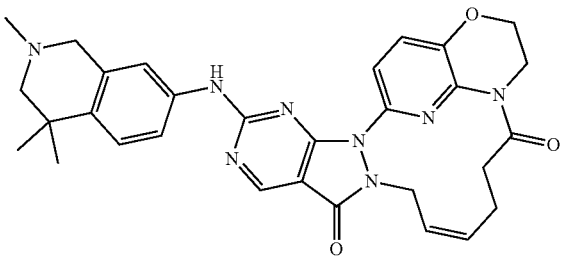

Compound 8-1-1 (cis) was synthesized following the synthetic method to the one used for compound 1-1-1, by replacing compound 1.1 to 23.2 in step 1 and 4-(N-methylpiperazin)aniline to compound 11.5 in step 4.

m/z: [M+H]$^+$ 553.4; $^1$H NMR (400 MHz, CDCl$_3$): δ 8.84 (s, 1H), 7.52-7.46 (m, 3H), 7.32-7.29 (m, 2H), 5.90-5.81 (m, 1H), 5.78-5.66 (m, 1H), 4.78-4.65 (m, 1H), 4.58 (d, J=7.6 Hz, 2H), 4.40-4.19 (m, 4H), 3.95-3.90 (m, 1H), 3.44-3.38 (m, 1H), 3.03 (s, 6H), 2.54 (s, 2H), 1.25 (d, J=4.0 Hz, 6H).

Embodiment 101: Synthesis of Compound 8-1-2

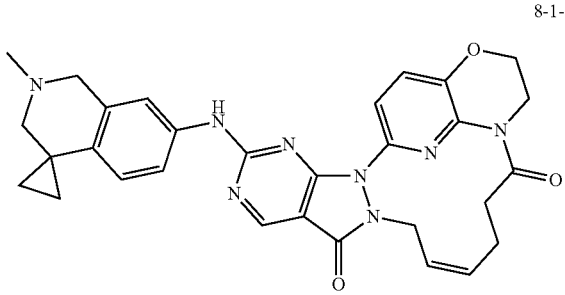

Compound 8-1-2 (cis) was synthesized following the synthetic method to the one used for compound 1-1-1, by replacing compound 1.1 to 23.2 in step 1 and 4-(N-methylpiperazin)aniline to compound 10.8 in step 4.

m/z: [M+H]$^+$ 550.8; $^1$H NMR (400 MHz, DMSO-d$_6$): δ 10.28 (d, J=3.6 Hz, 1H), 10.23 (d, J=3.6 Hz, 1H), 8.89 (s, 1H), 7.68 (d, J=5.2 Hz, 1H), 7.55 (s, 1H), 7.50-7.46 (m, 1H), 6.81 (d, J=8.8 Hz, 1H), 5.81-5.76 (m, 1H), 5.55-5.50 (m, 1H), 4.43 (d, J=6.8 Hz, 2H), 4.39-4.35 (m, 2H), 4.12-4.03 (m, 1H), 3.59-3.44 (m, 3H), 3.28 (d, J=8.4 Hz, 1H), 2.93-2.85 (m, 4H), 2.51-2.43 (m, 2H), 2.36 (d, J=8.0 Hz, 1H), 2.08-1.98 (m, 1H), 1.31-1.14 (m, 4H).

Embodiment 102: Synthesis of Compound 8-2-1

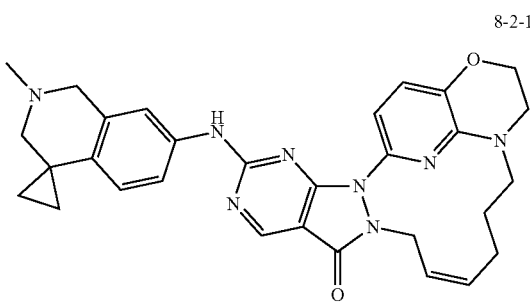 [SMILES: CN1Cc2cc(Nc3ncc4c(=O)n5n(c4n3)-c3ccc4c(n3)N(CCC/C=C\C5)CCO4)ccc2C2(CC2)C1]

Compound 8-2-1 (cis) was synthesized following the synthetic method to the one used for compound 1-1-1, by replacing compound 1.1 to 23.3 in step 1 and 4-(N-methylpiperazin)aniline to compound 10.8 in step 4.

m/z: [M+H]$^+$ 537.4; $^1$H NMR (400 MHz, DMSO-d$_6$): δ 10.23-10.19 (m, 2H), 8.84 (s, 1H), 7.69 (s, 1H), 7.55 (dd, J=2.4, 8.8 Hz, 1H), 7.26 (d, J=8.0 Hz, 1H), 6.86 (d, J=8.0 Hz, 1H), 6.84 (d, J=8.8 Hz, 1H), 5.86-5.83 (m, 1H), 5.50-5.47 (m, 1H), 4.51 (d, J=15.6 Hz, 1H), 4.43 (d, J=7.2 Hz, 1H), 4.25-4.21 (m, 4H), 3.54-3.49 (m, 4H), 3.24 (d, J=12.8 Hz, 2H), 2.94 (d, J=4.0 Hz, 3H), 2.08 (br. s, 2H), 1.71 (br. s, 2H), 1.35-0.95 (m, 4H).

Embodiment 103: Synthesis of Compound 8-2-2

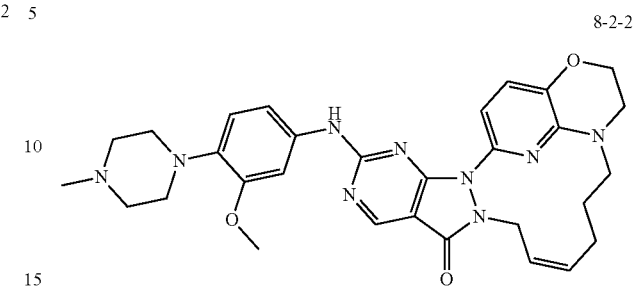

Compound 8-2-2 (cis) was synthesized following the synthetic method to the one used for compound 1-1-1, by replacing compound 1.1 to 23.3 in step 1 and 4-(N-methylpiperazin)aniline to 3-methoxy-4-(4-methylpiperazin-1-yl)aniline in step 4.

m/z: [M+H]$^+$ 570.4; $^1$H NMR (400 MHz, CDCl$_3$): δ 8.75 (s, 1H), 7.36 (d, J=4.0 Hz, 1H), 7.27 (s, 1H), 6.94 (d, J=8.0 Hz, 1H), 6.88 (dd, J=2.4, 8.4 Hz, 1H), 6.80 (d, J=8.4 Hz, 1H), 6.70 (d, J=8.0 Hz, 1H), 5.88 (dd, J=7.2, 11.2 Hz, 1H), 5.44 (dt, J=7.2, 11.2 Hz, 1H), 4.30 (d, J=7.6 Hz, 2H), 4.17 (t, J=4.8 Hz, 2H), 3.68-3.60 (m, 5H), 3.46 (t, J=4.8 Hz, 2H), 3.00 (br. s, 4H), 2.57 (br. s, 4H), 2.31 (s, 3H), 2.06 (br. s, 2H), 1.66 (s, 2H).

Embodiment 104: Synthesis of Compound 8-3-1

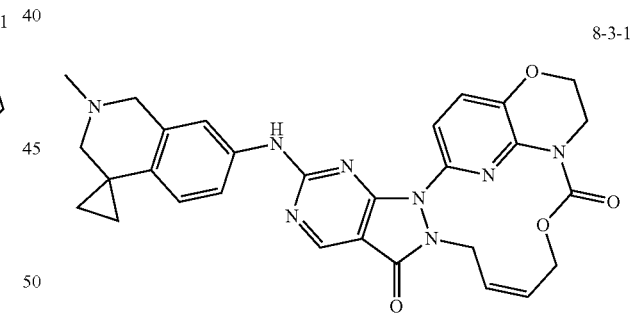

Compound 8-3-1 (cis) was synthesized following the synthetic method to the one used for compound 1-1-1, by replacing compound 1.1 to 23.4 in step 1 and 4-(N-methylpiperazin)aniline to compound 10.8 in step 4.

m/z: [M+H]$^+$ 552.8; $^1$H NMR (400 MHz, CDCl$_3$): δ 8.74 (s, 1H), 7.85 (t, J=4.0 Hz, 1H), 7.38 (s, 1H), 7.33 (d, J=2.0 Hz, 1H), 7.26 (d, J=8.4 Hz, 1H), 7.20 (d, J=8.0 Hz, 1H), 6.61 (d, J=8.4 Hz, 1H), 6.46-6.39 (m, 1H), 5.92-5.86 (m, 1H), 4.80 (s, 4H), 4.26 (t, J=4.4 Hz, 2H), 3.90 (s, 2H), 3.67 (s, 2H), 2.51 (s, 2H), 2.42 (s, 3H), 0.98-0.85 (m, 4H).

Embodiment 105: Synthesis of Compound 9-1-1

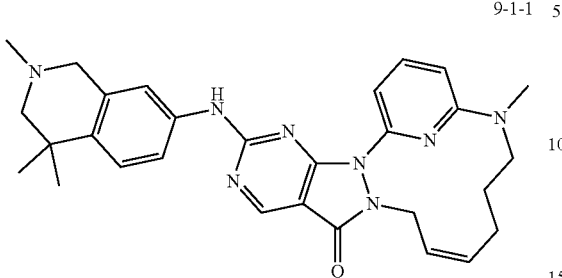

9-1-1

Compound 9-1-1 (cis) was synthesized following the synthetic method to the one used for compound 1-1-1, by replacing compound 1.1 to 2.6 in step 1 and 4-(N-methylpiperazin)aniline to compound 11.5 in step 4.

m/z: [M+H]$^+$ 511.0; $^1$H NMR (400 MHz, CDCl$_3$): δ 8.75 (s, 1H), 7.54 (dd, J=7.6, 8.4 Hz, 1H), 7.42 (s, 1H), 7.33 (s, 1H), 7.16-7.23 (m, 1H), 6.99 (d, J=7.6 Hz, 1H), 6.28 (d, J=8.4 Hz, 1H), 6.11 (dt, J=7.6, 10.8 Hz, 1H), 5.44 (dt, J=7.6, 10.8 Hz, 1H), 4.31 (d, J=7.6 Hz, 2H), 3.62 (br.s, 2H), 3.47 (s, 2H), 2.91 (s, 3H), 2.37 (s, 3H), 2.34 (d, J=2.4 Hz, 2H), 2.07 (br. s, 2H), 1.63-1.57 (m, 2H), 1.24 (s, 6H).

Embodiment 106: Synthesis of 2-((7-bromohept-2-yn-1-yl)oxy)tetrahydro-2H-pyran

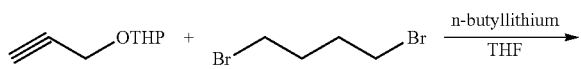

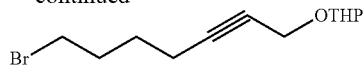

To a solution of pyran (4 g, 28.5 mmol) in anhydrous THF (40 mL) was added n-butyllithium (12.6 mL) under dry ice acetone bath at −78° C., the inner temperature of the system was kept under −70° C., and stirred at this temperature for 45 min and then a solution of 1,4-dibromobutane (18.5 g, 85.6 mmol) and hexamethylphosphoramide (8 mL) in anhydrous THF (40 mL) was added into the above reaction solution and stirred for another 1 h at this temperature, and then the reaction system was slowly warmed up to room temperature and stirred for overnight. The reaction was quenched by addition of saturated aqueous solution of ammonium chloride under ice-bath, diluted with H$_2$O and extracted with ethyl acetate (30 mL×3), the combined organic layers were successively washed with H$_2$O and brine, the organic layer was separated and concentrated, the residue was purified by column chromatography on silica gel (petroleum ether/ethyl acetate=10/1) to afford 2-((7-bromohept-2-yn-1-yl)oxy)tetrahydro-2H-pyran (7 g, yield: 87%) as an oil.

2-((6-bromohex-2-yn-1-yl)oxy)tetrahydro-2H-pyran was synthesized following the synthetic method to the one used for 2-((7-bromohept-2-yn-1-yl)oxy)tetrahydro-2H-pyran, by replacing 1,4-dibromobutane to 1,3-dibromopropane.

2-((8-bromooct-2-yn-1-yl)oxy)tetrahydro-2H-pyran was synthesized following the synthetic method to the one used for 2-((7-bromohept-2-yn-1-yl)oxy)tetrahydro-2H-pyran, by replacing 1,4-dibromobutane to 1,5-dibromopentane.

Embodiment 107: Synthesis of Compound 10-1-1

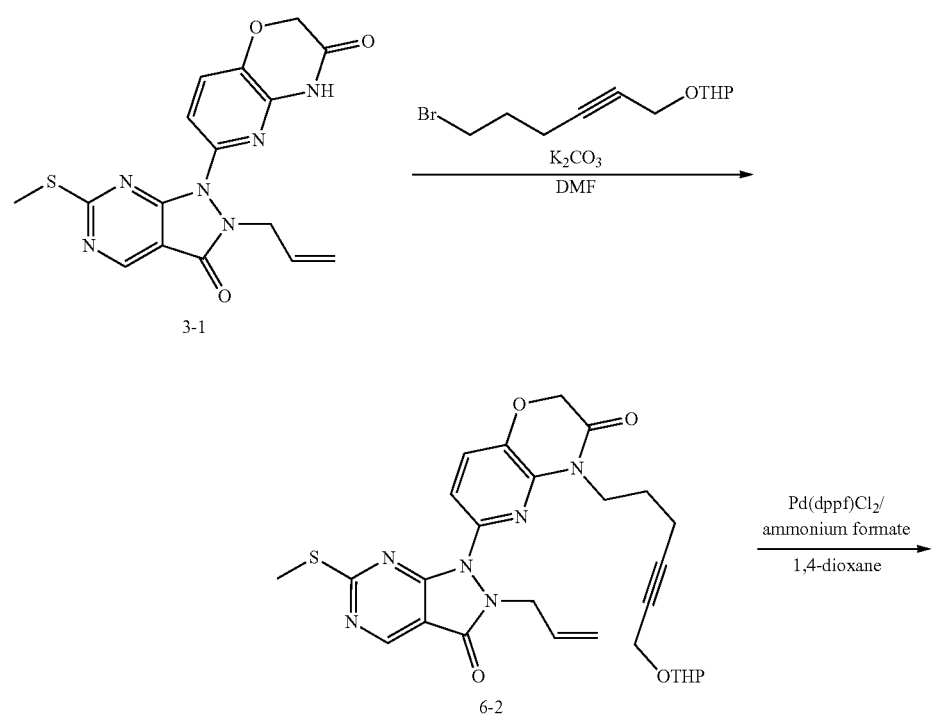

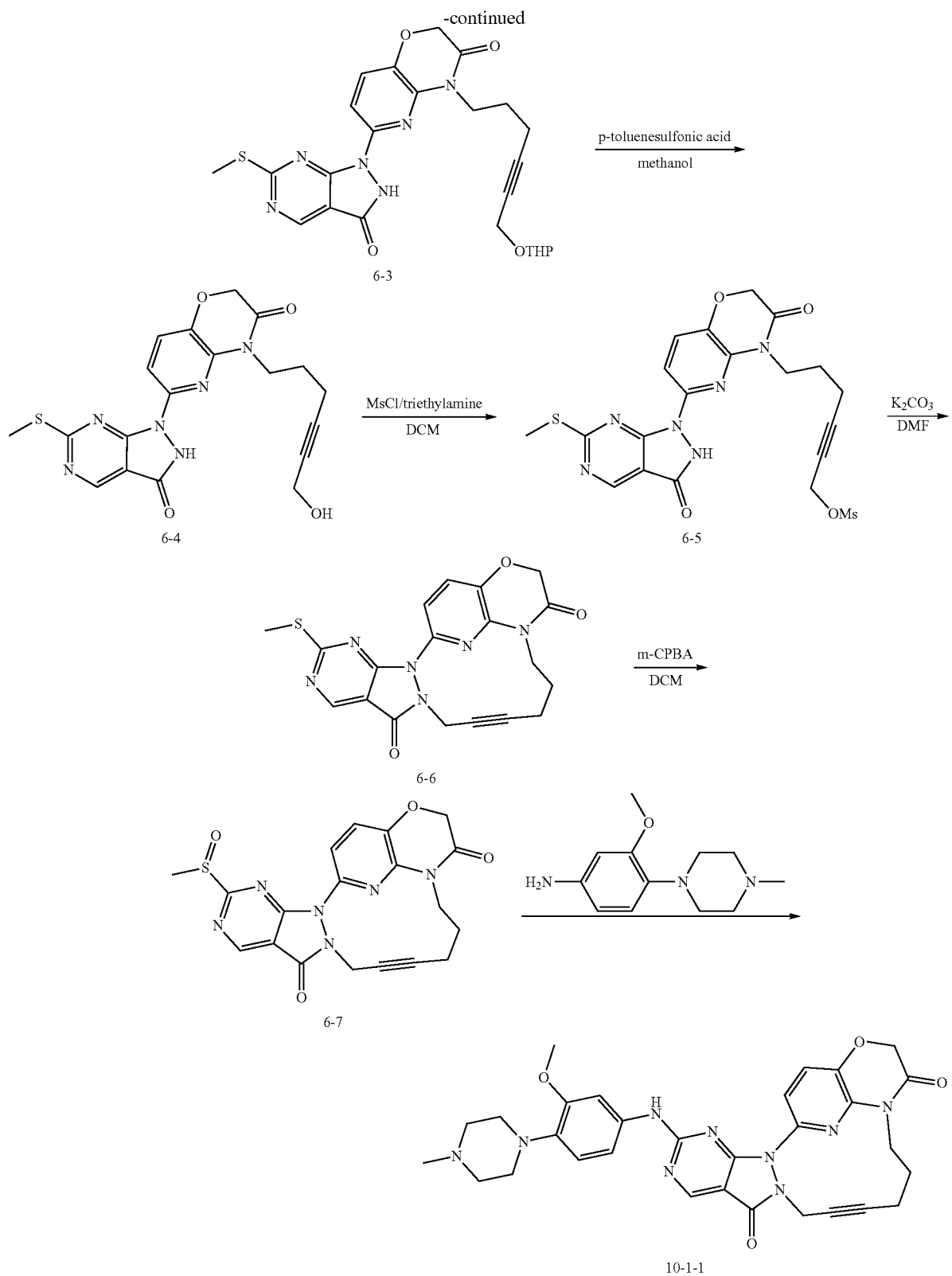

Step 1: To a solution of 2-((6-bromohex-2-yn-1-yl)oxy) tetrahydro-2H-pyran (303 mg, 1.16 mmol) and K₂CO₃ (481 mg, 3.48 mmol) in DMF (15 mL) was added compound 3-1 (430 mg, 1.16 mmol), the reaction system was stirred at room temperature for 3 h and then quenched by addition of H₂O, the aqueous layer was extracted with ethyl acetate (15 mL×3), the combined organic layers were washed with H₂O and brine, the organic layer was concentrated, the residue was purified by column chromatography on silica gel (petroleum ether/ethyl acetate=2/1) to afford compound 6-2 (333 mg, yield: 52%) as an oil.

Step 2: To a solution of compound 6-2 (140 mg, 0.25 mmol) and ammonium formate (32 mg, 0.51 mmol) in 1,4-dioxane was added Pd(dppf)Cl₂ dichloromethane complex (10.4 mg, 0.013 mmol), the reaction system was replaced with nitrogen for 3 times and then heated to 100° C. and stirred for 2 h under nitrogen. The reaction solution was cooled to room temperature, filtered, the filtrate was concentrated, the residue was purified by prep-TLC (DCM/methanol=10/1) to afford compound 6-3 (40 mg, yield: 31%) as a brown solid.

Step 3: To a solution of compound 6-3 (40 mg, 0.078 mmol) in methanol (5 mL) was added p-toluenesulfonic acid (3 mg, 0.016 mmol), the reaction system was heated to 50° C. and stirred for 2 h. The reaction solution was cooled to room temperature, filtered, the filtrate was concentrated, the residue was purified by prep-TLC (DCM/methanol=10/1) to afford compound 6-4 (15 mg, yield: 45%) as a brown solid.

m/z: [M+H]⁺ 427.2

Step 4: To a solution of compound 6-4 (77 mg, 0.18 mmol) and triethylamine (36.5 mg, 0.36 mmol) in DCM (10 mL) was added MsCl (31.1 mg, 0.27 mmol) under ice-bath, the reaction system was stirred at room temperature for 1 h, the reaction was quenched by addition of H₂O, the aqueous layer was extracted with DCM (5 mL×3), the combined organic layers were successively washed with H₂O and brine, the organic layer was concentrated to afford compound 6-5 (91 mg, crude), which was used directly for next step without further purification.

Step 5: To a solution of compound 6-5 (91 mg, 0.18 mmol) in DMF (15 mL) was added K₂CO₃ (74.5 mg, 0.54 mmol), the reaction system was stirred at room temperature for overnight, the reaction was quenched by addition of H₂O, the aqueous layer was extracted with ethyl acetate (15 mL×3), the combined organic layers were successively washed with H₂O and brine, the organic layer was concentrated, the residue was purified by column chromatography on silica gel (DCM/methanol=20/1) to afford compound 6-6 (20 mg, yield: 27%) as a brown solid.

m/z: [M+H]⁺ 409.2

Step 6: To a solution of compound 6-6 (20 mg, 0.05 mmol) in DCM (10 mL) was added m-CPBA (10 mg, 0.05 mmol), the reaction system was stirred at room temperature for 2 h and then directly concentrated to afford compound 6-7 (21.2 mg, crude), which was used directly for next step without further purification.

m/z: [M+H]⁺ 425.1

Step 7: To a solution of 3-methoxy-4-(4-methylpiperazin-1-yl)aniline (11.1 mg, 0.05 mmol) and N,N-diisopropylethylamine (12.9 mg, 0.1 mmol) in toluene (10 mL) was added compound 6-7 (21.2 mg, 0.05 mmol), the reaction system was heated to 70° C. and stirred for overnight and then directly concentrated, the residue was purified by prep-HPLC to afford compound 10-1-1 (9.3 mg, yield: 27%) as a yellow solid.

m/z: [M+H]⁺ 582.2; ¹H NMR (400 MHz, DMSO-d₆): δ 10.35 (s, 1H), 9.52 (s, 1H), 8.88 (s, 1H), 7.67 (d, J=8.4 Hz, 1H), 7.43 (s, 1H), 7.39 (d, J=8.4 Hz, 1H), 7.27 (dd, J=2.0, 8.8 Hz, 1H), 6.91 (d, J=8.8 Hz, 1H), 4.81 (s, 2H), 3.72 (s, 3H), 3.51-3.43 (m, 4H), 3.24-3.08 (m, 6H), 2.91-2.82 (m, 5H), 2.11 (br. s, 2H), 1.88-1.83 (m, 2H).

Embodiment 108: Synthesis of Compound 10-1-2

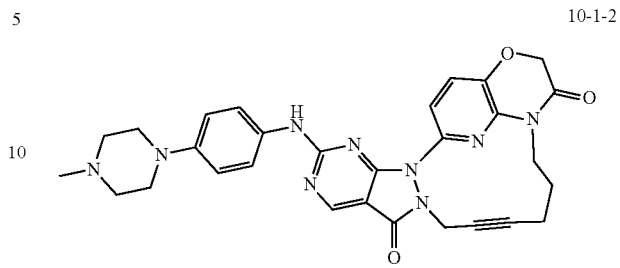

10-1-2

Compound 10-1-2 was synthesized following the synthetic method to the one used for compound 10-1-1, by replacing 3-methoxy-4-(4-methylpiperazin-1-yl)aniline to 4-(4-methyl piperazin-1-yl)aniline in step 8.

m/z: [M+H]⁺ 552.2; ¹H NMR (400 MHz, CDCl₃): δ 13.09-13.12 (br. s, 1H), 8.37-8.52 (d, J=6.0 Hz, 1H), 7.32-7.54 (m, 3H), 7.25-7.28 (m, 1H), 6.96-7.07 (m, 2H), 4.67 (s, 2H), 3.57-3.68 (m, 6H), 3.05-3.08 (br. s, 2H), 2.88 (s, 3H), 2.02 (s, 2H), 2.15 (s, 2H), 1.41-1.43 (m, 2H), 0.93-0.95 (m, 2H).

Embodiment 109: Synthesis of Compound 10-1-3

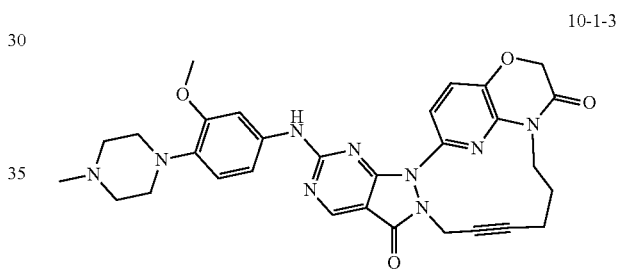

10-1-3

Compound 10-1-3 was synthesized following the synthetic method to the one used for compound 10-1-1, by replacing 2-((6-bromohex-2-yn-1-yl)oxy)tetrahydro-2H-pyran to 2-((7-bromohept-2-yn-1-yl)oxy)tetrahydro-2H-pyran in step 2.

m/z: [M+H]⁺ 596.3; ¹H NMR (400 MHz, CDCl₃): δ 12.89-12.91 (br. s, 1H), 8.87 (s, 1H), 7.39-7.48 (m, 3H), 7.13-7.22 (m, 1H), 6.92-6.94 (d, J=8.4 Hz, 1H), 4.74 (s, 2H), 4.55 (s, 2H), 4.25-4.29 (m, 2H), 3.83 (s, 3H), 3.44-3.58 (m, 6H), 3.14-3.19 (br. s, 2H), 3.14 (s, 3H), 2.36-2.39 (t, J=6.4 Hz, 2H), 1.89-1.96 (br. s, 2H), 1.62-1.66 (m, 2H).

Embodiment 110: Synthesis of Compound 10-1-4

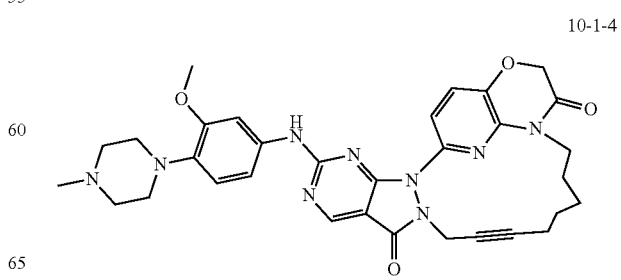

10-1-4

Compound 10-1-4 was synthesized following the synthetic method to the one used for compound 10-1-1, by replacing 2-((6-bromohex-2-yn-1-yl)oxy)tetrahydro-2H-pyran to 2-((8-bromooct-2-yn-1-yl)oxy)tetrahydro-2H-pyran in step 2.

m/z: [M+H]$^+$ 610.4; $^1$H NMR (400 MHz, CDCl$_3$): δ 8.85 (s, 1H), 7.54-7.56 (br. s, 1H), 7.39-7.41 (d, J=8.0 Hz, 1H), 7.28-7.29 (m, 1H), 7.02-7.10 (m, 2H), 6.86-6.88 (d, J=8.4 Hz, 1H), 4.76 (s, 2H), 4.47 (s, 2H), 4.21-4.25 (t, J=6.8 Hz, 2H), 3.73 (s, 3H), 3.20 (s, 4H), 2.53 (s, 3H), 2.20 (s, 2H), 1.93-1.98 (m, 2H), 1.51-1.59 (m, 4H).

Embodiment 110: Synthesis of Compound 7-2

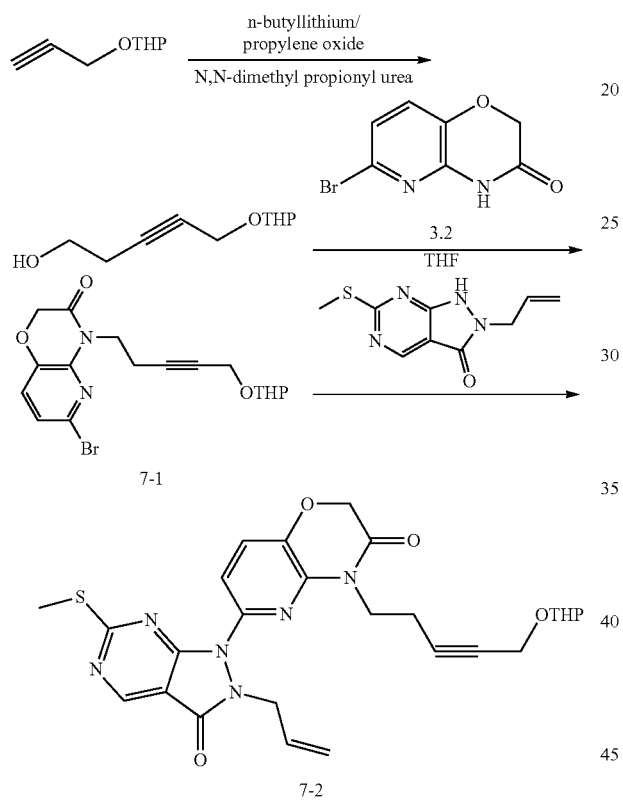

Step 1: To a solution of pyran (7 g, 50 mmol) and N,N-dimethyl propionyl urea (640 mg, 5.0 mmol) in anhydrous THF (100 mL) was added n-butyllithium (22 mL) under dry ice acetone bath at −78° C., the inner temperature of the system was kept under −70° C., and stirred at this temperature for 30 min and then propylene oxide (8.8 g, 200 mmol) was added into the above reaction solution and stirred for another 1 h at this temperature, and then the reaction system was slowly warmed up to room temperature and stirred for overnight. The reaction was quenched by addition of saturated solution of aqueous ammonium chloride under ice-bath, diluted with H$_2$O and extracted with ethyl acetate (30 mL×3), the combined organic layers were successively washed with H$_2$O and brine, the organic layer was dried over anhydrous sodium sulfate, filtered and concentrated, the residue was purified by column chromatography on silica gel (petroleum ether/ethyl acetate=3/1) to afford 5-((tetrahydro-2H-pyran-2-yl)oxy)pent-3-yn-1-ol (5.0 g, yield: 54%) as a colorless oil.

Step 2: To a solution of triphenylphosphine (1.15 g, 4.37 mmol) in anhydrous THF (10 mL) was added diisopropyl azodicarboxylate (883 mg, 4.37 mmol) under an ice-bath, the reaction system was stirred at 0° C. for 5 min, 5-((tetrahydro-2H-pyran-2-yl)oxy)pent-3-yn-1-ol (804 mg, 4.37 mmol) and compound 3.2 (1.0 g, 4.37 mmol) was added into the above reaction and stirred at room temperature for overnight, the reaction solution was directly concentrated, the residue was purified by column chromatography on silica gel (petroleum ether/ethyl acetate=5/1) to afford compound 7-1 (1.7 g, yield: 100%) as an oil.

Step 3: Compound 7-1 (1.7 g, 4.37 mmol), 2-allyl-6-(methylthio)-1H-pyrazolo[3,4-d]pyrimidin-3(2H)-one (971.3 mg, 4.37 mmol), cuprous iodide (835 mg, 4.37 mmol), N,N-dimethylethylenediamine (385 mg, 4.37 mmol) and K$_2$CO$_3$ (1.21 g, 8.74 mmol) was dissolved in a mixed solvent of 1,4-dioxane (40 mL) and DMF (4 mL), the reaction system was stirred at 100° C. for overnight. The reaction solution was cooled to room temperature, filtered, the filtrated was concentrated, the residue was purified by column chromatography on silica gel (petroleum ether/ethyl acetate=1/1) to afford compound 7-2 (270 mg, yield: 12%) as an oil.

m/z: [M+H]$^+$ 537.1

Embodiment 112: Synthesis of Compound 10-1-5

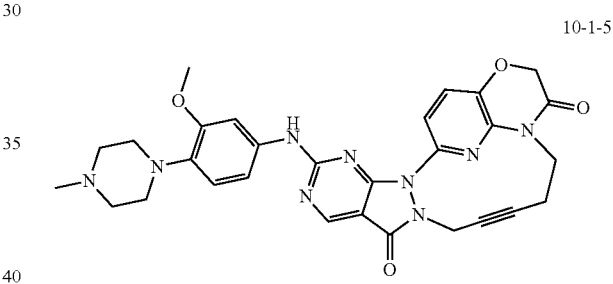

Compound 10-1-5 was synthesized following the synthetic method to the one used for compound 10-1-1 (Steps 3 to 8), by replacing compound 6-2 to 7-2.

m/z: [M+H]$^+$ 568.2; $^1$H NMR (400 MHz, CDCl$_3$): δ 8.85 (s, 1H), 7.38-7.48 (m, 3H), 7.18-7.20 (br. s, 1H), 6.92-6.94 (d, J=8.8 Hz, 1H), 5.02-5.10 (br. s, 1H), 4.77-4.78 (d, J=5.6 Hz, 2H), 4.39-4.49 (m, 2H), 3.80-3.89 (m, 4H), 3.44-3.55 (m, 5H), 3.15 (br. s, 2H), 2.86 (s, 3H), 2.53-2.57 (m, 2H), 1.61-1.69 (m, 2H).

EMBODIMENTS OF BIOASSAYS

Embodiment 1: Detection of Enzymatic Activity of Wee1

In the present disclosure, Wee1 enzyme catalysis assay was carried out using the ATP-Glo Max kinase luminescence detection kit (Promega). Kinase activity was assessed by quantitative detection of the amount of ATP retained in the solution following the kinase reaction. The luminescent signal in the assay is proportional to the amount of ATP and inversely proportional to the kinase activity. The concentration of the compound in the assay ranged from 0.5 nM to 30 μM. The compound was dissolved in 10% DMSO, and 5 μL of the solution was added to 50 μL of the reaction, and the concentration of DMSO in the final reaction was 1%. The reaction was carried out at 30° C. for 50 minutes. 40 mM trishydroxymetyl aminomethane, pH 7.4, 10 mM $MgCl_2$, 0.1 mg/ml BSA, 2 mM DTT, 0.1 mg/ml Poly (Lys, Tyr) substrate, 10 μM ATP and Wee1 were contained in the reaction mixture. After the enzymatic reaction, 50 μL of ATP-Glo Max kinase luminescence detection assay solution (Promega) was added and incubated for 15 minutes at room temperature. The luminescent signal was measured using a microplate reader. In some assays, a known Wee1 inhibitor was added as a positive control. Luminance data was analyzed using Graphpad software. The difference between the luminescence intensity in the absence of Wee1 and the luminescence intensity in the presence of Wee1 was defined as 100% activity (Lut−Luc). Using the luminescence intensity signal (Lu) in the presence of the compound, the % activity was calculated as follows:

% Activity={(Lut−Lu)/(Lut−Luc)}×100%, wherein,
Lu=luminous intensity of the compound Non-linear regression analysis was employed to plot the dose-effect curve of % activity value and the corresponding concentrations for the series of compounds. The equation is Y=B+(TB)/1+10((Log EC50−X)×Hill Slope), Y=% activity, B=minimum activity percentage, T=maximum activity percentage, X=logarithm of compound and Hill slope=slope factor or Hill coefficient. The $IC_{50}$ value was determined by the concentration of a compound that is required to obtain 50% of the maximum effect.

| Compound No. | $IC_{50}$ (nM) | Compound No. | $IC_{50}$ (nM) |
|---|---|---|---|
| 1-1-1 | 6.7 | 1-1-2 | 32 |
| 1-1-3 | 7.3 | 1-1-4 | 30.2 |
| 1-1-5 | 6.1 | 1-1-6 | 6.8 |
| 1-2-1 | 5.4 | 1-2-2 | 10.3 |
| 1-3-1 | 8.1 | 1-3-2 | 23.8 |
| 2-1-1 | 75.2 | 2-1-2 | 62.5 |
| 2-2-1 | 3.7 | 2-3-1 | 10.7 |
| 2-3-2 | 16.4 | 3-1-1 | 4.9 |
| 3-2-1 | 21.0 | 3-2-2 | 11.0 |
| 3-2-3 | 7.6 | 3-2-5 | 7.7 |
| 3-2-6 | 10.4 | 3-2-7 | 10.2 |
| 3-2-8 | 9.0 | 3-3-1 | 5.5 |
| 3-3-2 | 3.3 | 3-3-3 | 5.7 |
| 3-3-4 | 8.6 | 3-3-5 | 4.8 |
| 3-3-6 | 24.8 | 3-3-7 | 13.0 |
| 3-3-8 | 7.6 | 3-3-9 | 6.3 |
| 3-3-10 | 8.8 | 3-3-11 | 6.5 |
| 3-4-1 | 9.4 | 3-4-2 | 8.2 |
| 3-5-1 | 2.4 | 3-5-2 | 6.1 |
| 3-6-1 | 16.2 | 3-7-1 | 7.6 |
| 3-7-2 | 18.2 | 3-7-3 | 9.5 |
| 3-7-4 | 36.6 | 3-7-5 | 3.9 |
| 3-7-6 | 9.6 | 3-7-7 | 6.6 |
| 3-7-8 | 12.3 | 3-7-9 | 9.2 |
| 3-7-10 | 8.5 | 3-7-14 | 6.5 |
| 3-7-15 | 7.9 | 4-1-1 | 5.1 |
| 5-1-1 | 7.5 | 6-1-1 | 155 |
| 7-1-1 | 12.9 | 8-1-1 | 20.1 |
| 8-1-2 | 4.4 | 8-2-1 | 11.6 |
| 8-2-2 | 13.0 | 8-3-1 | 16.3 |
| 9-1-1 | 11.8 | 10-1-1 | 9.9 |
| 10-1-3 | 8.4 | 10-1-5 | 11.7 |
| AZD1775 | 8.7 | | |

Embodiment 2: Detection of the Cell Activity of Wee1 Based Onp-CDK1Y15ELISA Assay In the present disclosure, cellular assays were used to assess the biological activity of the compound. This assay was conducted using the human colon adenocarcinoma cell line WiDr. The activity of a specific Wee1 inhibitor was evaluated using p-CDK1Y15 ELISA assay method. The detailed assay method is described as follows:

WiDr cells were cultured in Dulbecco's Modified Eagle's medium containing 10% FBS at 37° C. and 5% $CO_2$. Compound concentrations ranged from 0.5 nM to 30 μM. The compound was diluted, added to a 24-well plate and incubated with the cells for 24 hours. DMSO was used as a negative control. A known Wee1 inhibitor was added as a positive control in some assays. According to the instruction of the manufacturer, in the p-CDK1Y15 assay, cells were lysed and tested by a colorimetric ELISA kit to determine the amount of p-CDK1Y15. The optical density was measured using a spectrophotometer. The OD data was analyzed using Graphpad software to obtain a fitted curve of $IC_{50}$ values against the compounds.

| Compound No. | $IC_{50}$ (nM) |
|---|---|
| 3-1-1 | 336 |
| 3-2-2 | 139 |
| 3-2-3 | 326 |
| 3-3-2 | 114 |
| 3-3-7 | 250 |
| 3-3-13 | 68.8 |
| 3-7-3 | 80.6 |
| 3-7-5 | 38.8 |
| 3-7-7 | 51.4 |
| 3-7-13 | 114 |
| 3-7-16 | 31.4 |
| AZD-1775 | 254 |

Embodiment 3: Cell Proliferation Assay

In the present disclosure, cell assays were used to assess the biological activity of the compound. Human osteosarcoma cell line MG63 (ATCC CRL-1427) was cultured in a 96-well plate of Dulbecco's Modified Eagle's medium, supplemented with 10% fetal bovine serum and 1% (v/v) L-glutamine, and the cultivation environment was 37° C. and 5% $CO_2$. Compound concentrations ranged from 4.5 nM to 30 μM. The Wee1 inhibitor stock solution was dissolved in DMSO, added to the medium with an indicated concentration and incubated for 72 hours. Negative control cells were only treated with vehicle. In some assays, a known Wee1 inhibitor was added as a positive control. Cell viability was measured using a Cell Counting Kit-8 (CCK-8, Sigma-Aldrich) under the instruction of the product specification. The data was analyzed using Graphpad software to obtain a fitted curve of $IC_{50}$ values against the compounds.

| Compound No. | $IC_{50}$ (nM) |
|---|---|
| 1-1-1 | 2405 |
| 1-2-1 | 593 |
| 2-2-1 | 439 |
| 3-1-1 | 1149 |
| 3-2-2 | 261 |
| 3-3-1 | 295 |
| 3-3-2 | 567 |
| 3-3-7 | 571 |
| 3-3-13 | 82.0 |
| 3-5-1 | 232 |
| 3-5-2 | 327 |
| 3-7-3 | 222 |
| 3-7-5 | 60.4 |
| 3-7-6 | 554 |
| 3-7-7 | 44.3 |
| 3-7-8 | 654 |
| 3-7-9 | 193 |

-continued

| Compound No. | IC$_{50}$(nM) |
| --- | --- |
| 3-7-10 | 56.4 |
| 3-7-13 | 150 |
| 3-7-15 | 211 |
| 3-7-16 | 99.1 |
| 3-7-17 | 270 |
| 3-8-1 | 160 |
| 8-1-2 | 323 |
| 10-1-1 | 490 |
| AZD1775 | 785 |

Remark: The positive controls for biological embodiment 1, 2 and 3 were AZD1775, chemical name for which is 2-allyl-1-(6-(2-hydroxypropan-2-yl)pyridin-2-yl)-6-((4-(4-methylpiperazin-1-yl)phenyl)amino)-1H-pyrazolo[3,4-d]pyrimidin-3 (2H)-one

What is claimed is:

1. A compound of formula I, an isomer, a prodrug, a stable isotope derivative or a pharmaceutically acceptable salt thereof;

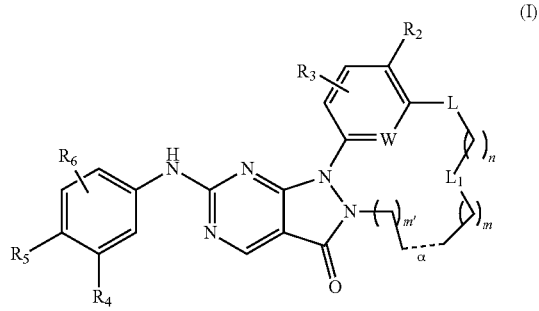

(I)

wherein, α bond is a single bond, a double bond or a triple bond;
L is CRR', O or NR'; L$_1$ is CRR$_1$, O or C(O); W is N or CR$_7$;
each of R and R$_1$ is independently H, halogen, —OR$_a$, —C(O)OR$_a$, —C(O)R$_a$, —C(O)NR$_a$R$_b$, —C(O)NR$_a$S(O)$_2$R$_b$, —S(O)$_{1-2}$R$_b$, —S(O)$_2$NR$_a$R$_b$, —S(O)$_2$N(R$_a$)C(O)R$_b$, —S(O)(=NCN)R$_a$, —S(O)(=NR$_c$)R$_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —NH$_2$, —NO$_2$, —SH, halogen, C$_{1-3}$ alkyl, C$_{1-3}$ alkoxyl and C$_{1-3}$ alkylamino; or R and R$_1$ together with the C atom to which they attached form a 3-8 membered cycloalkyl;
R' is H, —C(O)OR$_a$, —C(O)R$_a$, —C(O)NR$_a$R$_b$, —C(O)NR$_a$S(O)$_2$R$_b$, —S(O)$_{1-2}$R$_b$, —S(O)$_2$NR$_a$R$_b$, —S(O)$_2$N(R$_a$)C(O)R$_b$, —S(O)(=NCN)R$_a$, —S(O)(=NR$_c$)R$_a$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl; when the alkyl, cycloalkyl, heterocycloalkyl, cycloalkylalkyl or heterocycloalkylalkyl is substituted, it is substituted at any position by 1-3 substituents selected from the group consisting of —OH, —NH$_2$, —NO$_2$, —SH, halogen, C$_{1-3}$ alkyl, C$_{1-3}$ alkoxyl and C$_{1-3}$ alkylamino;
R$_2$ is H, halogen, hydroxyl, cyano, nitro, sulfydryl, amino, alkyl, alkoxyl, alkylthio, haloalkyl, haloalkoxyl, C$_{2-6}$ alkynyl, C$_{2-6}$ alkenyl, aryl, cycloalkyl, heterocycloalkyl, heteroaryl, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_0$, —S(O)$_{0-2}$R$_c$ or —S(O)$_2$N(R$_c$)$_2$;
or R' and R$_2$ are bonded to each other to form ring A; the ring A is substituted or unsubstituted C$_{3-15}$ cycloalkyl or substituted or unsubstituted 3-15 membered heterocycloalkyl; when the ring A is substituted, it is optionally substituted at any position by one or more substituents selected from the group consisting of oxo, thio, halogen, —CN, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, substituted or unsubstituted alkynyl; when the alkyl, cycloalkyl, heterocycloalkyl, cycloalkylalkyl, heterocycloalkylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;
R$_3$ is H, halogen, hydroxyl, cyano, nitro, sulfydryl, amino, alkyl, alkoxyl, alkylthio, haloalkyl, haloalkoxyl, C$_{2-6}$ alkynyl, C$_{2-6}$ alkenyl, aryl, cycloalkyl, heterocycloalkyl, heteroaryl, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —S(O)$_{0-2}$R$_c$ or —S(O)$_2$N(R$_c$)$_2$;
each of R$_4$ and R$_5$ is independently H, substituted or unsubstituted alkyl, substituted or unsubstituted alkoxyl, substituted or unsubstituted alkylamino, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, alkoxyl, alkylamino, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_d$, —OR$_d$, —OC(O)R$_d$, —OC(O)OR$_d$, —OC(O)

$NR_dR_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$ and —NR$_d$S(O)$_2$NR$_d$R$_e$;

or, $R_4$ and $R_5$ together with the ring atom to which they attached form a ring B, the ring B is substituted or unsubstituted monocyclic cycloalkyl, substituted or unsubstituted monocyclic heterocycloalkyl, substituted or unsubstituted spirocycloalkyl, substituted or unsubstituted spiroheterocyclyl, substituted or unsubstituted phenyl, or substituted or unsubstituted 5-12 membered heteroaryl; when the ring B is substituted, it is optionally substituted at any position by one or more substituents selected from the group consisting of oxo, halogen, —CN, —NO$_2$, —SR$_d$, —OR$_d$, —OC(O)R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_c$, —C(O)R$_c$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

$R_6$ is H, halogen, hydroxyl, sulfydryl, cyano, nitro, carboxyl, amino, alkyl, alkoxyl, alkylthio, alkylamino, haloalkyl, haloalkoxyl, $C_{2-6}$ alkynyl, $C_{2-6}$ alkenyl, hydroxyalkyl, aminoalkyl, aryl, cycloalkyl, substituted or unsubstituted heterocycloalkyl, heteroaryl or —CH$_2$OCH$_3$; when the heterocycloalkyl is substituted, it is optionally substituted at any position by 1-3 substituents selected from the group consisting of halogen, $C_{1-3}$ alkyl, $C_{1-3}$ alkoxyl and halo-$C_{1-3}$ alkyl;

$R_7$ is H, halogen, hydroxyl, sulfydryl, cyano, nitro, carboxyl, amino, alkyl, alkoxyl, alkylthio, alkylamino, haloalkyl, haloalkoxyl, $C_{2-6}$ alkynyl, $C_{2-6}$ alkenyl, hydroxyalkyl, aminoalkyl, aryl, cycloalkyl, substituted or unsubstituted heterocycloalkyl, or heteroaryl; when the heterocycloalkyl is substituted, it is optionally substituted at any position by 1-3 substituents selected from the group consisting of halogen, $C_{1-3}$ alkyl, $C_{1-3}$ alkoxyl and halo-$C_{1-3}$ alkyl;

each of $R_a$ and $R_b$ is independently selected from H, halogen, $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, 5-6 membered heteroaryl, $C_{3-8}$ cycloalkyl-$C_{1-6}$ alkyl, 3-8 membered heterocycloalkyl-$C_{1-6}$ alkyl, phenyl-$C_{1-6}$ alkyl, or 5-6 membered heteroaryl-$C_{1-6}$ alkyl; the $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, or 5-6 membered heteroaryl is unsubstituted or optionally substituted at any position by 1-3 substituents selected from the group consisting of halogen hydroxyl, amino, carboxyl, $C_{1-6}$ alkyl, halo-$C_{1-6}$ alkyl, $C_{1-6}$ alkoxyl and halo-$C_{1-6}$ alkoxyl;

each of $R_c$ is independently H, $C_{1-6}$ alkyl, halo-$C_{1-6}$ alkyl, $C_{3-8}$ cycloalkyl, 3-8 membered heterocycloalkyl, phenyl, 5-6 membered heteroaryl, 3-8 membered heterocycloalkyl-$C_{1-6}$ alkyl, $C_{3-8}$ cycloalkyl-$C_{1-6}$ alkyl, phenyl-$C_{1-6}$ alkyl or 5-6 membered heteroaryl-$C_{1-6}$ alkyl;

each of $R_d$ and $R_e$ is independently H, halogen, $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, 5-6 membered heteroaryl, $C_{3-8}$ cycloalkyl-$C_{1-6}$ alkyl, 3-8 membered heterocycloalkyl-$C_{1-6}$ alkyl, phenyl-$C_{1-6}$ alkyl, or 5-6 membered heteroaryl-$C_{1-6}$ alkyl; the $C_{1-6}$ alkyl, $C_{1-6}$ alkoxyl, $C_{2-6}$ alkenyl, $C_{2-6}$ alkynyl, $C_{3-8}$ cycloalkyl, 3-8 membered heterocycloalkyl, $C_{6-10}$ aryl, or 5-6 membered heteroaryl is unsubstituted or optionally substituted at any position by 1-3 substituents selected from the group consisting of halogen, hydroxyl, amino, carboxyl, $C_{1-6}$ alkyl, halo-$C_{1-6}$ alkyl, $C_{1-6}$ alkoxyl, $C_{1-6}$ alkylamino and halo-$C_{1-6}$ alkoxyl;

m' is an integer between 1-3;

each of m and n is independently an integer between 0-5.

2. The compound of formula I, the isomer, the prodrug, the stable isotope derivative or the pharmaceutically acceptable salt thereof of claim 1, wherein, α is a double bond; m' is 1.

3. The compound of formula I, the isomer, the prodrug, the stable isotope derivative or the pharmaceutically acceptable salt thereof of claim 1, wherein, α is a triple bond; m' is 1.

4. The compound of formula I, the isomer, the prodrug, the stable isotope derivative or the pharmaceutically acceptable salt thereof of claim 1, wherein, R' is H, —C(O)OR$_a$, —C(O)R$_a$, —C(O)NR$_a$R$_b$, —S(O)$_{1-2}$R$_b$, —C(O)NHS(O)$_2$R$_b$, —S(O)$_2$NR$_a$R$_b$, —S(O)$_2$NHC(O)R$_b$, —S(O)(=NCN)R$_a$, —S(O)(=NH)R$_a$, $C_{1-6}$ alkyl, or $C_{3-8}$ cycloalkyl;

and/or, $R_2$ is H;

and/or, $R_3$ is H, F, —OH, or $C_{1-6}$ alkoxyl;

and/or, $R_4$ is H, substituted or unsubstituted $C_{1-6}$alkyl, substituted or unsubstituted $C_{1-6}$ alkylamino, substituted or unsubstituted $C_{3-8}$ cycloalkyl, substituted or unsubstituted 3-9 membered heterocycloalkyl, substituted or unsubstituted phenyl, substituted or unsubstituted 5-6 membered heteroaryl, substituted or unsubstituted $C_{3-8}$ cycloalkyl-$C_{1-6}$ alkyl, substituted or unsubstituted 3-8 membered heterocycloalkyl-$C_{1-6}$ alkyl, substituted or unsubstituted phenyl-$C_{1-6}$ alkyl, substituted or unsubstituted 5-6 membered heteroaryl-$C_{1-6}$ alkyl, substituted or unsubstituted $C_{2-6}$ alkenyl, substituted or unsubstituted $C_{2-6}$ alkynyl;

and/or, $R_5$ is H, substituted or unsubstituted $C_{1-6}$ alkyl, substituted or unsubstituted $C_{1-6}$ alkylamino, substituted or unsubstituted $C_{3-8}$ cycloalkyl, substituted or unsubstituted 3-9 membered heterocycloalkyl, substituted or unsubstituted phenyl, substituted or unsubstituted 5-6 membered heteroaryl, substituted or unsubstituted $C_{3-8}$ cycloalkyl-$C_{1-6}$ alkyl, substituted or unsubstituted 3-8 membered heterocycloalkyl-$C_{1-6}$ alkyl, substituted or unsubstituted phenyl-$C_{1-6}$ alkyl, substituted or unsubstituted 5-6 membered heteroaryl-$C_{1-6}$ alkyl, substituted or unsubstituted $C_{2-6}$ alkenyl, substituted or unsubstituted $C_{2-6}$ alkynyl.

5. The compound of formula I, the isomer, the prodrug, the stable isotope derivative or the pharmaceutically acceptable salt thereof of claim 1, wherein, $R_4$ is

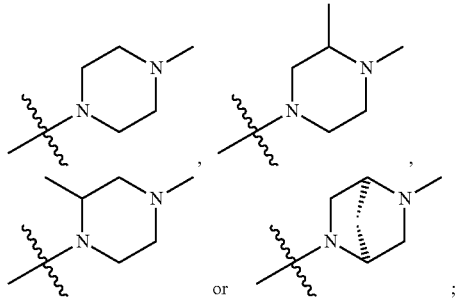

or, $R_5$ is

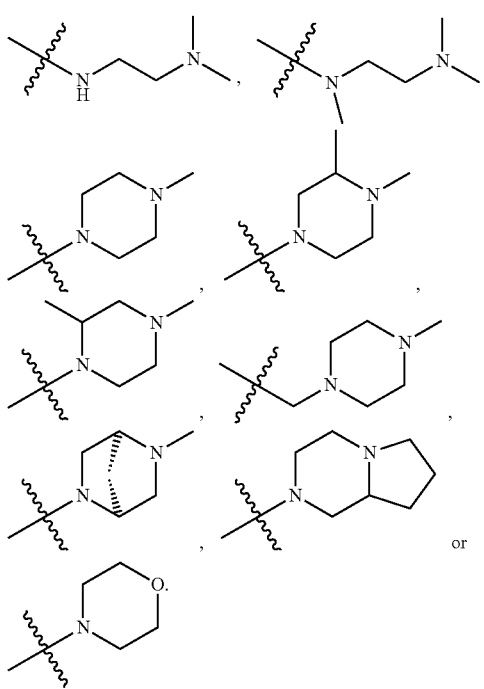

6. The compound of formula I, the isomer, the prodrug, the stable isotope derivative or the pharmaceutically acceptable salt thereof of claim 1, wherein, $R_2$ and R' are bonded to each other to form ring A; the ring A is a substituted or unsubstituted 5-8 membered heterocycloalkyl;

and/or, $R_4$ and $R_5$ together with the ring atom to which they attached form a ring B, the ring B is substituted or unsubstituted $C_{4-8}$ monocyclic cycloalkyl, substituted or unsubstituted 4-8 membered monocyclic heterocycloalkyl, substituted or unsubstituted $C_{7-12}$ spirocycloalkyl, substituted or unsubstituted 7-12 membered spiroheterocyclyl, substituted or unsubstituted phenyl, substituted or unsubstituted 5-10 membered heteroaryl.

7. The compound of formula I, the isomer, the prodrug, the stable isotope derivative or the pharmaceutically acceptable salt thereof of claim 1, wherein, the compound of formula I is the compound of formula II or II':

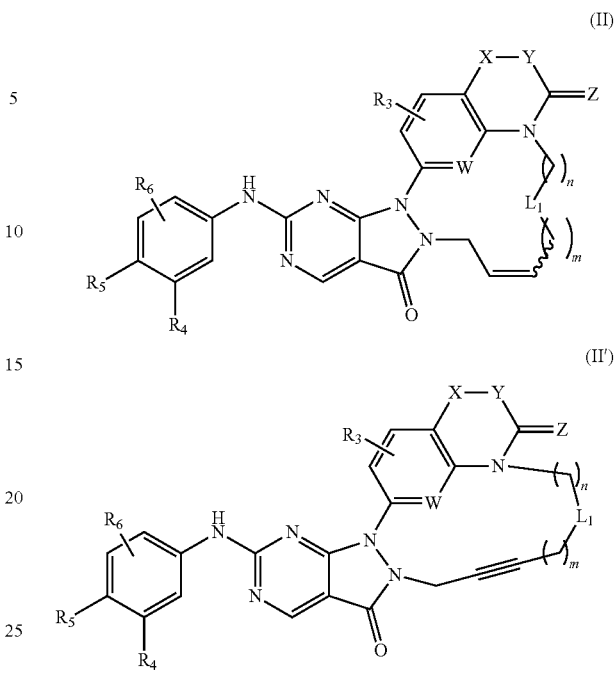

wherein, each of X and Y is a bond, —$CR_8R_{8a}$—, —$NR_9$—, —O—, —C(O)—, or —$S(O)_{1-2}$—;

Z is H/H, O or S;

each of $R_8$ and $R_9$ is H, halogen, —CN, —$SR_d$, —$OR_d$, —$OC(O)R_d$, —$OC(O)OR_d$, —$OC(O)NR_dR_e$, —C(O) $OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, —$NR_dS(O)_2NR_dR_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted alkenyl, substituted or unsubstituted alkynyl; when the alkyl, cycloalkyl, heterocycloalkyl, cycloalkylalkyl, heterocycloalkylalkyl, alkenyl or alkynylis substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_c$, —$C(O)R_c$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)_2N(R_c)_2$;

each of $R_{8a}$ is independently H, halogen or alkyl;

or each of $R_8$ and $R_{8a}$ together with the C atom to which they attached form a 3-8 membered cycloalkyl or heterocycloalkyl; the heterocycloalkyl comprises 1-2 heteroatoms or groups selected from the group consisting of N, O and $S(O)_{1-2}$;

$R_3$, $R_4$, $R_5$, $R_6$, W, $L_1$, m, n, $R_c$, $R_d$, $R_e$ are as defined in claim 1.

8. The compound of formula I, the isomer, the prodrug, the stable isotope derivative or the pharmaceutically acceptable salt thereof of claim 1, wherein, the compound of formula I is as shown in formula I-1, I-2, I-3 or I-6:

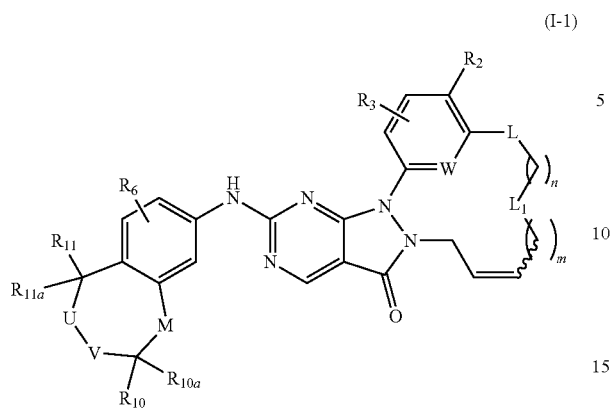

(I-1)

in I-1, M is a bond, —$CR_{12}R_{12a}$—, —$NR_{13}$—, or —O—;
U is a bond, —$CR_{12}R_{12a}$—, —$NR_{13}$—, —C(O)—, or —$S(O)_{1-2}$—;
V is a bond, —$NR_{13}$—, —O—, or —$CR_{12}R_{12a}$—;
each of $R_{10}$, $R_{11}$ and $R_{12}$ is independently H, halogen, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, —$NR_dS(O)_2NR_dR_e$, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_c$, —$C(O)R_c$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)_2N(R_c)_2$;
each of $R_{10a}$, $R_{11a}$ and $R_{12a}$ is independently H, hydroxyl, $C_{1-6}$ alkoxyl, halogen or alkyl;
or, each of $R_{10}$ and $R_{10a}$, $R_{11}$ and $R_{11a}$, $R_{12}$ and $R_{12a}$ together with the C atom to which they attached form a 3-8 membered cycloalkyl or heterocycloalkyl; the heterocycloalkyl comprises 1-2 heteroatomes or heterogroups selected from the group consisting of N, O, $S(O)_{1-2}$;
or, each of $R_{10}$ and $R_{10a}$, $R_{11}$ and $R_{11a}$, $R_{12}$ and $R_{12a}$ together with the C atom to which they attached form a —C(=O)—;
$R_{13}$ is H, —$OR_d$, —$C(O)OR_d$, —$C(O)R_d$, —$C(O)NR_dR_e$, —$S(O)_{1-2}R_e$, —$S(O)_2NR_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_c$, —$C(O)R_c$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)_2N(R_c)_2$;

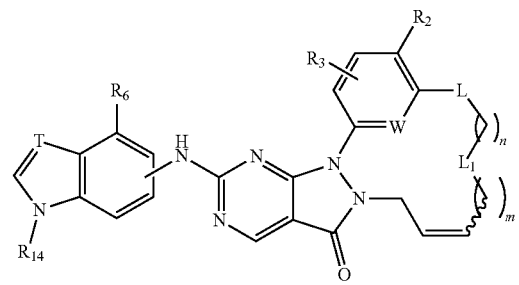

(I-2)

in I-2, T is N or $CR_{14}'$;
each of $R_{14}$ and $R_{14}'$ is H, —$OR_d$, —$C(O)OR_d$, —$C(O)R_d$, —$C(O)NR_dR_e$, —$S(O)_{1-2}R_e$, —$S(O)_2NR_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_c$, —$C(O)R_c$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)_2N(R_c)_2$;

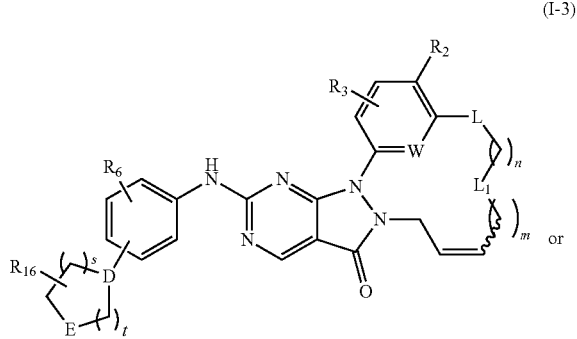

(I-3)

or

-continued

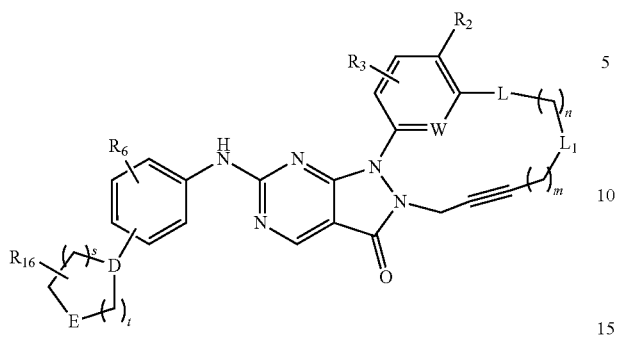

(I-6)

in I-3 or I-6, the moiety

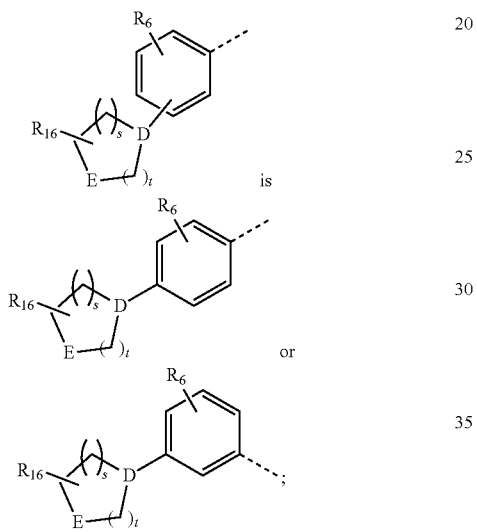

D is $CR_{17}$ or N;
E is —$CR_{17}R_{17a}$— or —$NR_{15}$—;
s is 0, 1 or 2;
t is 0, 1 or 2;
$R_{15}$ is H, —$OR_d$, —$C(O)OR_d$, —$C(O)R_d$, —$C(O)NR_dR_e$, —$S(O)_{1-2}R_e$, —$S(O)_2NR_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxy, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_d$, —$C(O)R_d$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)_2N(R_c)_2$;

$R_{16}$ is H, halogen, oxo, —CN, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, —$NR_dS(O)_2NR_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxy, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_d$, —$C(O)R_d$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)_2N(R_c)_2$;

$R_{17}$ is H, halogen, —CN, —$SR_d$, —$OR_d$, —$OC(O)R_d$, —$OC(O)OR_d$, —$OC(O)NR_dR_e$, —$C(O)OR_d$, —$C(O)R_d$, —$C(O)NR_dR_e$, —$NR_dR_e$, —$NR_dC(O)R_e$, —$N(R_d)C(O)OR_e$, —$N(R_d)C(O)NR_dR_e$, —$NR_dS(O)_2R_e$, —$NR_dC(=NH)R_e$, —$NR_dC(=NH)NR_dR_e$, —$S(O)_{1-2}R_e$, —$S(O)_2NR_dR_e$, —$NR_dS(O)_2NR_dR_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxy, hydroxyalkyl, aminoalkyl, alkenyl, alkynyl, —CN, —$NO_2$, —$SR_c$, —$OR_c$, —$OC(O)R_c$, —$OC(O)OR_c$, —$OC(O)N(R_c)_2$, —$C(O)OR_c$, —$C(O)R_c$, —$C(O)N(R_c)_2$, —$N(R_c)_2$, —$NHC(O)R_c$, —$NHC(O)OR_c$, —$NHC(O)N(R_c)_2$, —$NHS(O)_2R_c$, —$NHC(=NH)R_c$, —$NHC(=NH)N(R_c)_2$, —$S(O)_{1-2}R_c$, —$S(O)_2N(R_c)_2$ and —$NHS(O)N(R_c)_2$;

$R_{17a}$ is H, halogen or alkyl.

9. The compound of formula I, the isomer, the prodrug, the stable isotope derivative or the pharmaceutically acceptable salt thereof of claim 8, wherein, in I-1, $R_{10}$ and $R_{10a}$ together with the carbon atom to which they attached form a 3 membered ring, U is —$CH_2$—, $R_{11}$ and $R_{11a}$ are H;

or, $R_{11}$ and $R_{11a}$ together with the carbon atom to which they attached form a 3 membered ring, U is —$CH_2$—, $R_{10}$ and $R_{10a}$ are H;

or, each of R₁₁ and R₁₁ₐ is H; U is

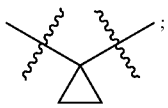 [SMILES: *C1(*)CC1]

each of R₁₀ and R₁₀ₐ is H;
or, each of R₁₁ and R₁₁ₐ is —CH₃; U is —CH₂—; each of R₁₀ and R₁₀ₐ is H;
and/or, R₃ is H.

10. The compound of formula I, the isomer, the prodrug, the stable isotope derivative or the pharmaceutically acceptable salt thereof of claim 8, wherein, in I-2, T is N or CH; R₁₄ is substituted or unsubstituted C₁₋₆ alkyl, substituted or unsubstituted C₃₋₈ cycloalkyl, substituted or unsubstituted 3-8 membered heterocycloalkyl, substituted or unsubstituted C₃₋₈ cycloalkyl-C₁₋₆ alkyl, or substituted or unsubstituted 3-8 membered heterocycloalkyl-C₁₋₆ alkyl; the C₁₋₆ alkyl, C₃₋₈ cycloalkyl, 3-8 membered heterocycloalkyl, C₃₋₈ cycloalkyl-C₁₋₆ alkyl or 3-8 membered heterocycloalkyl-C₁₋₆ alkyl is optionally substituted at any position by 1-3 substituents selected from the group consisting of halogen, C₁₋₄ alkyl, halo-C₁₋₃ alkyl, halo-C₁₋₃ alkoxyl, hydroxy-C₁₋₃ alkyl, amino-C₁₋₃ alkyl, —CN, —ORd, —C(O)ORd, —C(O)Rd, —C(O)NRdRe, —NRdRe, —S(O)₁₋₂Re, —S(O)₂NRdRe and —NRdS(O)₂NRdRe; each of Rd and Re is independently H or C₁₋₄ alkyl;

or, T is CR₁₄'; R₁₄' is substituted or unsubstituted C₁₋₆ alkyl, substituted or unsubstituted C₃₋₈ cycloalkyl, substituted or unsubstituted 3-8 membered heterocycloalkyl, substituted or unsubstituted C₃₋₈ cycloalkyl-C₁₋₆ alkyl, or substituted or unsubstituted 3-8 membered heterocycloalkyl-C₁₋₆ alkyl; the C₁₋₆ alkyl, C₃₋₈ cycloalkyl, 3-8 membered heterocycloalkyl, C₃₋₈ cycloalkylC₁₋₆ alkyl or 3-8 membered heterocycloalkyl-C₁₋₆ alkyl is optionally substituted at any position by 1-3 substituents selected from the group consisting of halogen, C₁₋₄ alkyl, halo-C₁₋₃ alkyl, halo-C₁₋₃ alkoxyl, hydroxy-C₁₋₃ alkyl, amino-C₁₋₃ alkyl, —CN, —ORd, —C(O)ORd, —C(O)Rd, —C(O)NRdRe, —NRdRe, —S(O)₁₋₂Re, —S(O)₂NRdRe and —NRdS (O)₂NRdRe; each of Rd and Re is independently H or C₁₋₄ alkyl; R₁₄ is H;

or, T is CH; R₁₄ is H or C₁₋₆ alkyl; R₆ is —N(CH₃)₂, piperazinyl, piperidinyl, pyrrolidinyl or azetidinyl; wherein the piperazinyl, piperidinyl, pyrrolidinyl or azetidinyl is optionally substituted at any position by one substituent selected from F, Cl, —CH₃, —OCH₃, —OCF₃, —CF₃, or —CHF₂.

11. The compound of formula I, the isomer, the prodrug, the stable isotope derivative or the pharmaceutically acceptable salt thereof of claim 8, wherein, in I-3 or I-6, D is N or CH;
and/or, R₆ is H, F, Cl, —CN, —CH₃, —CH₂OH, or —CH₂OCH₃;
and/or, R₁₅ is H, —ORd, —C(O)ORd, —C(O)Rd, —C(O)NRdRe, —S(O)₁₋₂Re, —S(O)₂NRdRe, substituted or unsubstituted C₁₋₄ alkyl; the C₁₋₄ alkyl is optionally substituted at any position by 1-3 substituents selected from the group consisting of halogen, halo-C₁₋₃ alkyl, —CN, —ORc and —N(Rc)₂; each of Rc, Rd and Re is independently H or C₁₋₄ alkyl;
and/or, R₁₆ is H, —CH₃, —CH₂OH, or —CH₂OCH₃.

12. The compound of formula I, the isomer, the prodrug, the stable isotope derivative or the pharmaceutically acceptable salt thereof of claim 7, wherein, the compound of formula I is the compound of formula II-1, II-2, II-3 or II-6:

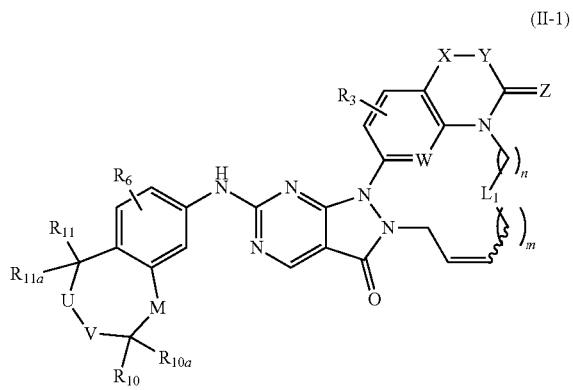

(II-1)

in II-1, each of X and Y is a bond, —CR₈R₈ₐ—, —NR₉—, O, —C(O)—, or —S(O)₁₋₂—;
Z is H/H, O or S;
M is a bond, —CR₁₂R₁₂ₐ—, —NR₁₃—, or —O—;
U is a bond, —CR₁₂R₁₂ₐ—, —NR₁₃—, —C(O)—, or —S(O)₁₋₂—;
V is a bond, —NR₁₃—, —O—, or —CR₁₂R₁₂ₐ—;
each of R₁₀, R₁₁ and R₁₂ is independently H, halogen, —SRd, —ORd, —OC(O)Rd, —OC(O)ORd, —OC(O)NRdRe, —C(O)ORd, —C(O)Rd, —C(O)NRdRe, —NRdRe, —NRdC(O)Re, —N(Rd)C(O)ORe, —N(Rd)C(O)NRdRe, —NRdS(O)₂Re, —NRdC(=NH)Re, —NRdC(=NH)NRdRe, —S(O)₁₋₂Re, —S(O)₂NRdRe, —NRdS(O)₂NRdRe, substituted or unsubstituted alkyl, substituted or unsubstituted cycloalkyl, substituted or unsubstituted heterocycloalkyl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO₂, —SRc, —ORc, —OC(O)Rc, —OC(O)ORc, —OC(O)N(Rc)₂, —C(O)ORc, —C(O)Rc, —C(O)N(Rc)₂, —N(Rc)₂, —NHC(O)Rc, —NHC(O)ORc, —NHC(O)N(Rc)₂, —NHS(O)₂Rc, —NHC(=NH)Rc, —NHC(=NH)N(Rc)₂, —S(O)₁₋₂Rc, —S(O)₂N(Rc)₂ and —NHS(O)₂N(Rc)₂;
each of R₁₀ₐ, R₁₁ₐ and R₁₂ₐ is independently H, hydroxyl, C₁₋₆ alkoxyl, halogen or alkyl;
or, each of R₁₀ and R₁₀ₐ, R₁₁ and R₁₁ₐ, R₁₂ and R₁₂ₐ together with the C atom to which they attached form a 3-8 membered cycloalkyl or heterocycloalkyl; the heterocycloalkyl comprises 1-2 heteroatomes or heterogroups selected from the group consisting of N, O, S(O)₁₋₂;
or, each of R₁₀ and R₁₀ₐ, R₁₁ and R₁₁ₐ, R₁₂ and R₁₂ₐ together with the C atom to which they attached form a —C(=O)—;

R₁₃ is H, —OR_d, —C(O)OR_d, —C(O)R_d, —C(O)NR_dR_e, —S(O)₁₋₂R_e, —S(O)₂NR_dR_e, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO₂, —SR_c, —OR_c, —OC(O)R_c, —OC(O)OR_c, —OC(O)N(R_c)₂, —C(O)OR_c, —C(O)R_c, —C(O)N(R_c)₂, —N(R_c)₂, —NHC(O)R_c, —NHC(O)OR_c, —NHC(O)N(R_c)₂, —NHS(O)₂R_c, —NHC(=NH)R_c, —NHC(=NH)N(R_c)₂, —S(O)₁₋₂R_c, —S(O)₂N(R_c)₂ and —NHS(O)₂N(R_c)₂;

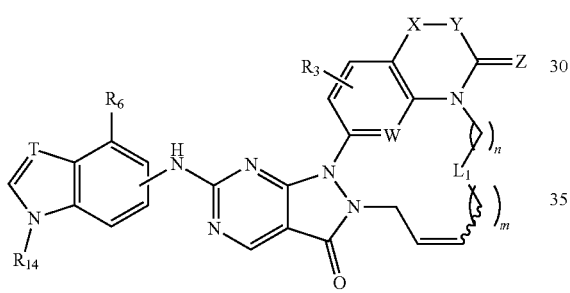

(II-2)

in II-2, each of X and Y is a bond, —CR₈R₈ₐ—, —NR₉—, O, —C(O)—, or —S(O)₁₋₂—;
Z is H/H, O or S;
T is N or CR₁₄';
each of R₁₄ and R₁₄' is H, —OR_d, —C(O)OR_d, —C(O)R_d, —C(O)NR_dR_e, —S(O)₁₋₂R_e, —S(O)₂NR_dR_e, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO₂, —SR_c, —OR_c, —OC(O)R_c, —OC(O)OR_c, —OC(O)N(R_c)₂, —C(O)OR_c, —C(O)R_c, —C(O)N(R_c)₂, —N(R_c)₂, —NHC(O)R_c, —NHC(O)OR_c, —NHS(O)₂R_c, —NHC(=NH)R_c, —NHC(=NH)N(R_c)₂, —S(O)₁₋₂R_c, —S(O)₂N(R_c)₂ and —NHS(O)₂N(R_c)₂;

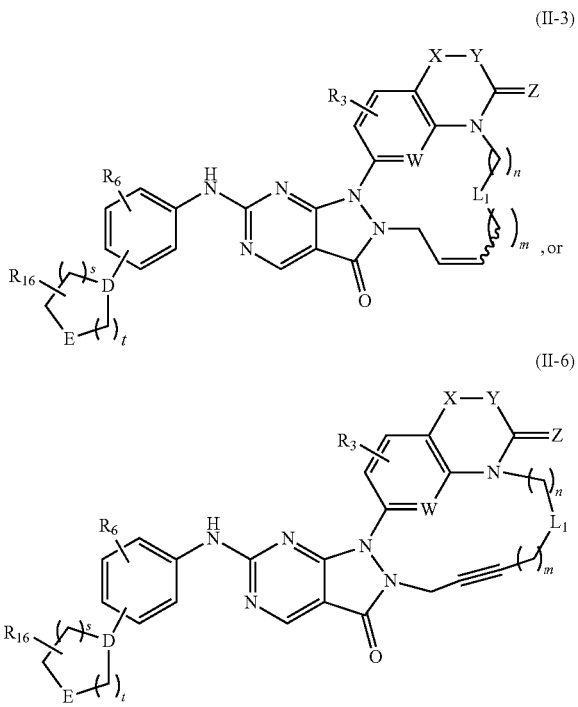

(II-3)

(II-6)

in II-3 or II-6, the moiety

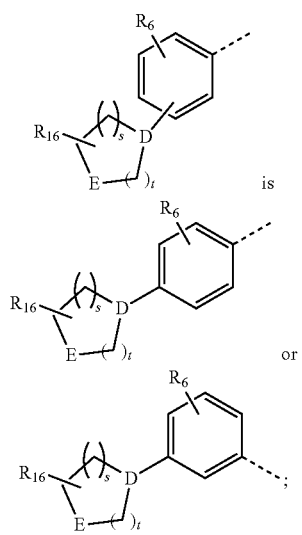

is each of X and Y is a bond, —CR₈R₈ₐ—, —NR₉—, O, —C(O)—, or —S(O)₁₋₂—;
Z is H/H, O or S;
D is CR₁₇ or N;
E is —CR₁₇R₁₇ₐ— or —NR₁₅—;
s is 0, 1 or 2;
t is 0, 1 or 2;
R₁₅ is H, —OR_d, —C(O)OR_d, —C(O)R_d, —C(O)NR_dR_e, —S(O)₁₋₂R_e, —S(O)₂NR_dR_e, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O)R$_c$, —OC(O)OR$_c$, —OC(O)N(R$_c$)$_2$, —C(O)OR$_d$, —C(O)R$_d$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N (R$_c$)$_2$, —S(O)$_{1-2}$R$_c$, —S(O)$_2$N(R$_c$)$_2$ and —NHS(O)$_2$N (R$_c$)$_2$;

R$_{16}$ is H, halogen, oxo, —CN, —SR$_d$, —OR$_d$, —OC(O) R$_d$, —OC(O)OR$_d$, —OC(O)NR$_d$R$_e$, —C(O)OR$_d$, —C(O)R$_d$, —C(O)NR$_d$R$_e$, —NR$_d$R$_e$, —NR$_d$C(O)R$_e$, —N(R$_d$)C(O)OR$_e$, —N(R$_d$)C(O)NR$_d$R$_e$, —NR$_d$S(O)$_2$R$_e$, —NR$_d$C(=NH)R$_e$, —NR$_d$C(=NH) NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, alkynyl, —CN, —NO$_2$, —SR$_c$, —OR$_c$, —OC(O) R$_c$, —OC(O)OR$_c$, —OC(O)N(R$_c$)$_2$, —C(O)OR$_d$, —C(O)R$_d$, —C(O)N(R$_c$)$_2$, —N(R$_c$)$_2$, —NHC(O)R$_c$, —NHC(O)OR$_c$, —NHC(O)N(R$_c$)$_2$, —NHS(O)$_2$R$_c$, —NHC(=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{17}$ is H, halogen, —CN, —SR$_d$, —OR$_d$, —OC(O)R$_d$, —OC(O)OR$_d$, —OC(O)NR$_d$R$_e$, —C(O)OR$_d$, —C(O) R$_d$, —C(O)NR$_d$R$_e$, —NR$_d$R$_e$, —NR$_d$C(O)R$_e$, —N(R$_d$) C(O)OR$_e$, —N(R$_d$)C(O)NR$_d$R$_e$, —NR$_d$S(O)$_2$R$_e$, —NR$_d$C(=NH)R$_e$, —NR$_d$C(=NH)NR$_d$R$_e$, —S(O)$_{1-2}$R$_e$, —S(O)$_2$NR$_d$R$_e$, —NR$_d$S(O)$_2$NR$_d$R$_e$, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, substituted or unsubstituted alkenyl, substituted or unsubstituted alkynyl; when the alkyl, cycloalkyl, heterocycloalkyl, aryl, heteroaryl, cycloalkylalkyl, heterocycloalkylalkyl, arylalkyl, heteroarylalkyl, alkenyl or alkynyl is substituted, it is optionally substituted at any position by one or more substituents selected from the group consisting of halogen, alkyl, haloalkyl, haloalkoxyl, hydroxyalkyl, aminoalkyl, alkenyl, —CN, —NO$_2$, —SR$_c$, —OR$_c$, —OC(O)R$_c$, —OC (O)OR$_c$, —OC(O)N(R$_c$)$_2$, —C(O)OR$_c$, —C(O)R$_c$, —C(O)N(R$_c$)$_2$, —N(R)$_2$, —NHC(O)R$_c$, —NHC(O) OR$_c$, —NHC(O)N(R$_c$)$_2$, —NHS(O)$_2$R$_c$, —NHC (=NH)R$_c$, —NHC(=NH)N(R$_c$)$_2$, —S(O)$_{1-2}$R$_c$, —S(O)$_2$N(R$_c$)$_2$ and —NHS(O)$_2$N(R$_c$)$_2$;

R$_{17a}$ is H, halogen or alkyl.

13. The compound of formula I, the isomer, the prodrug, the stable isotope derivative or the pharmaceutically acceptable salt thereof of claim 12, wherein, X is a bond or O; Y is —CH$_2$—, —CH(CH$_3$)—, or —C(CH$_3$)$_2$—.

14. The compound of formula I, the isomer, the prodrug, the stable isotope derivative or the pharmaceutically acceptable salt thereof of claim 1, wherein, the compound of formula I is selected from the group consisting of:

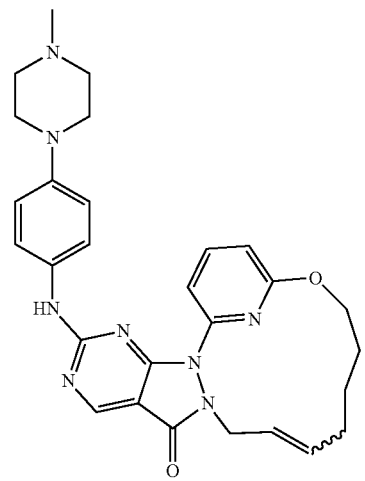

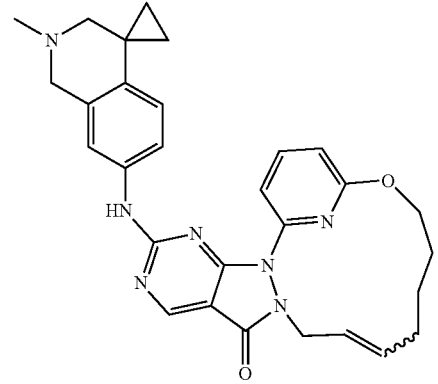

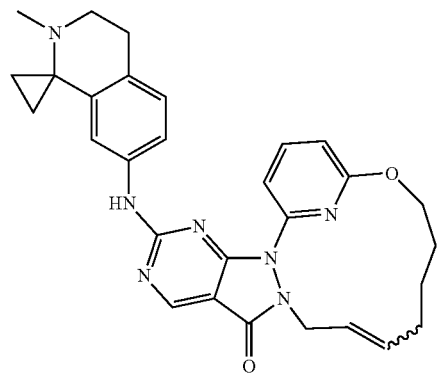

229
-continued
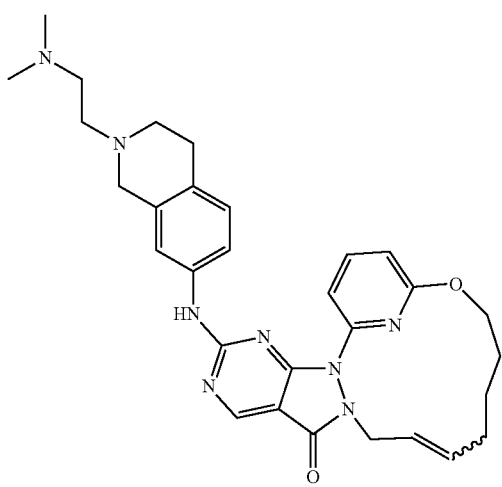
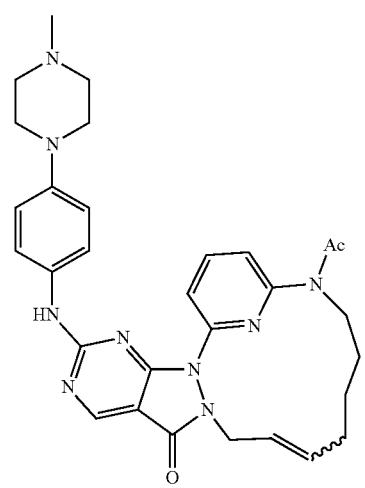
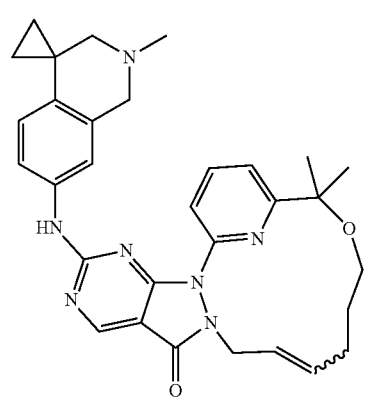
230
-continued
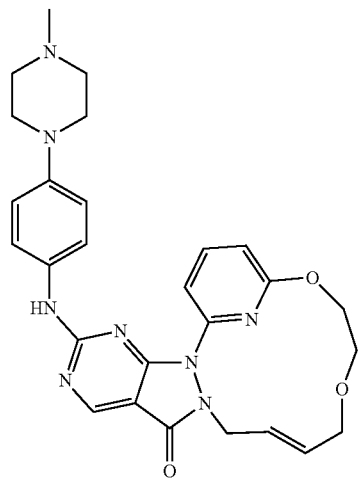
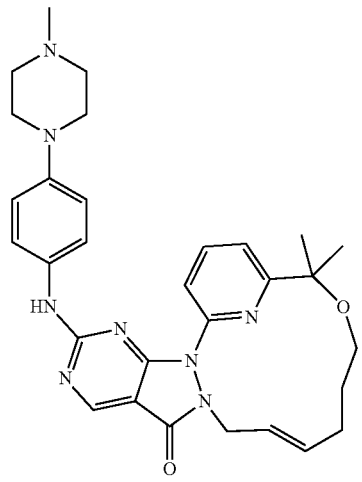
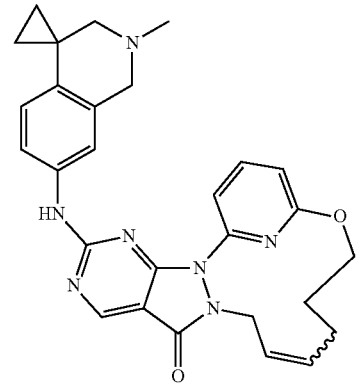
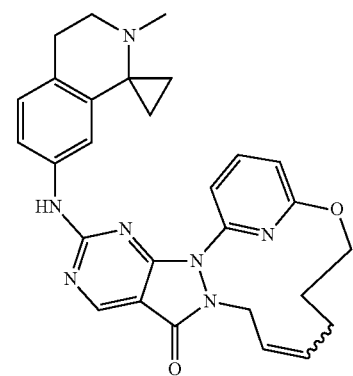

231
-continued
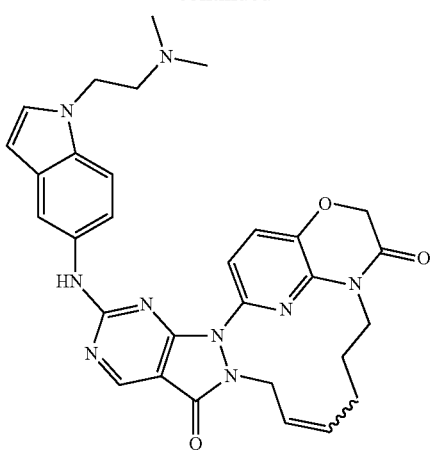
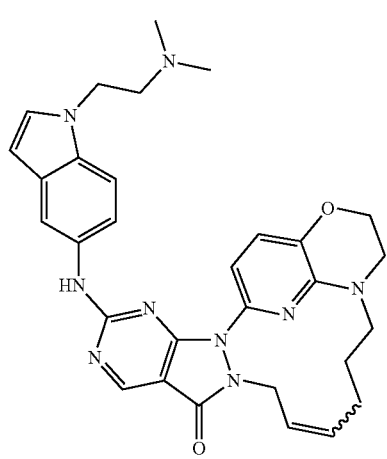
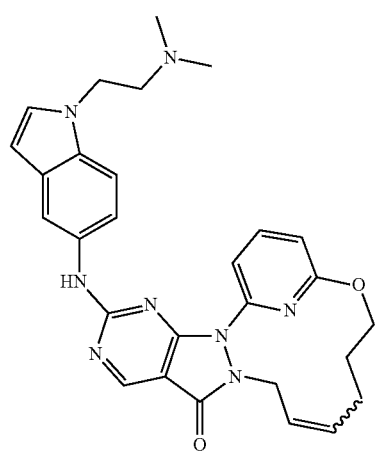
232
-continued
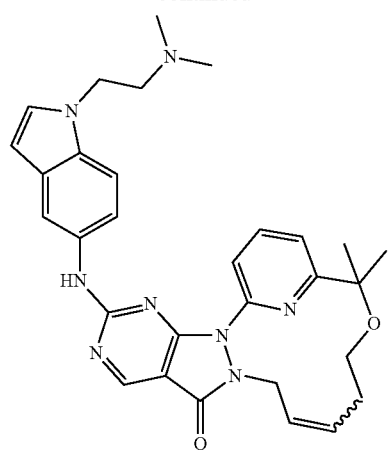
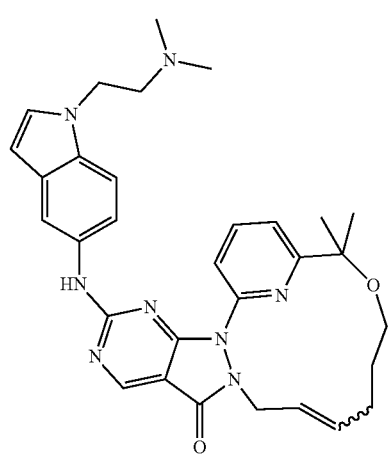
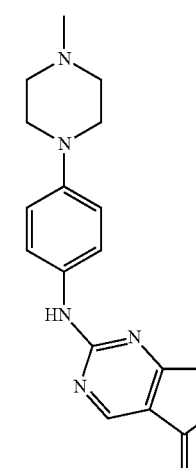

233
-continued
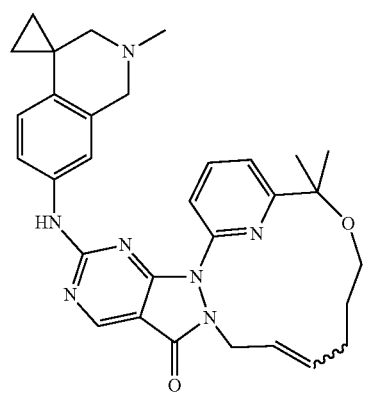
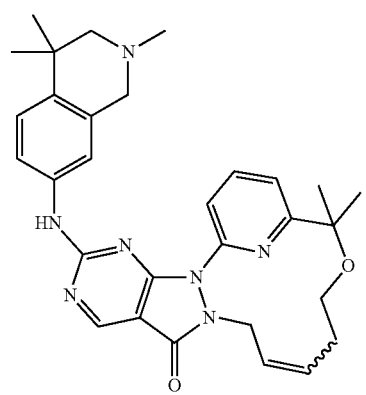
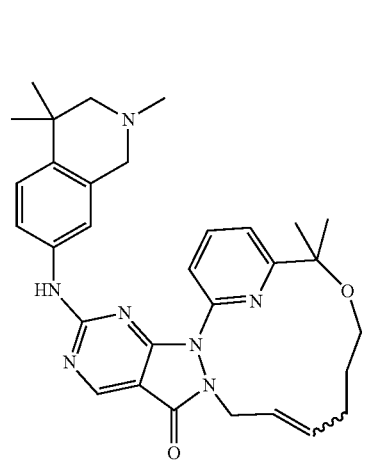
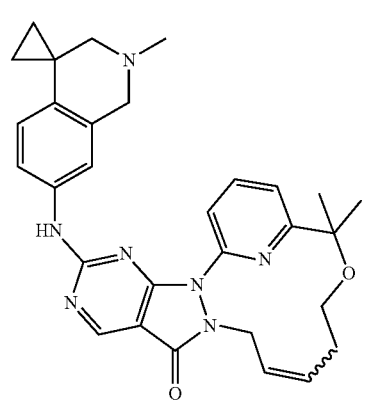
234
-continued
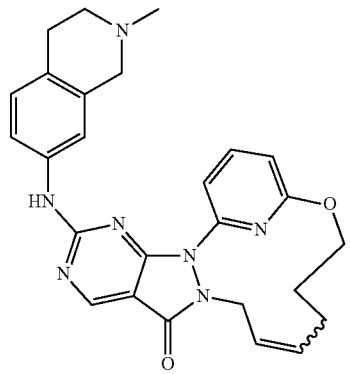
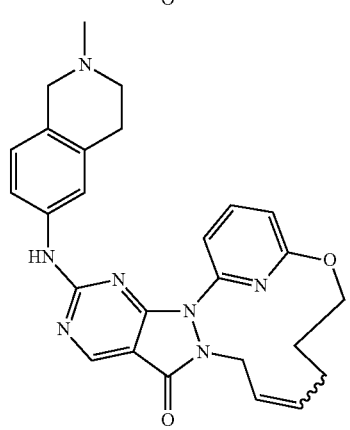
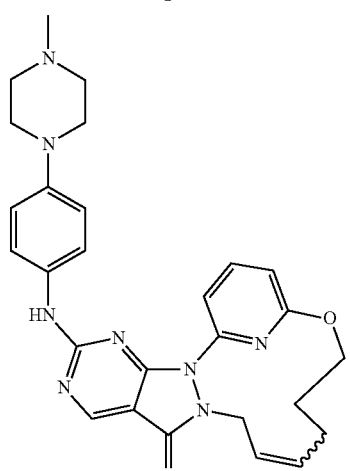
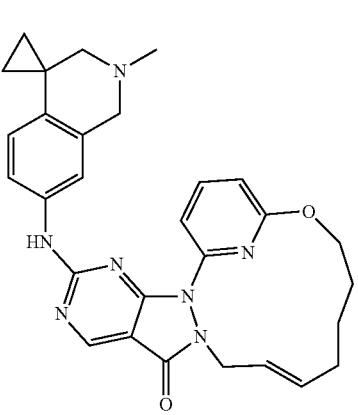

235
-continued
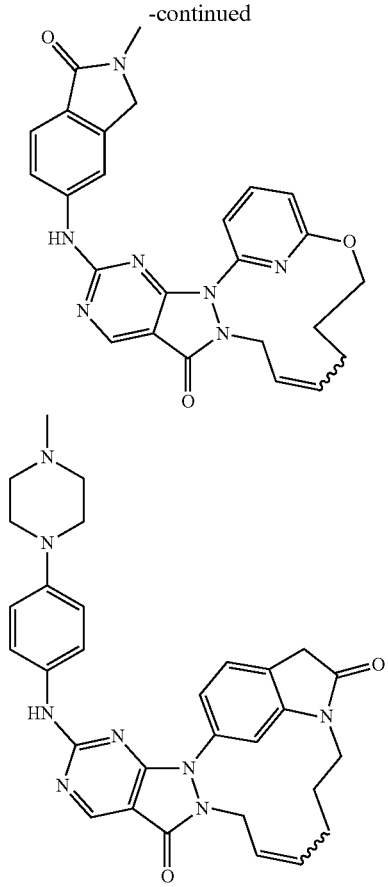
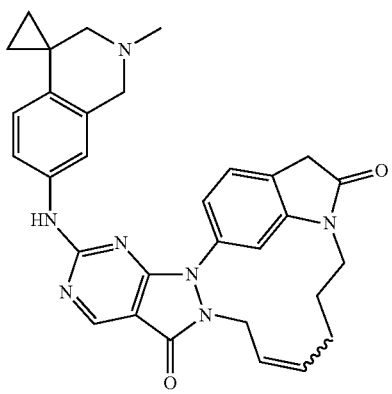
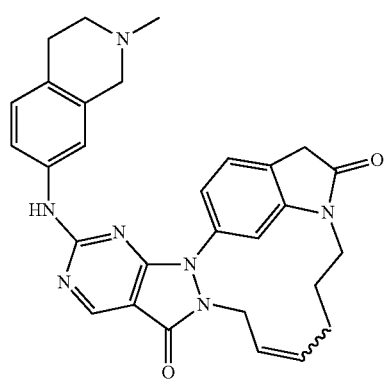
236
-continued
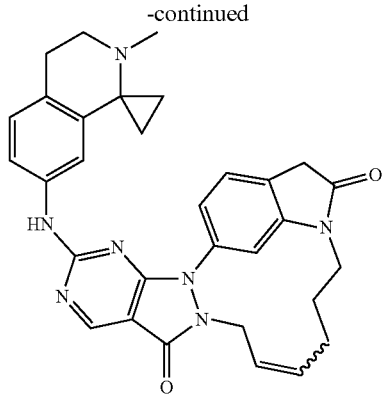
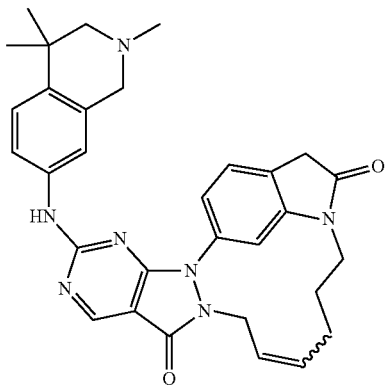
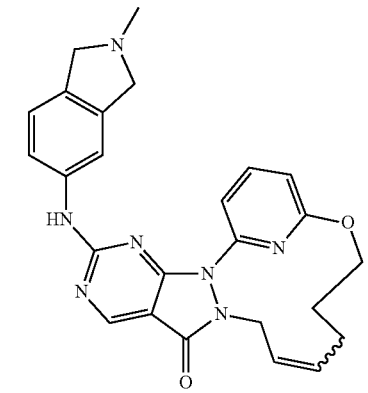
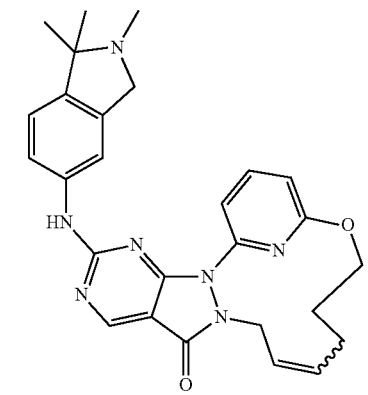

237
-continued
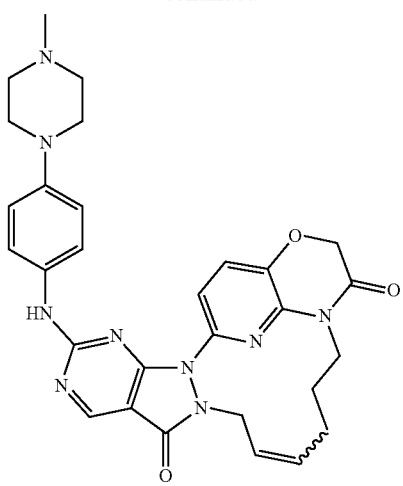
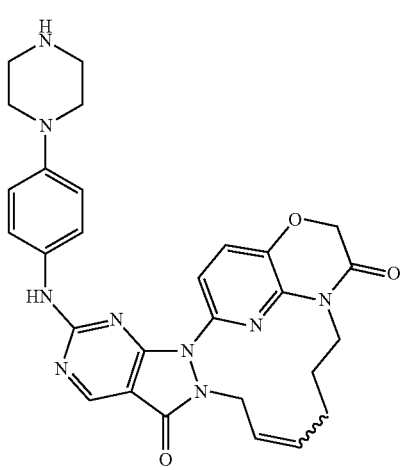
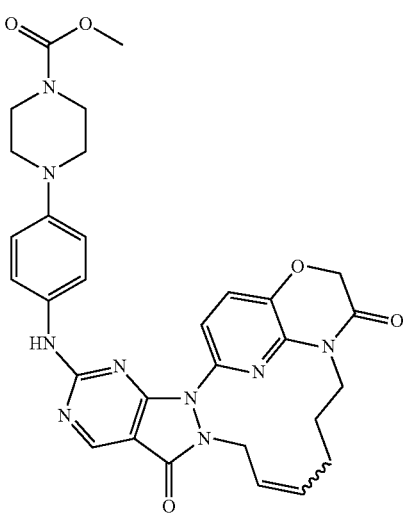
238
-continued
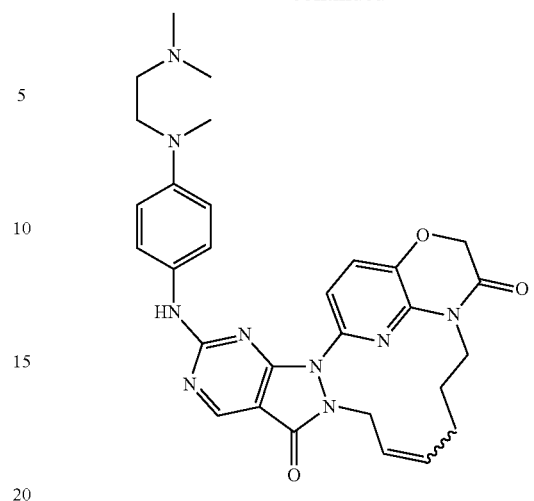
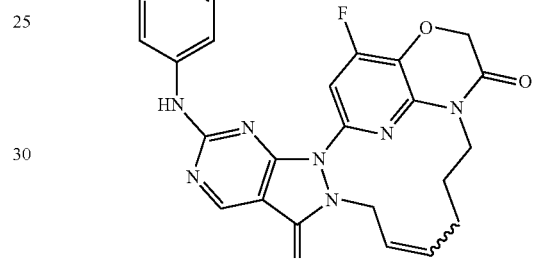
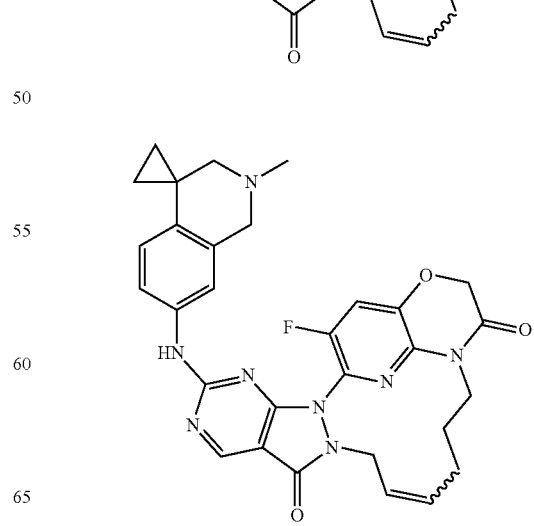

239
-continued
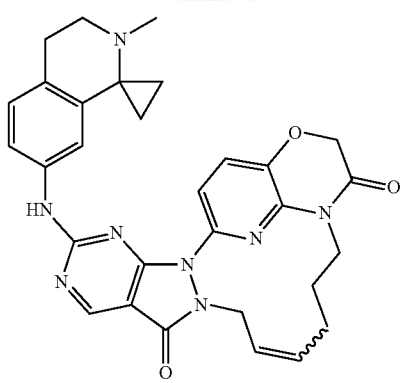
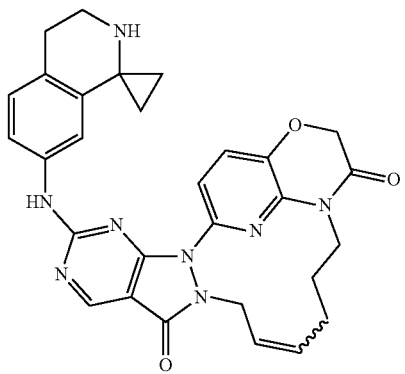
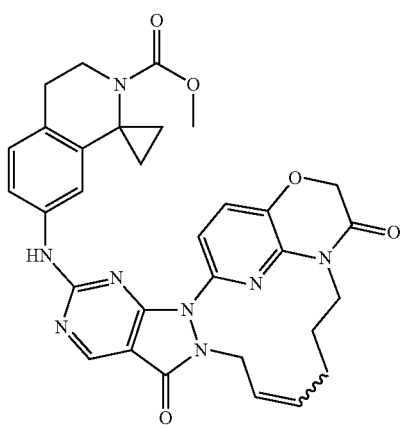
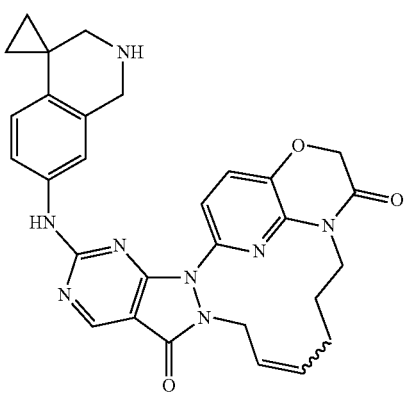
240
-continued
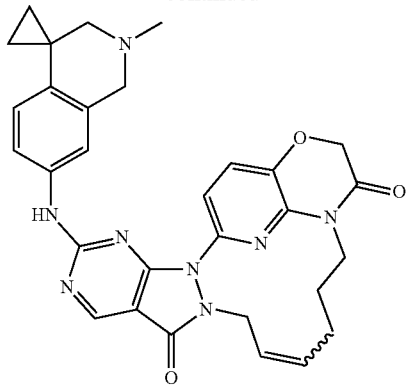
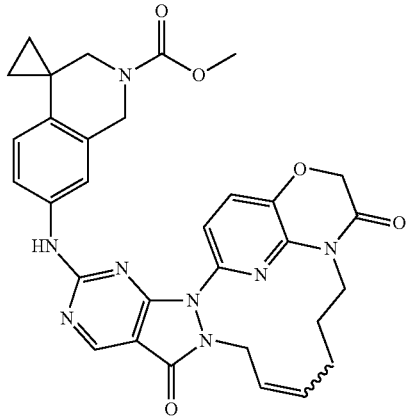
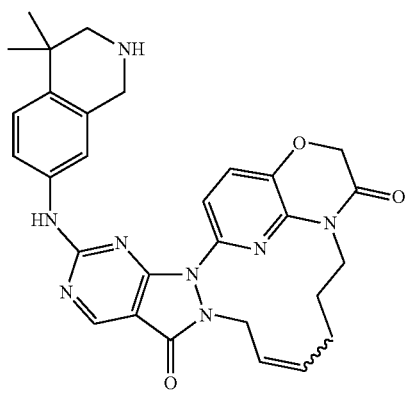
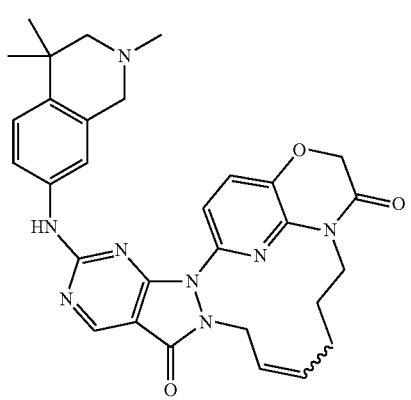

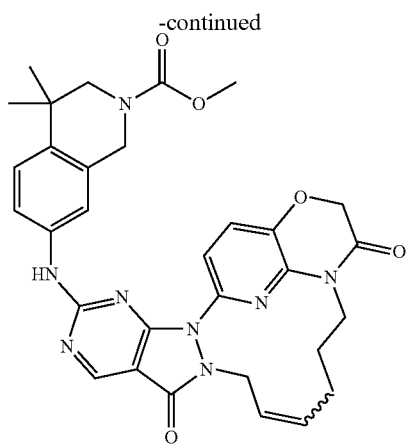
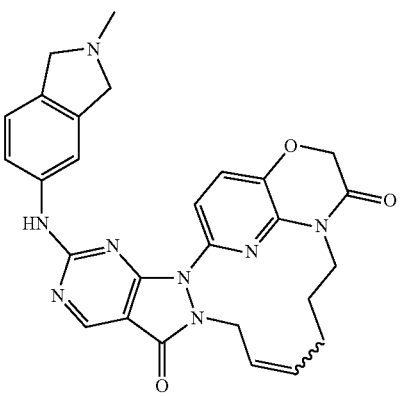
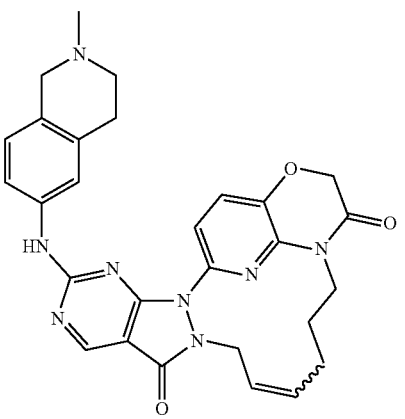
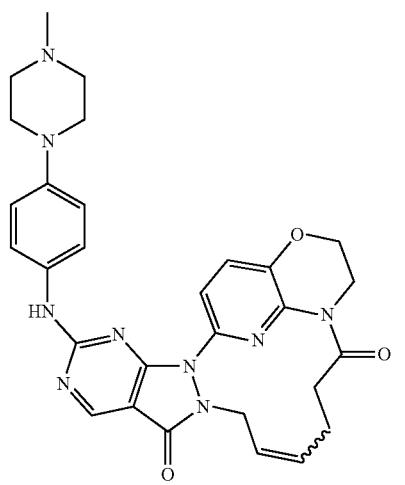
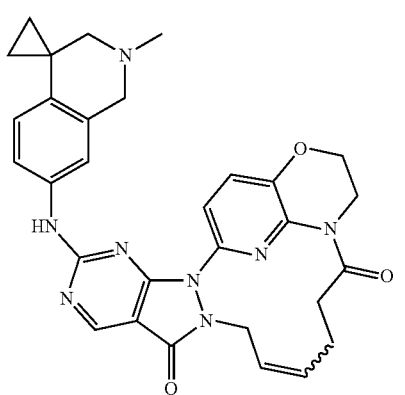

243
-continued
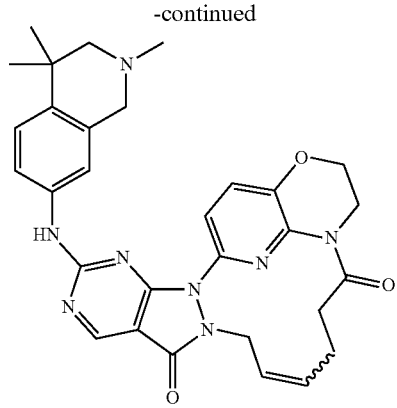
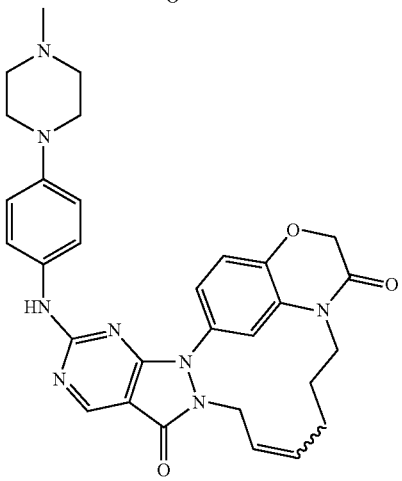
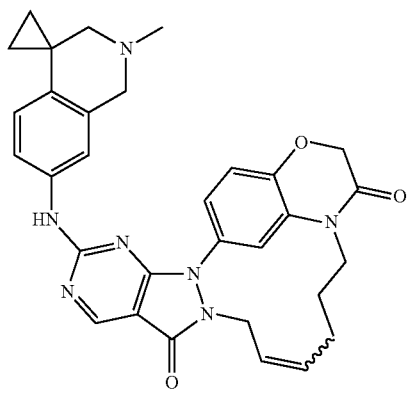
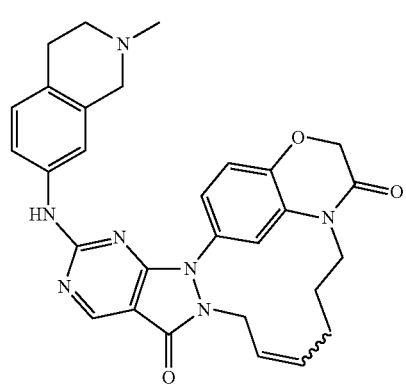
244
-continued
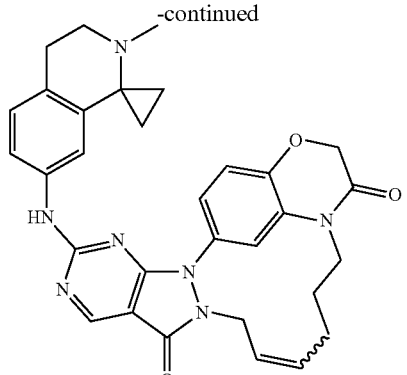
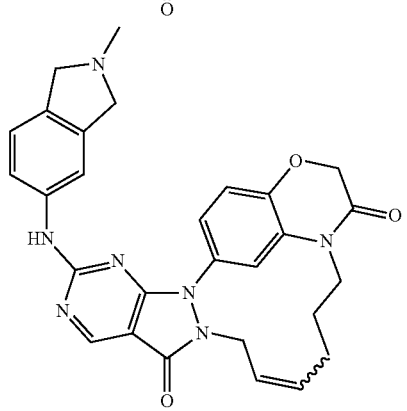
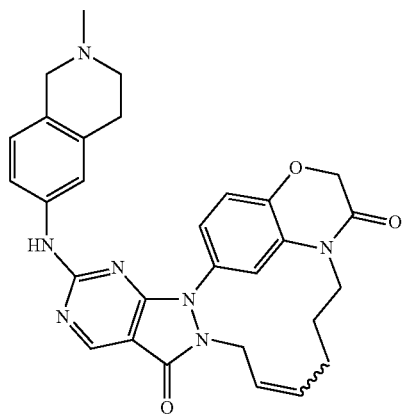
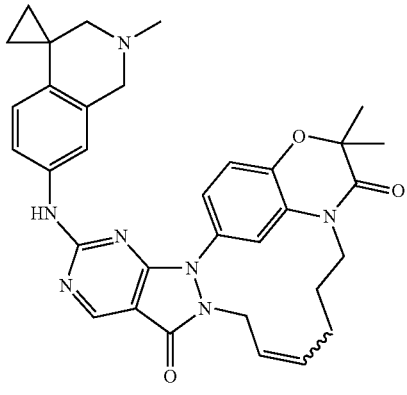

245
-continued
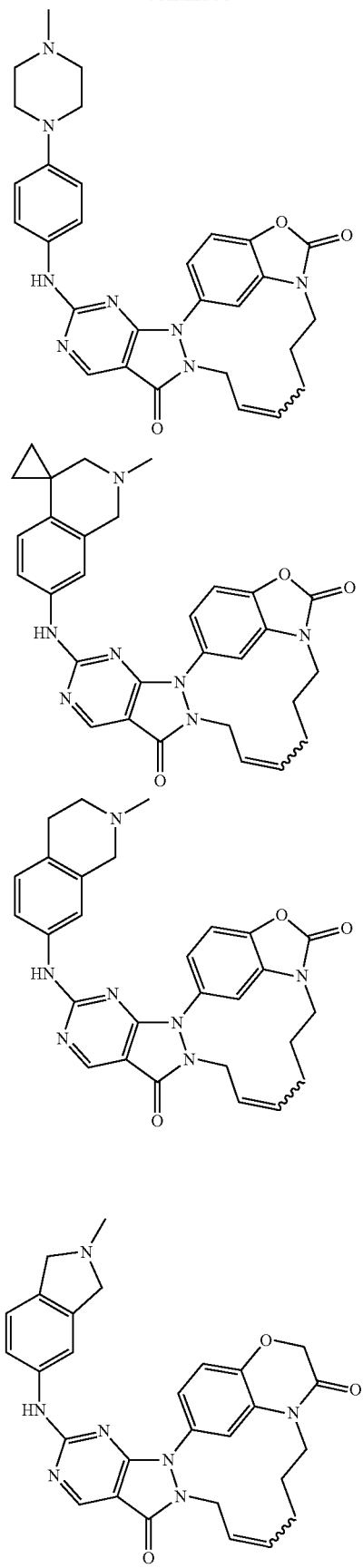
246
-continued
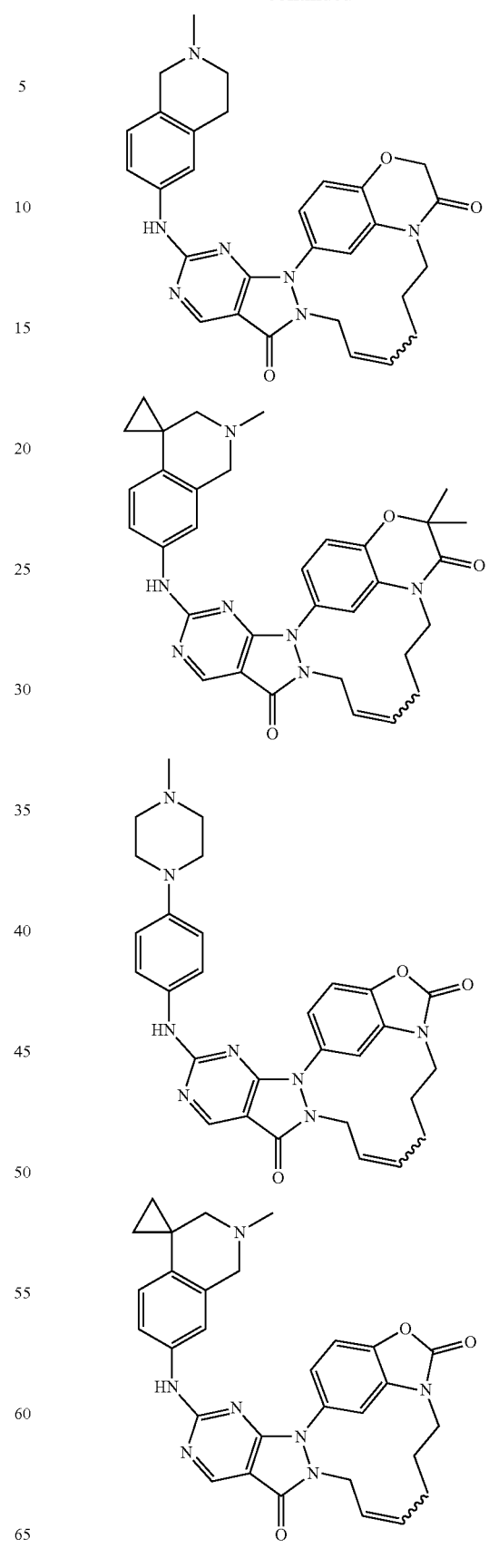

247
-continued
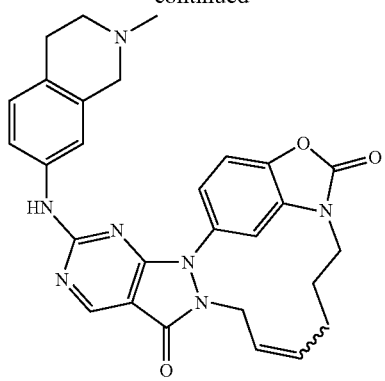
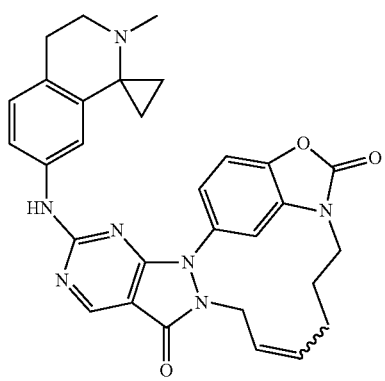
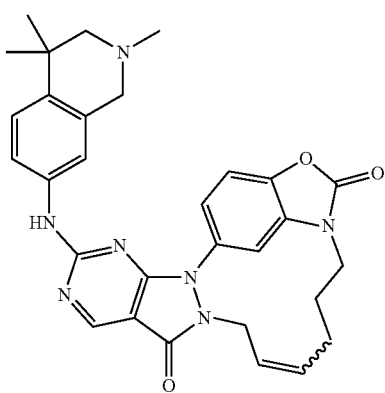
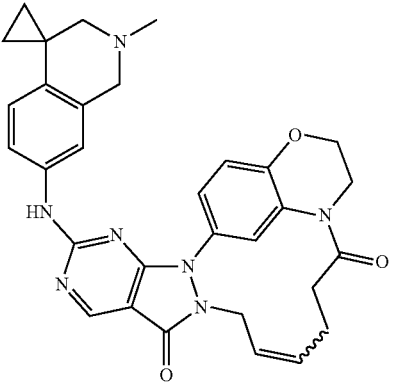
248
-continued
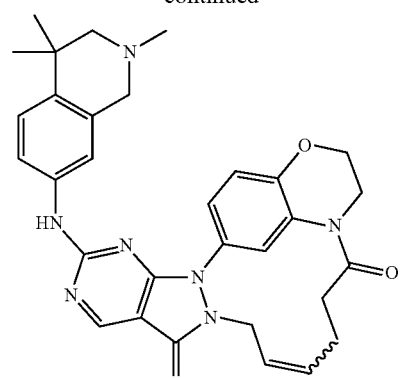
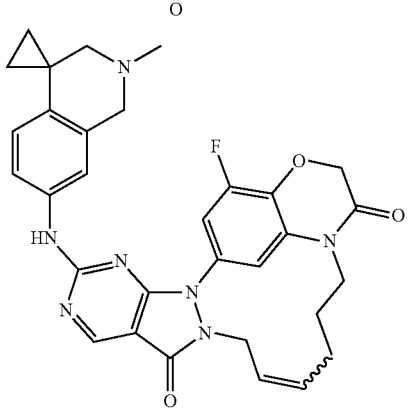
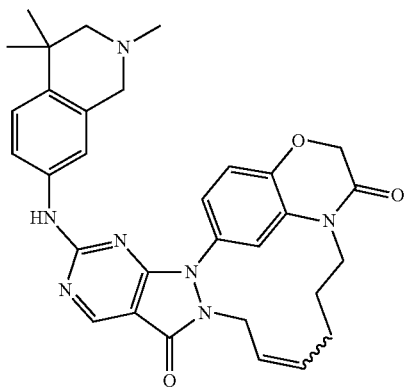
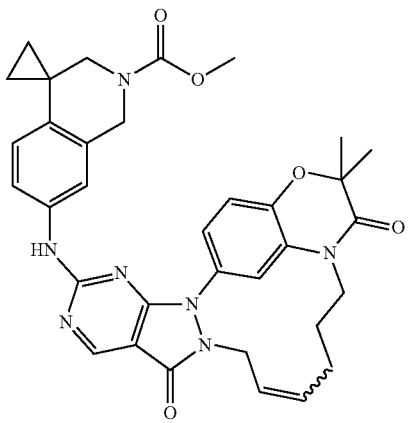

249
-continued
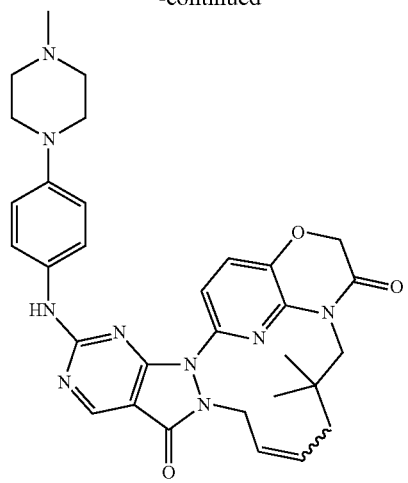
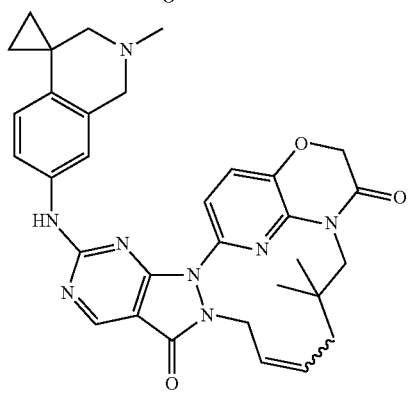
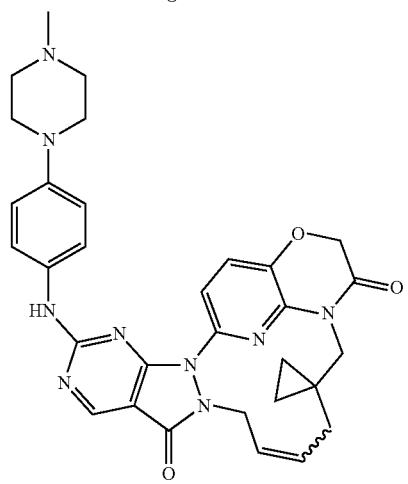
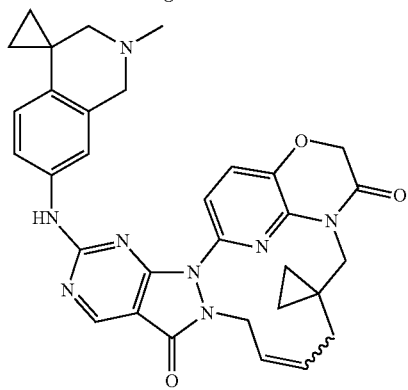
250
-continued
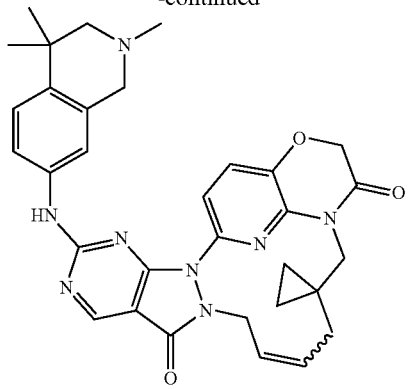
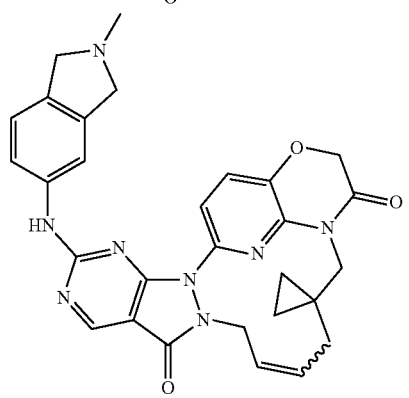
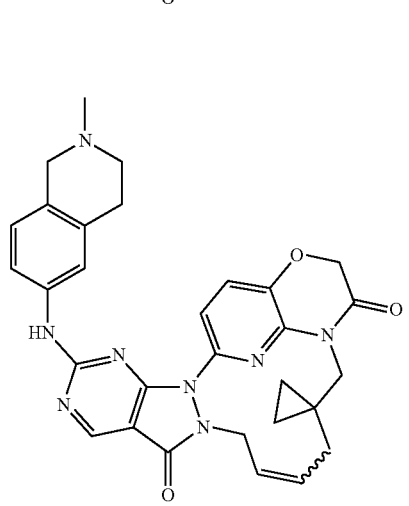
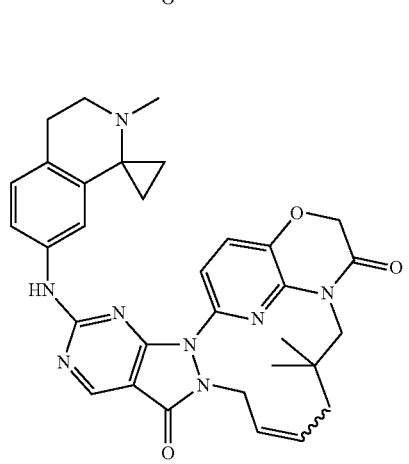

251
-continued
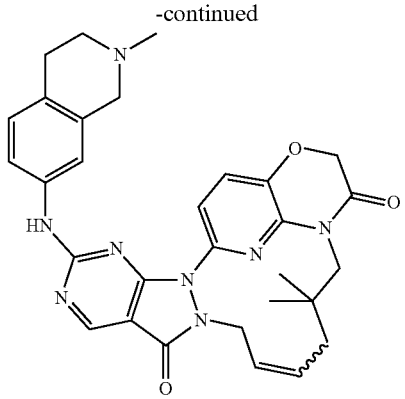
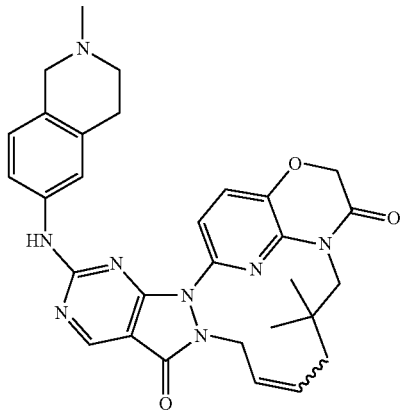
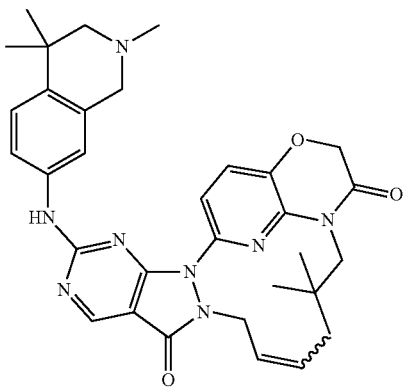
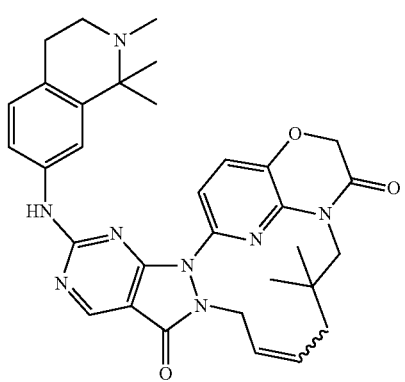
252
-continued
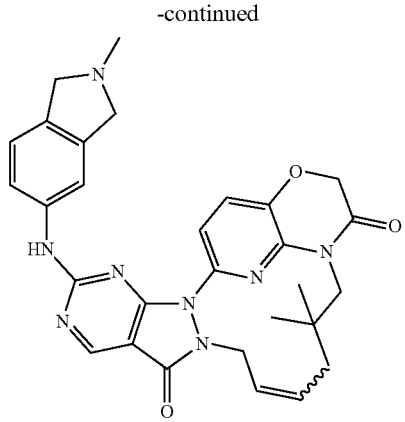
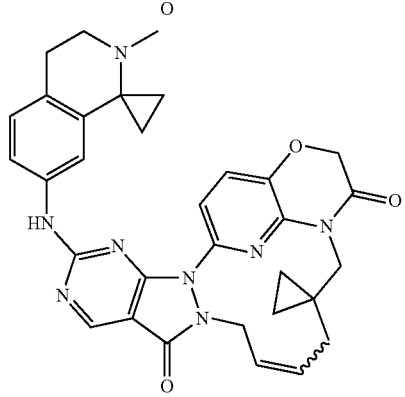
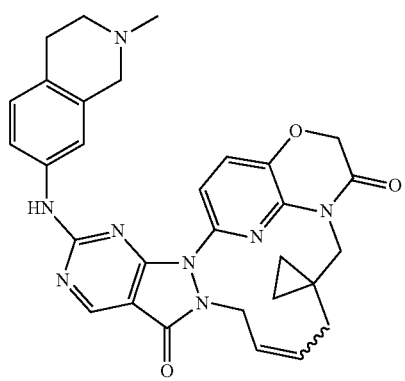
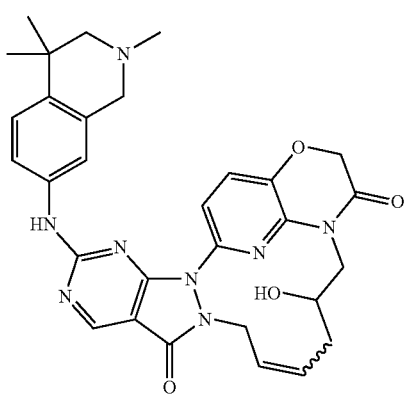

253
-continued
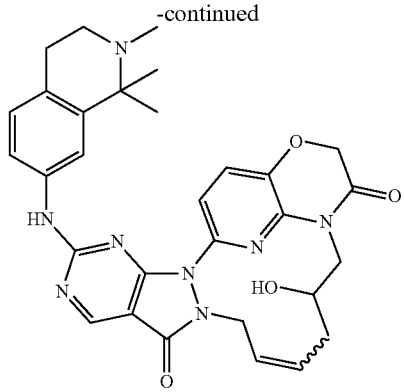
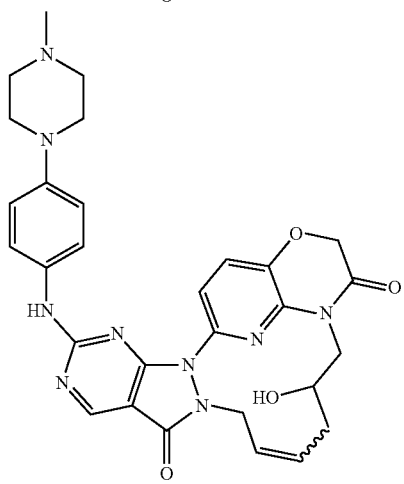
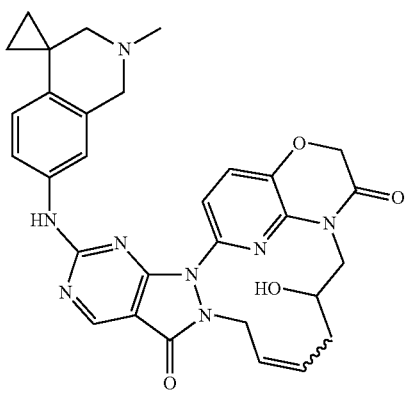
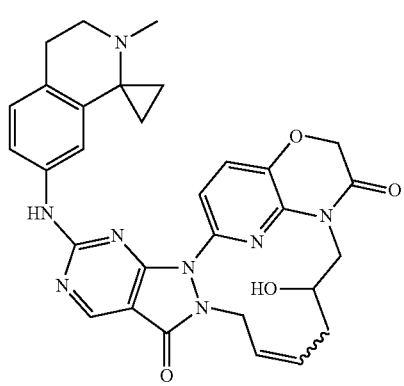
254
-continued
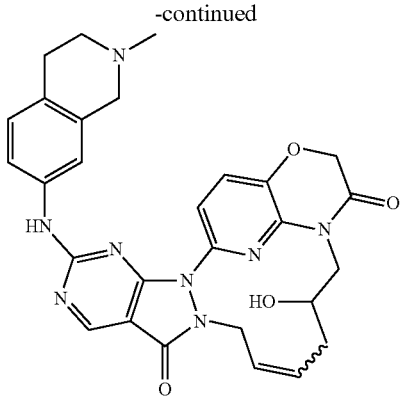
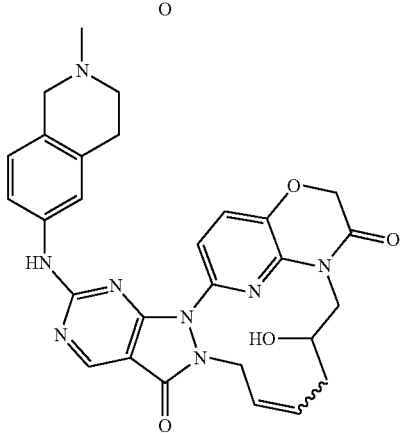
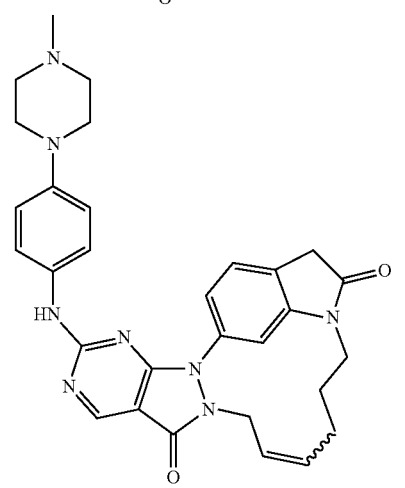
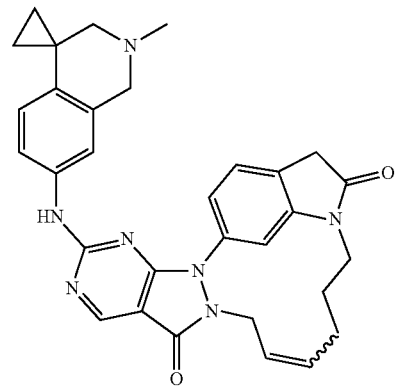

255
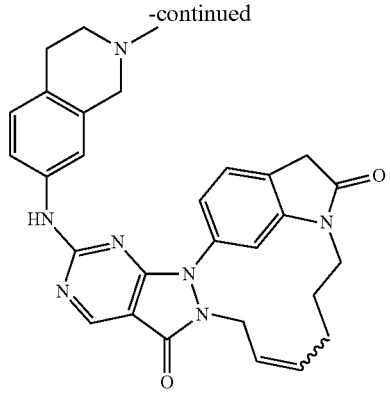
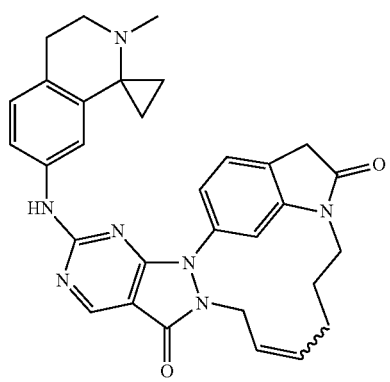
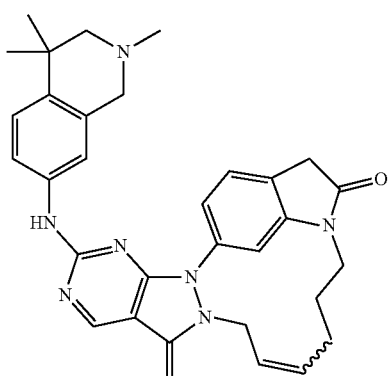
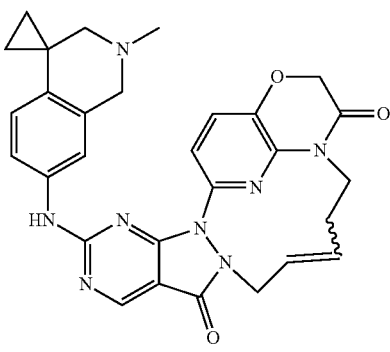
256
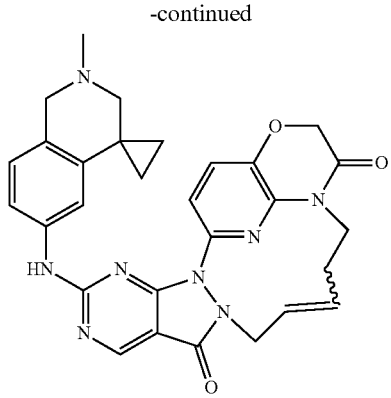
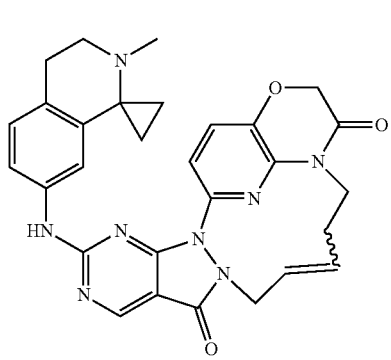
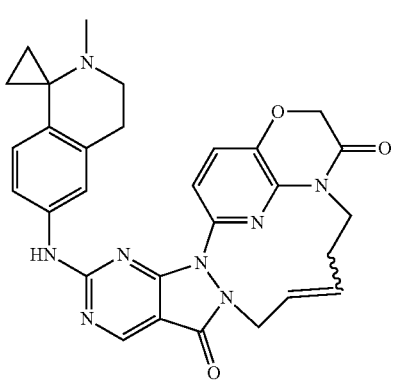
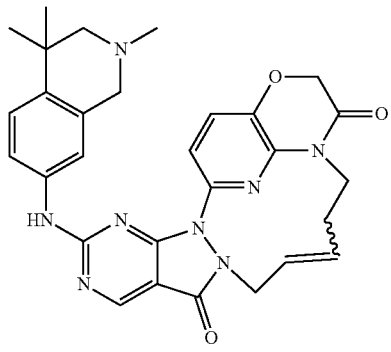

257
-continued
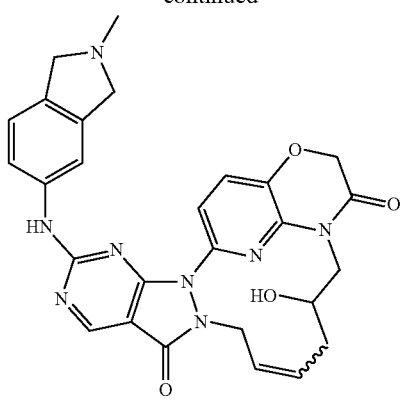
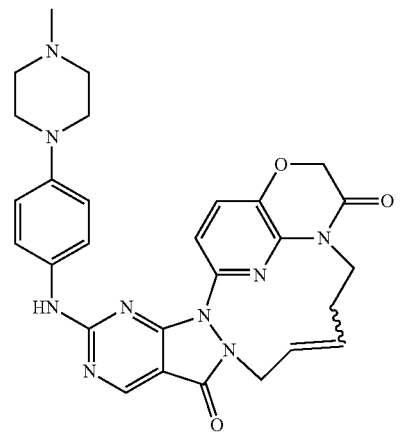
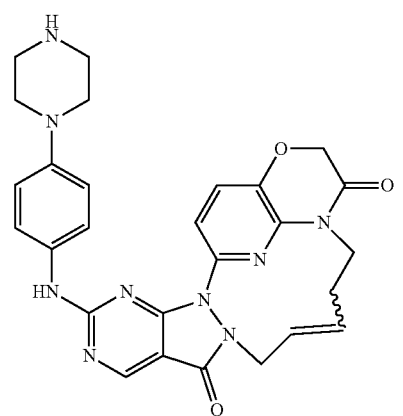
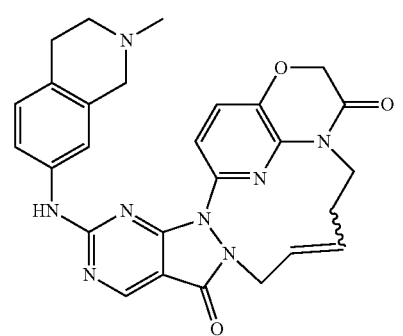
258
-continued
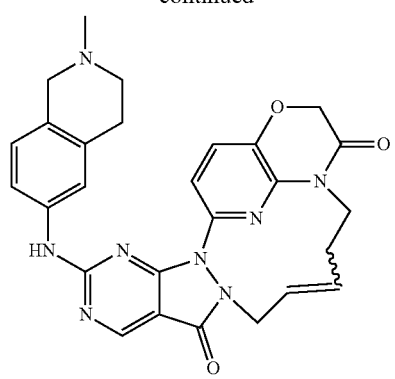
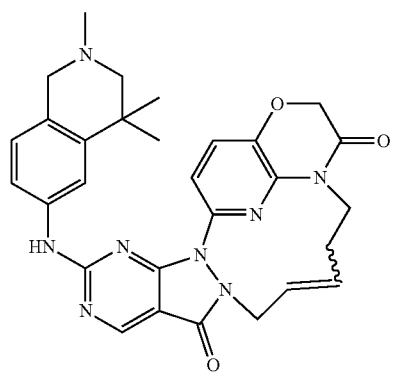
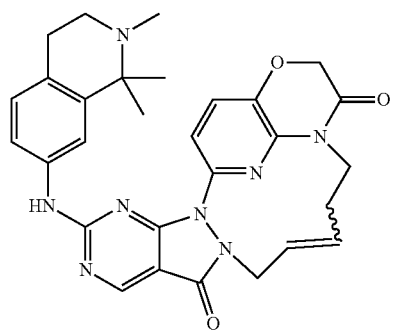
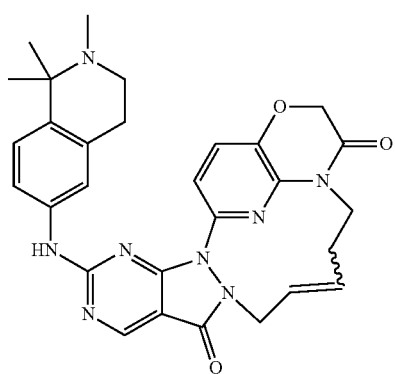

259
-continued
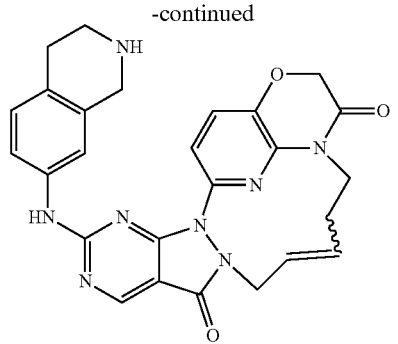
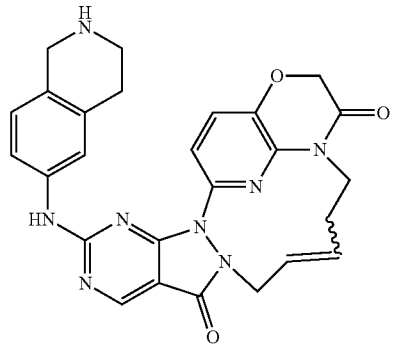
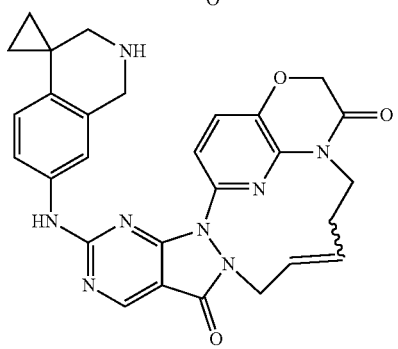
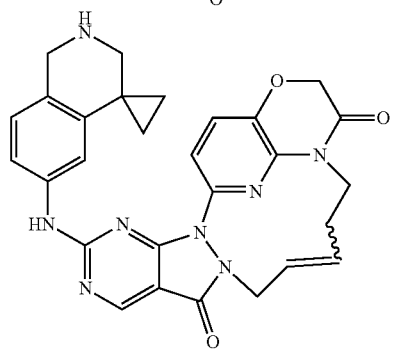
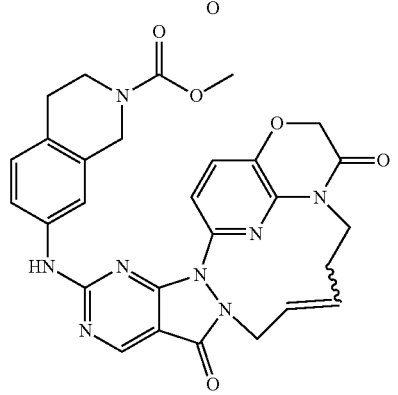
260
-continued
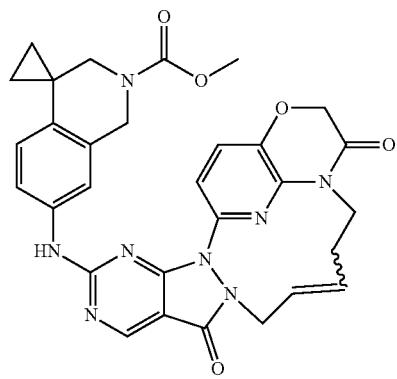
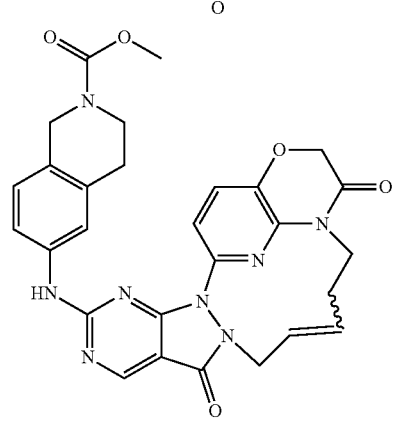
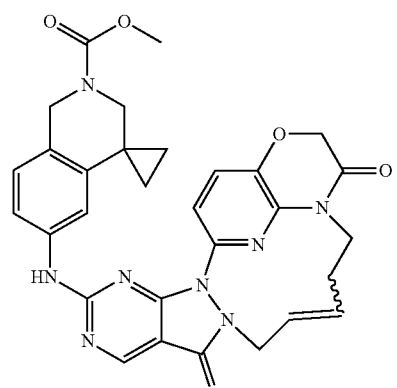
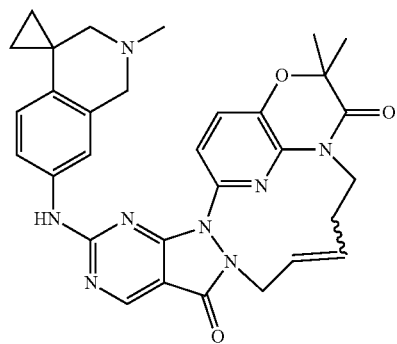

261
-continued
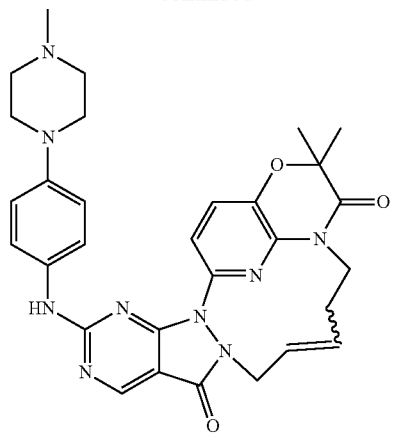
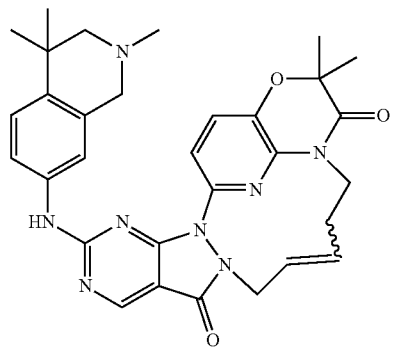
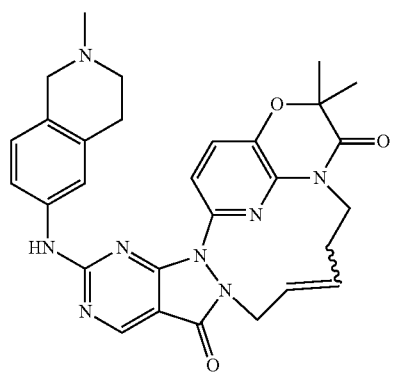
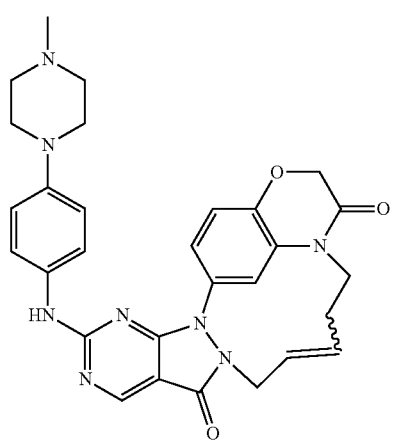
262
-continued
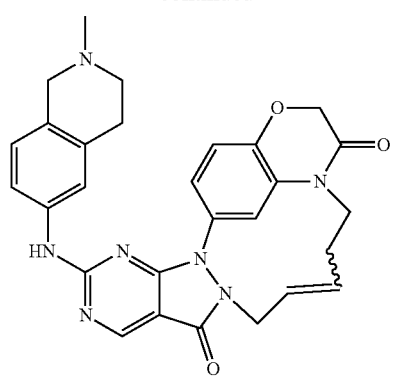
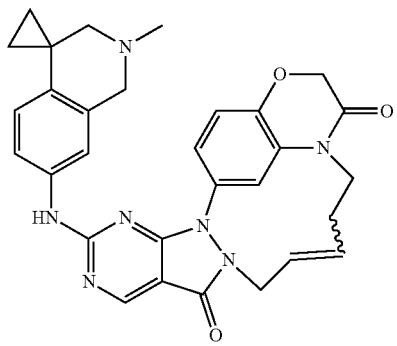
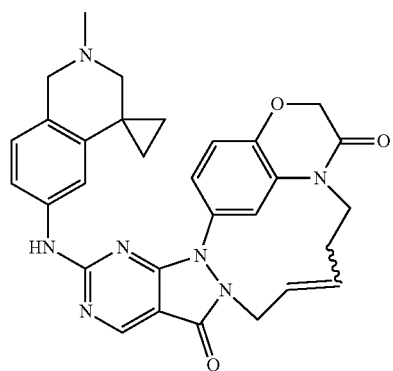
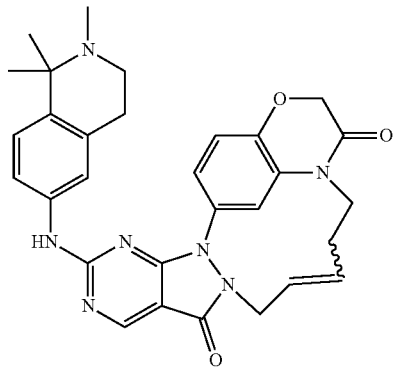

263
-continued
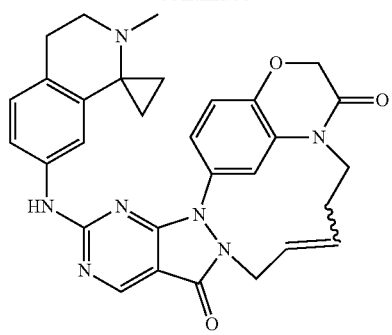
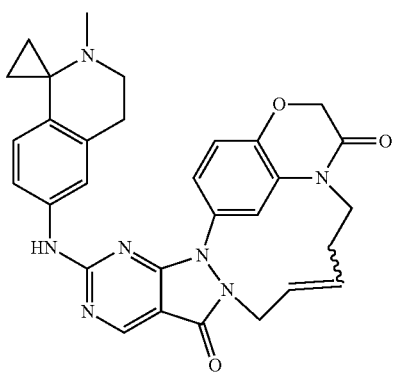
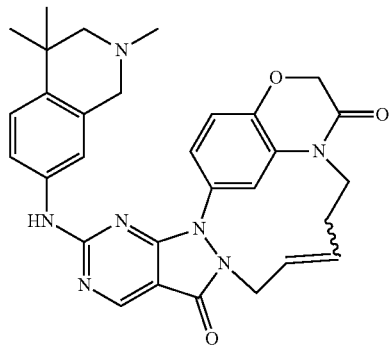
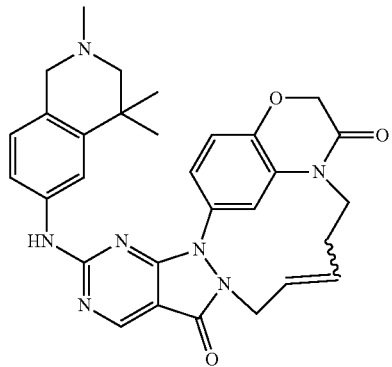
264
-continued
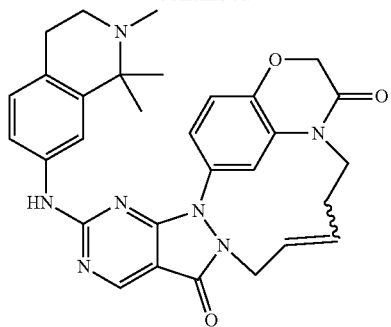
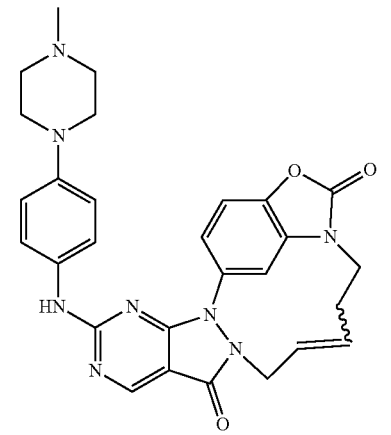
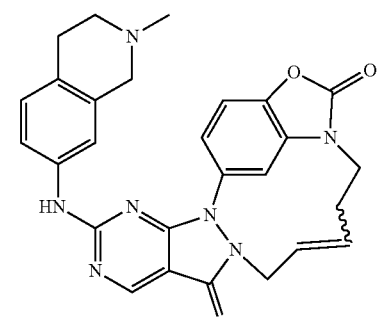
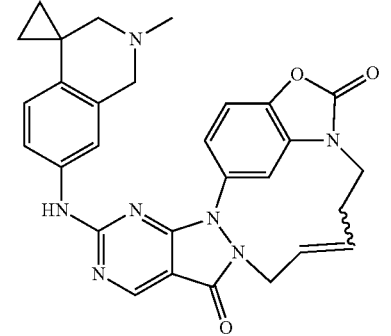

265
-continued
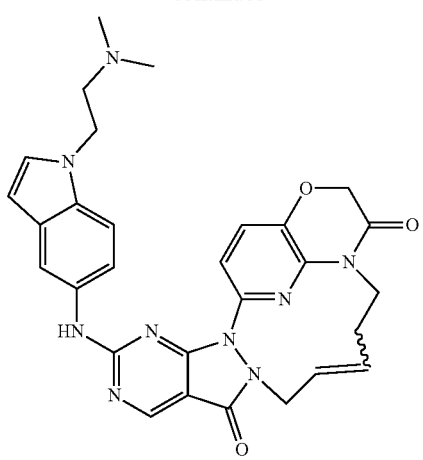
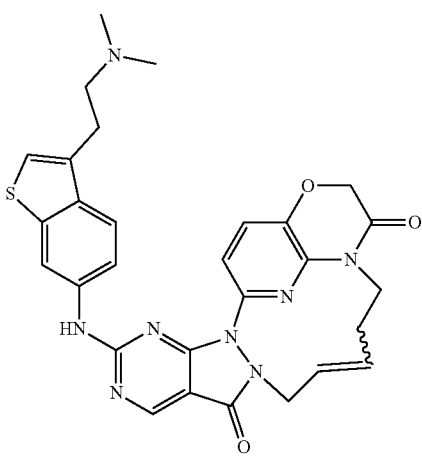
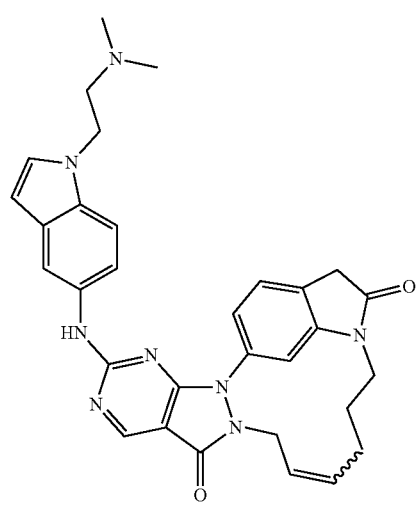
266
-continued
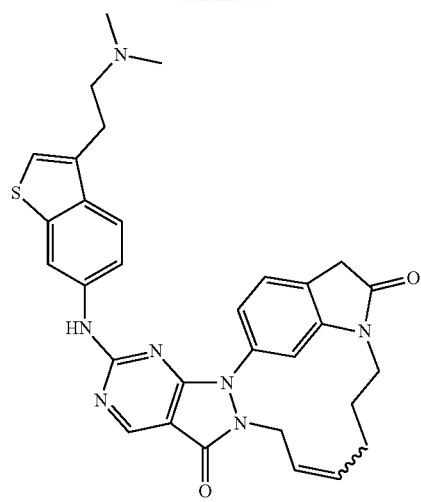
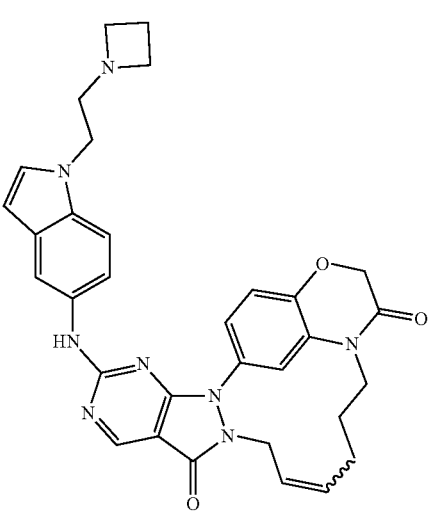
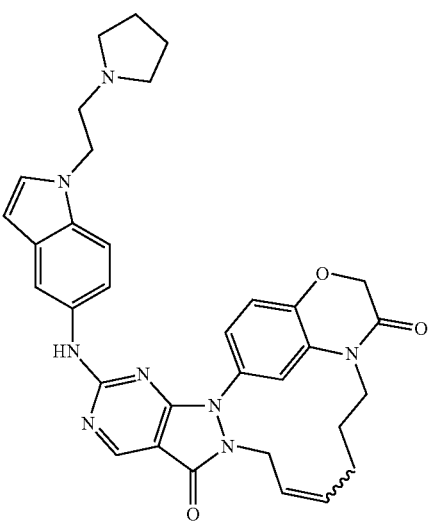

267
-continued
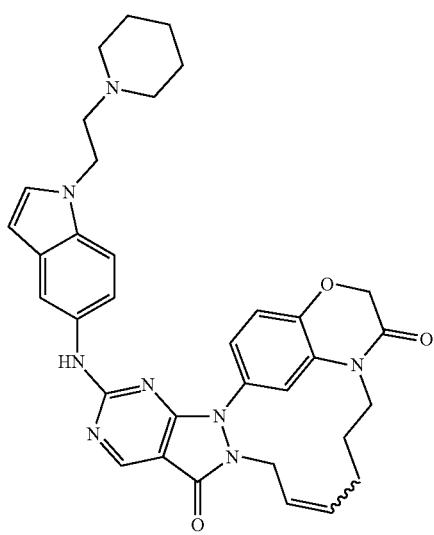
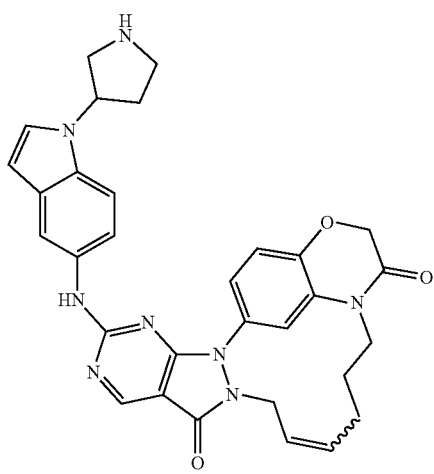
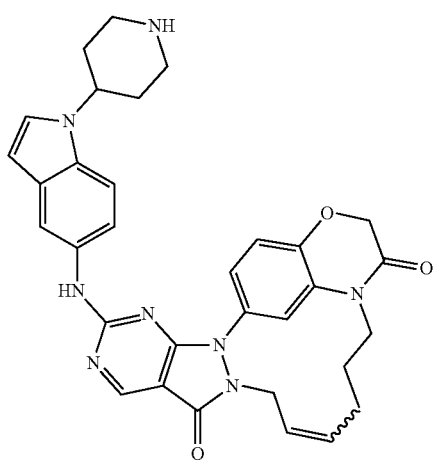
268
-continued
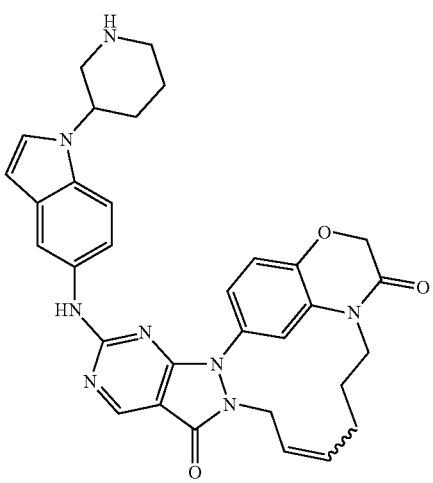
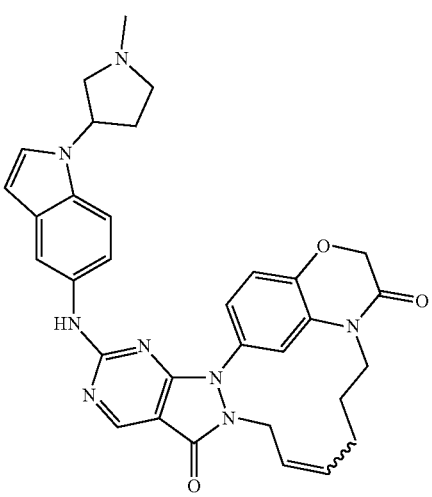

269
-continued
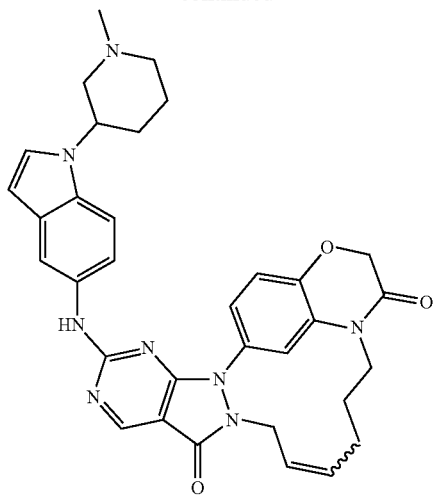
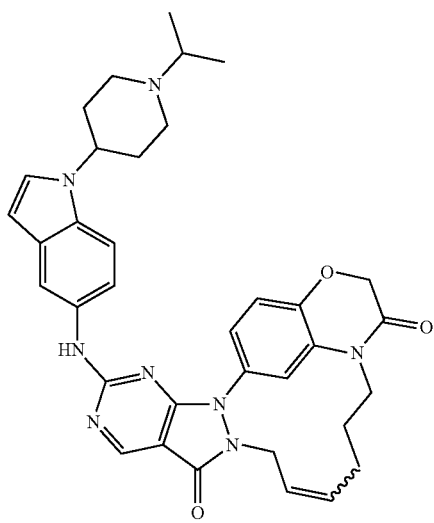
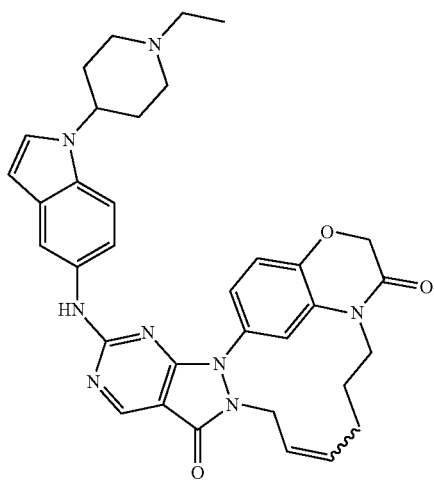
270
-continued
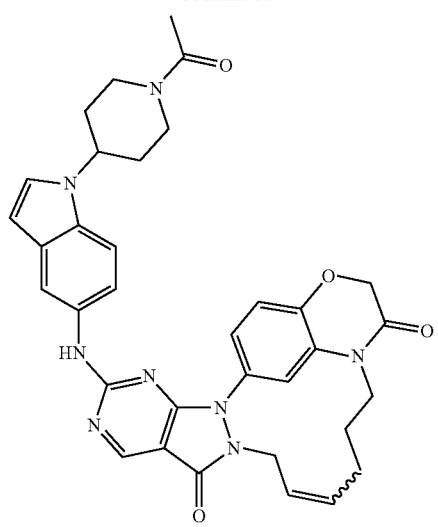
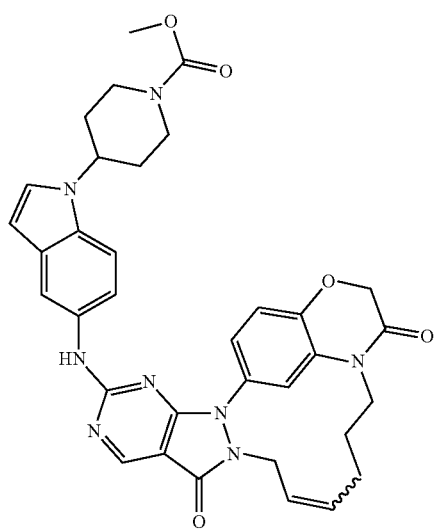
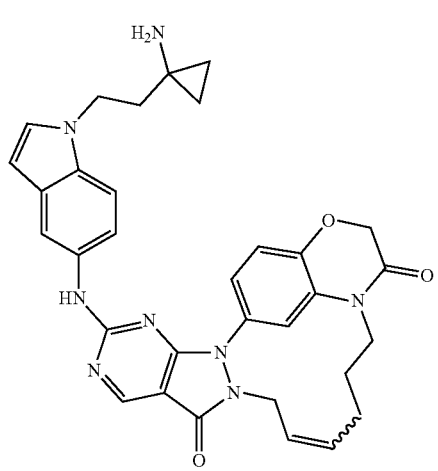

271
-continued
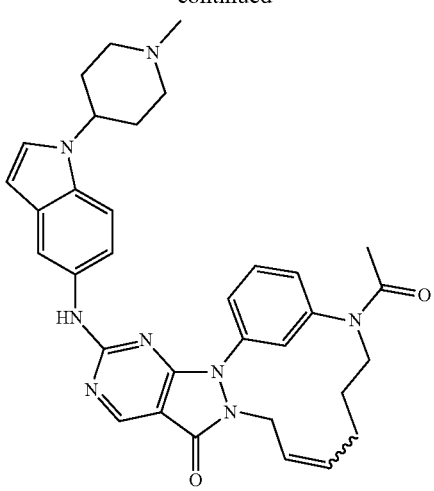
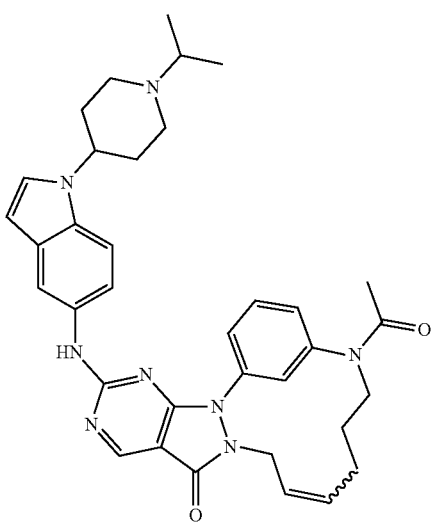
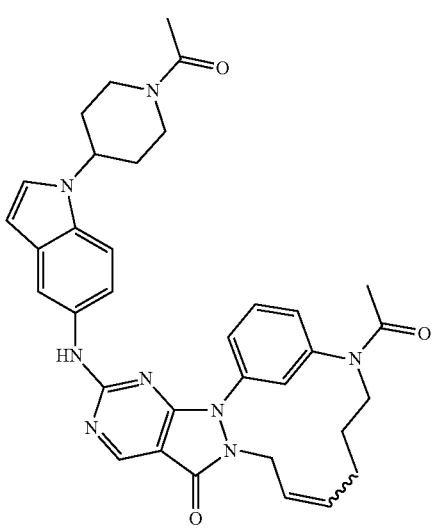
272
-continued
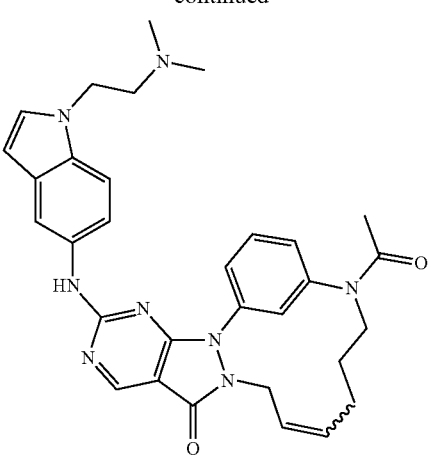
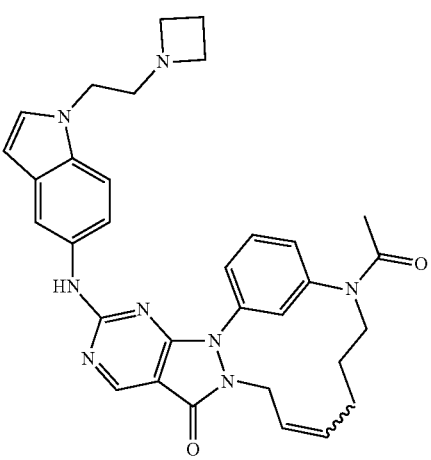
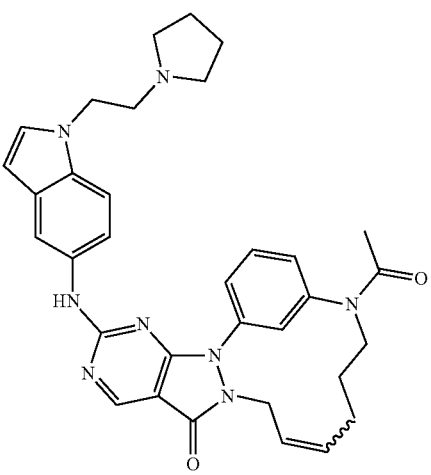

273
-continued
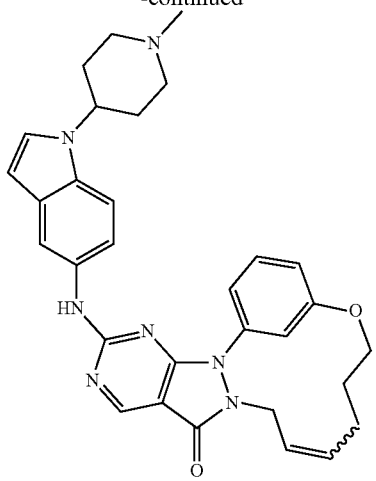
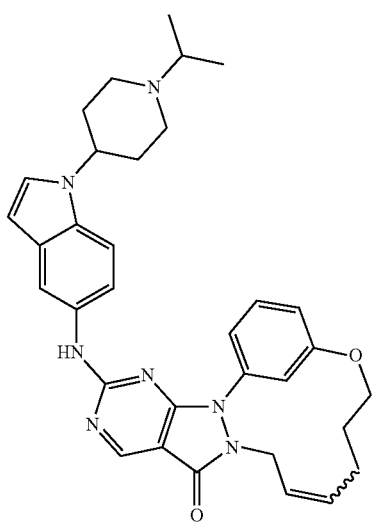
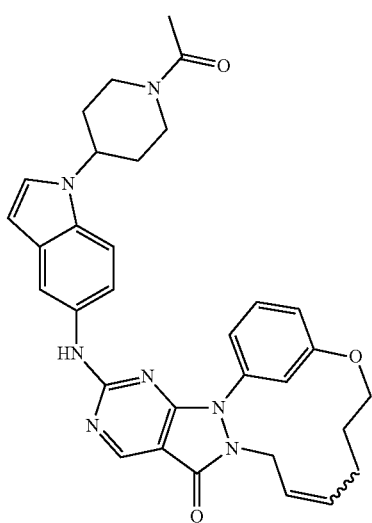
274
-continued
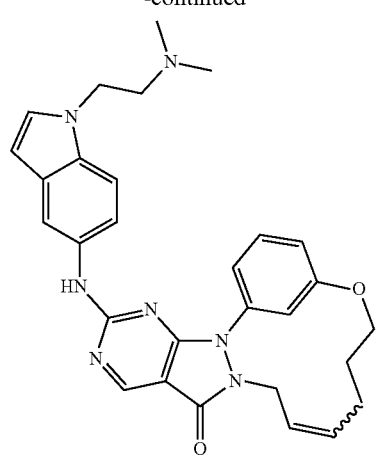
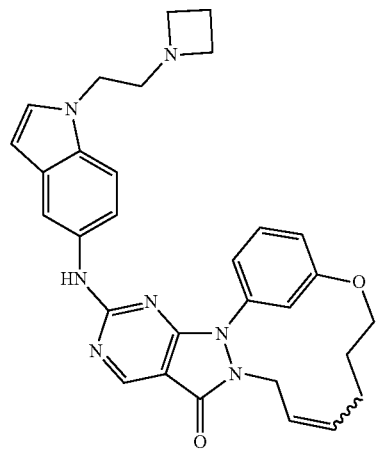
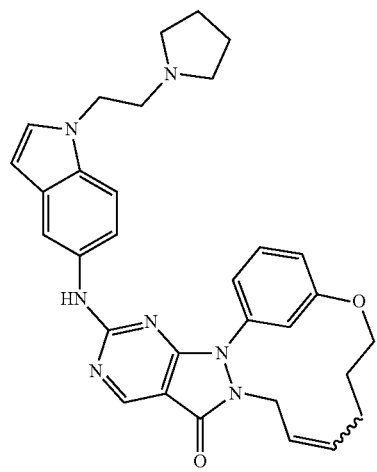

275
-continued
276
-continued
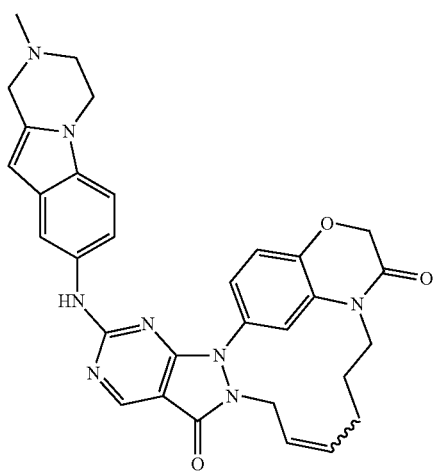
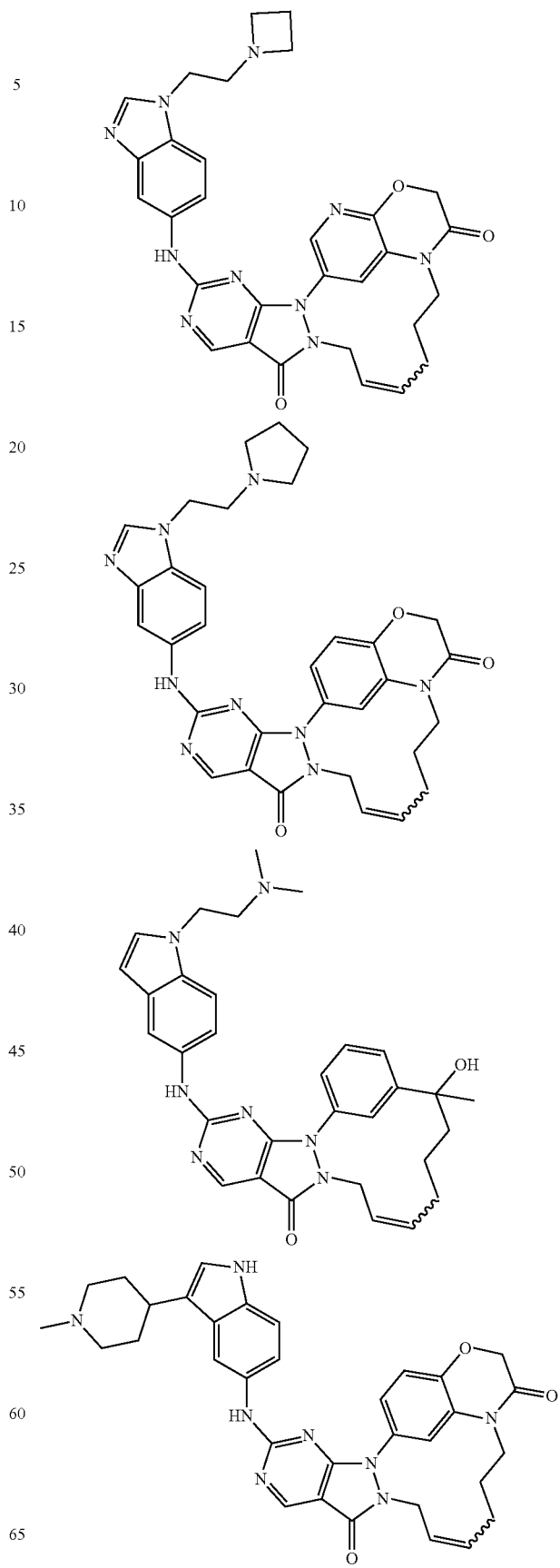

277
-continued
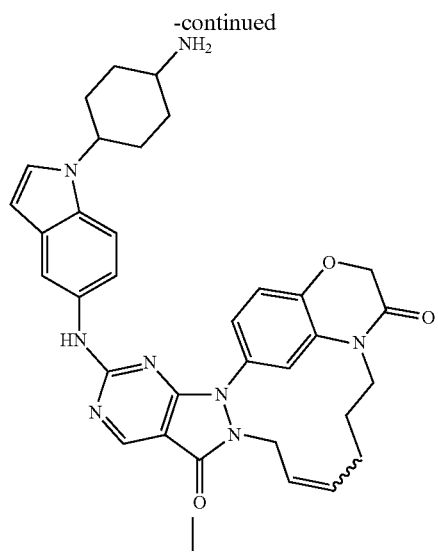
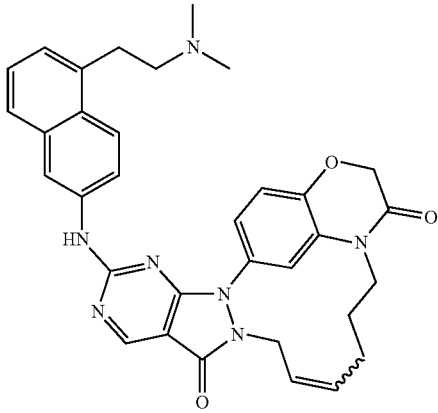
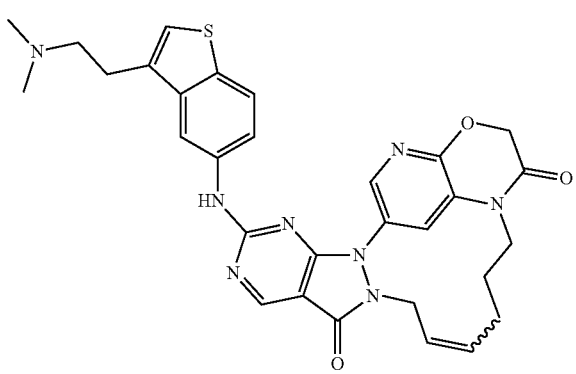
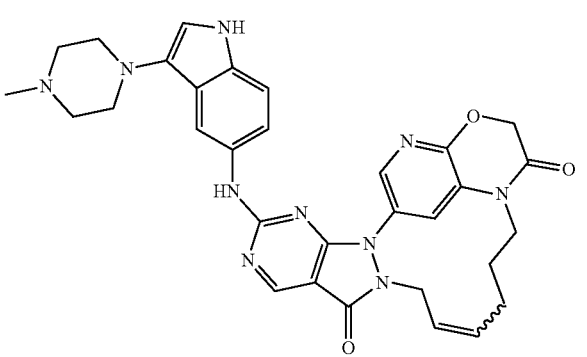
278
-continued
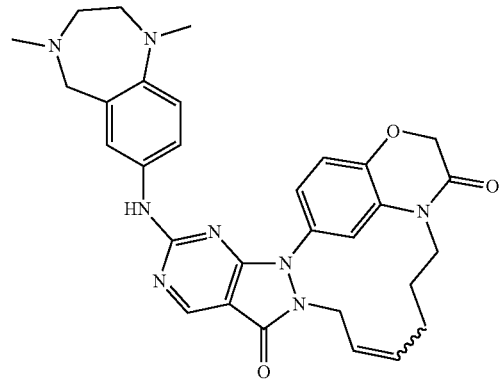
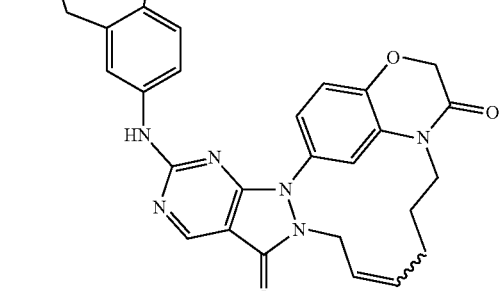
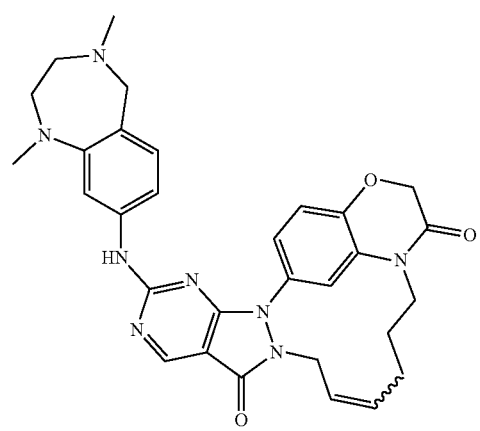
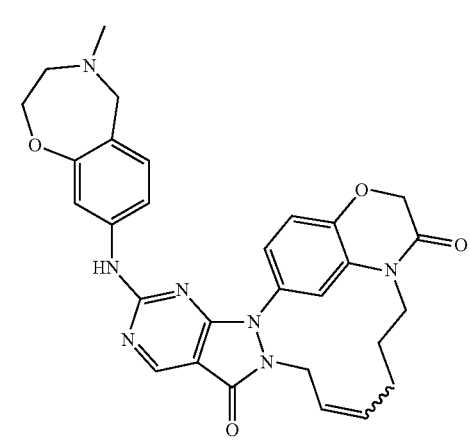

279
-continued
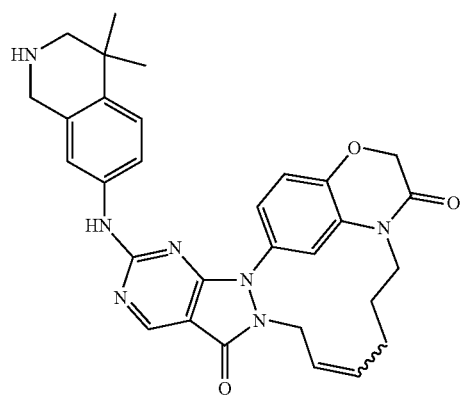
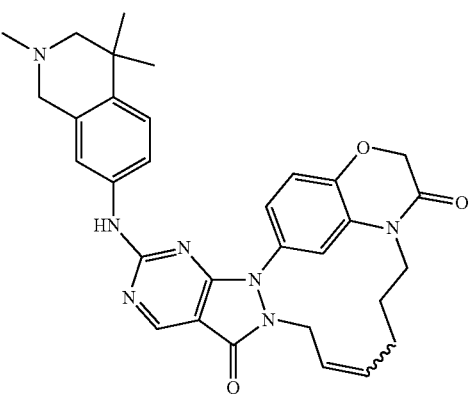
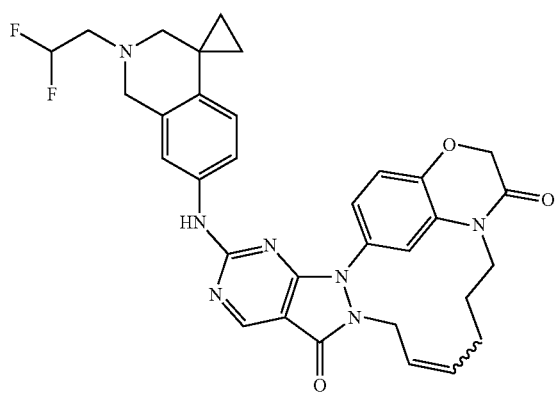
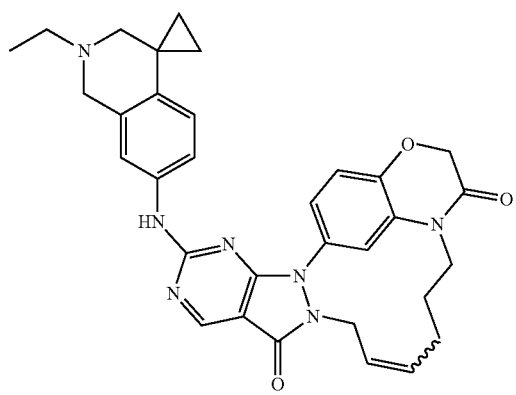
280
-continued
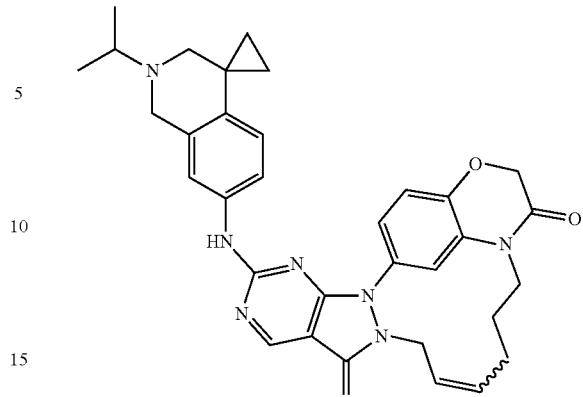
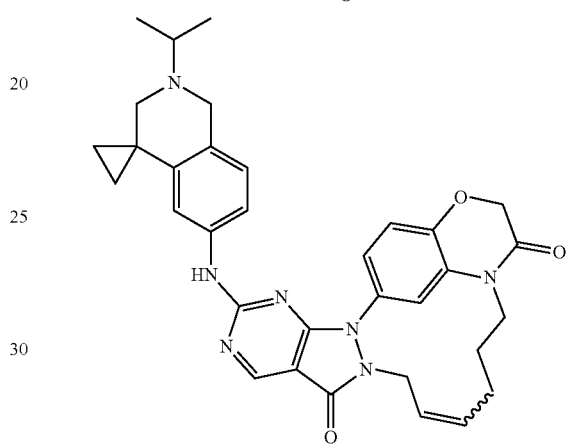
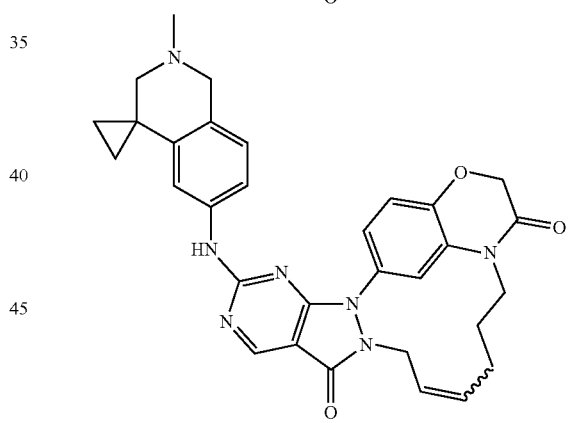
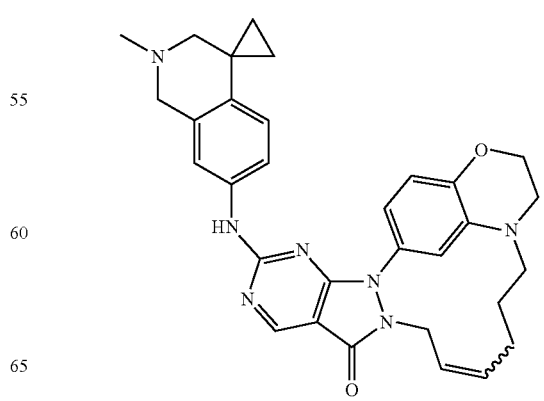

281
-continued
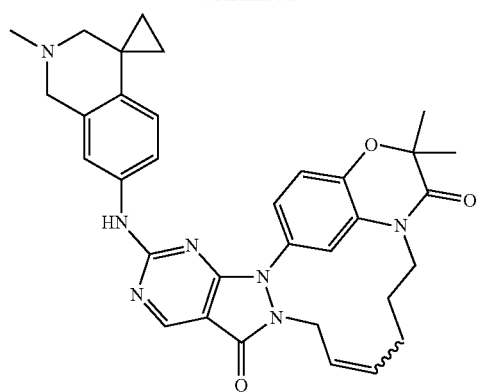
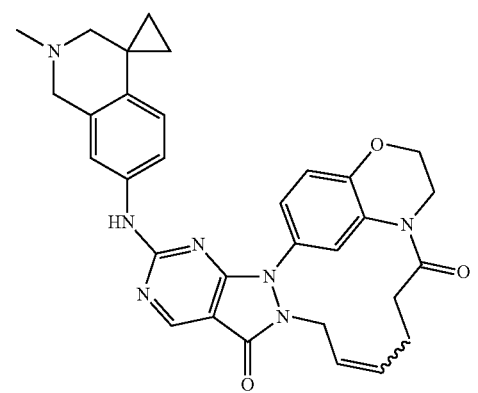
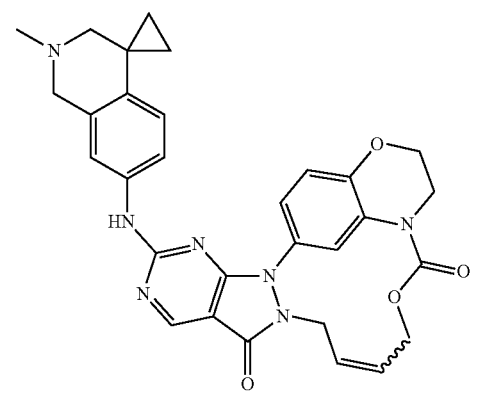
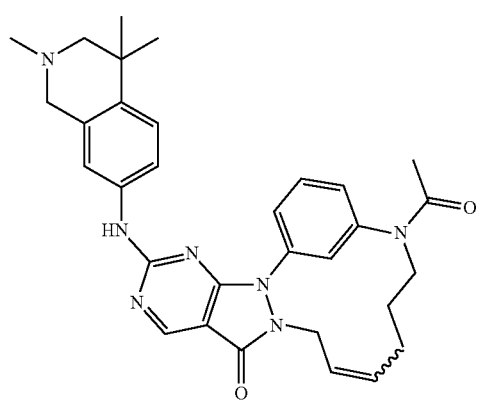
282
-continued
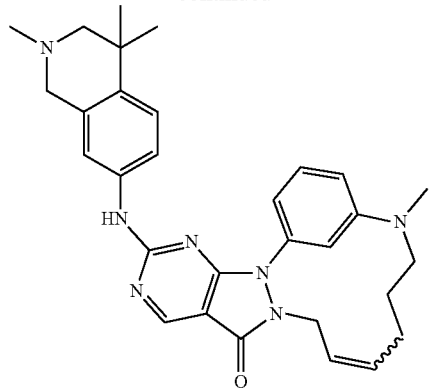
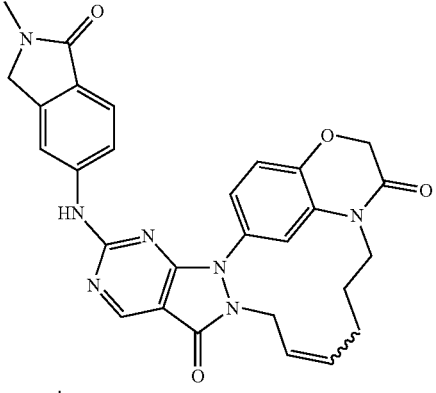
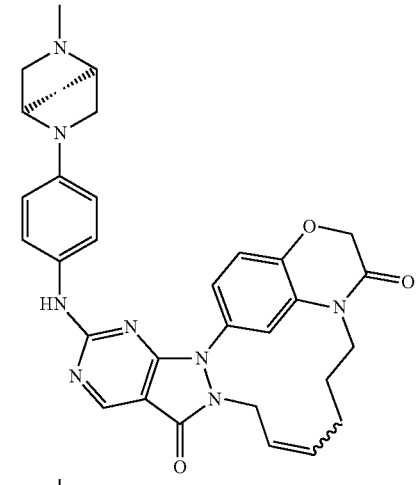
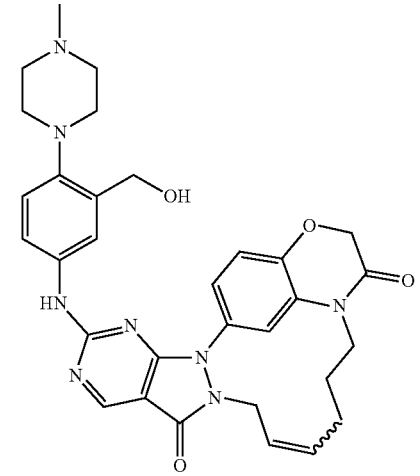

283
-continued
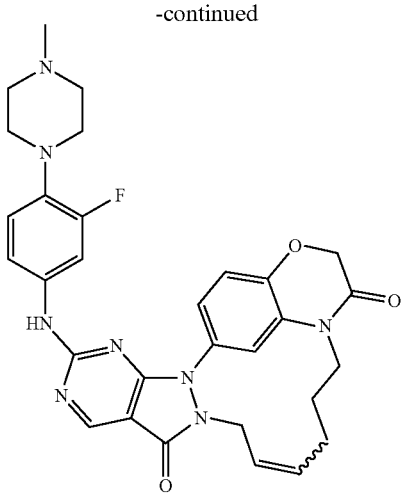
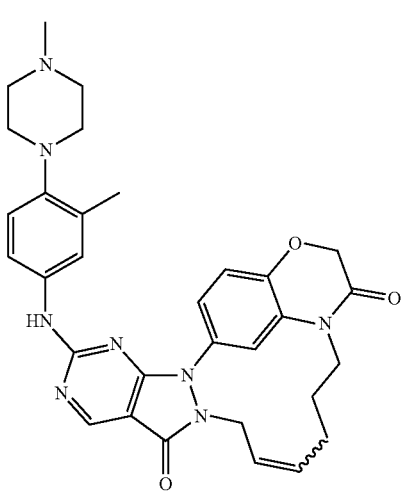
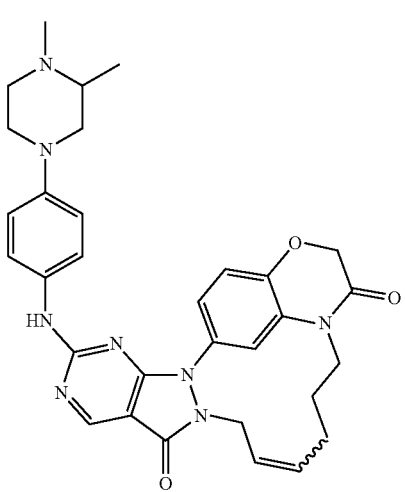
284
-continued
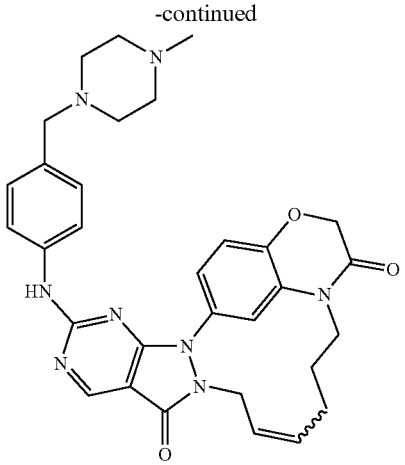
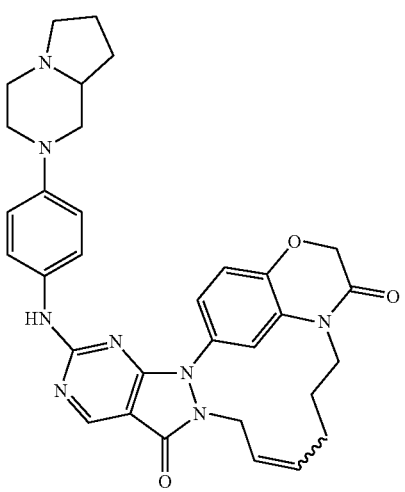
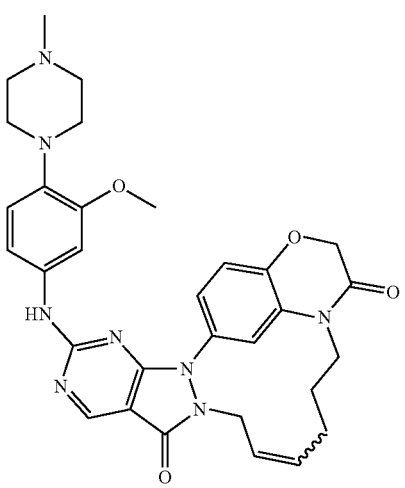

285
-continued
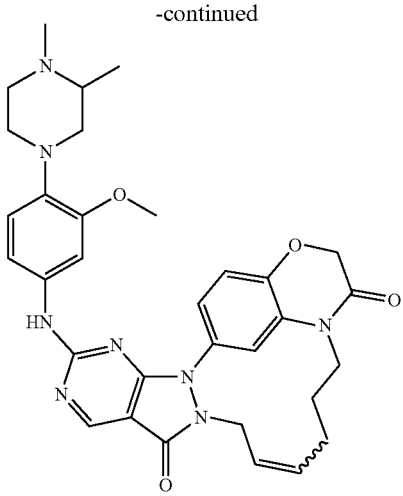
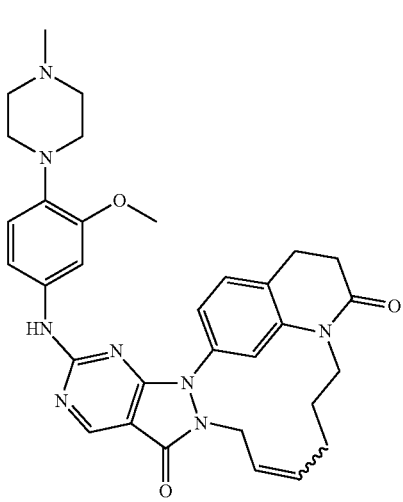
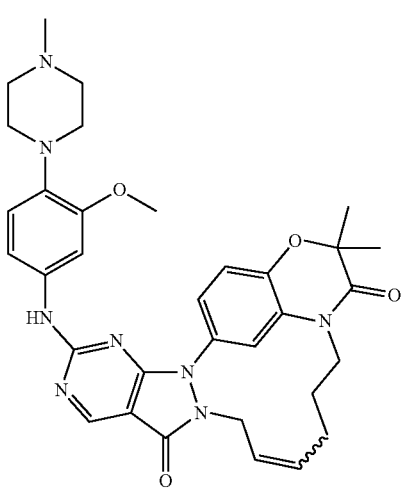
286
-continued
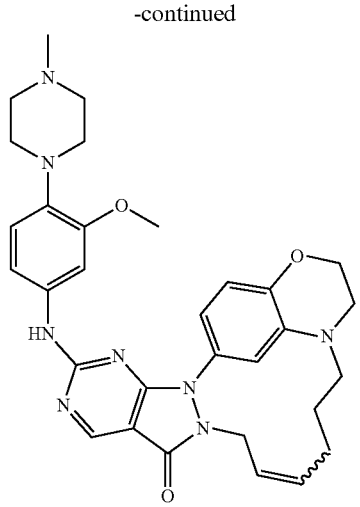
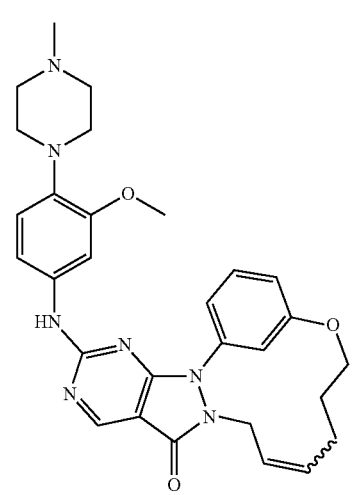
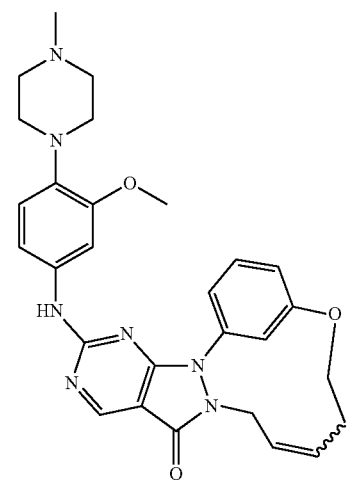

287
-continued
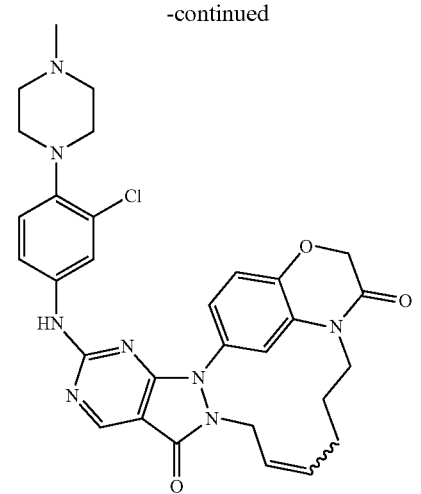
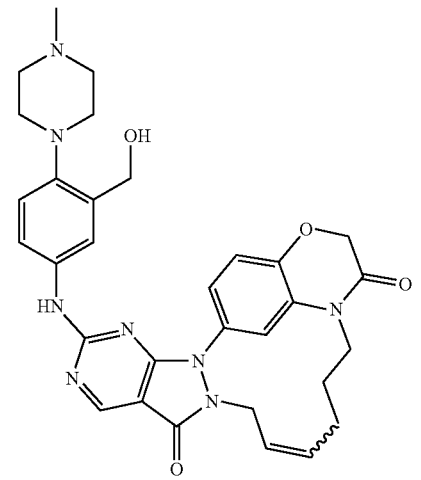
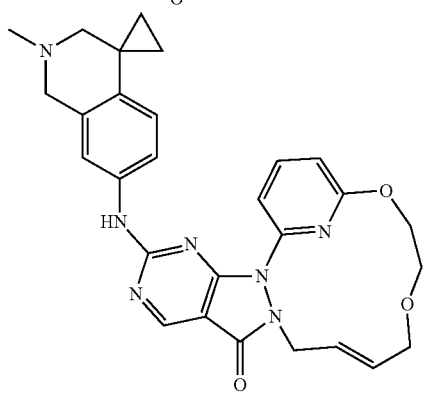
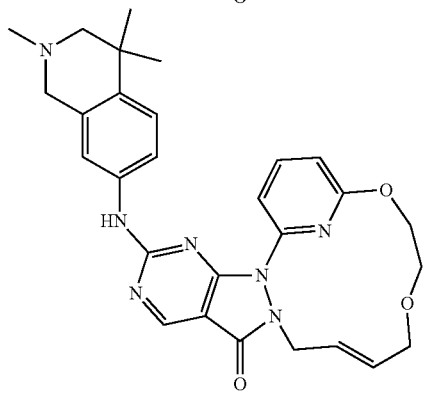
288
-continued
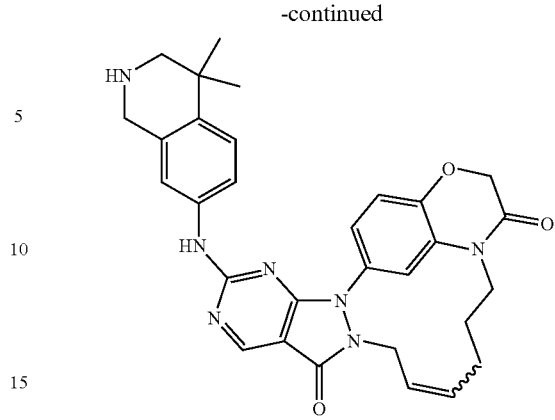
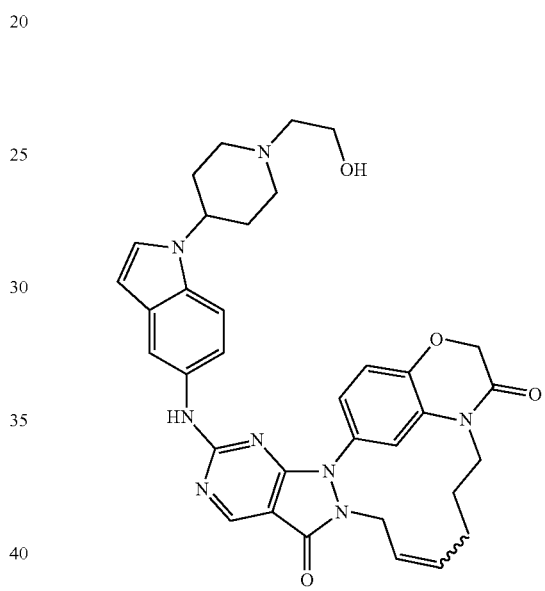
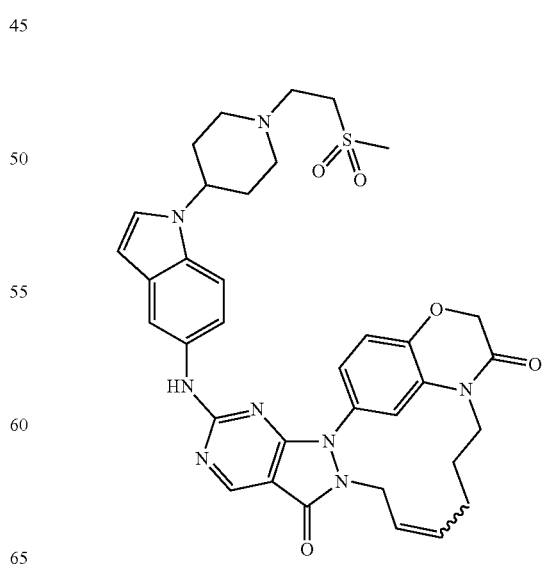

289
-continued
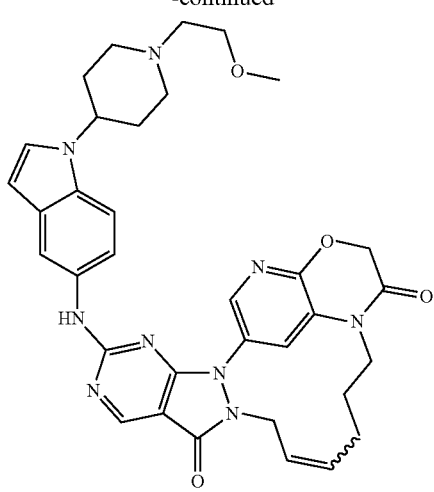
290
-continued
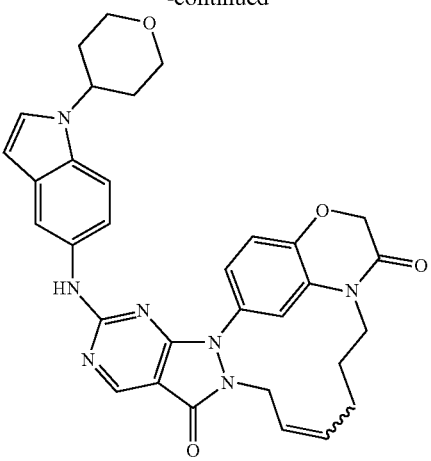
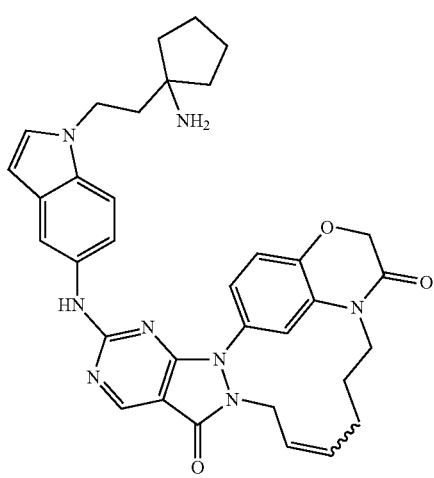
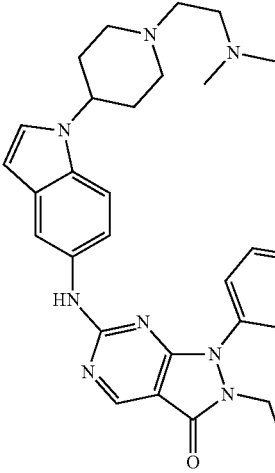
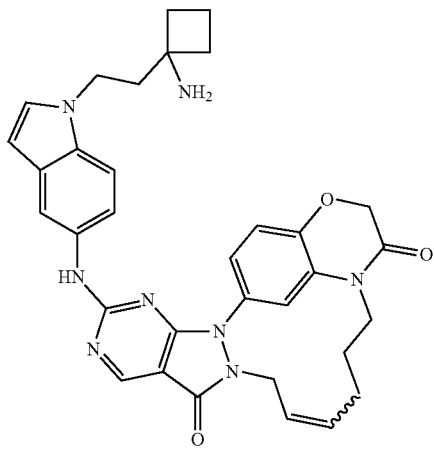
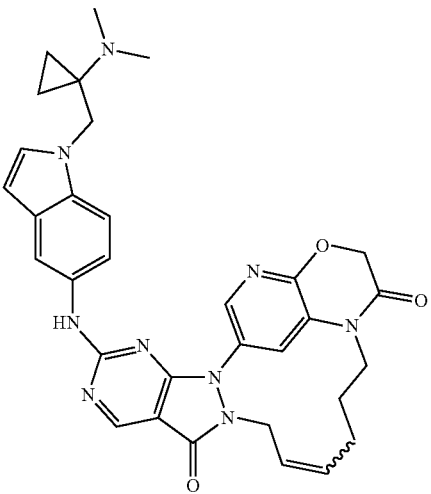

291
-continued
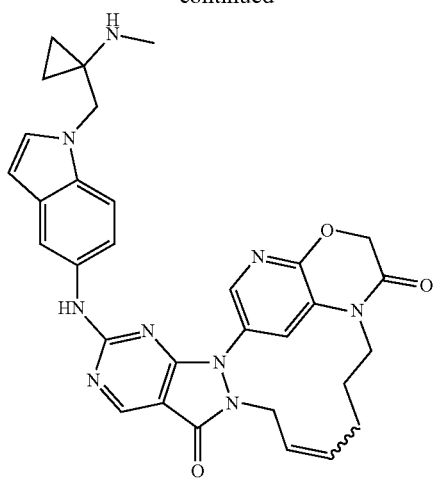
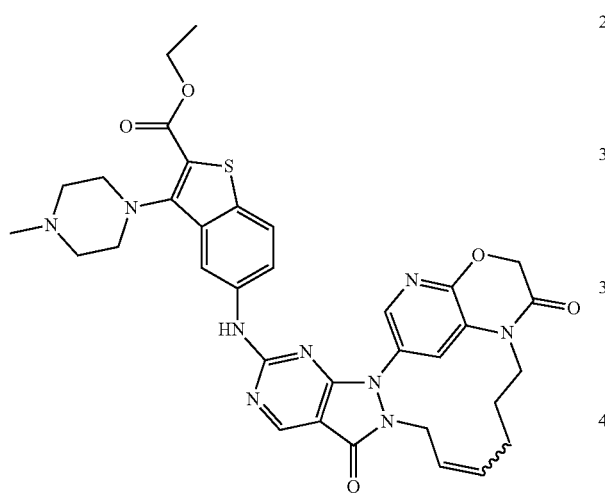
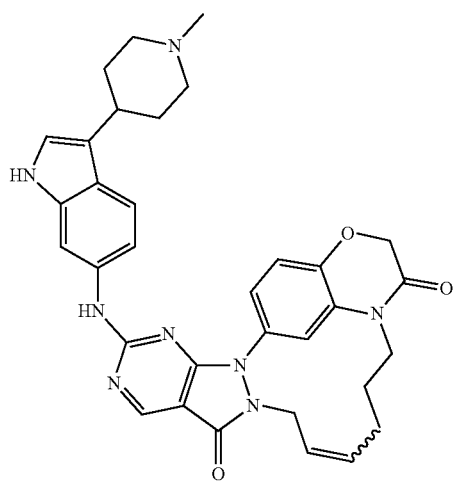
292
-continued
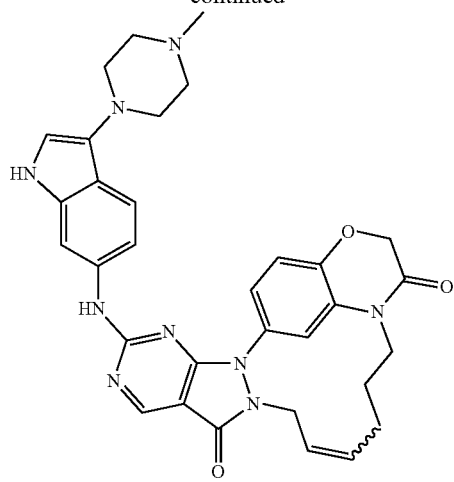
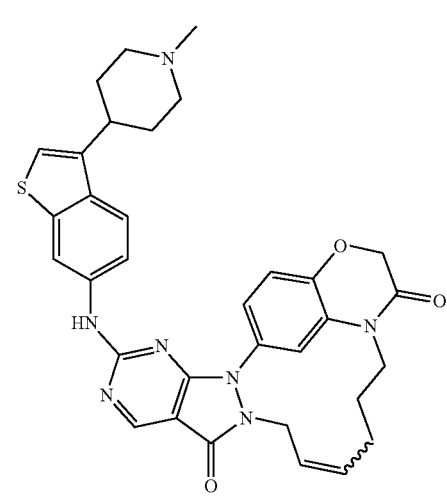
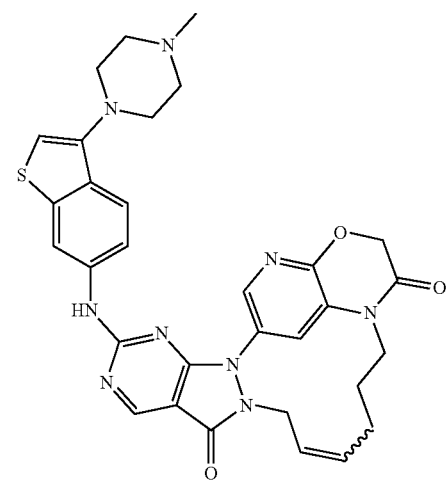

293
-continued
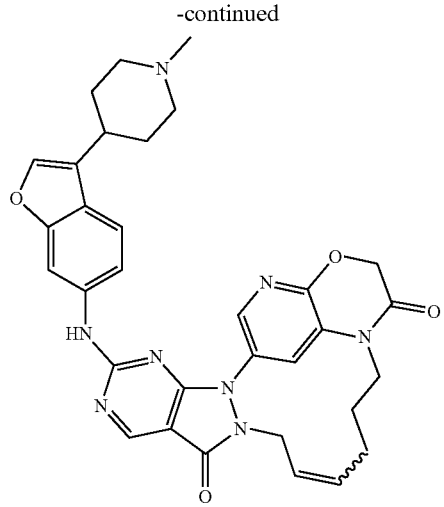
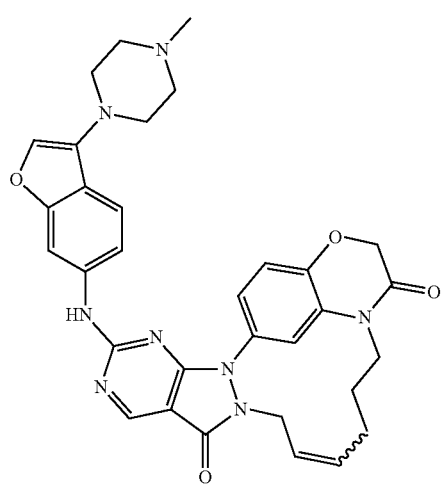
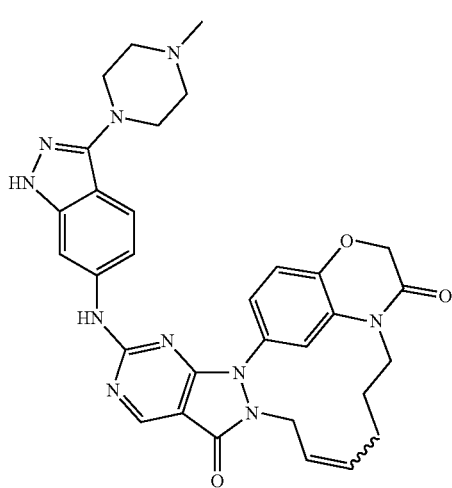
294
-continued
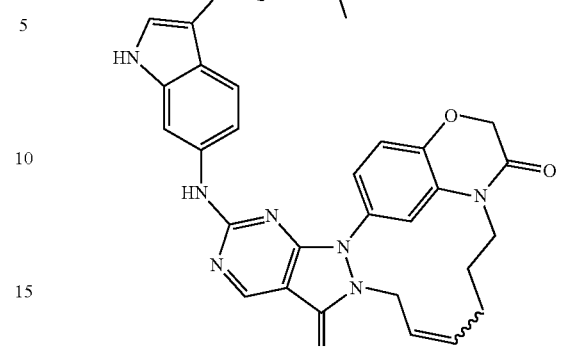
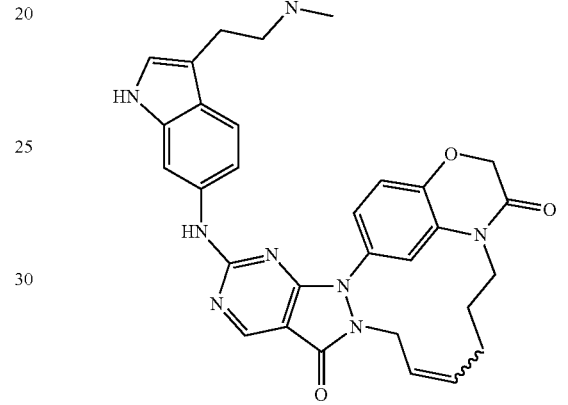
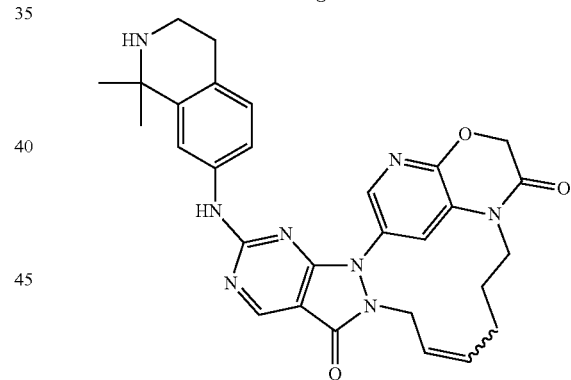
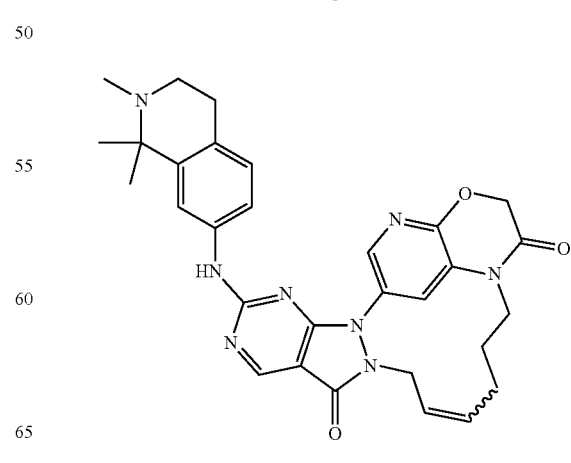

295
-continued
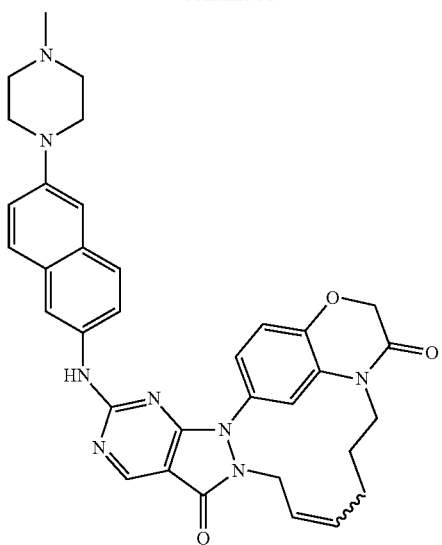
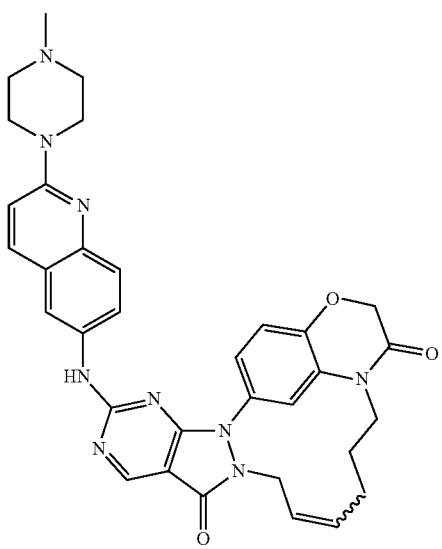
296
-continued
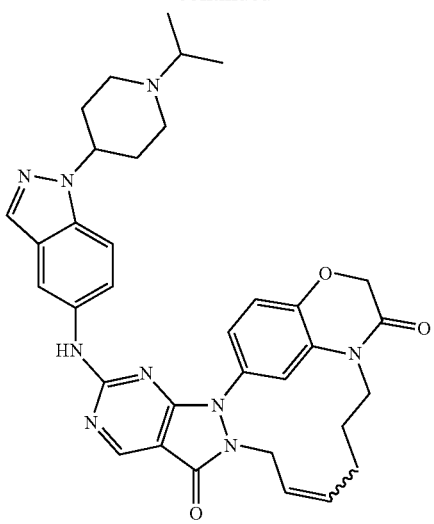
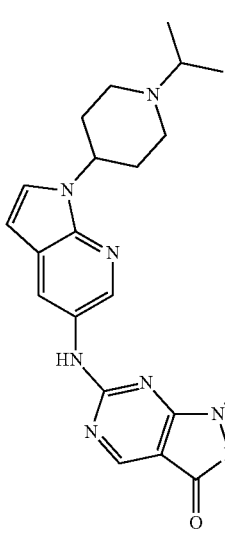
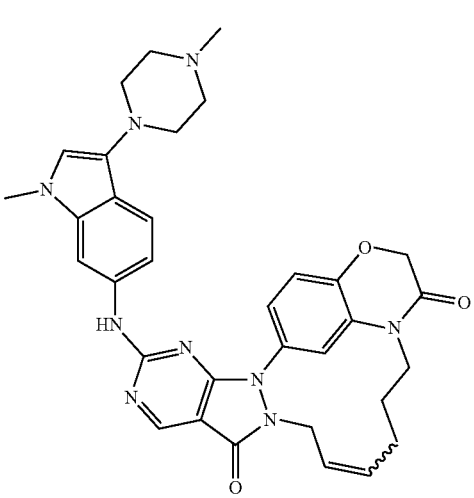

297
-continued
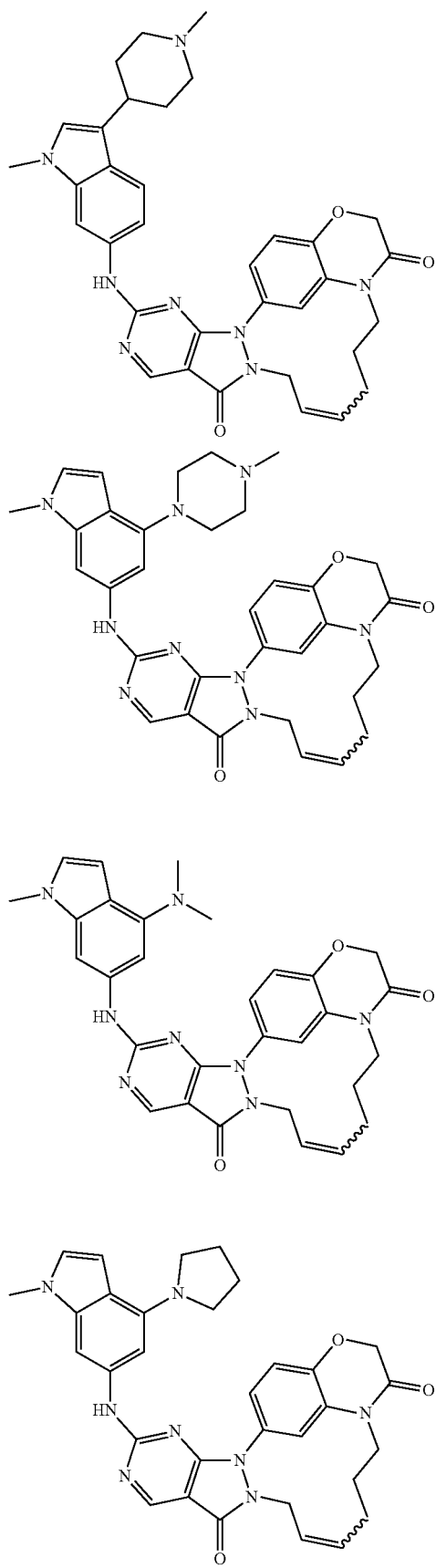
298
-continued
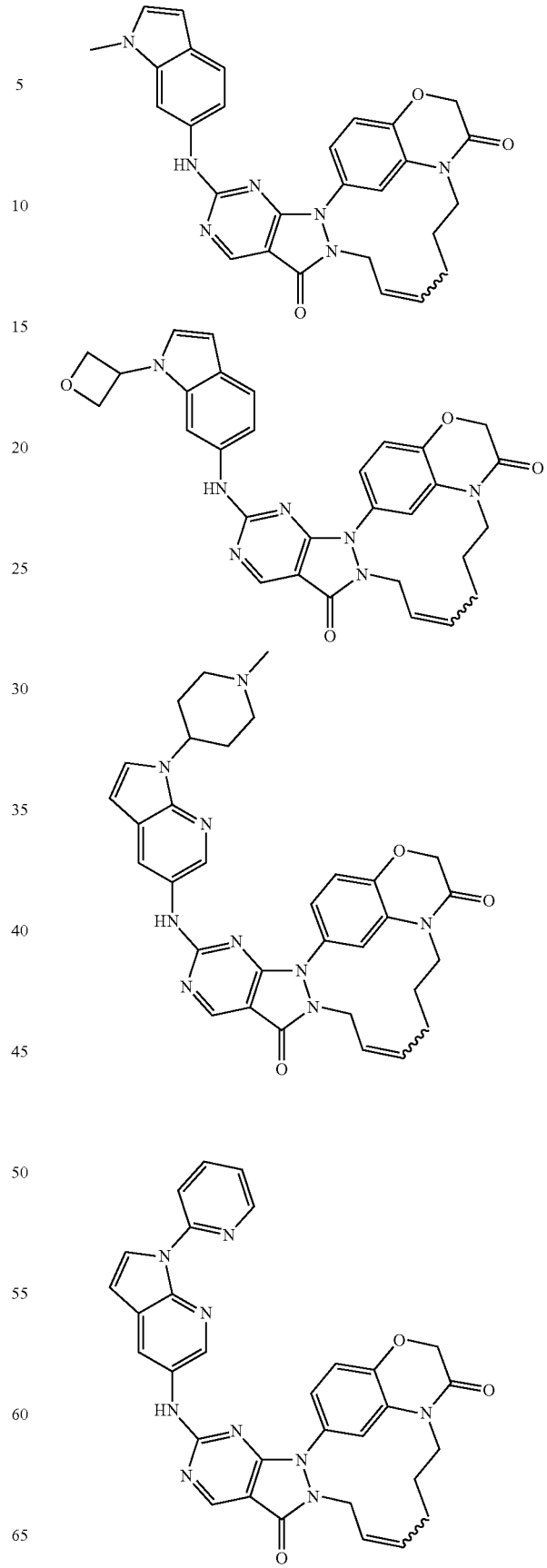

299
-continued
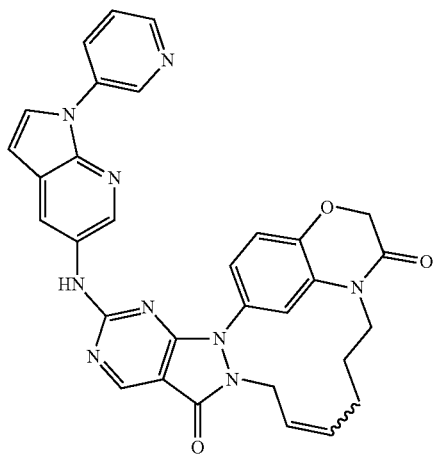
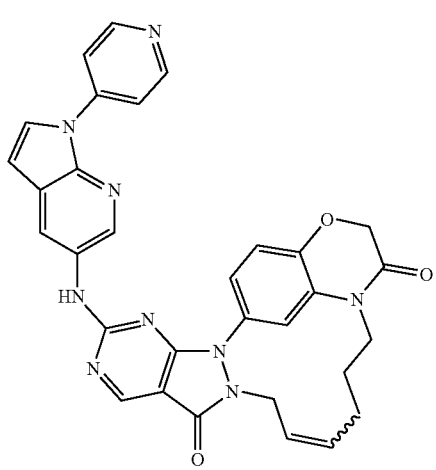
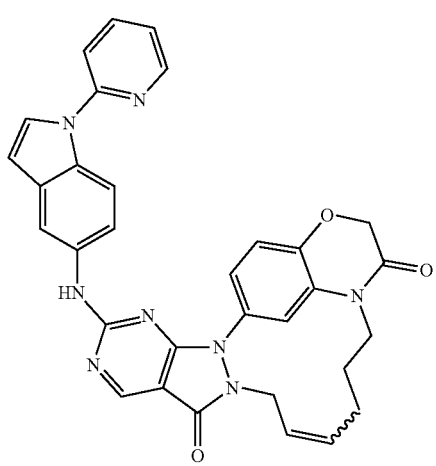
300
-continued
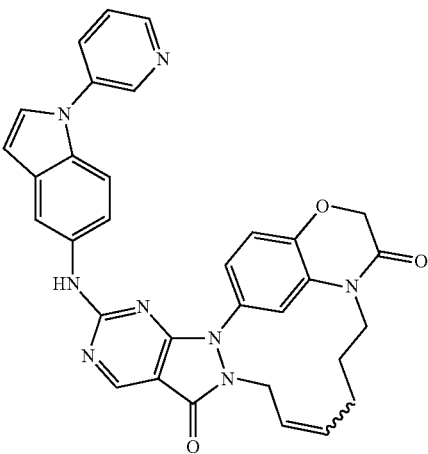
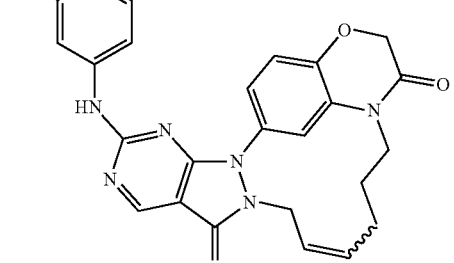
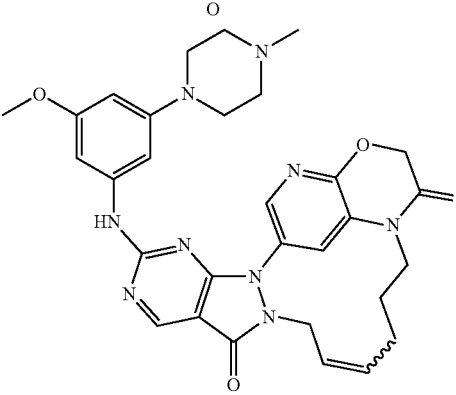
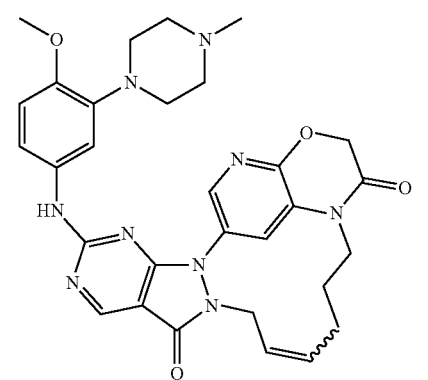

301
-continued
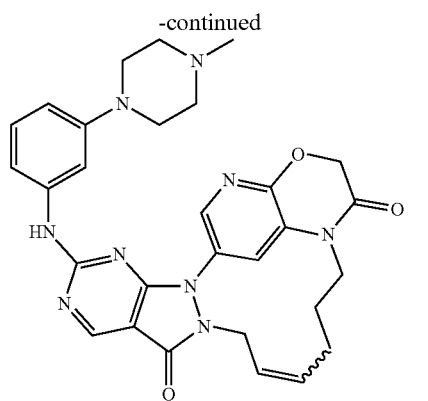
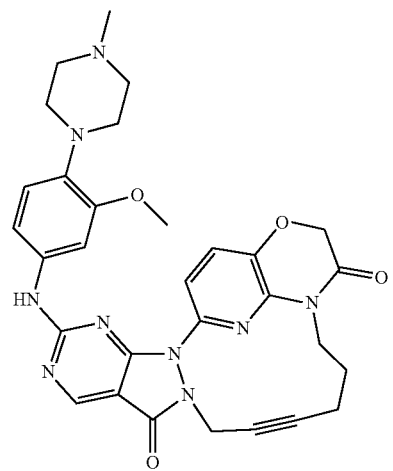
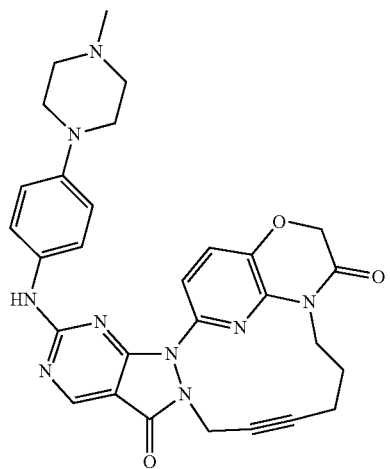
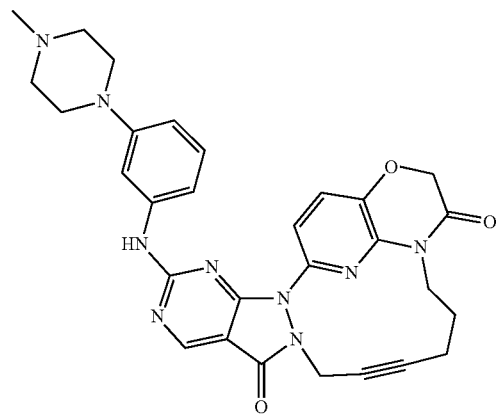
302
-continued
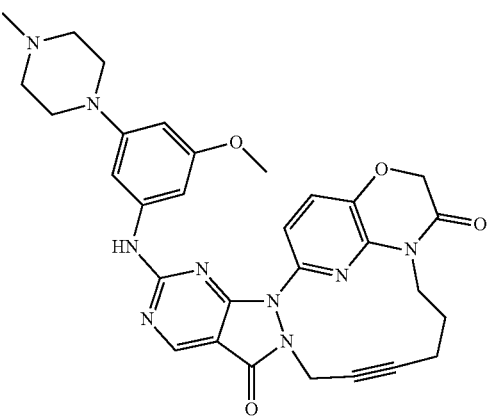
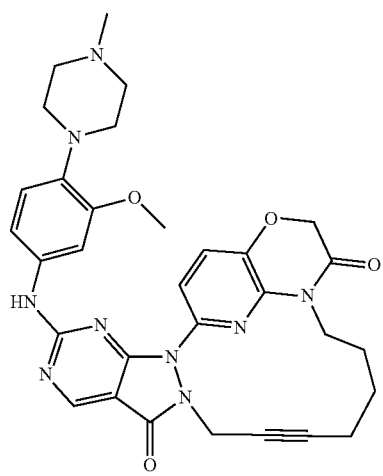
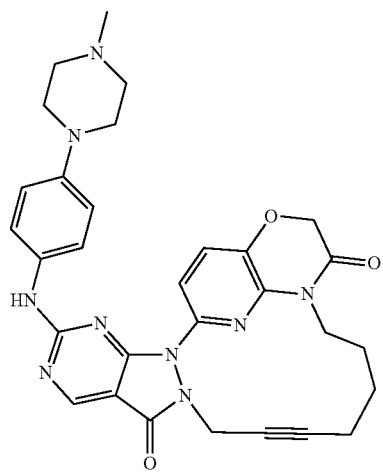

303
-continued
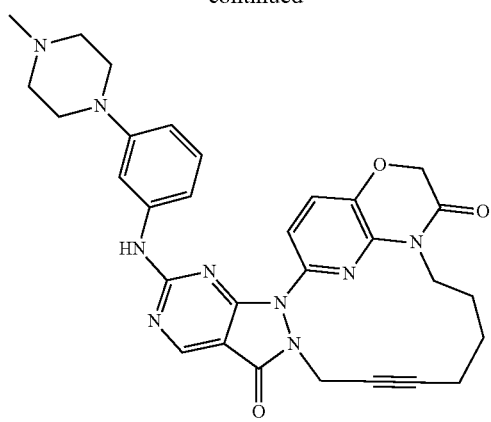
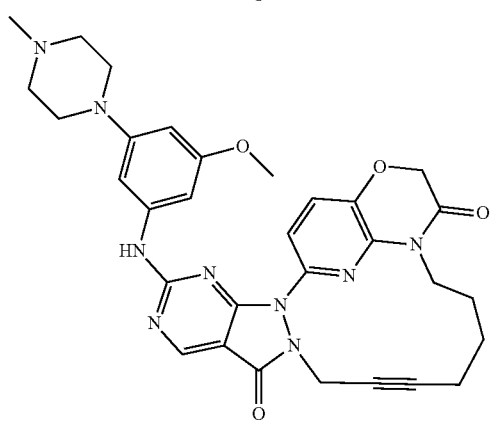
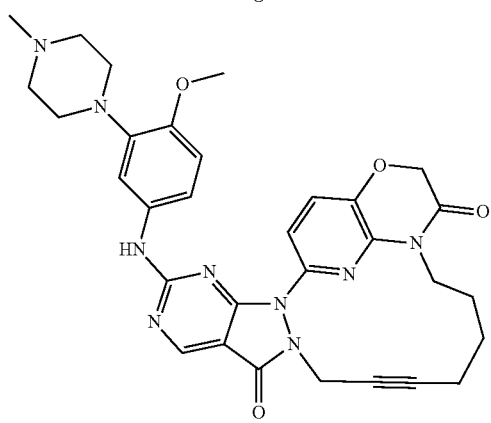
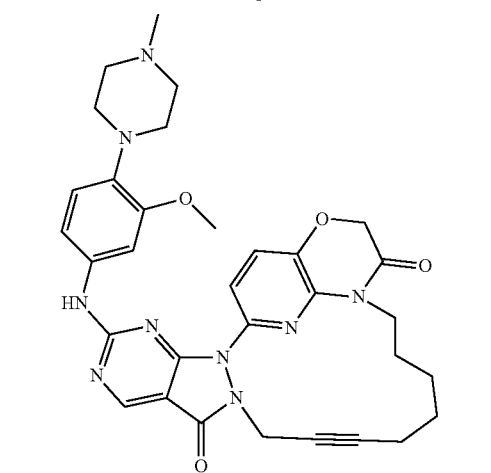
304
-continued
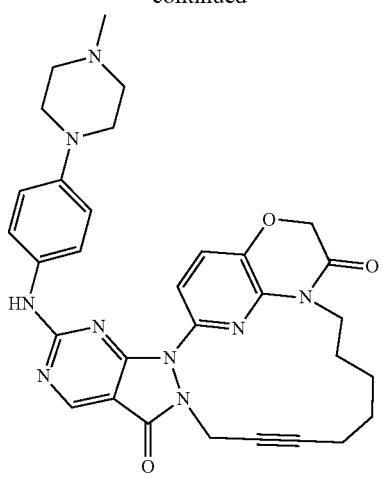
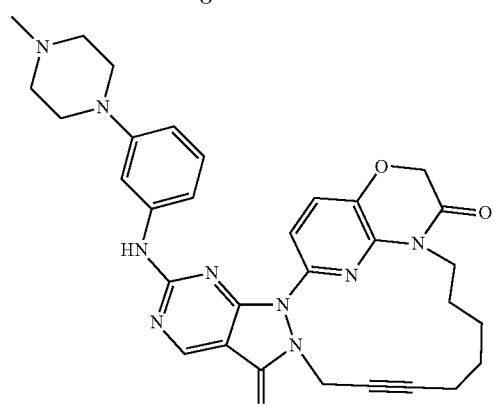
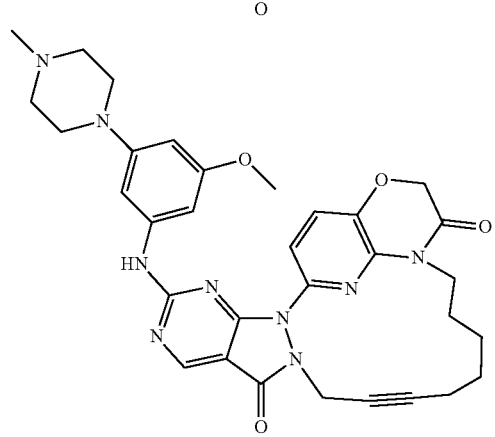
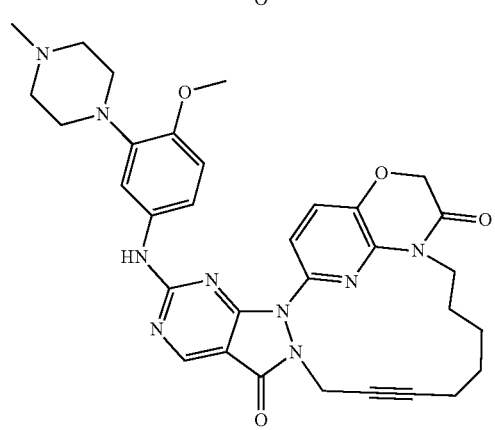

305
-continued

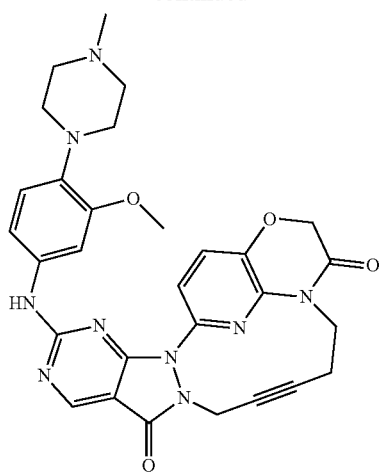

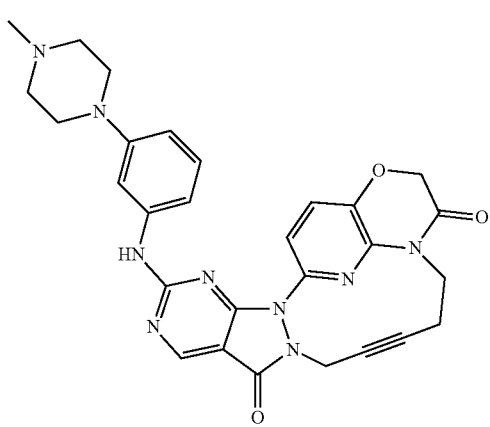

306
-continued

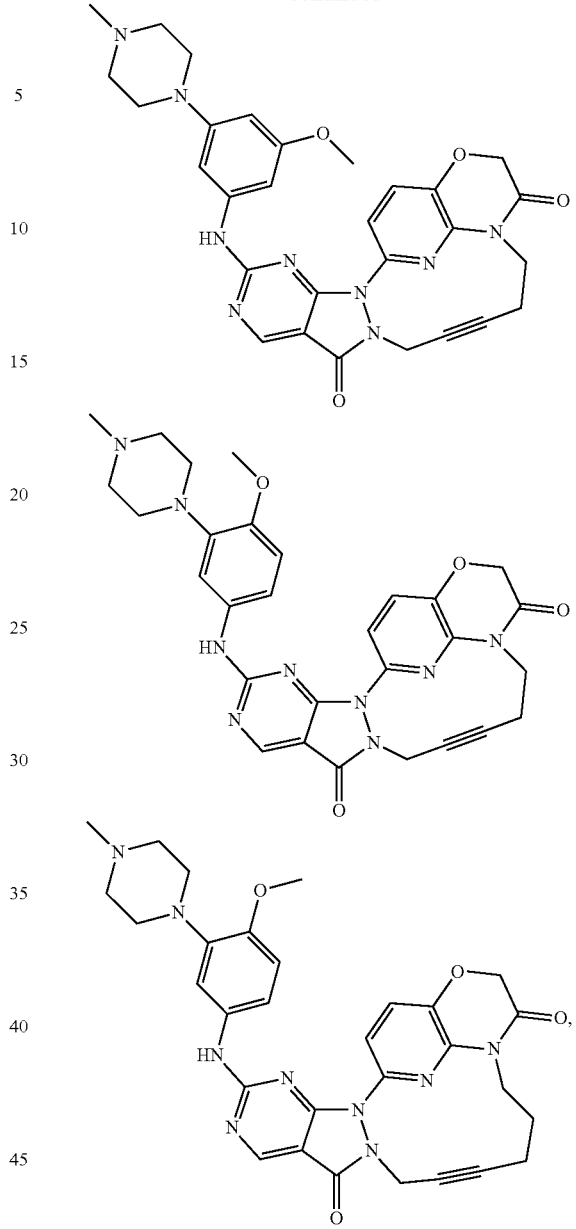

wherein " ∼ " refers to a cis-configuration, a trans-configuration, or an isomeric mixture of cis- and trans-configuration.

15. A pharmaceutical composition, comprising a therapeutic effective amount of active ingredient and a pharmaceutically acceptable adjuvant, the active ingredient comprises the compound of formula I, the isomer, the prodrug, the stable isotope derivative or the pharmaceutically acceptable salt thereof of claim 1, wherein the pharmaceutically acceptable adjuvant is a pharmaceutically acceptable carrier, diluent and/or excipient.

16. A method in sensitizing chemotherapy or radiotherapy of cancer in a subject in need thereof, comprising administering a pharmaceutically effective amount of the compound of formula I, the isomer, the prodrug, the stable isotope derivative or the pharmaceutically acceptable salt thereof of claim 1 to the subject.

17. A method in treating and/or alleviating cancer in a subject in need thereof, comprising administering a pharmaceutically effective amount of the compound of formula I, the isomer, the prodrug, the stable isotope derivative or the pharmaceutically acceptable salt thereof of claim 1 to the subject.

18. The method of claim 17, wherein, the compound of formula I, the isomer, the prodrug, the stable isotope derivative or the pharmaceutically acceptable salt thereof of claim 1 is used in combination with one or more than one other therapeutic agents and/or therapeutic methods.

19. A method in sensitizing chemotherapy or radiotherapy of cancer in a subject in need thereof, comprising administering a pharmaceutically effective amount of the pharmaceutical composition of claim 15 to the subject.

20. A method in treating and/or alleviating a cancer in a subject in need thereof, comprising administering a pharmaceutically effective amount of the pharmaceutical composition of claim 15 to the subject.

* * * * *